(12) United States Patent
Blaney et al.

(10) Patent No.: US 12,024,509 B2
(45) Date of Patent: Jul. 2, 2024

(54) THERAPEUTIC COMPOUNDS AS INHIBITORS OF THE OREXIN-1 RECEPTOR

(71) Applicant: C4X Discovery Limited, Manchester (GB)

(72) Inventors: Emma Louise Blaney, Manchester (GB); Barrie Phillip Martin, Manchester (GB); Thorsten Nowak, Manchester (GB); Martin John Watson, Manchester (GB)

(73) Assignee: C4X Discovery Limited, Manchester (GB)

( * ) Notice: Subject to any disclaimer, the term of this patent is extended or adjusted under 35 U.S.C. 154(b) by 0 days.

(21) Appl. No.: 16/814,328

(22) Filed: Mar. 10, 2020

(65) Prior Publication Data
US 2020/0270247 A1 Aug. 27, 2020

Related U.S. Application Data

(62) Division of application No. 15/508,392, filed as application No. PCT/GB2015/052546 on Sep. 3, 2015, now Pat. No. 10,611,760.

(30) Foreign Application Priority Data

Sep. 3, 2014 (GB) ...................... 1415569

(51) Int. Cl.
| | |
|---|---|
| *C07D 471/04* | (2006.01) |
| *A61K 31/4192* | (2006.01) |
| *A61K 31/435* | (2006.01) |
| *A61K 31/4439* | (2006.01) |
| *A61K 31/47* | (2006.01) |
| *A61P 3/04* | (2006.01) |
| *A61P 19/10* | (2006.01) |
| *A61P 25/00* | (2006.01) |
| *A61P 25/04* | (2006.01) |
| *A61P 25/06* | (2006.01) |
| *A61P 25/14* | (2006.01) |
| *A61P 25/16* | (2006.01) |
| *A61P 25/18* | (2006.01) |
| *A61P 25/20* | (2006.01) |
| *A61P 25/22* | (2006.01) |
| *A61P 25/24* | (2006.01) |
| *A61P 25/28* | (2006.01) |
| *A61P 25/30* | (2006.01) |
| *A61P 25/32* | (2006.01) |
| *A61P 25/34* | (2006.01) |

(Continued)

(52) U.S. Cl.
CPC .......... *C07D 471/04* (2013.01); *C07C 233/69* (2013.01); *C07C 233/78* (2013.01); *C07C 275/28* (2013.01); *C07C 275/40* (2013.01); *C07D 213/63* (2013.01); *C07D 213/64* (2013.01); *C07D 213/74* (2013.01); *C07D 231/38* (2013.01); *C07D 235/26* (2013.01); *C07D 235/30* (2013.01); *C07D 239/34* (2013.01); *C07D 239/42* (2013.01); *C07D 239/80* (2013.01); *C07D 239/84* (2013.01); *C07D 401/12* (2013.01); *C07D 401/14* (2013.01); *C07D 403/12* (2013.01); *C07D 413/12* (2013.01); *C07D 413/14* (2013.01); *C07D 417/12* (2013.01); *C07D 417/14* (2013.01)

(58) Field of Classification Search
CPC .......... A61P 25/20; A61P 25/00; A61P 25/14; A61P 25/18; A61P 25/36; A61P 25/16; A61P 25/34; A61P 25/22; A61P 25/30; A61P 25/28; A61P 25/32; A61P 25/06; A61P 25/24; A61P 25/04; A61P 19/10; A61P 3/04; A61P 43/00; C07D 471/04; C07D 239/34; C07D 239/84; C07D 239/80; C07D 239/42; C07D 401/12; C07D 401/14; C07D 213/74; C07D 213/64; C07D 213/63; C07D 235/30; C07D 235/26; C07D 413/14; C07D 413/12; C07D 417/14; C07D 417/12; C07D 403/12; C07D 231/38; C07C 233/69; C07C 233/78; C07C 257/40; C07C 257/28; A62K 31/435; A62K 31/47; A62K 31/4192; A62K 31/4439
See application file for complete search history.

(56) References Cited

U.S. PATENT DOCUMENTS

| | | |
|---|---|---|
| 5,968,965 A | 10/1999 | Dinsmore et al. |
| 6,066,738 A | 5/2000 | Dinsmore et al. |

(Continued)

FOREIGN PATENT DOCUMENTS

| | | |
|---|---|---|
| EP | 1349847 A1 | 10/2003 |
| EP | 1456203 A1 | 9/2004 |

(Continued)

OTHER PUBLICATIONS

Sharf et al., Brain Res., 2010, p. 1-15.*

(Continued)

*Primary Examiner* — Sun Jae Yoo
(74) *Attorney, Agent, or Firm* — Foley Hoag LLP; David P. Halstead; Alexander J. Chatterley

(57) ABSTRACT

The present invention relates to compounds that are inhibitors of the orexin-1 receptor. The compounds have the structural formula I defined herein. The present invention also relates to processes for the preparation of these compounds, to pharmaceutical compositions comprising them, and to their use in the treatment of diseases or disorders associated with orexin-1 receptor activity.

23 Claims, No Drawings

(51) Int. Cl.

| | | |
|---|---|---|
| A61P 25/36 | (2006.01) | |
| A61P 43/00 | (2006.01) | |
| C07C 233/69 | (2006.01) | |
| C07C 233/78 | (2006.01) | |
| C07C 275/28 | (2006.01) | |
| C07C 275/40 | (2006.01) | |
| C07D 213/63 | (2006.01) | |
| C07D 213/64 | (2006.01) | |
| C07D 213/74 | (2006.01) | |
| C07D 231/38 | (2006.01) | |
| C07D 235/26 | (2006.01) | |
| C07D 235/30 | (2006.01) | |
| C07D 239/34 | (2006.01) | |
| C07D 239/42 | (2006.01) | |
| C07D 239/80 | (2006.01) | |
| C07D 239/84 | (2006.01) | |
| C07D 401/04 | (2006.01) | |
| C07D 401/12 | (2006.01) | |
| C07D 401/14 | (2006.01) | |
| C07D 403/12 | (2006.01) | |
| C07D 413/12 | (2006.01) | |
| C07D 413/14 | (2006.01) | |
| C07D 417/12 | (2006.01) | |
| C07D 417/14 | (2006.01) | |

(56) References Cited

U.S. PATENT DOCUMENTS

| | | |
|---|---|---|
| 6,727,267 B2 | 4/2004 | Jaen et al. |
| 6,861,448 B2 | 3/2005 | Brouillette et al. |
| 6,905,739 B2 | 6/2005 | Cherkaoui et al. |
| 6,953,857 B2 | 10/2005 | Nazare et al. |
| 7,067,665 B2 | 6/2006 | Nazare et al. |
| 7,338,950 B2 | 3/2008 | Kelly et al. |
| 7,468,367 B2 | 12/2008 | Coulton et al. |
| 7,501,538 B2 | 3/2009 | Mjalli et al. |
| 7,544,699 B2 | 6/2009 | Mjalli et al. |
| 7,872,133 B2 | 1/2011 | Ohmoto et al. |
| 8,039,674 B2 | 10/2011 | Habashita et al. |
| 8,653,305 B2 | 2/2014 | Habashita et al. |
| 8,987,271 B2 | 3/2015 | Cardone et al. |
| 10,011,595 B2 | 7/2018 | Kim et al. |
| 10,611,760 B2 | 4/2020 | Blaney et al. |
| 10,696,654 B2 | 6/2020 | Martin |
| 11,130,746 B2 | 9/2021 | Martin |
| 11,753,398 B2 | 9/2023 | Martin |
| 2002/0198195 A1 | 12/2002 | Nazare et al. |
| 2004/0266732 A1 | 12/2004 | Galvez et al. |
| 2005/0080087 A1 | 4/2005 | Pendri et al. |
| 2005/0096083 A1* | 5/2005 | Chen .................... H04W 88/06 455/552.1 |
| 2008/0262046 A1 | 10/2008 | Coleman et al. |
| 2011/0212975 A1 | 9/2011 | Kao et al. |
| 2011/0263662 A1* | 10/2011 | Aissaoui ................ A61P 9/06 548/362.5 |
| 2012/0316147 A1 | 12/2012 | Bissantz et al. |
| 2017/0291897 A1 | 10/2017 | Blaney et al. |
| 2020/0255404 A1 | 8/2020 | Martin |
| 2021/0395227 A1 | 12/2021 | Martin |

FOREIGN PATENT DOCUMENTS

| | | |
|---|---|---|
| EP | 1637521 A1 | 3/2006 |
| EP | 1698335 A1 | 9/2006 |
| EP | 1760071 A1 | 3/2007 |
| EP | 1979341 A1 | 10/2008 |
| EP | 2462138 A1 | 6/2012 |
| EP | 2532661 A1 | 12/2012 |
| EP | 2730570 A1 | 5/2014 |
| EP | 2891489 A1 | 7/2015 |
| EP | 2891492 A1 | 7/2015 |
| GB | 240685 A | 10/1925 |
| JP | 2002/326980 A | 11/2002 |
| JP | 2003/012625 A | 1/2003 |
| JP | 2006/526653 A | 11/2006 |
| JP | 2007/537300 A | 12/2007 |
| JP | 2008/533151 A | 8/2008 |
| JP | 2008-239617 A | 10/2008 |
| JP | 2010/534626 A | 11/2010 |
| JP | 2012056871 A | 3/2012 |
| JP | 2013216634 A | 10/2013 |
| WO | WO-97027852 A1 | 8/1997 |
| WO | WO-0147862 A1 | 7/2001 |
| WO | WO-0177091 A2 | 10/2001 |
| WO | WO-2001/91558 A1 | 12/2001 |
| WO | WO-2003/051872 A1 | 6/2003 |
| WO | WO-05014532 A1 | 2/2005 |
| WO | WO-05014533 A2 | 2/2005 |
| WO | WO-05032493 A2 | 4/2005 |
| WO | WO-2005/090345 A1 | 9/2005 |
| WO | WO-2005/095327 A1 | 10/2005 |
| WO | WO-06038594 A1 | 4/2006 |
| WO | WO-2006/110626 A1 | 10/2006 |
| WO | WO-03006628 A3 | 10/2006 |
| WO | WO-2007/088999 A1 | 8/2007 |
| WO | WO-2007/126934 A2 | 11/2007 |
| WO | WO-08002671 A2 | 1/2008 |
| WO | WO-2008/061781 A1 | 5/2008 |
| WO | WO-2009/011775 A1 | 1/2009 |
| WO | WO-2009/022311 A2 | 2/2009 |
| WO | WO-2010012795 A1 | 2/2010 |
| WO | WO-2010/086366 A1 | 8/2010 |
| WO | WO-2011/015037 A1 | 2/2011 |
| WO | WO-2011/073316 A1 | 6/2011 |
| WO | WO-2012/021837 A2 | 2/2012 |
| WO | WO-2012/088438 A1 | 6/2012 |
| WO | WO-2013048942 A1 | 4/2013 |
| WO | WO-2013/066833 A1 | 5/2013 |
| WO | WO-2013076230 A1 | 5/2013 |
| WO | WO-2013158928 A2 | 10/2013 |
| WO | WO-2014/044738 A1 | 3/2014 |
| WO | WO-2014/159591 A1 | 10/2014 |
| WO | WO-2015/188073 A1 | 12/2015 |
| WO | WO-2016/034882 A1 | 3/2016 |
| WO | WO-2016/100161 A1 | 6/2016 |

OTHER PUBLICATIONS

Dubey et al, J. Pharmacol Pharmacother, 2015, 6(2), 118-121.*
Benting et al., "Preparation of arylalkylpyrazolecarboxamide derivatives and analogs for use as fungicides," Calpus, (2011).
Boss et al., "Recent Trends in Orexin Research—2010 to 2015," Bioorganic & Medicinal Chemistry Letters, 25:2875-2887 (2015).
Boss, "Orexin Receptor Antogonists—A Patent Review (2010 to Aug. 2014)," Expert Opinion, 24(12):1367-1381 (2014).
Braga et l., "Mild and efficient one-pot synthesis of chiral ß-chalcogen amides via 2-oxazoline ring-opening reaction mediated by indium," Journal of Organometallic Chemistry, 693:3563-3655 (2008).
Cai et al., "Antagonists of the Orexin Receptors," Expert Opinion, 16(5):631-646 (2006).
CAS Registry No. 1115194-20-1 (2009).
Clapp, "Reactions of ethylenimines with ammonia and amines," CAPLUS 1948:15572 (1948).
Coleman et al., "Discovery of [(2R,5R0-5-{[(5-Flouropyridin-2-yl)oxy]methyl}-2-methylpiperidin-1-yl][5-methyl-2-(pyrimidin-2-yl)phenyl]methanone (MK-6096): A Dual Orexin Receptor Antagonist with Potent Sleep-Promoting Properties," ChemMedChem, 7(3):415-424 (2012).
Coleman et al., "Discovery of Dual Orexin Receptor Antagonists (DORAs) for the Treatment of Insomnia," Currrent Topics in Medicinal Chemistry, 11:696-725 (2011).
Coleman et al., "Orexin Receptor Antagonists: A Review of Promising Compounds Patented Since 2006," Expert Opinion, 20(3):307-324 (2010).
Imperatore et al., "Effects of the Radical Savenger AVS on Behavioral and BBB Changes After Experimental Subarachnoid Hemmorrhage," Life Sciences, 66(9): 779-790 (2000).

(56) References Cited

OTHER PUBLICATIONS

International Search Report and Written Opinion for International Application No. PCT/EP2017/051960 dated Mar. 8, 2017.
International Search Report and Written Opinion for International Application No. PCT/GB2015/052546 dated Oct. 29, 2015.
Lebold et al., "Selective Orexin Receptor Antagonists," Bioorganic & Medicinal Chemistry Letters, 23:4761-4769 (2013).
Malherbe et al., "Mapping the Binding Pocket of Dual Antagonist almorexant to Human Orexin 1 and Orexin 2 Receptors: Comparison with the Selective OX1 Antagonist SB-674042 and the Selective OX2 Antagonist N-Ethyl-2[(6-methoxy-pyridin-3-yl)-(toluene-2-sufonyl)-amino]-N-pyridin-3-ylmethyl-acetamide (EMPA)," Mol. Pharmacol., 78:81-93 (2010).
McManus et al., "Coupling of bulky, electron-deficient partners in aryl amination in the preparation of tridentate bis(oxazoline) ligands for asymmetric catalysis," J Org Chem, 67:8566-8573 (2002).
Roecker et al., "Orexin Receptor Antagonists: Medicinal Chemistry and Therapeutic Potential," Current Topics in Medicinal Chemistry, 8:977-987 (2008).
U.K. Search Report for Application No. GB1601703.0 dated Nov. 9, 2016.
United Kingdom Search Report for United Kingdom Application No. GB 1415569.1 dated May 8, 2015.
Written Opinion issued by the Intellectual Property Office of Singapore in corresponding Application No. 11201701715P, dated Nov. 20, 2017.
Zhang et al., "Direct borylation of primary C—H bonds in functionalized molecules by palladium catalysis," Angew Chem Int Et, 53:3899-3903 (2014).
U.S. Appl. No. 16/073,429 (now U.S. Pat. No. 10,696,654, Granted.
U.S. Appl. No. 16/860,572, Allowed.
Baimel et al., "Orexin/hypocretin role in reward: implications for opioid and other addictions," British Journal of Pharmacology, 172: 334-348 (2015).
Mahler et al., "Multiple roles for orexin/hypocretin in addiction," Progress in Brain Research, 198: 49 pages (2012).
Rasmussen et al., "NIDA's medication development priorities in response to the Opioid Crisis: ten most wanted," Neuropsychopharmacology, 44: 657-659 (2019).
Thannickal et al., "Opiates increase the number of hypocretin-producing cells in human and mouse brain and reverse cataplexy in a mouse model of narcolepsy," Science Translational Medicine, 10: Article eaao4953 pp. 1-13 (2018).
Abbas et al., "Comprehensive Behavioral Analysis of Male Ox1r−/− Mice Showed Implication of Orexin Receptor-1 in Mood, Anxiety, and Social Behavior," Frontiers in Behavioral Neuroscience, 9: Article 324 pp. 1-10 (2015).
Kaufmann et al., "First-in-human study with ACT-539313, a novel selective orexin-1 receptor antagonist," British Journal of Clinical Pharmacology, 86(7): 1377-1386 (2020).
Piccoli et al., "Role of Orexin-1 Receptor Mechanisms on Compulsive Food Consumption in a Model of Binge Eating in Female Rats," Neuropsychopharmacology, 37: 1999-2011 (2012).
Salvadore et al., "Translational evaluation of novel selective orexin-1 receptor antagonist JNJ-61393215 in an experimental model for panic in rodents and humans," Translational Psychiatry, 10: 308 pp. 1-10 (2020).
Mirbolouk et al., "Chronic orexin-1 receptor blockage attenuates depressive behaviors and provokes PSD-95 expression in a rat model of depression", Behavioral Brain Research 437: 7 pages (2023).
Scott et al., "Hcrtr1 and 2 signaling differentially regulates depression-like behaviors", Behavioral Brain Research 222(2): 289-294 (2011).
Sekste et al., "Increase in the Level of Orexin Receptor 1 (OXJ R) mRNA in the Brain Structures of Rats Prone to Impulsivity in Behavior", Biomedical Chemistry, 6(1): 38-44 (2022).
Vickers et al., "Effects of Lisdexamfetamine in a rat model of binge-eating", Journal of Psychopharmacology, 29(12): 1290-1307 (2015).
Notice of Allowance for U.S. Appl. No. 17/459,598 dated May 2, 2023.

\* cited by examiner

THERAPEUTIC COMPOUNDS AS INHIBITORS OF THE OREXIN-1 RECEPTOR

RELATED APPLICATIONS

This application is a division of U.S. patent application Ser. No. 15/508,392, filed on Mar. 2, 2017, which is the National Stage Entry of PCT Application No. PCT/GB2015/052546, filed on Sep. 3, 2015, which claims the benefit of G.B. Patent Application No. 1415569.1, filed on Sep. 3, 2014.

INTRODUCTION

The present invention relates to therapeutic compounds. More specifically, the present invention relates to compounds that are inhibitors of the orexin-1 receptor. The present invention also relates to processes for the preparation of these compounds, to pharmaceutical compositions comprising them, and to their use in the treatment of diseases or disorders associated with orexin-1 receptor activity.

BACKGROUND OF THE INVENTION

The neuropeptides Orexin-A (OxA) and Orexin-B (OxB) (also known as Hypocretin-1 and Hypocretin-2) originate from the same prepro-peptide, which is expressed exclusively in the hypothalamus (1). Cleavage of the prepro-peptide (prepro-orexin) yields OxA a 33 amino acid polypeptide which is extensively post-translationally modified (C-terminal amidation, N-terminally cyclised with a pyroglutamyl residue). OxA shares a 46% sequence identity with OxB which is a 28 amino acid, C-terminally amidated linear polypeptide which likely forms a helical secondary structure (3).

The fully functional mature peptide neurotransmitters act as agonists on the orexin-1 ($OX_1$) and orexin-2 ($OX_2$) 7-transmembrane G-protein coupled receptors (also known as HCRTR1 and HCRTR2) that, like the orexin neuropeptides, share a high sequence homology across species (2, 6). $OX_1$ binds both OxA and OxB, albeit, with differential affinity (OxA has >10-fold higher affinity than OxB). On the contrary $OX_2$, which shares a 64% sequence identity with $OX_1$, binds both polypeptides with nearly equivalent affinity (2). The primary G-protein mediated mechanism through which both receptors act is $G_{q/11}$ activation of phospholipase C catalysing the liberation of inositol-1,4,5-triphosphate ($IP_3$), which in turn acts on $IP_3$ receptors to release calcium from intracellular stores. $OX_2$ has also been reported to modulate cAMP levels via activation of $G_s$ and $G_i$ and $OX_1$ appears capable of signalling through $G_{i/o}$ to also modulate cAMP levels (5, 8). The high degree of sequence similarity in the peptides and receptors across species translates into similar in vitro pharmacology (7).

The hypothalamus, where orexin is predominately expressed, regulates a broad array of physiological and behavioural activities. Orexin expression in this brain structure has been mapped immunohistochemically to only a very restricted number of neurons that reside specifically in the perifornical (50%), lateral and dorsomedial areas (4). The projection fields of these neurons have been identified in numerous brain regions, including the cortex, thalamus, hypothalamus, brainstem, and spinal cord, but not the cerebellum (9). This extensive coverage of the brain suggests that the orexin ligand/receptor system is implicated directly or indirectly in the regulation of multiple brain functions. Notably, knockout experiments in mice suggested that the orexin system is a key regulator of behavioural arousal, sleep and wakefulness. Indeed, the observed phenotype in orexin knockout mice was very similar to that of narcolepsy in humans (10, 11). Narcolepsy in humans is a chronic and disabling disorder characterized by excessive sleepiness during the day, fragmented sleep and cataplexy. Studies in dogs have linked the cause of the disorder to the disruption of the $OX_2$ gene or a loss of orexin peptide expression (12). Further supporting evidence that in particular the disruption of $OX_2$ function and or the absence of mature OxB ligand are associated with narcolepsy came from studies in knockout mice (17). Subsequent clinical studies comparing the levels of OxA in the cerebrospinal fluid of narcoleptic patients to normal individuals confirmed that the disruption of the orexin system shows a causal relationship with the occurrence of narcolepsy in humans (13). Additional studies in unusual early onset human narcolepsy resulted in the identification of a mutation in the orexin gene that further strengthened the link between narcolepsy and the orexin system in humans (14). More recently, clinical data demonstrating the pharmacological relevance of the orexins in CNS disorders has emerged. Most notably, clinical trials with small molecule dual $OX_1$ and $OX_2$ antagonists (DO-RAs) such as BELSOMRA® (Suvorexant), have clearly demonstrated the potential utility of such agents in treating sleep disorders (15, 16, 18). These data together with the pre-clinical evidence presented above clearly implicate $OX_2$ in sleep regulation.

The differential brain expression of $OX_1$ and $OX_2$ coupled with the diversity of neuro-biological effects attributed to the orexins strongly suggests drugs modulating $OX_1$ or $OX_2$ will elicit different biological effects. To this end, recent reports linking the $OX_1$/OxA system specifically to feeding and behavioural disorders are important.

Given that prepro-orexin mRNA levels are mainly found in the lateral and posterior hypothalamus, areas of the brain classically implicated in the regulation of food intake and energy balance/body weight, a link between the orexin system and feeding behaviour is not unexpected (19). The role of the $OX_1$/OxA system in such functions has been strengthened by a series of pre-clinical studies. Thus intracerebroventricular (i.c.v.) administration of OxA (20) has been shown to induce feeding and specific anti-orexin antibodies dose-dependently suppress food intake (21). In particular, the latter study indicates that orexin receptor antagonists should have a beneficial effect on orexin stimulated feeding. This hypothesis is supported by independent in vivo studies, which clearly identify $OX_1$ as the dominant receptor of the orexin system in the regulation of food intake and energy balance. Thus, experiments conducted with selective $OX_1$ and $OX_2$ receptor antagonists have shown that $OX_1$ selective compounds alter food intake and energy balance in circumstances of concurrent exposure to stress (22, 23). The dominant effect of the $OX_1$ on regulating feeding behaviour and energy balance is further supported by observations which show that $OX_1$ expression is selectively up-regulated in response to fasting, whereas those of $OX_2$ are unaffected (24). Finally, studies with an $OX_1$ specific antibody strongly suggests that a selective $OX_1$ antagonist should suppress food intake and thus have potential therapeutic utility for the treatment of feeding related disorders such as binge eating or obesity.

Elevated $OX_1$ levels have also been associated with psychiatric conditions including schizophrenia, anxiety and mood disorders, panic attacks, reward seeking behaviours and addiction (25, 26, 27). Studies with selective $OX_1$ antagonists (SB334867, SB408124) clearly demonstrated a beneficial effect in a clinically relevant animal model of panic thus implying that $OX_1$ antagonist could provide a novel therapeutic approach for the treatment of panic disorders (27).

Indirect evidence for the involvement of the orexin system in reward seeking behaviour comes from studies which show that orexinergic neurons project to reward associated brain regions such as the nucleus accumbens and ventral tegmental area (28). Direct experimental evidence comes from studies involving the intracerebroventricular (icv) infusion of orexin, which led to a dose-dependent reinstatement of cocaine seeking. The work by Boutrel et al. also links stress pathways to the effect of orexin on addiction and reward (29). Notably, stress is considered a prominent stimulus for relapse in abstinent addicts (31). The link between stress, addiction and orexin was further strengthened by pharmacological studies in a foot-shock model. These showed activation of orexin neurons in specific areas of the posterior and dorsomedial hypothalamus, which are particularly associated with stress but not the lateral hypothalamus, which has a strong link to reward (32). Moreover orexin as a mediator of stress-induced reinstatement of addictive behaviour was also shown for alcohol seeking (30). Importantly the effects of stress induced reinstatement of alcohol and cocaine seeking in animal models can be attenuated with the selective $OX_1$ antagonist SB334867 supporting the therapeutic use of $OX_1$ selective antagonists in these conditions (29, 30).

Finally the Orexin/$OX_1$ pathway has been implicated in nicotine self-administration (33, 34) and re-instatement of nicotine seeking (35, 36). Such data suggest that $OX_1$ antagonists could find utility as smoking cessation therapies.

Taken together the orexin system, in particular the $OX_1$ pathway may be considered a target for the treatment of reward seeking behaviours, addiction and related disorders.

There is therefore a need for compounds capable of attenuating orexin-1 ($OX_1$) activity. There is a further need for compounds capable of selectively modulating orexin-1 ($OX_1$) function.

SUMMARY OF THE INVENTION

In one aspect, the present invention provides a compound, or a pharmaceutically acceptable salt or solvate thereof as defined herein.

In another aspect, the present invention provides a pharmaceutical composition comprising a compound of the invention as defined herein, or a pharmaceutically acceptable salt or solvate thereof, and one or more pharmaceutically acceptable excipients.

In another aspect, the present invention relates to a compound of the invention as defined herein, or a pharmaceutically acceptable salt or solvate thereof, or a pharmaceutical composition as defined herein, for use in therapy.

In another aspect, the present invention relates to a compound of the invention as defined herein, or a pharmaceutically acceptable salt or solvate thereof, or a pharmaceutical composition as defined herein, for use in the treatment of diseases or conditions in which orexin-1 ($OX_1$) activity is implicated.

In another aspect, the present invention relates to the use of a compound of the invention as defined herein, or a pharmaceutically acceptable salt or solvate thereof, in the manufacture of a medicament for use in the treatment of diseases or conditions in which orexin-1 ($OX_1$) activity is implicated.

In another aspect, the present invention relates to a method of treating a disease or condition in which orexin-1 ($OX_1$) activity is implicated, said method comprising administering to a subject in need of such treatment a therapeutically effective amount of a compound of the invention as defined herein, or a pharmaceutically acceptable salt or solvate thereof, or a pharmaceutical composition as defined herein.

Examples of conditions in which orexin-1 ($OX_1$) activity is implicated include behavioural arousal, eating disorders (e.g. binge eating, obesity), psychiatric conditions (e.g. schizophrenia, anxiety, mood disorders, reward seeking behaviours, alcohol or drug (e.g. nicotine) addiction, panic disorders (such as panic attacks) and/or anxiety).

In another aspect, the present invention provides a compound, or a pharmaceutically acceptable salt or solvate thereof, or a pharmaceutical composition as defined herein, for use in the treatment of behavioural arousal, eating disorders (e.g. binge eating, obesity), psychiatric conditions (e.g. schizophrenia, anxiety, mood disorders, reward seeking behaviours, alcohol or drug (e.g. nicotine) addiction, panic disorders (such as panic attacks) and/or anxiety).

In another aspect, the present invention provides the use of a compound, or a pharmaceutically acceptable salt or solvate thereof, in the manufacture of a medicament for use in the treatment of behavioural arousal, eating disorders (e.g. binge eating, obesity), psychiatric conditions (e.g. schizophrenia, anxiety, mood disorders, reward seeking behaviours, alcohol or drug (e.g. nicotine) addiction, panic disorders (such as panic attacks) and/or anxiety).

In another aspect, the present invention provides a method of treating behavioural arousal, eating disorders (e.g. binge eating, obesity), psychiatric conditions (e.g. schizophrenia, anxiety, mood disorders, reward seeking behaviours, alcohol or drug (e.g. nicotine) addiction, panic disorders (such as panic attacks) and/or anxiety), said method comprising administering to a subject in need of such treatment a therapeutically effective amount of a compound, or a pharmaceutically acceptable salt or solvate thereof, or a pharmaceutical composition as defined herein.

In another aspect, the present invention provides a compound, or a pharmaceutically acceptable salt or solvate thereof, or a pharmaceutical composition as defined herein, for use in the production of an orexin-1 inhibitory effect.

In another aspect, the present invention provides the use of a compound, or a pharmaceutically acceptable salt or solvate thereof, in the manufacture of a medicament for use in the production of an orexin-1 inhibitory effect.

In another aspect, the present invention provides a method of producing an orexin-1 inhibitory effect in vitro, said method comprising administering an effective amount of a compound, or a pharmaceutically acceptable salt or solvate thereof.

In another aspect, the present invention provides a method of producing an orexin-1 inhibitory effect in vivo, said method comprising administering an effective amount of a compound, or a pharmaceutically acceptable salt or solvate thereof.

In another aspect, the present invention provides a method of inhibiting orexin-1 ($OX_1$) in vitro or in vivo, said method comprising contacting a cell with an effective amount of a compound as defined herein, or a pharmaceutically acceptable salt or solvate thereof.

The present invention further provides a method of synthesising a compound, or a pharmaceutically acceptable salt or solvate thereof, as defined herein.

In another aspect, the present invention provides a compound, or a pharmaceutically acceptable salt or solvate thereof, obtainable by, or obtained by, or directly obtained by a method of synthesis as defined herein.

In another aspect, the present invention provides novel intermediates as defined herein which are suitable for use in any one of the synthetic methods set out herein.

Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

"Cycloalkyl" means a hydrocarbon ring containing from 3 to 8 carbon atoms, for example, cyclopropyl, cyclobutyl, cyclopentyl, cyclohexyl, cycloheptyl or bicycle[2.2.2]octane, bicycle[2.1.1]hexane, bicycle[1.1.1]pentane and bicyclo[2.2.1]heptyl.

The term "heteroalkyl" refers to an alkyl chain comprising 1-8 carbon atoms which additionally comprises one, two or three heteroatoms present within the alkyl chain which are selected from the group consisting of N, O, or S.

The term "halo" refers to fluoro, chloro, bromo and iodo.

The term "haloalkyl" or "haloalkoxy" is used herein to refer to an alkyl or alkoxy group respectively in which one or more hydrogen atoms have been replaced by halogen (e.g. fluorine) atoms. Examples of haloalkyl and haloalkoxy groups include fluoroalkyl and fluoroalkoxy groups such as —CHF$_2$, —CH$_2$CF$_3$, or perfluoroalkyl/alkoxy groups such as —CF$_3$, —CF$_2$CF$_3$ or —OCF$_3$.

The term "carbocyclyl", "carbocyclic" or "carbocycle" means a non-aromatic saturated or partially saturated monocyclic, or a fused, bridged, or spiro bicyclic carbocyclic ring system(s). Monocyclic carbocyclic rings contain from about 3 to 12 (suitably from 3 to 7) ring atoms. Bicyclic carbocycles contain from 7 to 17 carbon atoms in the rings, suitably 7 to 12 carbon atoms, in the rings. Bicyclic carbocyclic rings may be fused, spiro, or bridged ring systems.

The term "heterocyclyl", "heterocyclic" or "heterocycle" means a non-aromatic saturated or partially saturated monocyclic, fused, bridged, or spiro bicyclic heterocyclic ring system(s). Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or SO$_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. Suitably, the term "heterocyclyl", "heterocyclic" or "heterocycle" will refer to 4, 5, 6 or 7 membered monocyclic rings as defined above.

By "bridged ring systems" is meant ring systems in which two rings share more than two atoms, see for example *Advanced Organic Chemistry*, by Jerry March, 4$^{th}$ Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

By "spiro bi-cyclic ring systems" we mean that the two ring systems share one common spiro carbon atom, i.e. the heterocyclic ring is linked to a further carbocyclic or heterocyclic ring through a single common spiro carbon atom.

Examples of spiro ring systems include 6-azaspiro[3.4]octane, 2-oxa-6-azaspiro[3.4]octane, 2-azaspiro[3.3]heptanes and 2-oxa-6-azaspiro[3.3]heptanes.

"Heterocyclyl(m-nC)alkyl" means a heterocyclyl group covalently attached to a (m-nC)alkylene group, both of which are defined herein.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Suitably, the term "heteroaryl" or "heteroaromatic" will refer to 5 or 6 membered monocyclic hetyeroaryl rings as defined above.

Non-limiting examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydro-pyrido[2,3-b]pyrazinyl and 3,4-dihydro-2H-pyrido[3,2-b][1,4]oxazinyl.

Non-limiting examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Non-limiting examples of six membered heteroaryl groups include but are not limited to pyridyl, pyrazinyl, pyridazinyl, pyrimidinyl and triazinyl.

A bicyclic heteroaryl group may be, for example, a group selected from:

a) a benzene ring fused to a 5- or 6-membered ring containing 1, 2 or 3 ring heteroatoms;
b) a pyridine ring fused to a 5- or 6-membered ring containing 1, 2 or 3 ring heteroatoms;
c) a pyrimidine ring fused to a 5- or 6-membered ring containing 1 or 2 ring heteroatoms;
d) a pyrrole ring fused to a 5- or 6-membered ring containing 1, 2 or 3 ring heteroatoms;
e) a pyrazole ring fused to a 5- or 6-membered ring containing 1 or 2 ring heteroatoms;
f) a pyrazine ring fused to a 5- or 6-membered ring containing 1 or 2 ring heteroatoms;
g) an imidazole ring fused to a 5- or 6-membered ring containing 1 or 2 ring heteroatoms;
h) an oxazole ring fused to a 5- or 6-membered ring containing 1 or 2 ring heteroatoms;
i) an isoxazole ring fused to a 5- or 6-membered ring containing 1 or 2 ring heteroatoms;
j) a thiazole ring fused to a 5- or 6-membered ring containing 1 or 2 ring heteroatoms;
k) an isothiazole ring fused to a 5- or 6-membered ring containing 1 or 2 ring heteroatoms;
l) a thiophene ring fused to a 5- or 6-membered ring containing 1, 2 or 3 ring heteroatoms;
m) a furan ring fused to a 5- or 6-membered ring containing 1, 2 or 3 ring heteroatoms;
n) a cyclohexyl ring fused to a 5- or 6-membered heteroaromatic ring containing 1, 2 or 3 ring heteroatoms; and
o) a cyclopentyl ring fused to a 5- or 6-membered heteroaromatic ring containing 1, 2 or 3 ring heteroatoms.

Particular non-limiting examples of bicyclic heteroaryl groups containing a six membered ring fused to a five membered ring include but are not limited to benzofuranyl, benzothiophenyl, benzimidazolyl, benzoxazolyl, benzisoxazolyl, benzothiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl, pyrrolopyridine, and pyrazolopyridinyl groups.

Particular non-limiting examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl(m-nC)alkyl" means a heteroaryl group covalently attached to a (m-nC)alkylene group, both of which are defined herein. Examples of heteroaralkyl groups include pyridin-3-ylmethyl, 3-(benzofuran-2-yl)propyl, and the like.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In this particular embodiment, an aryl is phenyl or naphthyl, especially phenyl.

The term "aryl(m-nC)alkyl" means an aryl group covalently attached to a (m-nC)alkylene group, both of which are defined herein. Examples of aryl-(m-nC)alkyl groups include benzyl, phenylethyl, and the like.

This specification also makes use of several composite terms to describe groups comprising more than one functionality. Such terms will be understood by a person skilled in the art. For example heterocyclyl(m-nC)alkyl comprises (m-nC)alkyl substituted by heterocyclyl.

The term "optionally substituted" refers to either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Compounds of the Invention

In a first aspect, the present invention provides a compound of Formula I

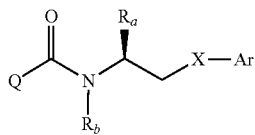

wherein:

X is a group:

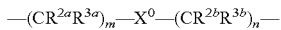

wherein $X^0$ is selected from —O—, —N($R^1$)—, —N($R^1$)—C(O)—, —C(O)—N($R^1$)—, —N($R^1$)C(O)N($R^1$)—, —S—, —SO—, —SO$_2$—, —S(O)$_2$N($R^1$)—, —N($R^1$)SO$_2$— or —C$R^4R^5$—;

m and n are each independently selected from 0 or 1;

$R^1$ is selected from hydrogen or a (1-6C)alkyl, (3-6C)cycloalkyl, (3-6C)cycloalkyl(1-2C)alkyl group which is optionally substituted by one or more (e.g. one to five) substituents selected from fluoro, cyano, hydroxyl, mercapto, N$R^{1a}R^{1b}$, (1-4C)alkoxy, (1-4C)haloalkoxy, (1-4C)alkylthio, (1-4C)alkylsulphinyl, (1-4C)alkylsulphonyl, (1-4C)alkoxycarbonyl, (2-4C)alkanoyl, (2-4C)alkanoyloxy;

$R^{1a}$ and $R^{1b}$ are each independently selected from hydrogen or (1-4C)alkyl or $R^{1a}$ and $R^{1b}$ are linked such that, together with the nitrogen atom to which they are attached, they form a 4, 5 or 6 membered heterocyclic ring which is optionally substituted by fluoro or (1-4C)alkyl;

$R^{2a}$, $R^{3a}$, $R^{2b}$, $R^{3b}$, $R^4$ and $R^5$ are each independently selected from hydrogen, halo, hydroxy or a (1-6C)alkyl, (3-6C)cycloalkyl, (3-6C)cycloalkyl(1-2C)alkyl group which is optionally substituted by one or more (e.g. one to five) fluoro substituents;

or $R^{2a}$ and $R^{3a}$, $R^{2b}$ and $R^{3b}$, $R^4$ and $R^5$ are optionally linked to such that, together with the carbon atom to which they are attached, they form a (3-6C)cycloalkyl ring which is optionally substituted by one or more (e.g. one to five) fluoro substituents;

Ar is aryl or heteroaryl, each of which is optionally substituted with one or more substituents selected from the group consisting of halo, cyano, nitro or a group of the formula:

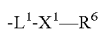

wherein $L^1$ is absent or a linker group of the formula —[C$R^7R^8$]$_r$— in which r is an integer selected from 1, 2, 3 or 4, and $R^7$ and $R^8$ are each independently selected from hydrogen, halo, hydroxy or a (1-4C)alkyl, (3-6C)cycloalkyl, (3-6C)cycloalkyl(1-2C)alkyl group which is optionally substituted by one or more (e.g. one to five) fluoro substituents; or $R^7$ and $R^8$ are optionally linked to such that, together with the carbon atom to which they are attached, they form a (3-6C)cycloalkyl ring which is optionally substituted by one or more (e.g. one to five) fluoro substituents;

$X^1$ is absent or selected from —O—, —C(O)—, —C(O)O—, —OC(O)—, —N($R^9$)—, —N($R^9$)—C(O)—, —C(O)—N($R^9$)—, —N($R^9$)—C(O)O—, —OC(O)—N($R^9$)—, —N($R^9$)C(O)N($R^{10}$)—, —S—, —SO—, —SO$_2$—, —S(O)$_2$N($R^9$)—, —N($R^9$)SO$_2$— or —S(O)(=N$R^{10}$)—, wherein $R^9$ and $R^{10}$ are selected from hydrogen, (1-4C)alkyl, (1-4C)fluoroalkyl or (3-6C)cycloalkyl; and $R^6$ is hydrogen, (1-6C)alkyl, (2-6C)alkenyl, (2-6C)alkynyl, aryl, aryl(1-2C)alkyl, (3-6C)cycloalkyl, (3-6C)cycloalkyl(1-2C)alkyl, heterocyclyl, heterocyclyl-(1-2C)alkyl, heteroaryl, or heteroaryl-(1-2C)alkyl, and wherein $R^6$ is optionally further substituted by one or more substituent groups independently selected from oxo, halo, cyano, nitro, or a group of the formula:

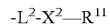

wherein $L^2$ is absent or a linker group of the formula —[C$R^{12}R^{13}$]$_s$— in which s is an integer selected from 1, 2, 3 or 4, and $R^{12}$ and $R^{13}$ are each independently selected from hydrogen or a (1-4C)alkyl, (3-6C)cycloalkyl, (3-6C)cycloalkyl(1-2C)alkyl group which is optionally substituted by one or more (e.g. one to five) fluoro substituents; or $R^{12}$ and $R^{13}$ are optionally linked to such that, together with the carbon atom to which they are attached, they form a (3-6C)cycloalkyl ring which is optionally substituted by one or more (e.g. one to five) fluoro substituents;

$X^2$ is absent or selected from —O—, —C(O)—, —C(O)O—, —OC(O)—, —N($R^{14}$)—, —N($R^{14}$)—C(O)—, —C(O)—N($R^{14}$)—, —N($R^{14}$)—C(O)O—, —OC(O)—N($R^{14}$)—, —N($R^{14}$)C(O)N($R^{15}$)—, —S—, —SO—, —SO$_2$—, —S(O)$_2$N($R^{14}$)—, —N($R^{14}$)SO$_2$— or —S(O)(=N$R^{14}$)—, wherein $R^{14}$ and $R^{15}$ are selected from hydrogen, (1-4C)alkyl, (1-4C)fluoroalkyl or (3-6C)cycloalkyl; and $R^{11}$ is hydrogen or a (1-6C)alkyl (3-6C)cycloalkyl, (3-6C)cycloalkyl(1-2C)alkyl group which is optionally substituted by one or more (e.g. one to five) fluoro substituents;

Q is aryl or heteroaryl, each of which is optionally substituted with one or more $R^z$ substituents, wherein $R^z$ is selected from the group consisting of halo, cyano, nitro, or a group of the formula:

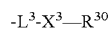

wherein $L^3$ is absent or a linker group of the formula —[C$R^{31}R^{32}$]$_t$— in which t is an integer selected from 1, 2, 3 or 4, and $R^{31}$ and $R^{32}$ are each independently selected from hydrogen or a (1-4C)alkyl, (3-6C)cycloalkyl, (3-6C)cycloalkyl(1-2C)alkyl group which is optionally substituted by one or more (e.g. one to five) fluoro substituents; or $R^{31}$ and $R^{32}$ are optionally linked to such that, together with the carbon atom to which they are attached, they form a (3-6C)cycloalkyl ring which is optionally substituted by one or more (e.g. one to five) fluoro substituents;

$X^3$ is absent or selected from —O—, —C(O)—, —C(O)O—, —OC(O)—, —N($R^{33}$)—, —N($R^{33}$)—C(O)—, —C(O)—N($R^{33}$)—, —N($R^{33}$)—C(O)O—, —OC(O)—N($R^{33}$)—, —N($R^{33}$)C(O)N($R^{34}$)—, —S—, —SO—, —SO$_2$—, —S(O)$_2$N($R^{33}$)—, —N($R^{33}$)SO$_2$— or —S(O)(=N$R^{33}$)—, wherein $R^{33}$ and $R^{34}$ are selected from hydrogen, (1-4C)alkyl, (1-4C)fluoroalkyl or (3-6C)cycloalkyl; and $R^{30}$ is hydrogen, (1-6C)alkyl, (2-6C)alkenyl, (2-6C)alkynyl, aryl, aryl(1-2C)alkyl, (3-6C)cycloalkyl, (3-6C)cycloalkyl(1-2C)alkyl, heterocyclyl, heterocyclyl-(1-2C)alkyl, heteroaryl, or heteroaryl-(1-2C)alkyl, and wherein $R^{30}$ is optionally further substituted by one or more substituent groups independently selected from oxo, halo, cyano, nitro, or a group of the formula:

-$L^4$-$X^4$—$R^{35}$ wherein $L^4$ is absent or a linker group of the formula —[C$R^{36}R^{37}$]$_u$— in which u is an integer selected from 1, 2, 3 or 4, and $R^{36}$ and $R^{37}$ are each independently selected from hydrogen or a (1-4C)alkyl, (3-6C)cycloalkyl, (3-6C)cycloalkyl(1-2C)alkyl group which is optionally substituted by one or more (e.g. one to five) fluoro substituents; or $R^{36}$ and $R^{37}$ are optionally linked to such that, together with the carbon atom to which they are attached, they form a (3-6C)cycloalkyl ring which is optionally substituted by one or more (e.g. one to five) fluoro substituents;

$X^4$ is absent or selected from —O—, —C(O)—, —C(O)O—, —OC(O)—, —N($R^{38}$)—, —N($R^{38}$)—C(O)—, —C(O)—N($R^{38}$)—, —N($R^{38}$)—C(O)O—, —OC(O)—N($R^{38}$)—, —N($R^{38}$)C(O)N($R^{39}$)—, —S—, —SO—, —SO$_2$—, —S(O)$_2$N($R^{38}$)—, —N($R^{38}$)SO$_2$— or —S(O)(=N$R^{38}$)—, wherein $R^{38}$ and $R^{39}$ are selected from hydrogen, (1-4C)alkyl, (1-4C)fluoroalkyl or (3-6C)cycloalkyl; and $R^{35}$ is hydrogen or a (1-6C)alkyl, (3-6C)cycloalkyl, (3-6C)cycloalkyl(1-2C)alkyl group which is optionally substituted by one or more (e.g. one to five) fluoro substituents;

$R_a$ is selected from:
(i) a (1-4C)alkyl which is optionally substituted by one or more $R^c$;
(ii) a (1-4C)fluoroalkyl;
(iii) a (3-6C)cycloalkyl which is optionally substituted by one or more $R^c$;
(iv) a (3-6C)cycloalkyl(1-2C)alkyl which is optionally substituted by one or more $R^c$;
(v) a 3 to 6-membered heterocyclic ring which is optionally substituted by one or more $R^c$;
(vi) a 3 to 6-membered heterocyclyl(1-2C)alkyl which is optionally substituted by one or more $R^c$;
(vii) aryl, which is optionally substituted by one or more $R^d$;
(viii) aryl(1-2C)alkyl which is optionally substituted by one or more $R^d$;
(ix) 5 or 6-membered heteroaryl which is optionally substituted by one or more $R^d$;
(x) 5 or 6-membered heteroaryl(1-2C)alkyl, which is optionally substituted by one or more $R^d$;

$R_b$ is selected from:
(i) hydrogen;
(ii) a (1-4C)alkyl which is optionally substituted by one or more fluoro;
(iii) a (3-6C)cycloalkyl which is optionally substituted by one or more fluoro;
(iv) a (3-6C)cycloalkyl(1-2C)alkyl which is optionally substituted by one or more fluoro;

each $R^c$ group present is independently selected from oxo, halo, or a group of the formula:

—$X^5$—$R^{50}$ wherein $X^5$ is absent or selected from —O—, —N($R^{51}$)— or —S—, wherein $R^{51}$ is selected from hydrogen, (1-4C)alkyl, (1-4C)fluoroalkyl or (3-6C)cycloalkyl; and $R^{50}$ is hydrogen, (1-4C)alkyl, (1-4C)fluoroalkyl, (3-6C)cycloalkyl, (3-6C)cycloalkyl(1-2C)alkyl;

each $R^d$ group present is selected from halo, cyano, hydroxyl, mercapto, amino, carbamoyl, sulphamoyl, (1-2C)alkyl, (1-2C)haloalkyl, (1-2C)alkoxy, (1-2C)haloalkoxy, (1-2C)alkylamino, di-[(1-2C)alkyl]amino, (1-2C)alkylthio, (1-2C)alkylsulphinyl, (1-2C)alkylsulphonyl, (1-2C)alkoxycarbonyl, N-(1-2C)alkylcarbamoyl, N,N-di-[(1-2C)alkyl]carbamoyl, (2C)alkanoyl, (2C)alkanoyloxy, (2C)alkanoylamino, N-(1-2C)alkylsulphamoyl and N,N-di-[(1-2C)alkyl]sulphamoyl;

or a pharmaceutically acceptable salt or solvate thereof.

In a further aspect, the present invention provides a compound of Formula I shown above, wherein:

$R_a$ is ethyl, propyl, isopropyl, cyclopropyl, n-butyl, isobutyl, sec-butyl, t-butyl, or cyclopropylmethyl, each of which is optionally substituted by one or more fluoro;

$R_b$ is selected from:
(i) hydrogen;
(ii) a (1-4C)alkyl which is optionally substituted by one or more fluoro;
(iii) a (3-6C)cycloalkyl which is optionally substituted by one or more fluoro; or
(iv) a (3-6C)cycloalkyl(1-2C)alkyl which is optionally substituted by one or more fluoro;

X is a group:

—(C$R^{2a}R^{3a}$)$_m$—$X^0$—(C$R^{2b}R^{3b}$)$_n$— wherein $X^0$ is selected from —O—, —N($R^1$)—, —N($R^1$)—C(O)—, —C(O)—N($R^1$)—, —N($R^1$)C(O)N($R^1$)— or —S—;

m is 0;

n is 0 or 1;

$R^1$ is selected from hydrogen or a (1-2C)alkyl group which is optionally substituted by one or more (e.g. one to five) substituents selected from fluoro, hydroxyl, N$R^{1a}R^{1b}$, (1-2C)alkoxy or (1-2C)haloalkoxy;

$R^{1a}$ and $R^{1b}$ are each independently selected from hydrogen or (1-2C)alkyl or $R^{1a}$ and $R^{1b}$ are linked such that, together with the nitrogen atom to which they are attached, they form a 4, 5 or 6 membered heterocyclic ring;

$R^{2a}$, $R^{3a}$, $R^{2b}$, and $R^{3b}$ are all hydrogen; and

Ar and Q are as defined above;

or a pharmaceutically acceptable salt or solvate thereof.

Particular compounds of the invention include, for example, compounds of the formula I, or pharmaceutically acceptable salts thereof, wherein, unless otherwise stated, each of X, $X^0$, m, n, $R^1$, $R^{1a}$, $R^{1b}$, $R^{2a}$, $R^{3a}$, $R^{2b}$, $R^{3b}$, $R^4$, $R^5$, Ar, $L^1$, $R^7$, $R^8$, $X^1$, $R^9$, $R^{10}$, $R^6$, $L^2$, $X^2$, $R^{14}$, $R^{15}$, $R^{11}$, Q, $L^3$, $X^3$, $R^{33}$, $R^{34}$, $R^{30}$, $L^4$, $X^4$, $R^{38}$, $R^{39}$, $R^{35}$, $R^{z1}$, $R^{z2}$, $R^a$, $R^b$, $R^c$, $X^5$, $R^{50}$, and $R^d$ has any of the meanings defined hereinbefore or in any of paragraphs (1) to (70) hereinafter:—

(1) X is a group:

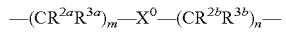

wherein
$X^0$ is selected from —O—, —N($R^1$)—, —N($R^1$)—C(O)—, —C(O)—N($R^1$)—, —N($R^1$)C(O)N($R^1$)—, —S—, —SO—, —$SO_2$—, —S(O)$_2$N($R^1$)—, or —N(R')$SO_2$—;
m and n are each independently selected from 0 or 1;
$R^1$ is selected from hydrogen or a (1-4C)alkyl, (3-4C)cycloalkyl, (3-4C)cycloalkyl(1-2C)alkyl group which is optionally substituted by one or more (e.g. one to five) substituents selected from fluoro, cyano, hydroxyl, mercapto, $NR^{1a}R^{1b}$, (1-2C)alkoxy, (1-2C)haloalkoxy, (1-2C)alkylthio, (1-2C)alkylsulphinyl, (1-2C)alkylsulphonyl, (1-2C)alkoxycarbonyl, (2C)alkanoyl, (2C)alkanoyloxy;
$R^{1a}$ and $R^{1b}$ are each independently selected from hydrogen or (1-2C)alkyl or $R^{1a}$ and $R^{1b}$ are linked such that, together with the nitrogen atom to which they are attached, they form a 4, 5 or 6 membered heterocyclic ring which is optionally substituted by fluoro or (1-2C)alkyl;
$R^{2a}$, $R^{3a}$, $R^{2b}$, and $R^{3b}$ are each independently selected from hydrogen, halo, hydroxy or a (1-4C)alkyl, (3-4C)cycloalkyl, (3-4C)cycloalkyl(1-2C)alkyl group which is optionally substituted by one or more (e.g. one to five) fluoro substituents;
or $R^{2a}$ and $R^{3a}$, and $R^{2b}$ and $R^{3b}$, are optionally linked to such that, together with the carbon atom to which they are attached, they form a (3-4C)cycloalkyl ring which is optionally substituted by one or more (e.g. one to five) fluoro substituents;

(2) X is a group:

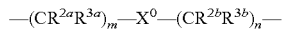

wherein
$X^0$ is selected from —O—, —N($R^1$)—, —N($R^1$)—C(O)—, —C(O)—N($R^1$)—, —N($R^1$)C(O)N($R^1$)—, —S—, —SO—, —$SO_2$—, —S(O)$_2$N($R^1$)—, or —N(R')$SO_2$—;
m and n are each independently selected from 0 or 1;
$R^1$ is selected from hydrogen or a (1-4C)alkyl, (3-4C)cycloalkyl, (3-4C)cycloalkyl(1-2C)alkyl group which is optionally substituted by one or more (e.g. one to five) substituents selected from fluoro, hydroxyl, $NR^{1a}R^{1b}$, (1-2C)alkoxy, or (1-2C)haloalkoxy;
$R^{1a}$ and $R^{1b}$ are each independently selected from hydrogen or (1-2C)alkyl or $R^{1a}$ and $R^{1b}$ are linked such that, together with the nitrogen atom to which they are attached, they form a 4, 5 or 6 membered heterocyclic ring which is optionally substituted by fluoro;
$R^{2a}$, $R^{3a}$, $R^{2b}$, and $R^{3b}$ are each independently selected from hydrogen, or a (1-2C)alkyl group which is optionally substituted by one or more (e.g. one to five) fluoro substituents;

(3) X is a group:

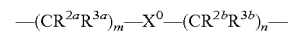

wherein
$X^0$ is selected from —O—, —N($R^1$)—, —N($R^1$)—C(O)—, —C(O)—N($R^1$)—, —N(R')C(O)N($R^1$)— or —S—;
m and n are each independently selected from 0 or 1;
$R^1$ is selected from hydrogen or a (1-2C)alkyl group which is optionally substituted by one or more (e.g. one to five) substituents selected from fluoro, hydroxyl, $NR^{1a}R^{1b}$, (1-2C)alkoxy, or (1-2C)haloalkoxy;
$R^{1a}$ and $R^{1b}$ are each independently selected from hydrogen or (1-2C)alkyl or $R^{1a}$ and $R^{1b}$ are linked such that, together with the nitrogen atom to which they are attached, they form a 4, 5 or 6 membered heterocyclic ring;
$R^{2a}$, $R^{3a}$, $R^{2b}$, and $R^{3b}$ are each independently from hydrogen, or a (1-2C)alkyl group which is optionally substituted by one or more (e.g. one to five) fluoro substituents;

(4) X is a group:

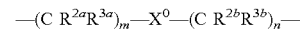

wherein
$X^0$ is selected from —O—, —N($R^1$)—, —N($R^1$)—C(O)—, —C(O)—N($R^1$)—, —N(R')C(O)N($R^1$)— or —S—;
m is 0;
n is 0 or 1;
$R^1$ is selected from hydrogen or a (1-2C)alkyl group which is optionally substituted by one or more (e.g. one to five) substituents selected from fluoro, hydroxyl, $NR^{1a}R^{1b}$, (1-2C)alkoxy or (1-2C)haloalkoxy;
$R^{1a}$ and $R^{1b}$ are each independently selected from hydrogen or (1-2C)alkyl or $R^{1a}$ and $R^{1b}$ are linked such that, together with the nitrogen atom to which they are attached, they form a 4, 5 or 6 membered heterocyclic ring;
$R^{2a}$, $R^{3a}$, $R^{2b}$, and $R^{3b}$ are all hydrogen;

(5) X is a group:

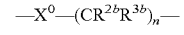

wherein
$X^0$ is selected from —O—, —N($R^1$)—, —N($R^1$)—C(O)—, —C(O)—N($R^1$)—, —N(R')C(O)N($R^1$)—, —S—, —SO—, —$SO_2$—, —S(O)$_2$N($R^1$)—, or —N(R')$SO_2$—;
n is selected from 0 or 1;
$R^1$ is selected from hydrogen or a (1-4C)alkyl, (3-4C)cycloalkyl, (3-4C)cycloalkyl(1-2C)alkyl group which is optionally substituted by one or more (e.g. one to five) substituents selected from fluoro, cyano, hydroxyl, mercapto, $NR^{1a}R^{1b}$, (1-2C)alkoxy, (1-2C)haloalkoxy, (1-2C)alkylthio, (1-2C)alkylsulphinyl, (1-2C)alkylsulphonyl, (1-2C)alkoxycarbonyl, (2C)alkanoyl, (2C)alkanoyloxy;
$R^{1a}$ and $R^{1b}$ are each independently selected from hydrogen or (1-2C)alkyl or $R^{1a}$ and $R^{1b}$ are linked such that, together with the nitrogen atom to which they are attached, they form a 4, 5 or 6 membered heterocyclic ring which is optionally substituted by fluoro or (1-2C)alkyl;
$R^{2b}$ and $R^{3b}$ are each independently selected from hydrogen, halo, hydroxy or a (1-4C)alkyl, (3-4C)cycloalkyl, (3-4C)cycloalkyl(1-2C)alkyl group which is optionally substituted by one or more (e.g. one to five) fluoro substituents;

or $R^{2b}$ and $R^{3b}$, are optionally linked to such that, together with the carbon atom to which they are attached, they form a (3-4C)cycloalkyl ring which is optionally substituted by one or more (e.g. one to five) fluoro substituents;

(6) X is a group:

$$-X^0-(CR^{2b}R^{3b})_n-$$

wherein $X^0$ is selected from —O—, —N($R^1$)—, —N($R^1$)—C(O)—, —C(O)—N($R^1$)—, —N(R')C(O)N($R^1$)—, —S—, —SO—, —$SO_2$—, —$S(O)_2$N($R^1$)—, or —N(R')$SO_2$—;

n is selected from 0 or 1;

$R^1$ is selected from hydrogen or a (1-4C)alkyl, (3-4C)cycloalkyl, (3-4C)cycloalkyl(1-2C)alkyl group which is optionally substituted by one or more (e.g. one to five) substituents selected from fluoro, hydroxyl, $NR^{1a}R^{1b}$, (1-2C)alkoxy, or (1-2C)haloalkoxy;

$R^{1a}$ and $R^{1b}$ are each independently selected from hydrogen or (1-2C)alkyl or $R^{1a}$ and $R^{1b}$ are linked such that, together with the nitrogen atom to which they are attached, they form a 4, 5 or 6 membered heterocyclic ring which is optionally substituted by fluoro;

$R^{2b}$ and $R^{3b}$ are each independently selected from hydrogen or a (1-2C)alkyl group which is optionally substituted by one or more (e.g. one to five) fluoro substituents;

(7) X is a group:

$$-X^0-(CR^{2b}R^{3b})_n-$$

wherein $X^0$ is selected from —O—, —N($R^1$)—, —N($R^1$)—C(O)—, —C(O)—N($R^1$)—, —N($R^1$)C(O)N($R^1$)— or —S—;

n is selected from 0 or 1;

$R^1$ is selected from hydrogen or a (1-2C)alkyl group which is optionally substituted by one or more (e.g. one to five) substituents selected from fluoro, hydroxyl, $NR^{1a}R^{1b}$, (1-2C)alkoxy, or (1-2C)haloalkoxy;

$R^{1a}$ and $R^{1b}$ are each independently selected from hydrogen or (1-2C)alkyl or $R^{1a}$ and $R^{1b}$ are linked such that, together with the nitrogen atom to which they are attached, they form a 4, 5 or 6 membered heterocyclic ring;

$R^{2b}$ and $R^{3b}$ are hydrogen;

(8) X is a group:

$$-X^0-(CR^{2b}R^{3b})_n-$$

wherein $X^0$ is selected from —O—, —N($R^1$)—, —N($R^1$)—C(O)—, —C(O)—N($R^1$)—, —N($R^1$)C(O)N($R^1$)— or —S—;

n is 0 or 1;

$R^1$ is selected from hydrogen or (1-2C)alkyl;

$R^{2b}$ and $R^{3b}$ are hydrogen;

(9) X is a group:

$$-X^0-(CR^{2b}R^{3b})_n-$$

wherein $X^0$ is selected from —O—, —N($R^1$)—, —C(O)—N($R^1$)—, —N($R^1$)C(O)N($R^1$)—, —S—, —SO—, —$SO_2$—, —$S(O)_2$N($R^1$)—, or —N($R^1$)$SO_2$—;

n is selected from 0 or 1;

$R^1$ is selected from hydrogen or a (1-4C)alkyl, (3-4C)cycloalkyl, (3-4C)cycloalkyl(1-2C)alkyl group which is optionally substituted by one or more (e.g. one to five) substituents selected from fluoro, cyano, hydroxyl, mercapto, $NR^{1a}R^{1b}$, (1-2C)alkoxy, (1-2C)haloalkoxy, (1-2C)alkylthio, (1-2C)alkylsulphinyl, (1-2C)alkylsulphonyl, (1-2C)alkoxycarbonyl, (2C)alkanoyl, (2C)alkanoyloxy;

$R^{1a}$ and $R^{1b}$ are each independently selected from hydrogen or (1-2C)alkyl or $R^{1a}$ and $R^{1b}$ are linked such that, together with the nitrogen atom to which they are attached, they form a 4, 5 or 6 membered heterocyclic ring which is optionally substituted by fluoro or (1-2C)alkyl;

$R^{2b}$ and $R^{3b}$ are each independently selected from hydrogen, halo, hydroxy or a (1-4C)alkyl, (3-4C)cycloalkyl, (3-4C)cycloalkyl(1-2C)alkyl group which is optionally substituted by one or more (e.g. one to five) fluoro substituents;

or $R^{2b}$ and $R^{3b}$, are optionally linked to such that, together with the carbon atom to which they are attached, they form a (3-4C)cycloalkyl ring which is optionally substituted by one or more (e.g. one to five) fluoro substituents;

(10) X is a group:

$$-X^0-(CR^{2b}R^{3b})_n-$$

wherein $X^0$ is selected from —O—, —N($R^1$)—, —N($R^1$)C(O)N($R^1$)—, —S—, —SO—, —$SO_2$—, —$S(O)_2$N($R^1$)—, or —N($R^1$)$SO_2$—;

n is selected from 0 or 1;

$R^1$ is selected from hydrogen or a (1-4C)alkyl, (3-4C)cycloalkyl, (3-4C)cycloalkyl(1-2C)alkyl group which is optionally substituted by one or more (e.g. one to five) substituents selected from fluoro, hydroxyl, $NR^{1a}R^{1b}$, (1-2C)alkoxy, or (1-2C)haloalkoxy;

$R^{1a}$ and $R^{1b}$ are each independently selected from hydrogen or (1-2C)alkyl or $R^{1a}$ and $R^{1b}$ are linked such that, together with the nitrogen atom to which they are attached, they form a 4, 5 or 6 membered heterocyclic ring which is optionally substituted by fluoro;

$R^{2b}$ and $R^{3b}$ are each independently selected from hydrogen or a (1-2C)alkyl group which is optionally substituted by one or more (e.g. one to five) fluoro substituents;

(11) X is a group:

$$-X^0-(CR^{2b}R^{3b})_n-$$

wherein $X^0$ is selected from —O—, —N($R^1$)—, —N($R^1$)C(O)N($R^1$)— or —S—;

n is selected from 0 or 1;

$R^1$ is selected from hydrogen or a (1-2C)alkyl group which is optionally substituted by one or more (e.g. one to five) substituents selected from fluoro, hydroxyl, $NR^{1a}R^{1b}$, (1-2C)alkoxy, or (1-2C)haloalkoxy;

$R^{1a}$ and $R^{1b}$ are each independently selected from hydrogen or (1-2C)alkyl or $R^{1a}$ and $R^{1b}$ are linked such that, together with the nitrogen atom to which they are attached, they form a 4, 5 or 6 membered heterocyclic ring;
$R^{2b}$ and $R^{3b}$ are hydrogen;

(12) X is a group:

$$-X^0-(CR^{2b}R^{3b})_n-$$

wherein
$X^0$ is selected from $-O-$, $-N(R^1)-$, $-N(R^1)-C(O)-$, $-C(O)-N(R^1)-$, $-N(R^1)C(O)N(R^1)-$ or $-S-$;
n is 0 or 1;
$R^1$ is selected from hydrogen or (1-2C)alkyl;

(13) $R^{2b}$ and $R^{3b}$ are hydrogen; Ar is aryl or heteroaryl, each of which is optionally substituted with one or more substituents selected from the group consisting of halo, cyano, nitro or a group of the formula:

-L$^1$-X$^1$—R$^6$ wherein
$L^1$ is absent or a linker group of the formula $-[CR^7R^8]_r-$ in which r is an integer selected from 1, 2 or 3, and $R^7$ and $R^8$ are each independently selected from hydrogen, halo, hydroxy or a (1-4C)alkyl, (3-4C)cycloalkyl, (3-4C)cycloalkyl(1-2C)alkyl group which is optionally substituted by one or more (e.g. one to five) fluoro substituents; or $R^7$ and $R^8$ are optionally linked to such that, together with the carbon atom to which they are attached, they form a (3-4C)cycloalkyl ring which is optionally substituted by one or more (e.g. one to five) fluoro substituents;
$X^1$ is absent or selected from $-O-$, $-C(O)-$, $-N(R^9)-$, $-N(R^9)-C(O)-$, $-C(O)-N(R^9)-$, $-N(R^9)C(O)N(R^{10})-$, $-S-$, $-SO-$, $-SO_2-$, $-S(O)_2N(R^9)-$, $-N(R^9)SO_2-$ or $-S(O)(=NR^{10})-$, wherein $R^9$ and $R^{10}$ are selected from hydrogen, (1-4C)alkyl, (1-4C)fluoroalkyl or (3-4C)cycloalkyl; and
$R^6$ is hydrogen, (1-6C)alkyl, aryl, aryl(1-2C)alkyl, (3-6C)cycloalkyl, (3-6C)cycloalkyl(1-2C)alkyl, heterocyclyl, heterocyclyl-(1-2C)alkyl, heteroaryl, or heteroaryl-(1-2C)alkyl,
and wherein $R^6$ is optionally further substituted by one or more substituent groups independently selected from oxo, halo, cyano, nitro, or a group of the formula:

-L$^2$-X$^2$—R$^{11}$ wherein
$L^2$ is absent or a linker group of the formula $-[CR^{12}R^{13}]_s-$ in which s is an integer selected from 1, 2 or 3, and $R^{12}$ and $R^{13}$ are each independently selected from hydrogen or a (1-4C)alkyl group which is optionally substituted by one or more (e.g. one to five) fluoro substituents; or $R^{12}$ and $R^{13}$ are optionally linked to such that, together with the carbon atom to which they are attached, they form a (3-6C)cycloalkyl ring which is optionally substituted by one or more (e.g. one to five) fluoro substituents;
$X^2$ is absent or selected from $-O-$, $-C(O)-$, $-N(R^{14})-$, $-N(R^{14})-C(O)-$, $-C(O)-N(R^{14})-$, $-N(R^{14})-C(O)O-$, $-N(R^{14})C(O)N(R^{15})-$, $-S-$, $-SO-$, $-SO_2-$, $-S(O)_2N(R^{14})-$, $-N(R^{14})SO_2-$ or $-S(O)(=NR^{14})-$, wherein $R^{14}$ and $R^{15}$ are selected from hydrogen, (1-4C)alkyl, (1-4C)fluoroalkyl or (3-6C)cycloalkyl; and
$R^{11}$ is hydrogen or a (1-6C)alkyl (3-6C)cycloalkyl, (3-6C)cycloalkyl(1-2C)alkyl group which is optionally substituted by one or more (e.g. one to five) fluoro substituents;

(14) Ar is aryl or heteroaryl, each of which is optionally substituted with one or more substituents selected from the group consisting of halo, cyano, nitro or a group of the formula:

-L$^1$-X$^1$—R$^6$ wherein
$L^1$ is absent or a linker group of the formula $-[CR^7R^8]_r-$ in which r is an integer selected from 1 or 2, and $R^7$ and $R^8$ are each independently selected from hydrogen, halo, or a (1-4C)alkyl group which is optionally substituted by one or more (e.g. one to five) fluoro substituents;
$X^1$ is absent or selected from $-O-$, $-C(O)-$, $-N(R^9)-$, $-N(R^9)-C(O)-$, $-C(O)-N(R^9)-$, $-N(R^9)C(O)N(R^{10})-$, $-S-$, $-SO-$, $-SO_2-$, $-S(O)_2N(R^9)-$, $-N(R^9)SO_2-$ or $-S(O)(=NR^{10})-$, wherein $R^9$ and $R^{10}$ are selected from hydrogen, (1-4C)alkyl or (1-4C)fluoroalkyl; and
$R^6$ is hydrogen, (1-4C)alkyl, phenyl, phenyl(1-2C)alkyl, (3-4C)cycloalkyl, (3-4C)cycloalkyl(1-2C)alkyl, 3-6-membered heterocyclyl, 3-6-membered heterocyclyl-(1-2C)alkyl, 5-6-membered heteroaryl, or 5-6-membered heteroaryl-(1-2C)alkyl,
and wherein $R^6$ is optionally further substituted by one or more substituent groups independently selected from oxo, halo, cyano, nitro, or a group of the formula:

-L$^2$-X$^2$—R$^{11}$ wherein
$L^2$ is absent or a linker group of the formula $-[CR^{12}R^{13}]_s-$ in which s is an integer selected from 1 or 2, and $R^{12}$ and $R^{13}$ are each independently selected from hydrogen or a (1-2C)alkyl group which is optionally substituted by one or more (e.g. one to five) fluoro substituents;
$X^2$ is absent or selected from $-O-$, $-N(R^{14})-$, $-N(R^{14})-C(O)-$, $-C(O)-N(R^{14})-$, $-S-$, $-SO-$, $-SO_2-$, $-S(O)_2N(R^{14})-$, $-N(R^{14})SO_2-$ or $-S(O)(=NR^{14})-$, wherein $R^{14}$ is selected from hydrogen or (1-2C)alkyl; and
$R^{11}$ is hydrogen or a (1-4C)alkyl (3-4C)cycloalkyl, (3-4C)cycloalkyl(1-2C)alkyl group which is optionally substituted by one or more (e.g. one to five) fluoro substituents;

(15) Ar is aryl or heteroaryl, each of which is optionally substituted with one or more substituents selected from the group consisting of halo, cyano, nitro or a group of the formula:

-L$^1$-X$^1$—R$^6$ wherein
$L^1$ is absent or a linker group of the formula $-[CR^7R^8]_r-$ in which r is an integer selected from 1 or 2, and $R^7$ and $R^8$ are each independently selected from hydrogen, halo, or a (1-2C)alkyl group which is optionally substituted by one or more (e.g. one to five) fluoro substituents;

X¹ is absent or selected from —O—, —N(R⁹)—, —S—, —SO—, or —SO₂—, wherein R⁹ is selected from hydrogen or (1-2C)alkyl; and R⁶ is hydrogen, (1-4C)alkyl, phenyl, phenyl(1-2C)alkyl, (3-4C)cycloalkyl, (3-4C)cycloalkyl(1-2C)alkyl, 3-6-membered heterocyclyl, 3-6-membered heterocyclyl-(1-2C)alkyl, 5-6-membered heteroaryl, or 5-6-membered heteroaryl-(1-2C)alkyl, and wherein R⁶ is optionally further substituted by one or more substituent groups independently selected from oxo, halo, cyano, nitro, or a group of the formula:

-L²-X²—R¹¹ wherein

L² is absent or a linker group of the formula —[CR¹²R¹³]ₛ— in which s is an integer selected from 1 or 2, and R¹² and R¹³ are each independently selected from hydrogen or a (1-2C)alkyl group X² is absent or selected from —O—, —N(R¹⁴)—, —S—, —SO—, or —SO₂—, wherein R¹⁴ is selected from hydrogen or (1-2C)alkyl; and R¹¹ is hydrogen or a (1-4C)alkyl group which is optionally substituted by one or more (e.g. one to five) fluoro substituents;

(16) Ar is aryl or heteroaryl, each of which is optionally substituted with one or more substituents selected from the group consisting of halo, cyano, nitro or a group of the formula:

-L¹-X¹—R⁶ wherein

L¹ is absent;

X¹ is absent or selected from —O—, —N(R⁹)—, —S—, —SO—, or —SO₂—, wherein R⁹ is selected from hydrogen or (1-2C)alkyl; and R⁶ is hydrogen, (1-4C)alkyl, phenyl, phenyl(1-2C)alkyl, (3-4C)cycloalkyl, (3-4C)cycloalkyl(1-2C)alkyl, 3-6-membered heterocyclyl, 3-6-membered heterocyclyl-(1-2C)alkyl, 5-6-membered heteroaryl, or 5-6-membered heteroaryl-(1-2C)alkyl, and wherein R⁶ is optionally further substituted by one or more substituent groups independently selected from oxo, halo, cyano, nitro, or a group of the formula:

-L²-X²—R¹¹ wherein

L² is absent;

X² is absent or selected from —O—, —N(R¹⁴)—, —S—, —SO—, or —SO₂—, wherein R¹⁴ is selected from hydrogen or (1-2C)alkyl; and R¹¹ is hydrogen or a (1-2C)alkyl group which is optionally substituted by one or more (e.g. one to five) fluoro substituents;

(17) Ar is phenyl, naphthyl or a mono or bicyclic heteroaryl, each of which is optionally substituted by a substituent group as defined in any one of paragraphs (13) to (16) above;

(18) Ar is phenyl or a mono or bicyclic heteroaryl, each of which is optionally substituted by a substituent group as defined in any one of paragraphs (13) to (16) above;

(19) Ar is phenyl or a 5- or 6-membered heteroaryl ring, each of which is optionally substituted by a substituent group as defined in any one of paragraphs (13) to (16) above;

(20) Q is aryl or heteroaryl, each of which is optionally substituted with one or more Rᶻ substituents, wherein Rᶻ is selected from the group consisting of halo, cyano, nitro, or a group of the formula:

-L³-X³—R³⁰ wherein

L³ is absent or a linker group of the formula —[CR³¹R³²]ₜ— in which t is an integer selected from 1, 2 or 3, and R³¹ and R³² are each independently selected from hydrogen or a (1-4C)alkyl, (3-4C)cycloalkyl, (3-4C)cycloalkyl(1-2C)alkyl group which is optionally substituted by one or more (e.g. one to five) fluoro substituents; or R³¹ and R³² are optionally linked to such that, together with the carbon atom to which they are attached, they form a (3-4C)cycloalkyl ring which is optionally substituted by one or more (e.g. one to five) fluoro substituents;

X³ is absent or selected from —O—, —C(O)—, —N(R³³)—, —N(R³³)—C(O)—, —C(O)—N(R³³)—, —N(R³³)C(O)N(R³⁴)—, —S—, —SO—, —SO₂—, —S(O)₂N(R³³)—, —N(R³³)SO₂— or —S(O)(=NR³³)—, wherein R³³ and R³⁴ are selected from hydrogen, (1-4C)alkyl, (1-4C)fluoroalkyl or (3-4C)cycloalkyl; and R³⁰ is hydrogen, (1-6C)alkyl, aryl, aryl(1-2C)alkyl, (3-6C)cycloalkyl, (3-6C)cycloalkyl(1-2C)alkyl, heterocyclyl, heterocyclyl-(1-2C)alkyl, heteroaryl, or heteroaryl-(1-2C)alkyl, and wherein R³⁰ is optionally further substituted by one or more substituent groups independently selected from oxo, halo, cyano, nitro, or a group of the formula:

-L⁴-X⁴—R³⁵ wherein

L⁴ is absent or a linker group of the formula —[CR³⁶R³⁷]ᵤ— in which u is an integer selected from 1, 2 or 3, and R³⁶ and R³⁷ are each independently selected from hydrogen or a (1-4C)alkyl group which is optionally substituted by one or more (e.g. one to five) fluoro substituents; or R³⁶ and R³⁷ are optionally linked to such that, together with the carbon atom to which they are attached, they form a (3-4C)cycloalkyl ring which is optionally substituted by one or more (e.g. one to five) fluoro substituents;

X⁴ is absent or selected from —O—, —C(O)—, —N(R³⁸)—, —N(R³⁸)—C(O)—, —C(O)—N(R³⁸)—, —N(R³⁸)C(O)N(R³⁹)—, —S—, —SO—, —SO₂—, —S(O)₂N(R³⁸)—, —N(R³⁸)SO₂— or —S(O)(=NR³⁸)—, wherein R³⁸ and R³⁹ are selected from hydrogen, (1-4C)alkyl, (1-4C)fluoroalkyl or (3-6C)cycloalkyl; and R³⁵ is hydrogen or a (1-6C)alkyl, (3-6C)cycloalkyl, (3-6C)cycloalkyl(1-2C)alkyl group which is optionally substituted by one or more (e.g. one to five) fluoro substituents;

(21) Q is aryl or heteroaryl, each of which is optionally substituted with one or more Rᶻ substituents, wherein Rᶻ is selected from the group consisting of halo, cyano, nitro, or a group of the formula:

-L³-X³—R³⁰ wherein

L³ is absent or a linker group of the formula —[CR³¹R³²]ₜ— in which t is an integer selected from 1 or 2, and $R^{31}$ and $R^{32}$ are each independently selected from hydrogen or a (1-4C)alkyl group which is optionally substituted by one or more (e.g. one to five) fluoro substituents;

$X^3$ is absent, or selected from —O—, —C(O)—, —N($R^{33}$)—, —N($R^{33}$)—C(O)—, —C(O)—N($R^{33}$)—, —N($R^{33}$)C(O)N($R^{34}$)—, —S—, —SO—, —SO$_2$—, —S(O)$_2$N($R^{33}$)—, —N($R^{33}$)SO$_2$— or —S(O)(=N$R^{33}$)—, wherein $R^{33}$ and $R^{34}$ are selected from hydrogen or (1-4C)alkyl; and $R^{30}$ is hydrogen, (1-4C)alkyl, phenyl, phenyl(1-2C)alkyl, (3-4C)cycloalkyl, (3-4C)cycloalkyl(1-2C)alkyl, 3-6-membered heterocyclyl, 3-6-membered heterocyclyl-(1-2C)alkyl, 5-6-membered heteroaryl, or 5-6-membered heteroaryl-(1-2C)alkyl, and wherein $R^{30}$ is optionally further substituted by one or more substituent groups independently selected from oxo, halo, cyano, nitro, or a group of the formula:

-$L^4$-$X^4$—$R^{35}$ wherein $L^4$ is absent or a linker group of the formula —[C$R^{36}R^{37}$]$_u$— in which u is an integer selected from 1 or 2, and $R^{36}$ and $R^{37}$ are each independently selected from hydrogen or a (1-2C)alkyl group which is optionally substituted by one or more (e.g. one to five) fluoro substituents;

$X^4$ is absent or selected from —O—, —N($R^{38}$)—, —N($R^{38}$)—C(O)—, —C(O)—N($R^{38}$)—, —N($R^{38}$)C(O)N($R^{39}$)—, —S—, —SO—, —SO$_2$—, —S(O)$_2$N($R^{38}$)—, —N($R^{38}$)SO$_2$— or —S(O)(=N$R^{38}$)—, wherein $R^{38}$ and $R^{39}$ are selected from hydrogen or (1-4C)alkyl; and $R^{35}$ is hydrogen or a (1-4C)alkyl, (3-4C)cycloalkyl, (3-4C)cycloalkyl(1-2C)alkyl group which is optionally substituted by one or more (e.g. one to five) fluoro substituents;

(22) Q is aryl or heteroaryl, each of which is optionally substituted with one or more $R^z$ substituents, wherein $R^z$ is selected from the group consisting of halo, cyano, nitro, or a group of the formula:

-$L^3$-$X^3$—$R^{30}$ wherein $L^3$ is absent or a linker group of the formula —[C$R^{31}R^{32}$]$_t$— in which t is an integer selected from 1 or 2, and $R^{31}$ and $R^{32}$ are each independently selected from hydrogen or a (1-4C)alkyl group;

$X^3$ is absent, or selected from —O—, —N($R^{33}$)—, —N($R^{33}$)—C(O)—, —C(O)—N($R^{33}$)—, —S—, —SO—, or —SO$_2$—, wherein $R^{33}$ is selected from hydrogen or (1-2C)alkyl; and $R^{30}$ is hydrogen, (1-4C)alkyl, phenyl, phenyl(1-2C)alkyl, (3-4C)cycloalkyl, (3-4C)cycloalkyl(1-2C)alkyl, 3-6-membered heterocyclyl, 3-6-membered heterocyclyl-(1-2C)alkyl, 5-6-membered heteroaryl, or 5-6-membered heteroaryl-(1-2C)alkyl, and wherein $R^{30}$ is optionally further substituted by one or more substituent groups independently selected from oxo, halo, cyano, nitro, or a group of the formula:

-$L^4$-$X^4$—$R^{35}$ wherein $L^4$ is absent or a linker group of the formula —[C$R^{36}R^{37}$]$_u$— in which u is an integer selected from 1 or 2, and $R^{36}$ and $R^{37}$ are each independently selected from hydrogen or a (1-2C)alkyl group;

$X^4$ is absent or selected from —O—, —N($R^{38}$)—, —S—, —SO—, or —SO$_2$—, wherein $R^{38}$ is selected from hydrogen or (1-2C)alkyl; and $R^{35}$ is hydrogen or a (1-4C)alkyl group which is optionally substituted by one or more (e.g. one to five) fluoro substituents;

(23) Q is aryl or heteroaryl, each of which is optionally substituted with one or more $R^z$ substituents, wherein $R^z$ is selected from the group consisting of halo, cyano, nitro, or a group of the formula:

-$L^3$-$X^3$—$R^{30}$ wherein $L^3$ is absent;

$X^3$ is absent, or selected from —O—, —N($R^{33}$)—, —S—, —SO—, or —SO$_2$—, wherein $R^{33}$ is selected from hydrogen or (1-2C)alkyl; and $R^{30}$ is hydrogen, (1-4C)alkyl, phenyl, phenyl(1-2C)alkyl, (3-4C)cycloalkyl, (3-4C)cycloalkyl(1-2C)alkyl, 3-6-membered heterocyclyl, 3-6-membered heterocyclyl-(1-2C)alkyl, 5-6-membered heteroaryl, or 5-6-membered heteroaryl-(1-2C)alkyl, and wherein $R^{30}$ is optionally further substituted by one or more substituent groups independently selected from oxo, halo, cyano, nitro, or a group of the formula:

-$L^4$-$X^4$—$R^{35}$ wherein $L^4$ is absent;

$X^4$ is absent or selected from —O—, —N($R^{38}$)—, —S—, —SO—, or —SO$_2$—, wherein $R^{38}$ is selected from hydrogen or (1-2C)alkyl; and $R^{35}$ is hydrogen or a (1-2C)alkyl group which is optionally substituted by one or more (e.g. one to five) fluoro substituents;

(24) Q is aryl or heteroaryl, each of which is substituted with one or more $R^z$ substituents, wherein $R^z$ is halo or a group of the formula:

-$L^3$-$X^3$—$R^{30}$ wherein $L^3$ is absent;

$X^3$ is absent, or selected from —O—, —N($R^{33}$)—, —S—, —SO—, or —SO$_2$—, wherein $R^{33}$ is selected from hydrogen or (1-2C)alkyl; and $R^{30}$ is (1-4C)alkyl, phenyl or a 5-6-membered heteroaryl ring, and wherein $R^{30}$ is optionally further substituted by one or more substituent groups independently selected from halo, cyano or a group of the formula:

-$L^4$-$X^4$—$R^{35}$ wherein $L^4$ is absent;

$X^4$ is absent or selected from —O—, —N($R^{38}$)—, —S—, —SO—, or —SO$_2$—, wherein $R^{38}$ is selected from hydrogen or (1-2C)alkyl; and $R^{35}$ is hydrogen or a (1-2C)alkyl group which is optionally substituted by one or more (e.g. one to five) fluoro substituents;

(25) Q is aryl or heteroaryl, each of which is substituted with one or more $R^z$ substituents, wherein $R^z$ is a group of the formula:

-$L^3$-$X^3$—$R^{30}$ wherein
$L^3$ is absent;
$X^3$ is absent; and
$R^{30}$ is phenyl or a 5-6-membered heteroaryl ring, and wherein $R^{30}$ is optionally further substituted by one or more substituent groups independently selected from halo, cyano or a group of the formula:

-$L^4$-$X^4$—$R^{35}$ wherein
$L^4$ is absent;
$X^4$ is absent; and
$R^{35}$ is hydrogen or a (1-2C)alkyl group which is optionally substituted by one or more (e.g. one to five) fluoro substituents;
(26) Q is phenyl, naphthyl or a mono or bicyclic heteroaryl, each of which is optionally substituted with one or more $R^z$ substituents as defined in any one of paragraphs (20) to (25) above;
(27) Q is phenyl or a mono or bicyclic heteroaryl, each of which is optionally substituted with one or more $R^z$ substituents as defined in any one of paragraphs (20) to (25) above;
(28) Q is phenyl, naphthyl or a mono or bicyclic heteroaryl, each of which is substituted with one or more $R^z$ substituents as defined in any one of paragraphs (20) to (25) above;
(29) Q is phenyl, or a mono or bicyclic heteroaryl, each of which is substituted with one or more $R^z$ substituents as defined in any one of paragraphs (20) to (25) above;
(30) Q is selected from phenyl, naphthyl, 5-6 membered monocyclic heteroaryl, or 9-10 membered bicyclic heteroaryl, each of which is optionally substituted in an ortho position in relation to the point of attachment to the —C(O)—N($R_b$)— motif by a $R^z$ substituent group as defined in any one of paragraphs (20) to (25) above (especially paragraph (25) above), and is optionally further substituted in any other position by one or more $R^z$ substituent groups as defined in any one of paragraphs (20) to (25) above;
(31) Q is selected from phenyl, 5-6 membered monocyclic heteroaryl, or 9-10 membered bicyclic heteroaryl, each of which is substituted in an ortho position in relation to the point of attachment to the —C(O)—N($R_b$)— motif by a substituent group as defined in any one of paragraphs (20) to (25) above (especially paragraph (25) above), and is optionally further substituted in any other position by one or more substituent groups as defined in any one of paragraphs (20) to (25) above;
(32) Q is a group having the following structure:

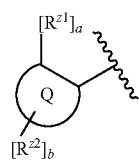

wherein ring Q is selected from phenyl, a 5-6 membered monocyclic heteroaryl, or a 9-10 membered bicyclic heteroaryl; a is an integer 0-1; and b is an integer 0-5; and $R^{z1}$ and $R^{z2}$ are substituent groups $R^z$ on Q as defined in any one of paragraphs (20) to (25) above, or $R^{z1}$ is as defined in any one of paragraphs (37), (38) or (39) below and $R^{z2}$ is as defined in any one of paragraphs (40), (41) or (42) below;
(33) Q is a group having any one of the following structures, W1-W7:

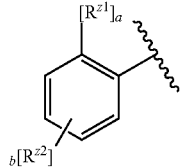
W1

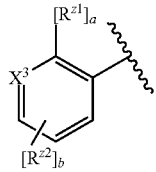
W2

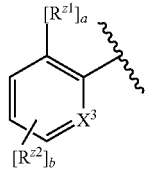
W3

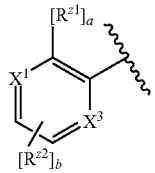
W4

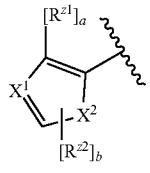
W5

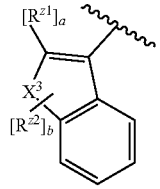
W6

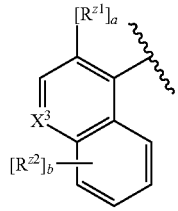
W7 wherein $X^1$, $X^2$ and $X^3$ are each a heteroatom selected from O, N or S; a is an integer 0-1; and b is an integer 0-5; and $R^{z1}$ and $R^{z2}$ are substituent groups $R^z$ on Q as defined in any one of paragraphs (20) to (25)

above, or $R^{z1}$ is as defined in any one of paragraphs (37), (38) or (39) below and $R^{z2}$ is as defined in any one of paragraphs (40), (41) or (42) below;

(34) Q is a group as defined in paragraph (32) or (33) above, wherein a is 1; and b is an integer 0 or 1;

(35) Q is a group selected from any one of the following structures:

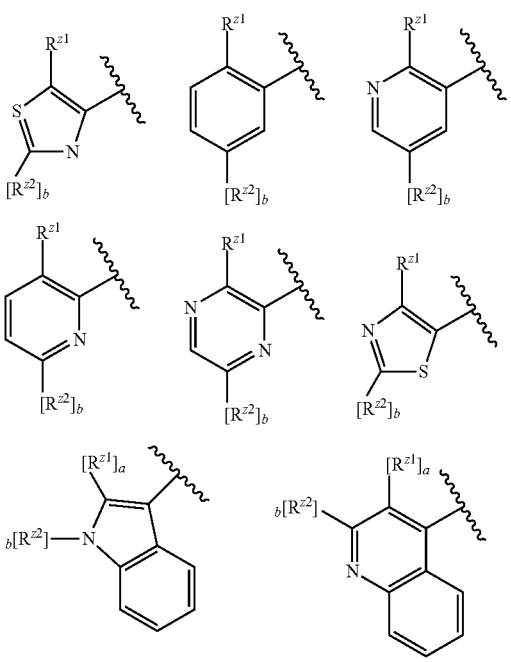

wherein a and b are each independently an integer 0-1; and $R^{z1}$ and $R^{z2}$ are substituent groups $R^z$ on Q as defined in any one of paragraphs (20) to (25) above, or $R^{z1}$ is as defined in any one of paragraphs (37), (38) or (39) below and $R^{z2}$ is as defined in any one of paragraphs (40), (41) or (42) below;

(36) Q is a group selected from any one of the following structures:

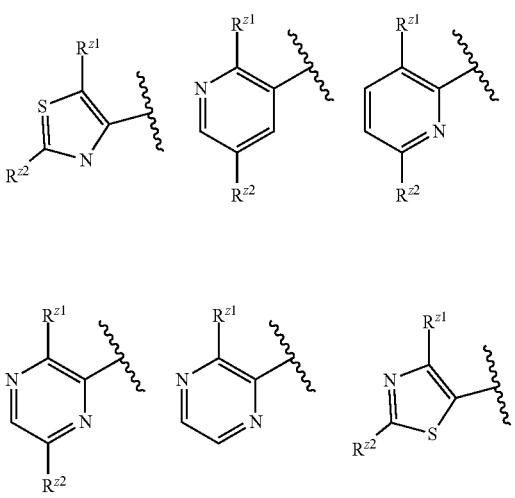

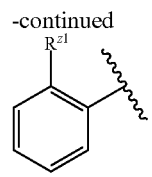

wherein $R^{z1}$ and $R^{z2}$ are substituent groups $R^z$ on Q as defined in any one of paragraphs (20) to (25) above, or $R^{z1}$ is as defined in any one of paragraphs (37), (38) or (39) below and $R^{z2}$ is as defined in any one of paragraphs (40), (41) or (42) below;

(37) $R^{z1}$ is a substituent group of the formula:

$$-L^3-X^3-R^{30}$$

wherein
$L^3$ is absent;
$X^3$ is absent, or selected from —O—, —N($R^{33}$)—, —S—, —SO— or —SO$_2$—, wherein $R^{33}$ is selected from hydrogen or (1-2C)alkyl; and
$R^{30}$ is hydrogen, (1-4C)alkyl, phenyl, (3-4C)cycloalkyl, (3-4C)cycloalkyl(1-2C)alkyl, 3-6-membered heterocyclyl, 3-6-membered heterocyclyl-(1-2C)alkyl, 5-6-membered heteroaryl, or 5-6-membered heteroaryl-(1-2C)alkyl,
and wherein $R^{30}$ is optionally further substituted as defined in any one of paragraphs (20) to (25) above;

(38) $R^{z1}$ is a substituent group of the formula:

$$-L^3-X^3-R^{30}$$

wherein
$L^3$ is absent;
$X^3$ is absent; and
$R^{30}$ is phenyl or a C- or N-linked 5-6 membered heteroaryl,
and wherein $R^{30}$ is optionally further substituted as defined in any one of paragraphs (20) to (25) above;

(39) $R^{z1}$ is a substituent group of the formula:

$$-L^3-X^3-R^{30}$$

wherein
$L^3$ is absent;
$X^3$ is absent; and
$R^{30}$ is phenyl or N-linked 1,2,3-triazolyl,
and wherein $R^{30}$ is optionally further substituted as defined in any one of paragraphs (20) to (25) above;

(40) $R^{z2}$ is a substituent group $R^z$ as defined in any one of paragraphs (20) to (25) above;

(41) $R^{z2}$ is selected from the group consisting of halo, cyano, nitro, or a group of the formula:

$$-L^3-X^3-R^{30}$$

wherein
$L^3$ is absent;
$X^3$ is absent, or selected from —O—, —N($R^{33}$)—, —N($R^{33}$)—C(O)—, —C(O)—N($R^{33}$)—, —S—, —SO—, or —SO$_2$—, wherein $R^{33}$ is selected from hydrogen or (1-2C)alkyl; and
$R^{30}$ is hydrogen, (1-4C)alkyl, (3-4C)cycloalkyl, (3-4C)cycloalkyl(1-2C)alkyl, 3-6-membered heterocyclyl, 3-6-membered heterocyclyl-(1-2C)alkyl, 5-6-membered heteroaryl, or 5-6-membered heteroaryl-(1-2C)alkyl, and wherein $R^{30}$ is optionally further substituted by one or more substituent groups as defined in any one of paragraphs (20) to (25) above;

(42) $R^{z2}$ is selected from the group consisting of halo, cyano, or a group of the formula:

$$-L^3-X^3-R^{30}$$

wherein
$L^3$ is absent;
$X^3$ is absent, or selected from —O—, —N($R^{33}$)—, —N($R^{33}$)—C(O)—, —C(O)—N($R^{33}$)—, —S—, —SO—, or —SO$_2$—, wherein $R^{33}$ is selected from hydrogen or (1-2C)alkyl; and
$R^{30}$ is hydrogen or (1-4C)alkyl,
and wherein $R^{30}$ is optionally further substituted by one or more fluoro atoms;

(43) $R_a$ is selected from:
  (i) a (1-4C)alkyl which is optionally substituted by one or more $R^c$;
  (ii) a (1-4C)fluoroalkyl;
  (iii) a (3-6C)cycloalkyl which is optionally substituted by one or more $R^c$;
  (iv) a (3-6C)cycloalkyl(1-2C)alkyl which is optionally substituted by one or more $R^c$;
  (v) a 3 to 6-membered heterocyclic ring which is optionally substituted by one or more $R^c$;
  (vi) a 3 to 6-membered heterocyclyl(1-2C)alkyl which is optionally substituted by one or more $R^c$;
  (vii) phenyl, which is optionally substituted by one or more $R^d$;
  (viii) phenyl(1-2C)alkyl which is optionally substituted by one or more $R^d$;
  (ix) 5 or 6-membered heteroaryl which is optionally substituted by one or more $R^d$;
  (x) 5 or 6-membered heteroaryl(1-2C)alkyl, which is optionally substituted by one or more $R^d$;

(44) $R_a$ is selected from:
  (i) a (1-4C)alkyl which is optionally substituted by one or more $R^c$;
  (ii) a (1-4C)fluoroalkyl;
  (iii) a (3-6C)cycloalkyl which is optionally substituted by one or more $R^c$; or
  (iv) a (3-6C)cycloalkyl(1-2C)alkyl which is optionally substituted by one or more $R^c$;

(45) $R_a$ is selected from:
  (i) a (1-4C)alkyl which is optionally substituted by one or more $R^c$;
  (ii) a (1-4C)fluoroalkyl;
  (iii) a (3-4C)cycloalkyl which is optionally substituted by one or more $R^c$; or
  (iv) a (3-4C)cycloalkyl(1-2C)alkyl which is optionally substituted by one or more $R^c$;

(46) $R_a$ is methyl, ethyl, propyl, isopropyl, cyclopropyl, n-butyl, isobutyl, sec-butyl, t-butyl, or cyclopropylmethyl, each of which is optionally substituted by one or more $R^c$;

(47) $R_a$ is methyl, ethyl, propyl, isopropyl, cyclopropyl, n-butyl, isobutyl, sec-butyl, t-butyl, cyclopropyl, or cyclopropylmethyl, each of which is optionally substituted by one or more fluoro;

(48) $R_a$ is methyl, ethyl, isopropyl, cyclopropyl, isobutyl or t-butyl, each of which is optionally substituted by one or more fluoro;

(49) $R_a$ is methyl, ethyl, isopropyl, cyclopropyl or isobutyl, each of which is optionally substituted by one or more fluoro;

(50) $R_a$ is methyl, ethyl, isopropyl or cyclopropyl, each of which is optionally substituted by one or more fluoro;

(51) $R_a$ is selected from:
  (i) a (2-4C)alkyl which is optionally substituted by one or more $R^c$;
  (ii) a (2-4C)fluoroalkyl;
  (iii) a (3-6C)cycloalkyl which is optionally substituted by one or more $R^c$;
  (iv) a (3-6C)cycloalkyl(1-2C)alkyl which is optionally substituted by one or more $R^c$;
  (v) a 3 to 6-membered heterocyclic ring which is optionally substituted by one or more $R^c$;
  (vi) a 3 to 6-membered heterocyclyl(1-2C)alkyl which is optionally substituted by one or more $R^c$;
  (vii) phenyl, which is optionally substituted by one or more $R^d$;
  (viii) phenyl(1-2C)alkyl which is optionally substituted by one or more $R^d$;
  (ix) 5 or 6-membered heteroaryl which is optionally substituted by one or more $R^d$;
  (x) 5 or 6-membered heteroaryl(1-2C)alkyl, which is optionally substituted by one or more $R^d$;

(52) $R_a$ is selected from:
  (i) a (2-4C)alkyl;
  (ii) a (2-4C)fluoroalkyl;
  (iii) a (3-6C)cycloalkyl which is optionally substituted by one or more fluoro; or
  (iv) a (3-6C)cycloalkyl(1-2C)alkyl which is optionally substituted by one or more fluoro;

(53) $R_a$ is selected from:
  (i) a (2-4C)alkyl;
  (ii) a (2-4C)fluoroalkyl;
  (iii) a (3-4C)cycloalkyl; or
  (iv) a (3-4C)cycloalkyl(1-2C)alkyl;

(54) $R_a$ is ethyl, propyl, isopropyl, cyclopropyl, n-butyl, isobutyl, sec-butyl, t-butyl, cyclopropyl, or cyclopropylmethyl, each of which is optionally substituted by one or more fluoro;

(55) $R_a$ is ethyl, isopropyl, cyclopropyl, isobutyl or t-butyl, each of which is optionally substituted by one or more fluoro;

(56) $R_a$ is ethyl, isopropyl, cyclopropyl or isobutyl, each of which is optionally substituted by one or more fluoro;

(57) $R_a$ is ethyl, cyclopropyl or isopropyl, each of which is optionally substituted by one or more fluoro;

(58) $R_a$ is ethyl or cyclopropyl, each of which is optionally substituted by one or more fluoro;

(59) $R_a$ is ethyl optionally substituted by one or more fluoro;

(60) $R_a$ is ethyl;

(61) $R_b$ is selected from:
  (i) hydrogen;
  (ii) a (1-4C)alkyl which is optionally substituted by one or more fluoro;
  (iii) a (3-4C)cycloalkyl which is optionally substituted by one or more fluoro;
  (iv) a (3-4C)cycloalkyl(1-2C)alkyl which is optionally substituted by one or more fluoro;

(62) $R_b$ is selected from:
  (i) hydrogen;
  (ii) a (1-4C)alkyl which is optionally substituted by one or more fluoro;

(63) $R_b$ is H or methyl;

(64) $R_b$ is methyl;

(65) each $R^c$ group present is independently selected from halo or a group of the formula:

—$X^5$—$R^{50}$ wherein
$X^5$ is absent or selected from —O—, —N($R^{51}$)— or —S—, wherein $R^{51}$ is selected from hydrogen, (1-4C)alkyl, or (1-4C)fluoroalkyl; and
$R^{50}$ is hydrogen, (1-4C)alkyl, (1-4C)fluoroalkyl, (3-6C)cycloalkyl, (3-6C)cycloalkyl(1-2C)alkyl;
(66) each $R^c$ group present is independently selected from fluoro or a group of the formula:

—$X^5$—$R^{50}$ wherein
$X^5$ is absent or selected from —O—, —N($R^{51}$)— or —S—, wherein $R^{51}$ is selected from hydrogen, (1-2C)alkyl, or (1-2C)fluoroalkyl; and
$R^{50}$ is hydrogen, (1-2C)alkyl, (1-2C)fluoroalkyl, (3-4C)cycloalkyl, (3-4C)cycloalkyl(1-2C)alkyl;
(67) each $R^c$ group present is independently selected from fluoro, hydroxyl or methoxy;
(68) each $R^c$ group present is fluoro;
(69) each $R^d$ group present is selected from halo, cyano, hydroxyl, mercapto, amino, (1-2C)alkyl, (1-2C)haloalkyl, (1-2C)alkoxy, (1-2C)haloalkoxy, (1-2C)alkylamino, di-[(1-2C)alkyl]amino, (1-2C)alkylthio, (1-2C)alkylsulphinyl, (1-2C)alkylsulphonyl;
(70) each $R^d$ group present is selected from fluoro, hydroxy, amino, (1-2C)alkyl, (1-2C)fluoroalkyl, (1-2C)alkoxy, (1-2C)fluoroalkoxy, (1-2C)alkylamino, di-[(1-2C)alkyl]amino, (1-2C)alkylthio, (1-2C)alkylsulphinyl, (1-2C)alkylsulphonyl.

Suitably, X is as defined in any one of paragraphs (1) to (12) above. In an embodiment, X is as defined in any one of paragraphs (2) to (4) above. In another embodiment, X is as defined in paragraph (3) or (4) above. In another embodiment, X is as defined in any one of paragraphs (5) or (8) above. In a further embodiment, X is as defined in paragraphs (7) or (8) above. In another embodiment, X is as defined in any one of paragraphs (9) to (12) above. In another embodiment, X is as defined in paragraphs (11) or (12) above.

Suitably, $X^0$, m, n, $R^1$, $R^{1a}$, $R^{1b}$, $R^{2a}$, $R^{3a}$, $R^{2b}$ and $R^{3b}$ are as defined in any one of paragraphs (1) to (4) above. In an embodiment, $X^0$, m, n, $R^1$, $R^{1a}$, $R^{1b}$, $R^{2a}$, $R^{3a}$, $R^{2b}$ and $R^{3b}$ are as defined in any one of paragraphs (2) to (4) above. In a particular embodiment, $X^0$, m, n, $R^1$, $R^{1a}$, $R^{1b}$, $R^{2a}$, $R^{3a}$, $R^{2b}$ and $R^{3b}$ are as defined in paragraph (3) or (4) above.

In a particular group of compounds of the invention, $X^0$, n, $R^1$, $R^{1a}$, $R^{1b}$, $R^{2b}$ and $R^{3b}$ are as defined in any one of paragraphs (5) to (12) above. In an embodiment, $X^0$, n, $R^1$, $R^{1a}$, $R^{1b}$, $R^{2b}$ and $R^{3b}$ are as defined in any one of paragraphs (7) or (8) above. In another embodiment, $X^0$, n, $R^1$, $R^{1a}$, $R^{1b}$, $R^{2b}$ and $R^{3b}$ are as defined in paragraphs (11) or (12) above.

Suitably, m is 0.
Suitably, n is 0 or 1, particularly 0.
Suitably, Ar is as defined in any one of paragraphs (13) to (19) above. In an embodiment, Ar is as defined in any one of paragraphs (15) to (19) above. In a particular embodiment, Ar is as defined in paragraph (17), (18) or (19) above.

Suitably, $L^1$, $R^7$, $R^8$, $X^1$, $R^9$, $R^{10}$, $R^6$, $L^2$, $X^2$, $R^{14}$, $R^{15}$ and $R^{11}$ are each as defined in any one of paragraphs (13) to (16) above. In an embodiment, $L^1$, $R^7$, $R^8$, $X^1$, $R^9$, $R^{10}$, $R^6$, $L^2$, $X^2$, $R^{14}$, $R^{15}$ and $R^{11}$ are each as defined in any one of paragraphs (15) or (16) above.

Suitably, Q is as defined in any one of paragraphs (20) to (36) above. In an embodiment, Q is as defined in any one of paragraphs (23) to (36) above. In a particular embodiment, Q is as defined in any one of paragraphs (28) to (36) above.

Suitably, $R^z$ is as defined in any one of paragraphs (20) to (25) above. In an embodiment, $R^z$ is as defined in any one of paragraphs (23) to (25) above. In a particular embodiment, $R^z$ is as defined in paragraphs (24) or (25) above.

Suitably, $L^3$, $X^3$, $R^{33}$, $R^{34}$, $R^{30}$, $L^4$, $X^4$, $R^{38}$, $R^{39}$ and $R^{35}$ are each as defined in any one of paragraphs (20) to (25) above. In an embodiment, $L^3$, $X^3$, $R^{33}$, $R^{34}$, $R^{30}$, $L^4$, $X^4$, $R^{38}$, $R^{39}$ and $R^{35}$ are each as defined in paragraphs (23) to (25) above. In a particular embodiment, $L^3$, $X^3$, $R^{33}$, $R^{34}$, $R^{30}$, $L^4$, $X^4$, $R^{38}$, $R^{39}$ and $R^{35}$ are each as defined in paragraphs (24) or (25) above.

Suitably, $R^{z1}$ is as defined in any one of paragraphs (37) to (39) above. In an embodiment, $R^{z1}$ is as defined in any one of paragraphs (38) or (39) above. In a particular embodiment, $R^{z1}$ is as defined in paragraph (39) above.

Suitably, $R^{z2}$ is as defined in any one of paragraphs (40) to (42) above. In an embodiment, $R^{z2}$ is as defined in any one of paragraphs (41) or (42) above. In a particular embodiment, $R^{z2}$ is as defined in paragraph (42) above.

Suitably, $R_a$ is as defined in any one of paragraphs (43) to (60) above. In an embodiment, $R_a$ is as defined in any one of paragraphs (53) to (60) above. In a particular embodiment, $R_a$ is as defined in any one of paragraphs (57) to (60) above. In a further embodiment, $R_a$ is ethyl.

Suitably, $R_b$ is as defined in any one of paragraphs (61) to (64) above. In an embodiment, $R_b$ is as defined in any one of paragraphs (62) to (64) above. In a particular embodiment, $R_b$ is as defined in paragraph (62) above.

Suitably, $R^c$ is as defined in any one of paragraphs (65) to (68) above. In an embodiment, $R^b$ is as defined in paragraphs (66) or (68) above.

Suitably, $R^d$ is as defined in paragraphs (69) or (70) above.

In a particular group of compounds, the compounds have the structural formula I, wherein
  $R_a$ is as defined in any one of paragraphs (43) to (50) or (57) to (60) above;
  $R_b$ is as defined in any one of paragraphs (61) to (64) above;
  and Q, X and Ar each have any one of the definitions set out hereinbefore.

In a particular group of compounds, the compounds have the structural formula I, wherein
  $R_a$ is as defined in any one of paragraphs (52) to (60) above;
  $R_b$ is as defined in any one of paragraphs (61) to (64) above;
  and Q, X and Ar each have any one of the definitions set out hereinbefore.

In a particular group of compounds, the compounds have the structural formula I, wherein
  $R_a$ is as defined in paragraph (53) above;
  $R_b$ is as defined in paragraph (62) above;
  and Q, X and Ar each have any one of the definitions set out hereinbefore.

In a further group of compounds, the compounds have the structural formula I, wherein
  $R_a$ is as defined in any one of paragraphs (44) to (50) or (57) to (60) above;
  $R_b$ is as defined in any one of paragraphs (61) to (64) above;
  and Q, X and Ar each have any one of the definitions set out hereinbefore.

In a further group of compounds, the compounds have the structural formula I wherein
R$_a$ is as defined in any one of paragraphs (54) to (60) above;
R$_b$ is as defined in any one of paragraphs (61) to (64) above;
and Q, X and Ar each have any one of the definitions set out hereinbefore.

In a further group of compounds, the compounds have the structural formula I wherein
R$_a$ is as defined in paragraph (54) above;
R$_b$ is as defined in paragraph (62) above;
and Q, X and Ar each have any one of the definitions set out hereinbefore.

In a further group of compounds, the compounds have the structural formula I, wherein
R$_a$ is ethyl or isopropyl, each of which is optionally substituted by fluoro;
and R$_b$, Q, X and Ar each have any one of the definitions set out hereinbefore.

In a further group of compounds, the compounds have the structural formula I, wherein
R$_a$ is ethyl optionally substituted by one or more fluoro atoms;
and R$_b$, Q, X and Ar each have any one of the definitions set out hereinbefore.

In a further group of compounds, the compounds have the structural formula I, wherein
R$_a$ is ethyl;
and R$_b$, Q, X and Ar each have any one of the definitions set out hereinbefore.

In a further group of compounds, the compounds have the structural formula I wherein
R$_a$ is as defined in any one of paragraphs (52) to (60) above;
R$_b$ is as defined in any one of paragraphs (61) to (64) above;
Q is as defined in any one of paragraphs (24) to (36) above;
X is as defined in any one of paragraphs (5) to (12) above; and
Ar is as defined in any one of paragraphs (13) to (19) above.

In a further group of compounds, the compounds have the structural formula I wherein
R$_a$ is as defined in paragraph (53) above;
R$_b$ is as defined in paragraph (62) above;
Q is as defined in paragraph (24) above;
X is as defined in paragraph (5) above; and
Ar is as defined in paragraph (13) above.

In a further group of compounds, the compounds have the structural formula I wherein
R$_a$ is ethyl or isopropyl, each of which is optionally substituted by fluoro;
R$_b$ is as defined in paragraph (62) above;
Q is as defined in paragraph (26) above;
X is as defined in paragraph (6) above; and
Ar is as defined in paragraph (14) above.

In a further group of compounds, the compounds have the structural formula I wherein
R$_a$ is ethyl optionally substituted by one or more fluoro atoms;
R$_b$ is as defined in paragraph (62) above;
Q is as defined in paragraph (27) above;
X is as defined in paragraph (7) above; and
Ar is as defined in any one of paragraphs (15) above.

In a further group of compounds, the compounds have the structural formula I wherein
R$_a$ is ethyl;
R$_b$ is as defined in paragraph (62) above;
Q is as defined in paragraph (35) above;
X is as defined in paragraph (8) above; and
Ar is as defined in paragraph (15) above.

In a further group of compounds, the compounds have the structural formula IA shown below

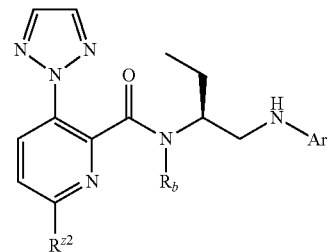

(IA)

wherein
R$_b$, R$^{z2}$ and Ar each have any one of the definitions set out hereinbefore.

In a further group of compounds, the compounds have the structural formula IA shown above, wherein
R$_b$ is as defined in any one of paragraphs (61) to (64) above;
R$^{z2}$ is as defined in any one of paragraphs (40) to (42) above; and
Ar is as defined in any one of paragraphs (13) to (19) above.

In a further group of compounds, the compounds have the structural formula IA shown above, wherein
R$_b$ is as defined in paragraph (63) above;
R$^{z2}$ is as defined in paragraph (41) above; and
Ar is as defined in paragraph (18) above.

In a further group of compounds, the compounds have the structural formula IA shown above, wherein
R$_b$ is as defined in paragraph (64) above;
R$^{z2}$ is as defined in paragraph (42) above; and
Ar is as defined in paragraph (19) above.

In a further group of compounds, the compounds have the structural formula IA shown above, wherein
R$_b$ is (1-4C)alkyl optionally substituted by fluoro;
R$^{z2}$ is selected from the group consisting of halo, cyano, nitro, or a group of the formula:

$$-L^3-X^3-R^{30}$$

wherein
L$^3$ is absent;
X$^3$ is absent, or selected from —O—, —N(R$^{33}$)—, —N(R$^{33}$)—C(O)—, —C(O)—N(R$^{33}$)—, —S—, —SO—, or —SO$_2$—, wherein R$^{33}$ is selected from hydrogen or (1-2C)alkyl; and
R$^{30}$ is hydrogen or (1-4C)alkyl;
and wherein R$^{30}$ is optionally further substituted by one or more fluoro atoms;
Ar is as defined hereinbefore.

In a further group of compounds, the compounds have the structural formula IA shown above, wherein
R$_b$ is methyl optionally substituted by fluoro;
R$^{z2}$ is selected from the group consisting of halo, methyl, methoxy, CF$_3$ or OCF$_3$;

Ar is pyridyl, pyrimidinyl, pyrazinyl, which is optionally substituted by one or more substituent groups selected from halo, cyano, hydroxyl, mercapto, amino, carbamoyl, sulphamoyl, (1-2C)alkyl, (1-2C)haloalkyl, (1-2C)alkoxy, (1-2C)haloalkoxy, (1-2C)alkylamino, di-[(1-2C)alkyl]amino, (1-2C)alkylthio, (1-2C)alkylsulphinyl, (1-2C)alkylsulphonyl, (1-2C)alkoxycarbonyl, N-(1-2C)alkylcarbamoyl, N,N-di-[(1-2C)alkyl]carbamoyl, (2C)alkanoyl, (2C)alkanoyloxy, (2C)alkanoylamino, N-(1-2C)alkylsulphamoyl and N,N-di-[(1-2C)alkyl]sulphamoyl.

Particular compounds of the present invention include any one of the following:

(S)—N-(1-((5-chloropyridin-2-yl)amino)butan-2-yl)-N,5-dimethyl-2-(2H-1,2,3-triazol-2-yl)benzamide (Example 1);

(S)—N-(1-((5-chloropyridin-2-yl)amino)butan-2-yl)-5-methyl-2-(2H-1,2,3-triazol-2-yl)benzamide (Example 2);

(S)—N-(1-((5-chloropyridin-2-yl)amino)butan-2-yl)-N-methyl-[1,1'-biphenyl]-2-carboxamide (Example 3);

(S)—N-(1-((5-chloropyridin-2-yl)amino)-3-methylbutan-2-yl)-[1,1'-biphenyl]-2-carboxamide (Example 4);

(S)—N-(1-((5-chloropyridin-2-yl)amino)-4-methylpentan-2-yl)-[1,1'-biphenyl]-2-carboxamide (Example 5);

(S)—N-(1-((5-chloropyridin-2-yl)amino)-3-methylbutan-2-yl)-2-methyl-4-phenylthiazole-5-carboxamide (Example 6);

(S)—N-(1-((5-chloropyridin-2-yl)amino)-4-methylpentan-2-yl)-2-methyl-4-phenylthiazole-5-carboxamide (Example 7);

(S)—N-(1-((5-chloropyridin-2-yl)amino)-4-methylpentan-2-yl)-N-methyl-[1,1'-biphenyl]-2-carboxamide (Example 8);

(S)—N-(1-((5-chloropyridin-2-yl)amino)-4-methylpentan-2-yl)-N,2-dimethyl-4-phenylthiazole-5-carboxamide (Example 9);

(S)—N-(1-((5-chloropyridin-2-yl)amino)-3-methylbutan-2-yl)-N-methyl-[1,1'-biphenyl]-2-carboxamide (Example 10);

(S)—N-(1-((5-chloropyridin-2-yl)amino)-3-methylbutan-2-yl)-N,2-dimethyl-4-phenylthiazole-5-carboxamide (Example 11);

(S)—N-(1-((5-chloropyridin-2-yl)amino)-3,3-dimethylbutan-2-yl)-N-methyl-[1,1'-biphenyl]-2-carboxamide (Example 12);

(S)—N-(2-((5-chloropyridin-2-yl)amino)-1-cyclopropylethyl)-N-methyl-[1,1'-biphenyl]-2-carboxamide (Example 13);

(S)—N-(1-((5-chloropyridin-2-yl)amino)propan-2-yl)-N-methyl-[1,1'-biphenyl]-2-carboxamide (Example 14);

(S)—N-(1-((5-chloropyridin-2-yl)amino)-3-methylbutan-2-yl)-N-cyclopropyl-[1,1'-biphenyl]-2-carboxamide (Example 15);

(S)-5-chloro-N-(1-((5-chloropyridin-2-yl)amino)butan-2-yl)-N-methyl-2-(2H-1,2,3-triazol-2-yl)benzamide (Example 16);

(S)—N-(1-((5-chloropyridin-2-yl)amino)butan-2-yl)-N-methyl-2-(2H-1,2,3-triazol-2-yl)-5-(trifluoromethyl)benzamide (Example 17);

(S)—N-(1-((5-chloropyridin-2-yl)amino)butan-2-yl)-5-fluoro-N-methyl-2-(2H-1,2,3-triazol-2-yl)benzamide (Example 18);

(S)-5-bromo-N-(1-((5-chloropyridin-2-yl)amino)butan-2-yl)-N-methyl-2-(2H-1,2,3-triazol-2-yl)benzamide (Example 19);

(S)—N-(1-((5-chloropyridin-2-yl)amino)butan-2-yl)-N-methyl-2-(2H-1,2,3-triazol-2-yl)-5-(trifluoromethoxy)benzamide (Example 20);

(S)—N-(1-((5-chloropyridin-2-yl)amino)butan-2-yl)-N,6-dimethyl-3-(2H-1,2,3-triazol-2-yl)picolinamide (Example 21);

(S)—N-(1-((5-chloropyridin-2-yl)amino)butan-2-yl)-N,5-dimethyl-2-morpholinobenzamide (Example 22);

(S)—N-(1-((5-chloropyridin-2-yl)amino)butan-2-yl)-5-(dimethylamino)-N-methyl-2-(2H-1,2,3-triazol-2-yl)benzamide (Example 23);

(S)—N-(1-((5-chloropyridin-2-yl)amino)butan-2-yl)-N-methyl-2-(2H-1,2,3-triazol-2-yl)-5-(trifluoromethyl)nicotinamide (Example 24);

(S)-5-chloro-N-(1-((5-chloropyridin-2-yl)amino)butan-2-yl)-2-(2H-1,2,3-triazol-2-yl)benzamide (Example 25);

(S)—N-(1-((5-chloropyridin-2-yl)amino)-3-methylbutan-2-yl)-N,2-dimethyl-5-phenylthiazole-4-carboxamide (Example 26);

(S)—N-(1-((5-chloropyridin-2-yl)amino)-3-methylbutan-2-yl)-N-methyl-2-phenyl-1H-indole-3-carboxamide (Example 27);

(S)—N-(1-((5-chloropyridin-2-yl)amino)-3-methylbutan-2-yl)-N-methyl-2-(2H-1,2,3-triazol-2-yl)benzamide (Example 28);

(S)—N-(1-((4-fluorobenzyl)oxy)-3-methylbutan-2-yl)-N-methyl-[1,1'-biphenyl]-2-carboxamide (Example 29);

(S)—N-(1-((4,6-dimethylpyrimidin-2-yl)oxy)-3-methylbutan-2-yl)-N-methyl-[1,1'-biphenyl]-2-carboxamide (Example 30);

(S)—N-methyl-N-(3-methyl-1-(quinazolin-2-yloxy)butan-2-yl)-[,1'-biphenyl]-2-carboxamide (Example 31);

(S)—N-methyl-N-(3-methyl-1-((4-phenylpyrimidin-2-yl)oxy)butan-2-yl)-[1,1'-biphenyl]-2-carboxamide (Example 32);

(S)—N-methyl-N-(3-methyl-1-((1-methyl-1H-benzo[d]imidazol-2-yl)oxy)butan-2-yl)-[1,1'-biphenyl]-2-carboxamide (Example 33);

(S)—N-(1-((5-chloropyridin-2-yl)oxy)-3-methylbutan-2-yl)-N-methyl-[1,1'-biphenyl]-2-carboxamide (Example 34);

(S)—N-methyl-N-(3-methyl-1-((4-phenylpyrimidin-2-yl)amino)butan-2-yl)-[1,1'-biphenyl]-2-carboxamide (Example 35);

(S)—N-methyl-N-(3-methyl-1-(quinazolin-2-ylamino)butan-2-yl)-[1,1'-biphenyl]-2-carboxamide (Example 36);

(S)—N-(1-((4,6-dimethylpyrimidin-2-yl)amino)-3-methylbutan-2-yl)-N-methyl-[1,1'-biphenyl]-2-carboxamide (Example 37);

(S)—N-methyl-N-(3-methyl-1-((1-methyl-1H-benzo[d]imidazol-2-yl)amino)butan-2-yl)-[1,1'-biphenyl]-2-carboxamide (Example 38);

(S)-5-chloro-N-methyl-2-(2H-1,2,3-triazol-2-yl)-N-(1-((5-(trifluoromethyl)pyrimidin-2-yl)amino)butan-2-yl)benzamide (Example 39);

(S)-5-chloro-N-methyl-2-(2H-1,2,3-triazol-2-yl)-N-(1-((5-(trifluoromethyl)pyrazin-2-yl)amino)butan-2-yl)benzamide (Example 40);

(S)-5-chloro-N-methyl-2-(2H-1,2,3-triazol-2-yl)-N-(1-((6-(trifluoromethyl)pyridazin-3-yl)amino)butan-2-yl)benzamide (Example 41);

(S)-5-chloro-N-methyl-2-(2H-1,2,3-triazol-2-yl)-N-(1-((5-(trifluoromethyl)pyridin-2-yl)amino)butan-2-yl)benzamide (Example 42);

(S)—N-(1-(benzo[d]oxazol-2-ylamino)butan-2-yl)-5-chloro-N-methyl-2-(2H-1,2,3-triazol-2-yl)benzamide (Example 43);

(S)—N-(1-(benzo[d]thiazol-2-ylamino)butan-2-yl)-5-chloro-N-methyl-2-(2H-1,2,3-triazol-2-yl)benzamide (Example 44);
(S)-5-chloro-N-(1-((5-chloro-3-nitropyridin-2-yl)amino)butan-2-yl)-N-methyl-2-(2H-1,2,3-triazol-2-yl)benzamide (Example 45);
(S)—N,6-dimethyl-3-(2H-1,2,3-triazol-2-yl)-N-(1-((5-(trifluoromethyl)pyrimidin-2-yl)amino)butan-2-yl)picolinamide (Example 46);
(S)—N,6-dimethyl-3-(2H-1,2,3-triazol-2-yl)-N-(1-((5-(trifluoromethyl)pyrazin-2-yl)amino)butan-2-yl)picolinamide (Example 47);
(S)—N,6-dimethyl-3-(2H-1,2,3-triazol-2-yl)-N-(1-((5-(trifluoromethyl)pyridin-2-yl)amino)butan-2-yl)picolinamide (Example 48);
(S)—N-(1-((5-chloropyridin-2-yl)amino)-3-methylbutan-2-yl)-N,5-dimethyl-2-(2H-1,2,3-triazol-2-yl)benzamide (Example 49);
(S)—N-(1-((5-chloropyridin-2-yl)amino)-3-methylbutan-2-yl)-N,1-dimethyl-1H-indole-3-carboxamide (Example 50);
(S)—N-(1-((5-chloropyridin-2-yl)amino)-3-methylbutan-2-yl)-N,2-dimethylquinoline-4-carboxamide (Example 51);
(S)—N-(1-((5-chloropyridin-2-yl)amino)-3-methylbutan-2-yl)-N-methyl-2-(trifluoromethoxy)benzamide (Example 52);
(S)-5-chloro-N-methyl-N-(1-((6-methylpyridin-2-yl)amino)butan-2-yl)-2-(2H-1,2,3-triazol-2-yl)benzamide (Example 53);
(S)-5-chloro-N-methyl-2-(2H-1,2,3-triazol-2-yl)-N-(1-((6-(trifluoromethyl)pyridin-3-yl)amino)butan-2-yl)benzamide (Example 54);
(S)—N,6-dimethyl-3-(2H-1,2,3-triazol-2-yl)-N-(1-((6-(trifluoromethyl)pyridin-3-yl)amino)butan-2-yl)picolinamide (Example 55);
(S)—N-(1-(4-fluorobenzamido)-3-methylbutan-2-yl)-N-methyl-[1,1'-biphenyl]-2-carboxamide (Example 56);
(S)—N-(1-((4-fluorobenzyl)amino)-3-methylbutan-2-yl)-N-methyl-[1,1'-biphenyl]-2-carboxamide (Example 57);
(S)—N-methyl-N-(3-methyl-1-(3-phenylureido)butan-2-yl)-[1,1'-biphenyl]-2-carboxamide (Example 58);
(S)—N-(1-((4-chlorophenyl)amino)-3-methylbutan-2-yl)-N-methyl-[1,1'-biphenyl]-2-carboxamide (Example 59);
(S)—N-(1-((3-amino-5-chloropyridin-2-yl)amino)butan-2-yl)-5-chloro-N-methyl-2-(2H-1,2,3-triazol-2-yl)benzamide (Example 60);
(S)—N,6-dimethyl-N-(1-(quinazolin-2-ylamino)butan-2-yl)-3-(2H-1,2,3-triazol-2-yl)picolinamide (Example 61);
(S)—N-(1-(benzo[d]oxazol-2-ylamino)butan-2-yl)-N,6-dimethyl-3-(2H-1,2,3-triazol-2-yl)picolinamide (Example 62);
(S)—N-(1-(benzo[d]thiazol-2-ylamino)butan-2-yl)-N,6-dimethyl-3-(2H-1,2,3-triazol-2-yl)picolinamide (Example 63);
(S)—N-(1-((5-chlorobenzo[d]oxazol-2-yl)amino)butan-2-yl)-N,6-dimethyl-3-(2H-1,2,3-triazol-2-yl)picolinamide (Example 64);
(S)—N,6-dimethyl-N-(1-(quinoxalin-2-ylamino)butan-2-yl)-3-(2H-1,2,3-triazol-2-yl)picolinamide (Example 65);
(S)—N,6-dimethyl-N-(3-methyl-1-((5-(trifluoromethyl)pyrimidin-2-yl)amino)butan-2-yl)-3-(2H-1,2,3-triazol-2-yl)picolinamide (Example 66);
(S)—N,6-dimethyl-N-(3-methyl-1-((5-(trifluoromethyl)pyrazin-2-yl)amino)butan-2-yl)-3-(2H-1,2,3-triazol-2-yl)picolinamide (Example 67);
(S)—N,6-dimethyl-N-(3-methyl-1-(quinazolin-2-ylamino)butan-2-yl)-3-(2H-1,2,3-triazol-2-yl)picolinamide (Example 68);
(S)—N,6-dimethyl-N-(3-methyl-1-((5-(trifluoromethyl)pyridin-2-yl)amino)butan-2-yl)-3-(2H-1,2,3-triazol-2-yl)picolinamide (Example 69);
(S)—N-ethyl-6-methyl-3-(2H-1,2,3-triazol-2-yl)-N-(1-((5-(trifluoromethyl)pyrazin-2-yl)amino)butan-2-yl)picolinamide (Example 70);
(S)—N-ethyl-6-methyl-3-(2H-1,2,3-triazol-2-yl)-N-(1-((5-(trifluoromethyl)pyridin-2-yl)amino)butan-2-yl)picolinamide (Example 71);
(S)—N-ethyl-6-methyl-N-(1-(quinazolin-2-ylamino)butan-2-yl)-3-(2H-1,2,3-triazol-2-yl)picolinamide (Example 72);
(S)—N-ethyl-6-methyl-3-(2H-1,2,3-triazol-2-yl)-N-(1-((5-(trifluoromethyl)pyrimidin-2-yl)amino)butan-2-yl)picolinamide (Example 73);
S)—N-(1-cyclopropyl-2-((5-(trifluoromethyl)pyrimidin-2-yl)amino)ethyl)-N,6-dimethyl-3-(2H-1,2,3-triazol-2-yl)picolinamide (Example 74);
(S)—N,6-dimethyl-N-(1-(quinolin-2-ylamino)butan-2-yl)-3-(2H-1,2,3-triazol-2-yl)picolinamide (Example 75);
(S)—N-(1-((1,5-naphthyridin-2-yl)amino)butan-2-yl)-N,6-dimethyl-3-(2H-1,2,3-triazol-2-yl)picolinamide (Example 76);
(S)-5-chloro-N-methyl-N-(1-(quinolin-2-ylamino)butan-2-yl)-2-(2H-1,2,3-triazol-2-yl)benzamide (Example 77);
(S)—N,3-dimethyl-N-(1-((5-(trifluoromethyl)pyrimidin-2-yl)amino)butan-2-yl)isoquinoline-1-carboxamide (Example 78);
(S)—N-methyl-N-(1-((5-(trifluoromethyl)pyrimidin-2-yl)amino)butan-2-yl)quinoline-8-carboxamide (Example 79);
(S)-6-chloro-N-methyl-N-(1-((5-(trifluoromethyl)pyrimidin-2-yl)amino)butan-2-yl)quinoline-8-carboxamide (Example 80);
(S)-3-(dimethylamino)-N-methyl-N-(1-((5-(trifluoromethyl)pyrimidin-2-yl)amino)butan-2-yl)isoquinoline-1-carboxamide (Example 81);
(S)—N,6-dimethyl-N-(1-(methyl(5-(trifluoromethyl)pyrimidin-2-yl)amino)butan-2-yl)-3-(2H-1,2,3-triazol-2-yl)picolinamide (Example 82);
(S)—N-(1-((2-methoxyethyl)(5-(trifluoromethyl)pyrimidin-2-yl)amino)butan-2-yl)-N,6-dimethyl-3-(2H-1,2,3-triazol-2-yl)picolinamide (Example 83);
(S)—N,6-dimethyl-3-(pyrimidin-2-yl)-N-(1-((5-(trifluoromethyl)pyrimidin-2-yl)amino)butan-2-yl)picolinamide formic acid salt (Example 84);
(S)—N-methyl-N-(1-((5-(trifluoromethyl)pyrimidin-2-yl)amino)butan-2-yl)isoquinoline-1-carboxamide (Example 85);
(S)—N-(1-((5-chloropyridin-2-yl)amino)butan-2-yl)-N,4,5-trimethyl-2-(2H-1,2,3-triazol-2-yl)benzamide (Example 86);
(S)—N-(1-((5-chloropyridin-2-yl)amino)butan-2-yl)-5-methoxy-N,4-dimethyl-2-(2H-1,2,3-triazol-2-yl)benzamide (Example 87);
(S)—N,6-dimethyl-3-(2H-1,2,3-triazol-2-yl)-N-(4,4,4-trifluoro-1-((5-(trifluoromethyl)pyrimidin-2-yl)amino)butan-2-yl)picolinamide (Example 88);
(S)—N,6-dimethyl-3-(1H-1,2,4-triazol-1-yl)-N-(1-((5-(trifluoromethyl)pyrimidin-2-yl)amino)butan-2-yl)picolinamide formic acid salt (Example 89);
(S)—N,6-dimethyl-3-(1H-pyrazol-1-yl)-N-(1-((5-(trifluoromethyl)pyrimidin-2-yl)amino)butan-2-yl)picolinamide formic acid salt (Example 90);

(S)-2-fluoro-N-methyl-6-(2H-1,2,3-triazol-2-yl)-N-(1-((5-(trifluoromethyl)pyrimidin-2-yl)amino)butan-2-yl)benzamide (Example 91);
(S)-6-methoxy-N-methyl-3-(2H-1,2,3-triazol-2-yl)-N-(1-((5-(trifluoromethyl)pyrimidin-2-yl)amino)butan-2-yl)picolinamide (Example 92); or a pharmaceutically acceptable salt or solvate thereof.

The various functional groups and substituents making up the compounds of the present invention are typically chosen such that the molecular weight of the compound does not exceed 1000. More usually, the molecular weight of the compound will be less than 750, for example less than 700, or less than 650, or less than 600, or less than 550. More preferably, the molecular weight is less than 525 and, for example, is 500 or less.

Suitable or preferred features of any compounds of the present invention may also be suitable features of any other aspect.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess orexin-1 inhibitory activity.

The present invention also encompasses compounds of the invention as defined herein which comprise one or more isotopic substitutions. For example, H may be in any isotopic form, including $^1H$, $^2H$ (D) and $^3H$ (T); C may be in any isotopic form including $^{12}C$, $^{13}C$, and $^{14}C$; and O may be in any isotopic form, including $^{16}O$ and $^{18}O$; and the like.

It is also to be understood that certain compounds of the invention may exist in solvated as well as unsolvated forms such as, for example, hydrated forms. It is to be understood that the invention encompasses all such solvated forms that possess orexin-1 inhibitory activity.

It is also to be understood that certain compounds of the invention may exhibit polymorphism, and that the invention encompasses all such forms that possess orexin-1 inhibitory activity.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

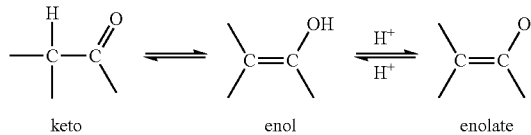

keto    enol    enolate

Compounds of the invention containing an amine function may also form N-oxides. A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The compounds of the invention may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the invention and in-vivo cleavable amide derivatives that may be formed at a carboxy group or an amino group in a compound of the invention.

Accordingly, the present invention includes those compounds of the formula I as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula I may be a synthetically-produced compound or a metabolically-produced compound.

A suitable pharmaceutically acceptable pro-drug of a compound of the formula I is one that is based on reasonable medical judgement as being suitable for administration to the human or animal body without undesirable pharmacological activities and without undue toxicity.

Various forms of pro-drug have been described, for example in the following documents:—
a) *Methods in Enzymoloqy*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the formula I that possesses a carboxy group is, for example, an in vivo cleavable ester thereof. An in vivo cleavable ester of a compound of the formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the formula I that possesses a hydroxy group is, for example, an in vivo cleavable ester or ether thereof. An in vivo cleavable ester or ether of a compound of the formula I containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the formula I that possesses a carboxy group is, for example, an in vivo cleavable amide thereof, for example an amide formed with an amine such as ammonia, a $C_{1-4}$alkylamine such as methylamine, a $(C_{1-4}$alkyl$)_2$ amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of the formula I that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the formula I may be exerted in part by one or more metabolites that are formed within the human or animal body after administration of a compound of the formula I. As stated hereinbefore, the in vivo effects of a compound of the formula I may also be exerted by way of metabolism of a precursor compound (a pro-drug).

It shall also be appreciated that compounds of the formula I may also be covalently linked (at any suitable position) to other groups such as, for example, solubilising moieties (for example, PEG polymers), moieties that enable them to be bound to a solid support (such as, for example, biotin-containing moieties), and targeting ligands (such as antibodies or antibody fragments).

Synthesis

In the description of the synthetic methods described below and in the referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example $BF_3 \cdot OEt_2$. A suitable alternative protecting group for a primary amino group is, for example, a phthaloyl group which may be removed by treatment with an alkylamine, for example dimethylaminopropylamine, or with hydrazine.

The person skilled in the art will recognise that the compounds of the invention may be prepared, in known manner, in a variety of ways. Compounds of formula I can be prepared by the methods given below, by the methods given in the experimental or by analogous methods. The routes described are merely illustrative of some of the methods that can be employed for the synthesis of compounds of formulae I and the person skilled in the art will appreciate that the order of the reaction steps is not limited to those described. It will also be appreciated that the assignment of nucleophile and electrophile is not limited to that described herein and in some cases it may be appropriate for the assignment to be reversed. Different approaches to synthetic chemistry strategy are described in "Organic Synthesis: The Disconnection Approach", $2^{nd}$ edition, S. Warren and P. Wyatt (2008).

A compound of formula I, or a pharmaceutically-acceptable salt thereof, wherein Q, X, Ar, $R_a$ and $R_b$ are as previously defined, may be prepared by reacting a compound of formula II, wherein Q is as previously defined in formula I, with an amine of formula III, wherein X, Ar, $R_a$ and $R_b$ are as previously defined in formula I (Scheme A, step i).

A suitably reactive derivative of a carboxylic acid of formula II is formed, for example: an acyl halide formed by the reaction of the acid and an inorganic acid chloride such as thionyl chloride; a mixed anhydride, formed by the reaction of the acid and a chloroformate such as isobutyl chloroformate; an ester, formed by reaction with an alcohol in the presence of acid or base; an activated ester, formed by the reaction of the acid with a phenol such as pentafluorophenyl trifluoroacetate or with an alcohol such as N-hydroxybenzotriazole; or the product of the reaction of the acid and an amide-coupling agent such as dicyclohexylcarbodiimide. Where a carboxylic acid of formula II is converted to an ester, for example by the reaction of an acyl chloride with an organic alcohol, such as methanol, this may be reacted with an amine of formula III in the presence of an organometallic activating agent, for example a Grignard reagent such as isopropylmagnesium bromide. Typically, a carboxylic acid of formula II and an amine of formula III, in a suitable solvent, such as DMF in the presence of a non-nucleophilic base, such as DIPEA, are treated with an amide-coupling agent, such as HATU.

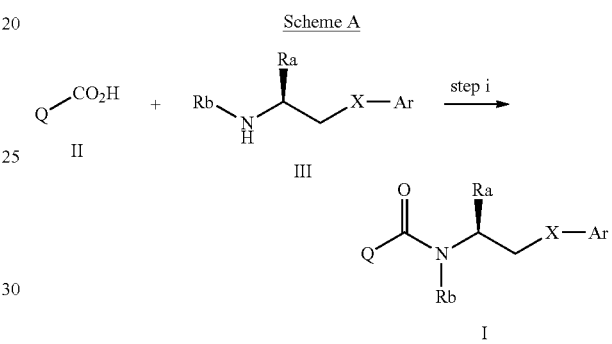

Scheme A

Compounds of formula II, wherein Q is as previously defined in formula I, may be commercially available or prepared by techniques known, or apparent to, those skilled in the art. Compounds of formula II may be prepared by: acid or base catalysed hydrolysis of an ester, an amide or a nitrile, such as the hydrolysis of a methyl ester with sodium hydroxide; transition metal catalysed oxidation of an aldehyde or alcohol; treatment of an organolithium or Grignard reagent with carbon dioxide; transition metal catalysed carbonylation of an aryl halide in the presence of water. Transition metal catalysed carbonylation of an aryl halide in the presence of an amine of formula III may form a compound of formula I directly.

It will be appreciated by those skilled in the art that compounds of formula I and formula III, wherein X, Ar, Q, $R_a$ and $R_b$ are as previously defined in formula I, may be prepared by incorporating suitable protecting group and route selection strategies into the general synthetic chemistry methodology described in Scheme B, wherein X, Ar, Q, $R_a$ and $R_b$ are as previously defined in formula I and Y is either: H; QC(O), wherein Q is as previously defined in formula I; or an amine protecting group such as benzyl, 3,4-dimethoxybenzyl p-methoxybenzyl, carbobenzyloxy, tert-butyloxycarbonyl, 9-fluorenylmethyloxycarbonyl, acetyl, benzoyl, p-methoxyphenyl, tosyl, nosyl or trifluoroacetyl.

A compound of formula IV, or a pharmaceutically-acceptable salt thereof, wherein Ar, $R_1$, $R_a$ and $R_b$ are as previously defined in formula I, may be prepared by reacting an amine of formula V, wherein $R_1$, $R_a$ and $R_b$ are as previously defined in formula I, with a compound of formula ZAr, wherein Ar is as previously defined in formula I and Z is a substituent amenable to transition-metal catalysed amination chemistry (Scheme B, step ii). A compound of formula ZAr, wherein Z is a halide such as bromide or chloride, a boronic acid or boronate ester, or an activated alcohol such as a triflate, may be converted to a compound of formula IV by reaction with an amine of formula V in the presence of a transition metal catalyst such as [1,1'-bis(diphenylphosphino)ferrocene]dichloropalladium(II) or $Pd_2(dba)_3$ in the presence of a base such as potassium carbonate or sodium tert-butoxide and a suitable ligand such as triphenylphosphine or 4,5-Bis(diphenylphosphino)-9,9-dimethylxanthene. Typically the reaction is carried out in toluene, at reflux, using $Pd_2(dba)_3$ as a catalyst in the presence of BINAP and sodium tert-butoxide.

Alternatively, a compound of formula IV may be prepared by reacting an amine of formula V with a compound of formula ZAr, wherein Ar is as previously defined in formula I and Z is a leaving group such as a halide, for example iodide or bromide, or an activated alcohol, for example tosylate or mesylate, in the presence of a non-nucleophilic base such as DBU, sodium tert-butoxide, potassium carbonate, a tertiary amine for example DIPEA, or a heterocyclic base for example pyridine (Scheme B, step ii). Typically the reaction is carried out using DIPEA, as a base, in NMP at 130° C.

A compound of formula IV, or a pharmaceutically-acceptable salt thereof, wherein Ar, $R_1$, $R_a$ and $R_b$ are as previously defined in formula I, may be prepared by reacting an amine of formula $HNR_1Ar$, wherein $R_1$ and Ar are as previously described in formula I, with an aldehyde of formula VI, wherein $R_a$ and $R_b$ are as previously defined in formula I (Scheme B, step iii). A compound of formula IV may be prepared by reductive amination of compounds of formula VI with an amine of formula $HNR_1Ar$ in the presence of a suitable reducing agent such as sodium cyanoborohydride, $NaBH(OAc)_3$ or sodium borohydride, in a polar solvent such as methanol, ethanol, THF, DCE or DCM either alone or in combination with an acid such as AcOH. Typically the reaction is carried out using $NaBH(OAc)_3$ in DCE at ambient temperature.

A compound of formula VII, or a pharmaceutically-acceptable salt thereof, wherein Ar, $R_a$ and $R_b$ are as previously defined in formula I, may be prepared by reacting an alcohol of formula VIII, wherein $R_a$ and $R_b$ are as previously defined in formula I, with a compound of formula ZAr, wherein Ar is as previously defined in formula I and Z is a leaving group such as a halide or an activated alcohol (Scheme B, step iv). A compound of formula ZAr, wherein Z is a leaving group such as halide, for example iodide or bromide, or an activated alcohol, for example tosylate or mesylate, may be converted to a compound of formula VII by reaction with an alcohol of formula VIII in the presence of a non-nucleophilic base such potassium carbonate, sodium hydride or lithium diisopropylamide. Alternatively, where Z is an alcohol, in-situ activation may be employed, for example with the use of diethylazadicarboxylate and triphenyl phosphine in a solvent such as THF. Typically the reaction is carried out wherein ZAr is an aryl halide using sodium hydride as base and THF as solvent at ambient temperature.

An amine of formula V may be prepared by reductive amination as previously described for Scheme B step iii, between an aldehyde of formula VI and an amine, amine equivalent or suitably protected amine, of formula $H_2NR_1$ (Scheme B, step v).

The person skilled in the art will recognise that aldehydes of formula VI can be prepared in a variety of ways. Typically aldehydes of formula VI are prepared by the oxidation of an alcohol of formula VIII in DCM using Dess-Martin's Periodinane and $NaHCO_3$ (Scheme B, step vi).

Compounds of formula V may also be prepared by reduction of an amide of formula IX with a hydride reagent such as $LiAlH_4$ or by catalytic hydrogenation (Scheme B, step vii). Typically the reaction is carried out in THF or diethyl ether using $LiAlH_4$ at 0° C. The person skilled in the art will recognise that the preparation of amines of formula V is not limited to the methods described herein and can be achieved in known manner, in a variety of ways.

The person skilled in the art will recognise that alcohols of formula VIII, wherein $R_a$ and $R_b$ are as previously defined in formula I, can be prepared in a variety of known ways. For example, alcohols of formula VIII may be prepared by reduction of carbonyl containing compounds such as aldehydes of formula VI (Scheme B, step viii), carboxylic acids or carboxylic acid equivalents, such as a carboxylic esters, of formula X (Scheme B, step ix) with a suitable reducing agent such as sodium borohydride, $LiAlH_4$, diisobutyl aluminium hydride or $LiBH_4$. Typically alcohols of formula VIII are prepared by reduction of carboxylic ester equivalents of carboxylic acids of formula X using $LiBH_4$ in THF at ambient temperature. It will be appreciated by a person skilled in the art that a carboxylic ester equivalent of a carboxylic acid of formula X can be prepared in a variety of known ways.

Scheme B

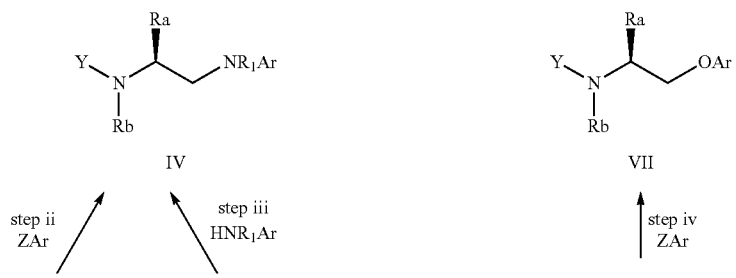

-continued

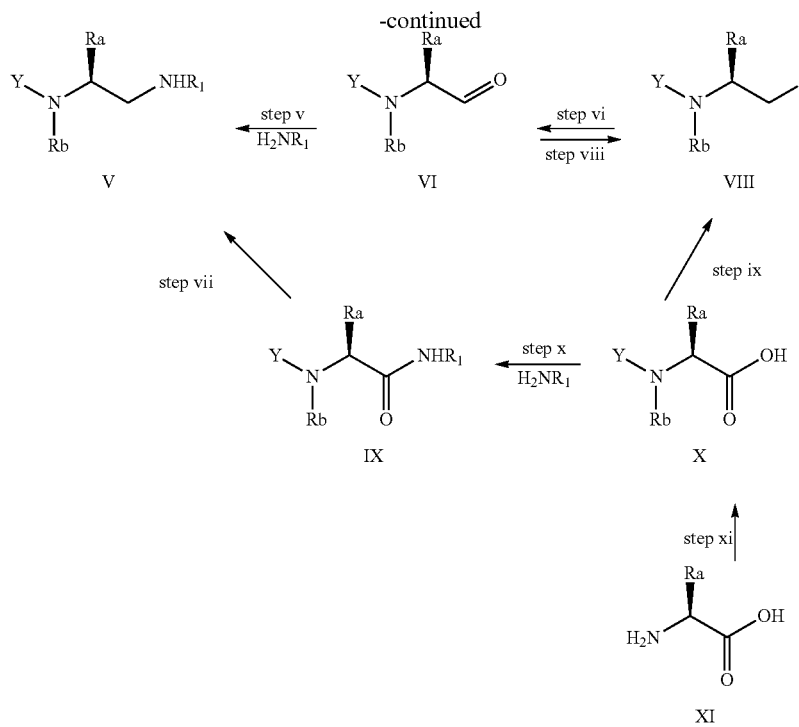

Compounds of formula X may be prepared from a suitably protected/activated derivative of an amino acid of formula XI (Scheme B, step xi). It will be appreciated by those skilled in the art that conversion of an amino acid of formula XI to a compound of formula X via a synthetic strategy of protection/activation may require multiple reaction steps, and can be achieved in a variety of ways of known manner. For example, compounds of formula X can be prepared by: conversion of an amino acid of formula XI to an activated amide such as a trifluoroacetamide by reaction with trifluoracetic anhydride, followed by deprotonation with a base such as sodium hydride, alkylation with an alkyl halide of formula $R_bZ$, wherein $R_b$ is as described in formula I and Z is a leaving group such as a halide or an activated alcohol, for example methyl iodide, and hydrolysis with a suitable base such as sodium hydroxide; benzylic protection by reaction of an amino acid of formula XI with a suitable aldehyde or aldehyde equivalent such as benzaldehyde, followed by reductive amination with an aldehyde of formula $R_bCHO$, or aldehyde equivalent followed by catalytic hydrogenation with a transition metal catalyst such as palladium under an atmosphere of hydrogen; conversion of an amino acid of formula XI to a carbamate by reaction with an anhydride or acid chloride such as with di-tert-butyl dicarbonate, followed by reduction with a metal-hydride such as $LiAlH_4$.

Natural and non-natural amino acids of formula XI and their derivatives are either commercially available or may be prepared by methods known to those skilled in the art. For reviews of the synthesis of amino acids, see (a) C. Najera and J. M. Sansano, *Chem. Rev.*, 2007, 107, 4584; (b) R. M. Williams and J. A. Hendrix, *Chem. Rev.*, 1992, 92, 889; (c) R. O. Duthaler, *Tetrahedron*, 1994, 50, 1539.

Pharmaceutical Compositions

According to a further aspect of the invention there is provided a pharmaceutical composition which comprises a compound of the invention as defined hereinbefore, or a pharmaceutically acceptable salt or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy of proliferative disease is an amount sufficient to symptomatically relieve in a warm-blooded animal, particularly a human the symptoms of infection, to slow the progression of infection, or to reduce in patients with symptoms of infection the risk of getting worse.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The compounds of the invention are selective inhibitors of orexin-1 activity. As a consequence, they are potentially useful therapeutic agents for the treatment of diseases or conditions in which orexin-1 receptor activity is implicated.

Thus, in one aspect, the present invention relates to a compound of the invention as defined herein, or a pharmaceutically acceptable salt or solvate thereof, or a pharmaceutical composition as defined herein, for use in therapy.

In another aspect, the present invention relates to a compound of the invention as defined herein, or a pharmaceutically acceptable salt or solvate thereof, or a pharmaceutical composition as defined herein, for use in the treatment of diseases or conditions in which orexin-1 ($OX_1$) activity is implicated.

In another aspect, the present invention relates to the use of a compound of the invention as defined herein, or a pharmaceutically acceptable salt or solvate thereof, in the manufacture of a medicament for use in the treatment of diseases or conditions in which orexin-1 ($OX_1$) activity is implicated.

In another aspect, the present invention relates to a method of treating a disease or condition in which orexin-1 ($OX_1$) activity is implicated, said method comprising administering to a subject in need of such treatment a therapeutically effective amount of a compound of the invention as defined herein, or a pharmaceutically acceptable salt or solvate thereof, or a pharmaceutical composition as defined herein.

Examples of particular diseases or conditions that the compounds of formula (I) and their pharmaceutically acceptable salts may be used to treat include, but are not limited to, any one of the following: schizophrenia and other psychotic disorders (e.g., psychotic disorder, psychosis or schizoaffective disorder); dementia and other cognitive disorders; anxiety disorders (e.g., generalized anxiety disorder, post-traumatic stress disorder, panic disorders, acute stress disorder, social anxiety disorder, phobias including agoraphobia, obsessive compulsive disorder, trichotillomania or body dismorphic disorder); mood disorders (e.g., depressive disorders, major depressive disorders, bipolar disorders including bipolar I and II, bipolar mania, bipolar depression); addiction including substance dependence (e.g. cocaine, opiates, *cannabis* or prescription drug dependence), alcohol dependence, nicotine dependence or gambling disorder; eating disorders (e.g. binge eating, bulimia nervosa, anorexia nervosa or obesity); sleep disorders (e.g. rapid eye movement sleep disorder); disorders usually first diagnosed in infancy, childhood, or adolescence (e.g., attention-deficit disorder, autistic spectrum disorders, Rett syndrome, Fragile X syndrome, Asperger syndrome and disruptive behaviour disorders); restless leg syndrome; pain (e.g. neuropathic pain including chemotherapy induced pain or migraine); osteoporosis and neurodegenerative disorders (e.g. Parkinson's or Alzheimer's disease).

In particular, the compounds of the invention (including pharmaceutically acceptable salts) may be used in the treatment of the positive symptoms of schizophrenia, schizophreniform disorder or schizoaffective disorder (e.g. voices or hallucinations), cognitive disorders (such as dementia and impaired learning), anxiety disorders (such as post-traumatic stress disorder or panic disorders), or addiction.

The invention also provides a compound of formula I as defined herein for use in the treatment of at least one symptom or condition associated with the treatment of any one of the following: schizophrenia and other psychotic disorders (e.g., psychotic disorder, psychosis or schizoaffective disorder); dementia and other cognitive disorders; anxiety disorders (e.g., generalized anxiety disorder, post-traumatic stress disorder, panic disorders, acute stress disorder, social anxiety disorder, phobias including agoraphobia, obsessive compulsive disorder, trichotillomania or body dismorphic disorder); mood disorders (e.g., depressive disorders, major depressive disorders, bipolar disorders including bipolar I and II, bipolar mania, bipolar depression); addiction including substance dependence (e.g. cocaine, opiates, *cannabis* or prescription drug dependence), alcohol dependence, nicotine dependence or gambling disorder; eating disorders (e.g. binge eating, bulimia nervosa, anorexia nervosa or obesity); sleep disorders (e.g. rapid eye movement sleep disorder); disorders usually first diagnosed in infancy, childhood, or adolescence (e.g., attention-deficit disorder, autistic spectrum disorders, Rett syndrome, Fragile X syndrome, Asperger syndrome and disruptive behaviour disorders); restless leg syndrome; pain (e.g. neuropathic pain including chemotherapy induced pain or migraine); osteoporosis and neurodegenerative disorders (e.g. Parkinson's or Alzheimer's disease) which comprises administering to a patient in need thereof a therapeutically effective amount of a compound of formula (I) or a pharmaceutically acceptable salt thereof as hereinbefore defined.

Such symptoms and conditions include, but are not limited to, anxiety, agitation, hostility, panic, an eating disorder, an affective symptom, a mood symptom, a negative and positive psychotic symptom commonly associated with psychosis and neurodegenerative disorder.

Further particular examples of conditions in which orexin-1 ($OX_1$) activity is implicated include behavioural arousal, eating disorders (e.g. binge eating, obesity), psychiatric conditions (e.g. schizophrenia, anxiety, mood disorders, reward seeking behaviours, alcohol or drug (e.g. nicotine) addiction, panic disorders (such as panic attacks) and/or anxiety).

In another aspect, the present invention provides a compound, or a pharmaceutically acceptable salt or solvate thereof, or a pharmaceutical composition as defined herein, for use in the treatment of schizophrenia and other psychotic disorders (e.g., psychotic disorder, psychosis or schizoaffective disorder); dementia and other cognitive disorders; anxiety disorders (e.g., generalized anxiety disorder, post-traumatic stress disorder, panic disorders, acute stress disorder, social anxiety disorder, phobias including agoraphobia, obsessive compulsive disorder, trichotillomania or body dismorphic disorder); mood disorders (e.g., depressive disorders, major depressive disorders, bipolar disorders including bipolar I and II, bipolar mania, bipolar depression); addiction including substance dependence (e.g. cocaine, opiates, *cannabis* or prescription drug dependence), alcohol dependence, nicotine dependence or gambling disorder; eating disorders (e.g. binge eating, bulimia nervosa, anorexia nervosa or obesity); sleep disorders (e.g. rapid eye movement sleep disorder); disorders usually first diagnosed in infancy, childhood, or adolescence (e.g., attention-deficit disorder, autistic spectrum disorders, Rett syndrome, Fragile X syndrome, Asperger syndrome and disruptive behaviour disorders); restless leg syndrome; pain (e.g. neuropathic pain including chemotherapy induced pain or migraine); osteoporosis and neurodegenerative disorders (e.g. Parkinson's or Alzheimer's disease).

In another aspect, the present invention provides a compound, or a pharmaceutically acceptable salt or solvate thereof, or a pharmaceutical composition as defined herein, for use in the treatment of behavioural arousal, eating disorders (e.g. binge eating, obesity), psychiatric conditions (e.g. schizophrenia, anxiety, mood disorders, reward seeking behaviours, alcohol or drug (e.g. nicotine) addiction, panic disorders (such as panic attacks) and/or anxiety).

In another aspect, the present invention provides the use of a compound, or a pharmaceutically acceptable salt or solvate thereof, in the manufacture of a medicament for use in the treatment of schizophrenia and other psychotic disorders (e.g., psychotic disorder, psychosis or schizoaffective disorder); dementia and other cognitive disorders; anxiety disorders (e.g., generalized anxiety disorder, post-traumatic stress disorder, panic disorders, acute stress disorder, social anxiety disorder, phobias including agoraphobia, obsessive compulsive disorder, trichotillomania or body dismorphic disorder); mood disorders (e.g., depressive disorders, major depressive disorders, bipolar disorders including bipolar I and II, bipolar mania, bipolar depression); addiction including substance dependence (e.g. cocaine, opiates, *cannabis* or prescription drug dependence), alcohol dependence, nicotine dependence or gambling disorder; eating disorders (e.g. binge eating, bulimia nervosa, anorexia nervosa or obesity); sleep disorders (e.g. rapid eye movement sleep disorder); disorders usually first diagnosed in infancy, childhood, or adolescence (e.g., attention-deficit disorder, autistic spectrum disorders, Rett syndrome, Fragile X syndrome, Asperger syndrome and disruptive behaviour disorders); restless leg syndrome; pain (e.g. neuropathic pain including chemotherapy induced pain or migraine); osteoporosis and neurodegenerative disorders (e.g. Parkinson's or Alzheimer's disease).

In another aspect, the present invention provides the use of a compound, or a pharmaceutically acceptable salt or solvate thereof, in the manufacture of a medicament for use in the treatment of behavioural arousal, eating disorders (e.g. binge eating, obesity), psychiatric conditions (e.g. schizophrenia, anxiety, mood disorders, reward seeking behaviours, alcohol or drug (e.g. nicotine) addiction, panic disorders (such as panic attacks) and/or anxiety).

In another aspect, the present invention provides a method of treating schizophrenia and other psychotic disorders (e.g., psychotic disorder, psychosis or schizoaffective disorder); dementia and other cognitive disorders; anxiety disorders (e.g., generalized anxiety disorder, post-traumatic stress disorder, panic disorders, acute stress disorder, social anxiety disorder, phobias including agoraphobia, obsessive compulsive disorder, trichotillomania or body dismorphic disorder); mood disorders (e.g., depressive disorders, major depressive disorders, bipolar disorders including bipolar I and II, bipolar mania, bipolar depression); addiction including substance dependence (e.g. cocaine, opiates, *cannabis* or prescription drug dependence), alcohol dependence, nicotine dependence or gambling disorder; eating disorders (e.g. binge eating, bulimia nervosa, anorexia nervosa or obesity); sleep disorders (e.g. rapid eye movement sleep disorder); disorders usually first diagnosed in infancy, childhood, or adolescence (e.g., attention-deficit disorder, autistic spectrum disorders, Rett syndrome, Fragile X syndrome, Asperger syndrome and disruptive behaviour disorders); restless leg syndrome; pain (e.g. neuropathic pain including chemotherapy induced pain or migraine); osteoporosis and neurodegenerative disorders (e.g. Parkinson's or Alzheimer's disease), said method comprising administering to a subject in need of such treatment a therapeutically effective amount of a compound, or a pharmaceutically acceptable salt or solvate thereof, or a pharmaceutical composition as defined herein.

In another aspect, the present invention provides a method of treating behavioural arousal, eating disorders (e.g. binge eating, obesity), psychiatric conditions (e.g. schizophrenia, anxiety, mood disorders, reward seeking behaviours, alcohol or drug (e.g. nicotine) addiction, panic disorders (such as panic attacks) and/or anxiety), said method comprising administering to a subject in need of such treatment a therapeutically effective amount of a compound, or a pharmaceutically acceptable salt or solvate thereof, or a pharmaceutical composition as defined herein.

In another aspect, the present invention provides a compound, or a pharmaceutically acceptable salt or solvate thereof, or a pharmaceutical composition as defined herein, for use in the production of an orexin-1 inhibitory effect.

In another aspect, the present invention provides the use of a compound, or a pharmaceutically acceptable salt or solvate thereof, in the manufacture of a medicament for use in the production of an orexin-1 inhibitory effect.

In another aspect, the present invention provides a method of producing an orexin-1 inhibitory effect in vitro, said method comprising administering an effective amount of a compound, or a pharmaceutically acceptable salt or solvate thereof.

In another aspect, the present invention provides a method of producing an orexin-1 inhibitory effect in vivo, said method comprising administering an effective amount of a compound, or a pharmaceutically acceptable salt or solvate thereof.

In another aspect, the present invention provides a method of inhibiting orexin-1 ($OX_1$) in vitro and/or in vivo, said method comprising contacting a cell with an effective amount of a compound as defined herein, or a pharmaceutically acceptable salt or solvate thereof.

Routes of Administration

The compounds of the invention or pharmaceutical composition comprising the active compound may be administered to a subject by any convenient route of administration, whether systemically/peripherally or topically (i.e. at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The compounds of the invention may be administered alone as a monotherapy or may administered in combination with one or more additional therapeutic agents. The selection of the one or more additional therapeutic agents will of course vary depending on the disease or condition to be treated and its severity.

It is commonplace to use combination therapies to treat certain medical conditions.

Therefore, the treatment defined hereinbefore may be applied as a sole therapy or may involve, in addition to the compound of the invention, treatment with one or more additional therapeutic agents.

Such conjoint/combination treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to a particular aspect of the invention there is provided a combination suitable for use in the treatment of a disease or condition in which orexin-1 receptor activity is implicated, comprising a compound of the invention as defined hereinbefore, or a pharmaceutically acceptable salt or solvate thereof, and another therapeutic agent.

According to this aspect of the invention there is provided a combination suitable for use in the treatment of behavioural arousal, eating disorders (e.g. binge eating, obesity), psychiatric conditions (e.g. schizophrenia, anxiety, mood disorders, reward seeking behaviours, alcohol or drug (e.g. nicotine) addiction and/or anxiety), the combination comprising a compound of the invention as defined hereinbefore, or a pharmaceutically acceptable salt or solvate thereof, and one or more additional therapeutic agents.

In a further aspect of the invention there is provided a compound of the invention or a pharmaceutically acceptable salt or solvate thereof, in combination with one or more additional therapeutic agents.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt or solvate thereof in combination with one or more additional therapeutic agents in association with a pharmaceutically acceptable diluent or carrier.

According to a particular aspect of the invention there is provided a combination suitable for use in the treatment of schizophrenia and other psychotic disorders (e.g., psychotic disorder, psychosis or schizoaffective disorder); dementia and other cognitive disorders; anxiety disorders (e.g., generalized anxiety disorder, post-traumatic stress disorder, panic disorders, acute stress disorder, social anxiety disorder, phobias including agoraphobia, obsessive compulsive disorder, trichotillomania or body dismorphic disorder); mood disorders (e.g., depressive disorders, major depressive disorders, bipolar disorders including bipolar I and II, bipolar mania, bipolar depression); addiction including substance dependence (e.g. cocaine, opiates, *cannabis* or prescription drug dependence), alcohol dependence, nicotine dependence or gambling disorder; eating disorders (e.g. binge eating, bulimia nervosa, anorexia nervosa or obesity); sleep disorders (e.g. rapid eye movement sleep disorder); disorders usually first diagnosed in infancy, childhood, or adolescence (e.g., attention-deficit disorder, autistic spectrum disorders, Rett syndrome, Fragile X syndrome, Asperger syndrome and disruptive behaviour disorders); restless leg syndrome; pain (e.g. neuropathic pain including chemotherapy induced pain or migraine); osteoporosis and neurodegenerative disorders (e.g. Parkinson's or Alzheimer's disease), the combination comprising a compound of the invention as defined hereinbefore, or a pharmaceutically acceptable salt or solvate thereof, and another therapeutic agent.

According to a particular aspect of the invention there is provided a combination suitable for use in the treatment of behavioural arousal, eating disorders (e.g. binge eating, obesity), psychiatric conditions (e.g. schizophrenia, anxiety, mood disorders, reward seeking behaviours, alcohol or drug (e.g. nicotine) addiction, panic disorders (such as panic attacks) and/or anxiety) comprising a compound of the invention as defined hereinbefore, or a pharmaceutically acceptable salt or solvate thereof, and another therapeutic agent.

Examples of other therapeutic agents that may be used as part of a combination therapy with a compound of the present invention include, but are not limited to, the following:

(i) antidepressants such as, for example, amitnptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, reboxetine, robaizotan, sertraline, sibutramine, tianeptine, thionisoxetine, tranylcypromaine, trazodone, trimipramine, venlafaxine, vortioxetine and equivalents and pharmaceutically active isomer(s) and/or metabolite(s) thereof;

(ii) antipsychotics including, for example, amisulpride, aripiprazole, asenapine, benzisoxidil, bifeprunox, brexpiprazole, carbamazepine, cariprazine, clozapine, chlorpromazine, debenzapine, divalproex, duloxetine, eszopiclone, haloperidol, iloperidone, lamotrigine, loxapine, lurasidone, mesoridazine, olanzapine, paliperidone, perlapine, perphenazine, phenothiazine, phenylbutylpiperidine, pimozide, prochlorperazine, quetiapine, risperidone, sertindole, sulpiride, suproclone, suri clone, thioridazine, trifluoperazine, trimetozine, valproate, valproic acid, zopiclone, zotepine, zicronapine, ziprasidone, and equivalents and pharmaceutically active isomer(s) and/or metabolite(s) thereof;

(iii) anxiolytics including, for example, alnespirone, azapirones, benzodiazepines, barbiturates, and equivalents and pharmaceutically active isomer(s) and/or metabolite(s) thereof. Example anxiolytics include adinazolam, alprazolam, balezepam, bentazepam, bromazepam, brotizolam, buspirone, clonazepam, clorazepate, chlordiazepoxide, cyprazeparn, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, and zolazepam; and equivalents and pharmaceutically active isomer(s) and/or metabolite(s) thereof;

(iv) anticonvulsants including, for example, carbamazepine, valproate, lamotrigine, levetiracetam and gabapentin, and equivalents and pharmaceutically active isomer(s) and/or metabolite(s) thereof;

(v) Alzheimer's therapies including, for example, donepezil, galantamine, memantine, rivastigmine, tacrine, and equivalents and pharmaceutically active isomer(s) and/or metabolite(s) thereof;

(vi) Parkinson's therapies including, for example, L-dopa, ropinirole, pramipexole, monoamine oxidase type B (MAO-B) inhibitors such as deprenyl, selegiline and rasagiline, catechol-O-methyS transferase (COMT) inhibitors such as entacapone or tolcapone, adenosine A-2 inhibitors, dopamine re-uptake inhibitors, NMDA antagonists, Nicotine agonists, and Dopamine agonists and inhibitors of neuronal nitric oxide synthase, and equivalents and pharmaceutically active isomer(s) and/or metabolite(s) thereof;

(vii) migraine therapies including, for example, almotriptan, amantadine, botulinum toxin A, bromocriptine, butalbital, cabergoline, dichloralphenazone, dihydroergotamine, eletriptan, frovatriptan, lisuride, naratriptan, pergolide, pramipexole, rizatriptan, ropinirole, sumatriptan, topiramate, zolmitriptan, and zolmitriptan, and equivalents and pharmaceutically active isomer(s) and/or metabolite(s) thereof;

(viii) stroke therapies including, for example, abciximab, activase, citicoline, desmoteplase, and equivalents and pharmaceutically active isomer(s) and/or metabolite(s) thereof;

(ix) urinary incontinence therapies including, for example, darafenacin, duloxetine, flavoxate, mirabegron, oxybutynin, propiverine, robalzotan, solifenacin, and tolterodine, and equivalents and pharmaceutically active isomer(s) and/or metabolite(s) thereof;

(x) neuropathic pain therapies including, for example, capsaicin, gabapentin, iidoderm, and pregabalin, and equivalents and pharmaceutically active isomer(s) and/or metabolite(s) thereof;

(xi) nociceptive pain therapies such as, for example, celecoxib, etoricoxib, lumiracoxib, rofecoxib, valdecoxib, diclofenac, loxoprofen, naproxen, and paracetamol, and equivalents and pharmaceutically active isomer(s) and/or metabolite(s) thereof;

(xii) insomnia therapies including, for example, allobarbital, alonimid, amobarbital, benzoctamine, butabarbital, capuride, chloral, cloperidone, clorethate, dexclamol, ethchlorvynol, eszopiclone, etomidate, glutethimide, halazepam, hydroxyzine, iorediplon, mecloqualone, melatonin, mephobarbital, methaqualone, midaflur, nisobamate, pentobarbital, phenobarbital, propofol, ralmeteon, roletamide, suvorexant, triclofos, secobarbital, zaleplon, and Zolpidem, zopiclone and equivalents and pharmaceutically active isomer(s) and/or metabolite(s) thereof;

(xiii) mood stabilizers including, for example, carbamazepine, divalproex, gabapentin, lamotrigine, lithium, olanzapine, quetiapine, valproate, valproic acid, and verapamil, and equivalents and pharmaceutically active isomer(s) and/or metabolite(s) thereof;

(xiv) 5HT1B ligands such as, for example, compounds disclosed in WO 99/05134 and WO 02/08212;

(xv) mGluR2 agonists;

(xvi) alpha 7 nicotinic agonists such as, for example, compounds disclosed in WO 96/006098, WO 97/030998, WO 99/003859, WO 00/042044, WO 01/029034, WO 01/60821, WO 01/36417, WO 02/096912, WO 03/087102, WO 03/087103, WO 03/087104, WO 2004/016617, WO 2004/016616, and WO 2004/019947; (xvii) chemokine receptor CCR1 inhibitors;

(xviii) delta opioid agonists such as, for example, compounds disclosed in WO 97/23466 and WO 02/094794; and (xviv) osteoporosis therapies such as, for example, bisphosphonates, denosumab, raloxifene, calcitonin, strontium ranelate, HRT, calcium and vitamin D.

Such combination therapies employ the compounds of this invention within the dosage range described herein and the other pharmaceutically active agent within approved dosage ranges and/or the dosage such as described in the publication reference.

EXAMPLES

Synthesis of Compounds
General Procedures:

Several methods for preparing the compounds of this invention are illustrated in the following Examples. Starting materials are made according to procedures known in the art or as illustrated herein, or are available commercially. Commercial reagents were used without further purification. Where no reaction temperature is included, the reaction was performed at ambient temperature which is typically 18-27° C.

Where ammonia solution is utilised in normal phase chromatography, a stock solution is made by a series of dilutions according to the following protocol:

A 7N solution of ammonia in methanol (30 mL) was diluted to a volume of 100 mL with methanol. This solution was further diluted to a volume of 1 L with DCM.

Where compounds described in the invention are characterized by $^1$H NMR spectroscopy, spectra were recorded on 400 MHz Bruker, Varian or JEOL instruments. Where no temperature is included the spectra were recorded at ambient temperature. Chemical shift values are expressed in parts per million (ppm). Where NMR spectra are complex due to the presence of interconverting isomers, approximate partial integrations of signals are reported. The following abbreviations are used for the multiplicity of the NMR signals: s=singlet, b=broad, t=triplet, q=quartet, m=multiplet, d=doublet.

Where compounds described in the invention are characterized by LCMS data, retention time and molecular weight are determined using the conditions listed below. In cases where compounds of the invention appear as slowly interconverting stereoisomers, multiple retention times are reported.

Method A: Agilent 1100 LC at 254 nM with MS detection (API electrospray). Column: Waters X-Select C18 (2.5 µm, 4.6×30 mm). Conditions: MeCN [eluent A]; 0.1% Formic acid [eluent B]. Gradient: 5% to 95% B over 4 min.

Method B: Agilent 1100 LC at 254 nM with MS detection (API electrospray). Column: Waters X-Select C18 (2.5 µm, 4.6×30 mm). Conditions: MeCN [eluent A]; 0.1% Ammonium bicarbonate [eluent B]. Gradient: 5% to 95% B over 4 min.

Method C: Agilent 1100 LC at 254 nM with MS detection (API electrospray). Column: Waters X-Select C18 (2.5 µm, 4.6×30 mm). Conditions: MeCN [eluent A]; 0.1% Ammonia [eluent B]. Gradient: 5% to 95% B over 4 min.

Method D: Agilent 1100 LC at 254 nM with MS detection (API electrospray). Column: Waters X-Select C18 (2.5 µm, 4.6×30 mm). Conditions: MeCN [eluent A]; 0.1% Formic acid [eluent B]. Gradient: 5% to 50% B over 4 min.

Method E: Shimadzu LCMS-2010 EV at 210-400 nM (ESI). Column: YMC ODS C18 (3 µm, 4.6×50 mm). Conditions: MeCN (containing 5% aqueous phase+0.1% formic acid) [eluent A]; 5 mM Ammonium formate+0.1% formic acid [eluent B]. Gradient: 20 to 95% B over 4 min.

Method F: Shimadzu LCMS-2010 EV at 210-400 nM (ESI). Column: YMC Triart C18 (3 µm, 4.6×50 mm). Conditions: MeCN (containing 5% aqueous phase+0.1% formic acid) [eluent A]; 5 mM Ammonium formate+0.1% formic acid [eluent B]. Gradient: 30 to 95% B over 4 min.

Method G: Shimadzu LCMS-2010 EV at 210-420 nm (ESI). Column: Kinetex Core-Shell C18 (5 µm, 2.1×50 mm). Conditions: Water+0.1% formic acid [eluent A]; MeCN+0.1% formic acid [eluent B]. Gradient: 5 to 100 to 5% B over 1.31 min.

Method H: Shimadzu LCMS-2010 EV at 210-420 nm (ESI). Column: Waters Atlantis dC18 (3 µm, 2.1×100 mm). Conditions: Water+0.1% formic acid [eluent A]; MeCN+0.1% formic acid [eluent B]. Gradient: 5 to 100 to 5% B over 7 min.

Method I: Waters Acquity UPLC System at 200-400 nm (ESI). Column: Phenomenex Kinetix—XB C18 (1.7 µm, 2.1×100 mm). Conditions: Water+0.1% formic acid [eluent A]; MeCN+0.1% formic acid [eluent B]. Gradient: 5 to 100 to 5% B over 7 min.

Method J: Waters ZQ MS with Agilent 1100 HPLC at 210-420 nm (ESI). Column: Phenomenex Gemini—NXC18 (3 µm, 2.0×50 mm). Conditions: 2 mM ammonium bicarbonate, buffered to pH10 [eluent A]; MeCN [eluent B]. Gradient: 1 to 100 to 1% B over 3.5 min.

Method K: Waters Acquity UPLC with diode array (210-350 nm) and SQD mass detector. Column: XBridge BEH C18 2.5 µm 2.1×50 mm (Flow 0.8 mL/min). Conditions: 10 mM ammonium bicarbonate pH 10 [eluent A]; MeCN [eluent B]. Gradient: 2-98% B over 1.30 min.

Method L: Waters Acquity UPLC with diode array (210-350 nm) and SQD mass detector. Column: XBridge BEH C18 2.5 µm 2.1×50 mm (Flow 0.8 mL/min). Conditions: 10 mM ammonium bicarbonate pH 10 [eluent A]; MeCN [eluent B]. Gradient: 2-98% B over 4.70 min.

Method M: Agilent 1260 LC with MS detection (API electrospray). Column: Phenomenex Kinetic XB C18 (2.6 µm, 4.6×50 mm). Conditions: Water+0.1% formic acid [eluent A]; MeCN [eluent B]. Gradient: 5 to 98 to 5% B over 2.3 min.

Method N: Agilent 1260 LC with MS detection (API electrospray). Column: Agilent Poroshell 120 EC-C18 (2.7 µm, 3.0×50 mm) Conditions: Water+0.1% formic acid [eluent A]; MeCN [eluent B]. Gradient: 5 to 95 to 5% B over 3.5 min.

Method O: Waters ZQ MS with Agilent 1100 HPLC at 210-420 nm (ESI). Column: Phenomenex Gemini—NXC18 (3 µm, 2.0×50 mm). Conditions: 2 mM ammonium bicarbonate, buffered to pH10 [eluent A]; MeCN [eluent B]. Gradient: 5 to 100 to 5% B over 7 min.

| Abbreviations: | |
|---|---|
| AcOH | Acetic acid |
| BINAP | (2,2'-bis(diphenylphosphino)-1,1'-binaphthyl) |

-continued

| Abbreviations: | |
|---|---|
| Boc$_2$O | Di-tert-butyl carbonate |
| CDI | Carbonyldiimidazole |
| Cs$_2$CO$_3$ | Cesium carbonate |
| CsF | Cesium fluoride |
| CuI | Copper iodide |
| DCE | Dichloroethane |
| DCM | Dichloromethane |
| DEAD | Diethyl azodicarboxylate |
| Dess Martin periodinane | 1,1,1-Triacetoxy-1,1-dihydro-1,2-benziodoxol-3(1H)-one |
| DIAD | Diisopropyl azodicarboxylate |
| DIPEA | N,N-Diisopropylethylamine |
| DMF | N,N-Dimethylformamide |
| DMSO | Dimethylsulfoxide |
| EtOAc | Ethylacetate |
| HATU | N-[(Dimethylamino)-1H-1,2,3-triazolo-[4,5-b]pyridin-1-ylmethylene]-N-methylmethanaminium hexafluorophosphate N-oxide |
| HBTU | N,N,N',N'-Tetramethyl-O-(1H-benzotriazol-1-yl)uranium hexafluorophosphate |
| HCl | Hydrogen chloride |
| HPLC | High Performance Liquid Chromatography |
| hr(s) | hour(s) |
| IPA | Isopropyl alcohol |
| LCMS | Liquid Chromatography Mass Spectrometry |
| LiAlH$_4$ | Lithium aluminium hydride |
| LiBH$_4$ | Lithium borohydride |
| LiOH | Lithium hydroxide |
| MeCN | Acetonitrile |
| MeMgCl | Methyl magnesium chloride |
| MgSO$_4$ | Magnesium sulfate |
| min(s) | minute(s) |
| NaBH(OAc)$_3$ | Sodium triacetoxyborohydride |
| NaCl | Sodium chloride |
| NaHCO$_3$ | Sodium bicarbonate |
| NaO$^t$Bu | Sodium tert-butoxide |
| NaOMe | Sodium methoxide |
| Na$_2$SO$_4$ | Sodium sulfate |
| Na$_2$SO$_4$•10H$_2$O | Sodium sulfate decahydrate |
| NMP | N-Methylpyrrollidinone |
| NMR | Nuclear magnetic resonance |
| Pd$_2$(dba)$_3$ | Tris(dibenzylideneacetone)dipalladium(0) |
| Pd(PPh$_3$)$_4$ | Tetrakis(triphenylphosphine) palladium (0) |
| SnCl$_2$•2H$_2$O | Tin(II) chloride dihydrate |
| TBAF | Tetrabutylammonium fluoride |
| tBME | tert-Butyl methyl ether |
| tBuXPhos | 2-Di-tert-butylphosphino-2',4',6'-triisopropylbiphenyl |
| THF | Tetrahydrofuran |
| TFA | Trifluoroacetic acid |

Synthesis of Intermediates

Preparation of (S)—N-(1-hydroxybutan-2-yl)-5-methyl-2-(2H-1,2,3-triazol-2-yl)benzamide (Intermediate 1a)

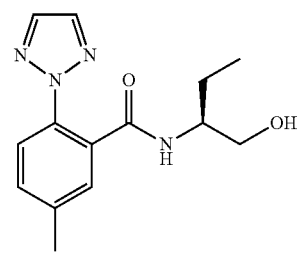 [SMILES: CC[C@@H](CO)NC(=O)c1cc(C)ccc1-n1nccn1]

To a solution of 5-methyl-2-(2H-1,2,3-triazol-2-yl)benzoic acid (0.60 g, 2.9 mmol) [prepared as described in WO 2012/148553], DIPEA (1.0 mL, 5.91 mmol) and (S)-2-aminobutan-1-ol (0.26 g, 2.9 mmol) in NMP (5 mL) was added HATU (1.23 g, 3.2 mmol) and the reaction mixture stirred overnight. It was then poured onto water (50 mL) and the crude product extracted into EtOAc (2×30 mL). The combined organics were dried over Na$_2$SO$_4$, filtered and concentrated in vacuo. The crude product was purified by chromatography on the Biotage Companion™ (40 g column, 0 to 100% EtOAc in isohexane) to afford the title compound as an oil (0.70 g).

LCMS (Method A): 1.32 min, 275 [M+H]$^+$

Preparation of (S)—N-(1-((tert-butyldimethylsilyl)oxy)butan-2-yl)-5-methyl-2-(2H-1,2,3-triazol-2-yl)benzamide (Intermediate 1b)

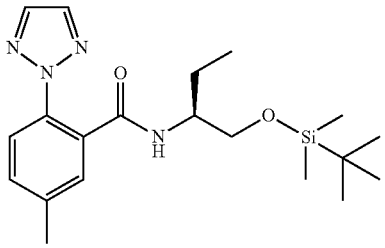 [SMILES: CC[C@@H](CO[Si](C)(C)C(C)(C)C)NC(=O)c1cc(C)ccc1-n1nccn1]

To a solution of Intermediate 1a (0.77 g, 2.8 mmol) and imidazole (0.21 g, 3.1 mmol) in anhydrous DMF (10 mL) was added tert-butyldimethylchlorosilane (0.46 g, 3.1 mmol) and the reaction mixture stirred for 48 hrs. It was then poured onto water (100 mL) and the crude product extracted into diethyl ether (2×30 mL). The combined organics were dried over Na$_2$SO$_4$, filtered and concentrated in vacuo. The crude product was purified by chromatography on the Biotage Companion™ (120 g column, 0 to 50% diethyl ether in isohexane) to afford the title compound as a solid (0.72 g).

LCMS (Method A): 2.83 min, 389 [M+H]$^+$

Preparation of (S)—N-(1-hydroxybutan-2-yl)-N,5-dimethyl-2-(2H-1,2,3-triazol-2-yl)benzamide (Intermediate 1)

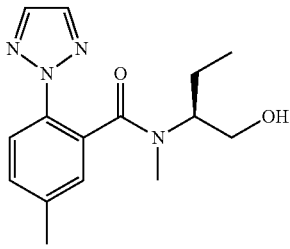 [SMILES: CC[C@@H](CO)N(C)C(=O)c1cc(C)ccc1-n1nccn1]

To a solution of Intermediate 1b (0.81 g, 2.1 mmol) in anhydrous DMF (10 mL) at 0-5° C. was added sodium hydride, 60% dispersion in mineral oil (92 mg, 2.3 mmol) and the reaction mixture stirred for 30 mins at this temperature. To the reaction was added iodomethane (0.52 mL, 8.3 mmol) and the mixture was allowed to warm to ambient temperature and stirred overnight. To this solution was added 1M TBAF in THF (4.2 mL, 4.2 mmol) and the reaction mixture stirred for 1 hr. It was then poured onto water (50 mL) and the crude product extracted with EtOAc (2×50 mL). The combined organics were washed with water and dried over Na$_2$SO$_4$, filtered and concentrated in vacuo. The crude product was purified by chromatography on the Biotage Companion™ (40 g column, 20 to 100% EtOAc in isohexane) to afford the title compound as an oil which solidified upon standing (0.55 g).

LCMS (Method A): Two peaks at 1.48 min and 1.61 min, 289 [M+H]$^+$

Preparation of (S)-methyl 2-([1,1'-biphenyl]-2-ylcarboxamido)butanoate (Intermediate 2a)

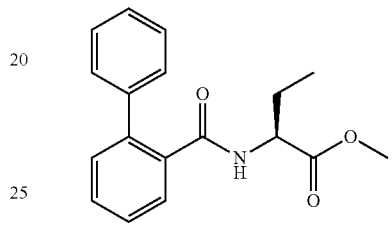

To a stirred solution of (S)-methyl 2-aminobutanoate hydrochloride (0.53 g, 3.4 mmol), [1,1'-biphenyl]-2-carboxylic acid (0.68 g, 3.4 mmol) and HATU (1.70 g, 4.5 mmol) in DMF (20 mL) was added DIPEA (2.4 mL, 13.7 mmol) and the reaction mixture was stirred overnight. It was then poured onto water (30 mL) and the crude product extracted with EtOAc. The combined organics were dried over Na$_2$SO$_4$, filtered and concentrated in vacuo. The crude product was purified by chromatography on the Biotage Companion™ (40 g column, 0 to 100% diethyl ether in isohexane) to afford the title compound as a gum (0.73 g).

LCMS (Method A): 2.05 min, 298 [M+H]$^+$

Preparation of (S)-methyl 2-(N-methyl-[1,1'-biphenyl]-2-ylcarboxamido) butanoate (Intermediate 2b)

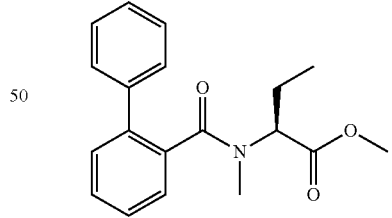

To a solution of Intermediate 2a (0.73 g, 2.4 mmol) in anhydrous THF (20 mL) at 0° C. was added sodium hydride, 60% dispersion in oil (0.11 g, 2.7 mmol) and the mixture was allowed to stir for 1 hr at 0° C. To this mixture was added iodomethane (0.31 mL, 4.9 mmol) and stirring continued for 2 hrs. The reaction mixture was quenched with water (30 mL) and the product was extracted into EtOAc (50 mL). The combined organics were washed with water (2×20 mL), dried over Na$_2$SO$_4$ filtered and concentrated in vacuo to afford the title compound as an oil (0.74 g).

LCMS (Method A): 2.33 min, 312 [M+H]$^+$

Preparation of (S)—N-(1-hydroxybutan-2-yl)-N-methyl-[1,1'-biphenyl]-2-carboxamide (Intermediate 2)

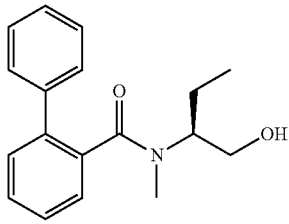 [SMILES: CC[C@@H](CO)N(C)C(=O)c1ccccc1-c1ccccc1]

A mixture of Intermediate 2b (0.67 g, 2.1 mmol) and 2M LiBH$_4$ in THF (5.4 mL, 10.8 mmol) was stirred for 4 hrs. The reaction mixture was quenched by the addition of AcOH (1 mL). It was then poured onto water and the crude product extracted into diethyl ether. The combined organics were washed with water, dried over Na$_2$SO$_4$, filtered and concentrated in vacuo. The crude product was purified by chromatography on the Biotage Companion™ (12 g column, 0 to 100% EtOAc in isohexane) to afford the title compound as a gum (0.44 g).

LCMS (Method A): Two peaks at 1.80 min and 1.88 min, 284 [M+H]$^+$

Preparation of (S)-methyl 2-([1,1'-biphenyl]-2-yl-carboxamido)-3-methylbutanoate (Intermediate 3a)

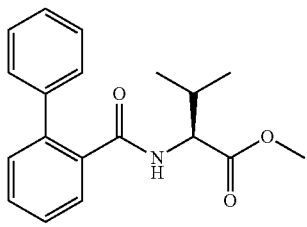

The title compound (7.2 g) was prepared as a gum from (S)-methyl 2-amino-3-methylbutanoate hydrochloride (5.0 g, 30 mmol) and [1,1'-biphenyl]-2-carboxylic acid (5.9 g, 30 mmol) using the method described for Intermediate 2a. The crude product was purified by chromatography on the Biotage Companion™ (120 g column, 0 to 100% diethyl ether in isohexane).

LCMS (Method A): 2.12 min, 312 [M+H]$^+$

Preparation of (S)—N-(1-hydroxy-3-methylbutan-2-yl)-[1,1'-biphenyl]-2-carboxamide (Intermediate 3)

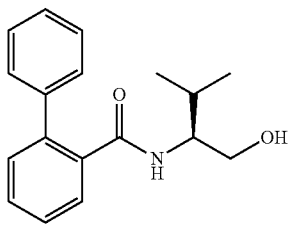 [SMILES: CC(C)[C@@H](CO)NC(=O)c1ccccc1-c1ccccc1]

The title compound (0.30 g) was prepared from Intermediate 3a (0.35 g, 1.1 mmol) using the method described for Intermediate 2. The crude product was used without further purification in subsequent reactions.

LCMS (Method A): 1.94 min, 284 [M+H]$^+$

Preparation of (S)-methyl 2-([1,1'-biphenyl]-2-yl-carboxamido)-4-methylpentanoate (Intermediate 4a)

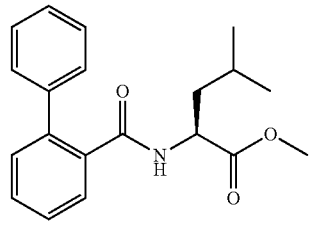

The title compound (0.18 g) was prepared from (S)-methyl 2-amino-4-methylpentanoate hydrochloride (0.50 g, 2.7 mmol) and [1,1'-biphenyl]-2-carboxylic acid (0.55 g, 2.7 mmol) using the method described for Intermediate 2a. The crude product used without further purification in subsequent reactions.

LCMS (Method A): 2.37 min, 326 [M+H]$^+$

Preparation of (S)—N-(1-hydroxy-4-methylpentan-2-yl)-[1,1'-biphenyl]-2-carboxamide (Intermediate 4)

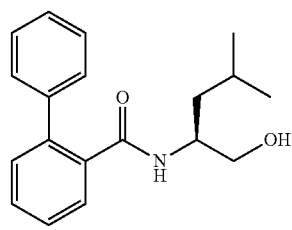 [SMILES: CC(C)C[C@@H](CO)NC(=O)c1ccccc1-c1ccccc1]

The title compound (0.10 g) was prepared from Intermediate 4a (0.18 g, 0.55 mmol) using the method described for Intermediate 2. The crude product was used without further purification in subsequent reactions LCMS (Method A): 2.03 min, 298 [M+H]$^+$ Preparation of (S)-methyl 3-methyl-2-(2-methyl-4-phenylthiazole-5-carboxamido)butanoate (Intermediate 5a)

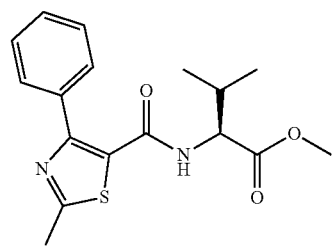 [SMILES: COC(=O)[C@@H](NC(=O)c1sc(C)nc1-c1ccccc1)C(C)C]

The title compound (0.22 g) was prepared from (S)-methyl 2-amino-3-methylbutanoate hydrochloride (0.15 g, 0.90 mmol) and 2-methyl-4-phenylthiazole-5-carboxylic acid (0.20 g, 0.90 mmol) using the method described for Intermediate 2a. The crude product used without further purification in subsequent reactions.

LCMS (Method A): 2.17 min, 333 [M+H]$^+$

Preparation of (S)—N-(1-hydroxy-3-methylbutan-2-yl)-2-methyl-4-phenylthiazole-5-carboxamide (Intermediate 5)

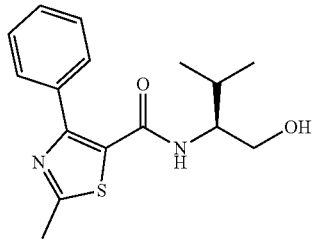 [SMILES: Cc1nc(-c2ccccc2)c(C(=O)N[C@H](CO)C(C)C)s1]

The title compound (0.20 g) was prepared from Intermediate 5a (0.22 g, 0.66 mmol) using the method described for Intermediate 2. The crude product was used without further purification in subsequent reactions LCMS (Method A): 1.97 min, 305 [M+H]$^+$ Preparation of (S)-methyl 4-methyl-2-(2-methyl-4-phenylthiazole-5-carboxamido)pentanoate (Intermediate 6a)

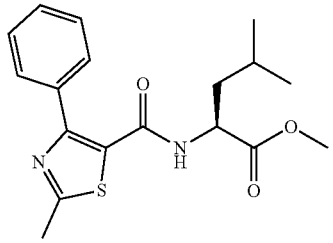 [SMILES: COC(=O)[C@H](CC(C)C)NC(=O)c1sc(C)nc1-c1ccccc1]

The title compound (0.28 g) was prepared from (S)-methyl 2-amino-4-methylpentanoate hydrochloride (0.17 g, 0.94 mmol) and 2-methyl-4-phenylthiazole-5-carboxylic acid (0.21 g, 0.94 mmol) using the method described for Intermediate 2a. The crude product used without further purification in subsequent reactions.

LCMS (Method A): 2.23 min, 347 [M+H]$^+$

Preparation of (S)—N-(1-hydroxy-4-methylpentan-2-yl)-2-methyl-4-phenylthiazole-5-carboxamide (Intermediate 6)

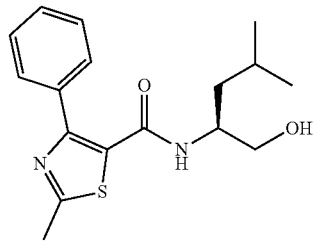 [SMILES: Cc1nc(-c2ccccc2)c(C(=O)N[C@H](CO)CC(C)C)s1]

The title compound (0.26 g) was prepared from Intermediate 6a (0.28 g, 0.81 mmol) using the method described for Intermediate 2. The crude product was used without further purification in subsequent reactions LCMS (Method A): 1.83 min, 319 [M+H]$^+$ Preparation of (S)-methyl 4-methyl-2-(N-methyl-[1,1'-biphenyl]-2-ylcarboxamido)pentanoate (Intermediate 7a)

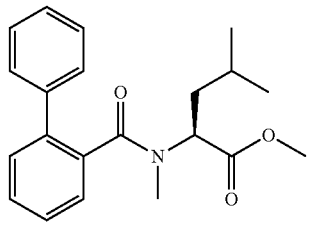 [SMILES: COC(=O)[C@H](CC(C)C)N(C)C(=O)c1ccccc1-c1ccccc1]

The title compound (0.57 g) was prepared as a gum from Intermediate 4a (0.59 g, 1.8 mmol) using the method described for Intermediate 2b. The crude product was used without further purification in subsequent reactions LCMS (Method A): 2.57 min, 340 [M+H]$^+$ Preparation of (S)—N-(1-hydroxy-4-methylpentan-2-yl)-N-methyl-[1,1'-biphenyl]-2-carboxamide (Intermediate 7)

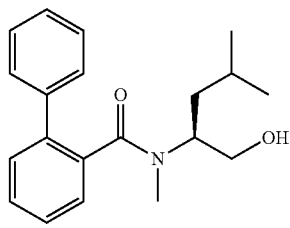 [SMILES: CC(C)C[C@@H](CO)N(C)C(=O)c1ccccc1-c1ccccc1]

The title compound (0.72 g, assumed quantitative yield) was prepared as a gum from Intermediate 7a (0.55 g, 1.62 mmol) using the method described for Intermediate 2. The crude product was used without further purification in subsequent reactions.

LCMS (Method A): 2.23 min, 312 [M+H]$^+$

Preparation of (S)-methyl 2-(N,2-dimethyl-4-phenylthiazole-5-carboxamido)-4-methylpentanoate (Intermediate 8a)

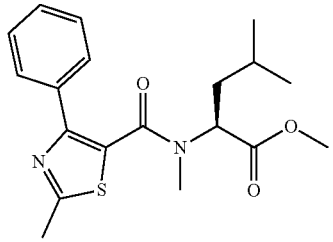 [SMILES: COC(=O)[C@H](CC(C)C)N(C)C(=O)c1sc(C)nc1-c1ccccc1]

The title compound (0.44 g) was prepared as a gum from Intermediate 6a (0.55 g, 1.59 mmol) using the method described for Intermediate 2b. The crude product was used without further purification in subsequent reactions.

LCMS (Method A): 2.38 min, 361 [M+H]$^+$

Preparation of (S)—N-(1-hydroxy-4-methylpentan-2-yl)-N,2-dimethyl-4-phenylthiazole-5-carboxamide (Intermediate 8)

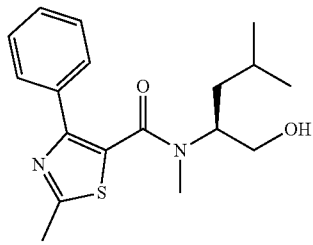 [SMILES: Cc1nc(-c2ccccc2)c(C(=O)N(C)[C@H](CO)CC(C)C)s1]

The title compound (0.26 g) was prepared from Intermediate 8a (0.30 g, 0.83 mmol) using the method described for Intermediate 2. The crude product was used without further purification in subsequent reactions.

LCMS (Method A): 1.83 min, 333 [M+H]$^+$

Preparation of (S)-methyl 3-methyl-2-(N-methyl-[1,1'-biphenyl]-2-ylcarboxamido)butanoate (Intermediate 9a)

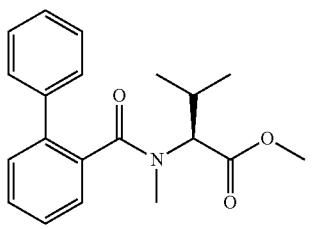 [SMILES: COC(=O)[C@H](C(C)C)N(C)C(=O)c1ccccc1-c1ccccc1]

The title compound (0.88 g) was prepared as a gum from (S)-methyl 3-methyl-2-(methylamino)butanoate hydrochloride (0.50 g, 2.7 mmol) and [1,1'-biphenyl]-2-carboxylic acid (0.55 g, 2.7 mmol) using the method described for Intermediate 2a. The crude product was isolated by extraction into diethyl ether and used without further purification in subsequent reactions.

LCMS (Method A): 2.45 min, 326 [M+H]$^+$

Preparation of (S)—N-(1-hydroxy-3-methylbutan-2-yl)-N-methyl-[1,1'-biphenyl]-2-carboxamide (Intermediate 9)

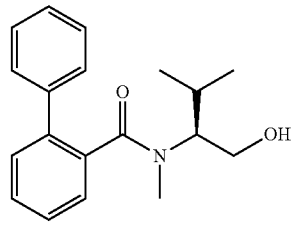 [SMILES: CC(C)[C@@H](CO)N(C)C(=O)c1ccccc1-c1ccccc1]

The title compound (0.72 g) was prepared as a gum from Intermediate 9a (0.85 g, 2.6 mmol) using the method described for Intermediate 2. The crude product was used without further purification in subsequent reactions.

LCMS (Method A): Two peaks at 1.96 min and 2.03 min, 298 [M+H]$^+$

Preparation of (S)-methyl 2-(N,2-dimethyl-4-phenylthiazole-5-carboxamido)-3-methylbutanoate (Intermediate 10a)

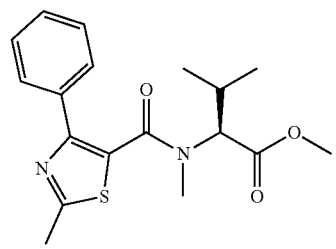 [SMILES: COC(=O)[C@H](C(C)C)N(C)C(=O)c1sc(C)nc1-c1ccccc1]

The title compound (0.83 g) was prepared as a solid from (S)-methyl 3-methyl-2-(methylamino)butanoate hydrochloride (0.45 g, 2.5 mmol) and 2-methyl-4-phenylthiazole-5-carboxylic acid (0.54 g, 2.5 mmol) using the method described for Intermediate 2a. The crude product was isolated by extraction into diethyl ether and used without further purification in subsequent reactions.

LCMS (Method A): 2.23 min, 347 [M+H]$^+$

Preparation of (S)—N-(1-hydroxy-3-methylbutan-2-yl)-N,2-dimethyl-4-phenylthiazole-5-carboxamide (Intermediate 10)

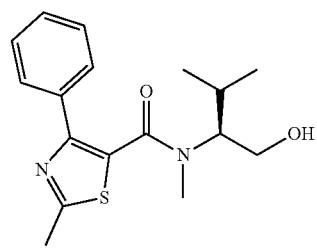 [SMILES: Cc1nc(-c2ccccc2)c(C(=O)N(C)[C@H](CO)C(C)C)s1]

The title compound (0.40 g) was prepared from Intermediate 10a (0.44 g, 1.3 mmol) using the method described for Intermediate 2. The crude product was used without further purification in subsequent reactions.
LCMS (Method A): 1.97 min, 319 [M+H]$^+$ Preparation of (S)-methyl 2-([1,1'-biphenyl]-2-yl-carboxamido)-3,3-dimethylbutanoate (Intermediate 11a)

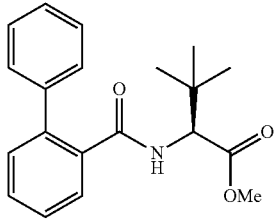 [SMILES: COC(=O)[C@@H](NC(=O)c1ccccc1-c1ccccc1)C(C)(C)C]

The title compound (0.43 g) was prepared as a gum from (S)-methyl 2-amino-3,3-dimethylbutanoate hydrochloride (0.25 g, 1.4 mmol) and [1,1'-biphenyl]-2-carboxylic acid (0.27 g, 1.4 mmol) using the method described for Intermediate 2a. The crude product was purified by chromatography on the Biotage Companion™ (40 g column, 0 to 100% diethyl ether in isohexane).
LCMS (Method A): 2.23 min, 326 [M+H]$^+$ Preparation of (S)-methyl 3,3-dimethyl-2-(N-methyl-[1,1'-biphenyl]-2-ylcarboxamido)butanoate (Intermediate 11b)

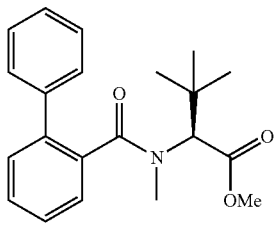 [SMILES: COC(=O)[C@@H](N(C)C(=O)c1ccccc1-c1ccccc1)C(C)(C)C]

The title compound (0.44 g) was prepared as an oil from Intermediate 11a (0.47 g, 1.4 mmol) using the method described for Intermediate 2b. The crude product was used without further purification in subsequent reactions.
LCMS (Method A): 2.56 min, 340 [M+H]$^+$ Preparation of (S)—N-(1-hydroxy-3,3-dimethylbutan-2-yl)-N-methyl-[1,1'-biphenyl]-2-carboxamide (Intermediate 11)

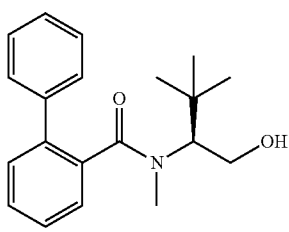 [SMILES: CN(C(=O)c1ccccc1-c1ccccc1)[C@H](CO)C(C)(C)C]

The title compound (0.38 g) was prepared as an oil from Intermediate 11b (0.47 g, 1.4 mmol) using the method described for Intermediate 2. The crude product was purified by chromatography on the Biotage Companion™ (12 g column, 0 to 100% diethyl ether in isohexane).
LCMS (Method A): 2.17 min, 312 [M+H]$^+$ Preparation of (S)-methyl 2-([1,1'-biphenyl]-2-yl-carboxamido)-2-cyclopropylacetate (Intermediate 12a)

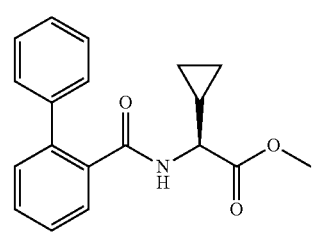

The title compound (0.60 g) was prepared as a gum from (S)-methyl 2-amino-2-cyclopropylacetate hydrochloride (0.42 g, 2.5 mmol) and [1,1'-biphenyl]-2-carboxylic acid (0.50 g, 2.5 mmol) using the method described for Intermediate 2a. The crude product was isolated by filtration from water and purified by chromatography on the Biotage Companion™ (40 g column, 0 to 100% EtOAc in isohexane).
LCMS (Method A): 2.08 min, 310 [M+H]$^+$ Preparation of (S)-methyl 2-cyclopropyl-2-(N-methyl-[1,1'-biphenyl]-2-ylcarboxamido)acetate (Intermediate 12b)

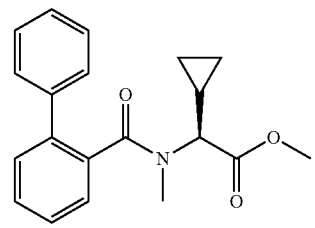 [SMILES: COC(=O)[C@H](C1CC1)N(C)C(=O)c1ccccc1-c1ccccc1]

The title compound (0.60 g) was prepared as an oil from Intermediate 12a (0.60 g, 1.9 mmol) using the method described for Intermediate 2b. The crude product was used without further purification in subsequent reactions.
LCMS (Method A): 2.26 min, 324 [M+H]$^+$ Preparation of (S)—N-(1-cyclopropyl-2-hydroxyethyl)-N-methyl-[1,1'-biphenyl]-2-carboxamide (Intermediate 12)

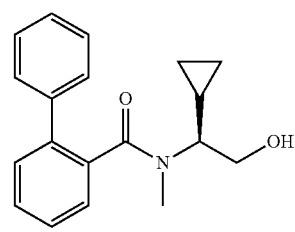 [SMILES: CN(C(=O)c1ccccc1-c1ccccc1)[C@H](CO)C1CC1]

The title compound (0.44 g) was prepared as a gum from Intermediate 12b (0.47 g, 1.4 mmol) using the method described for Intermediate 2. The crude product was purified by chromatography on the Biotage Companion™ (12 g column, 0 to 100% EtOAc in isohexane).

LCMS (Method A): 1.92 min, 296 [M+H]⁺

Preparation of (S)-methyl 2-([1,1'-biphenyl]-2-yl-carboxamido)propanoate (Intermediate 13a)

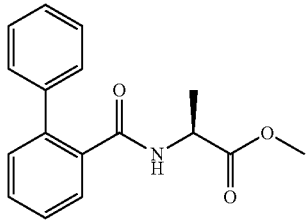 [SMILES: COC(=O)[C@H](C)NC(=O)c1ccccc1-c1ccccc1]

The title compound (0.56 g) was prepared as a gum from (S)-methyl 2-aminopropanoate hydrochloride (0.35 g, 2.5 mmol) and [1,1'-biphenyl]-2-carboxylic acid (0.50 g, 2.5 mmol) using the method described for Intermediate 2a. The crude product was isolated by extraction into EtOAc and purified by chromatography on the Biotage Companion™ (40 g column, 0 to 100% diethyl ether in isohexane).

LCMS (Method A): 2.00 min, 284 [M+H]⁺

Preparation of (S)-methyl 2-(N-methyl-[1,1'-biphenyl]-2-ylcarboxamido)propanoate (Intermediate 13b)

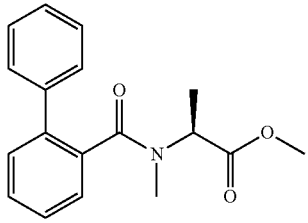 [SMILES: COC(=O)[C@H](C)N(C)C(=O)c1ccccc1-c1ccccc1]

The title compound (0.45 g) was prepared as an oil from Intermediate 13a (0.45 g, 1.6 mmol) using the method described for Intermediate 2b. The crude product was used without further purification in subsequent reactions.

LCMS (Method A): 2.05 min, 298 [M+H]⁺

Preparation of (S)—N-(1-hydroxypropan-2-yl)-N-methyl-[1,1'-biphenyl]-2-carboxamide (Intermediate 13)

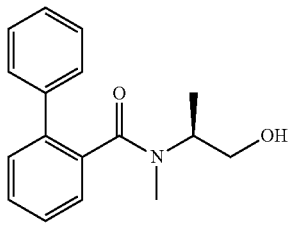 [SMILES: C[C@@H](CO)N(C)C(=O)c1ccccc1-c1ccccc1]

The title compound (0.41 g) was prepared as a gum from Intermediate 13b (0.45 g, 1.5 mmol) using the method described for Intermediate 2. The crude product was purified by chromatography on the Biotage Companion™ (12 g column, 0 to 100% EtOAc in isohexane).

LCMS (Method A): 1.68 min, 270 [M+H]⁺

Preparation of (S)-methyl 2-(benzylamino)-3-methylbutanoate (Intermediate 14a)

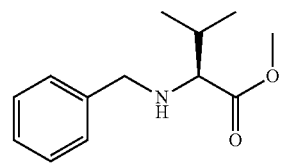 [SMILES: COC(=O)[C@@H](NCc1ccccc1)C(C)C]

A mixture of triethylamine (3.7 mL, 27 mmol), benzaldehyde (2.7 mL, 27 mmol), (S)-methyl 2-amino-3-methylbutanoate hydrochloride (4.5 g, 27 mmol) and NaBH(OAc)₃ (11.4 g, 54 mmol) in DCE (20 mL) was stirred overnight. The reaction mixture was concentrated in vacuo then the residue was dissolved in diethyl ether (200 mL). The solution was washed with water (3×100 mL), and then the organics were separated and extracted into 1M hydrochloric acid (100 mL). The aqueous layer was separated, basified with 2M sodium hydroxide solution, then the crude product was extracted into diethyl ether (200 mL) and washed with water (2×100 mL). The combined organics were dried over Na₂SO₄, filtered and concentrated in vacuo to afford the title compound as an oil (5.4 g).

LCMS (Method A): 0.81 min, 222 [M+H]⁺

Preparation of (S)-2-(benzylamino)-3-methylbutan-1-ol (Intermediate 14b)

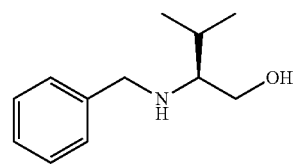

To an ice cooled solution of Intermediate 14a (1.8 g, 8.1 mmol) in anhydrous THF (20 mL) was added dropwise 2M LiAlH₄ in THF (8.1 mL, 16 mmol) and the reaction mixture stirred under ice bath cooling for 2 hrs. The reaction mixture was quenched by the addition of water (2 mL) followed by 2M sodium hydroxide solution (3 mL). The mixture was filtered through Celite® and concentrated in vacuo. The crude product was purified by chromatography on the Biotage Companion™ (40 g column, 0 to 5% ammonia solution in DCM) to afford the title compound as an oil (1.3 g).

LCMS (Method A): 1.65 min, 194 [M+H]⁺

Preparation of (S)-2-(benzyl(cyclopropyl)amino)-3-methylbutan-1-ol (Intermediate 14c)

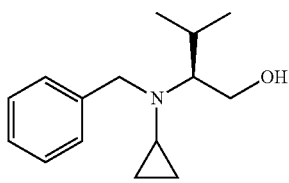 [SMILES: CC(C)[C@@H](CO)N(Cc1ccccc1)C1CC1]

To a solution of Intermediate 14b (1.8 g, 9.3 mmol) and (1-ethoxycyclopropoxy)trimethylsilane (4.9 g, 28 mmol) in methanol (100 mL) was added sodium cyanoborohydride (1.8 g, 28 mmol) and AcOH (0.7 mL) and the mixture heated at reflux for 10 hrs. The reaction mixture was concentrated in vacuo and the residue dissolved in EtOAc (40 mL). The solution was washed with water (2×20 mL), dried over $Na_2SO_4$, filtered and concentrated in vacuo to afford the title compound as an oil (2.3 g).

LCMS (Method A): 0.89 min, 234 $[M+H]^+$; (Method B): 2.63 min, 234 $[M+H]^+$

Preparation of (S)—N-cyclopropyl-N-(1-hydroxy-3-methylbutan-2-yl)-[1,1'-biphenyl]-2-carboxamide (Intermediate 14)

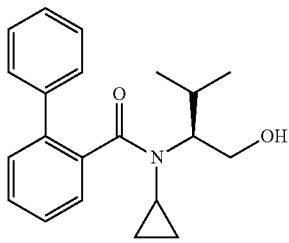 [SMILES: CC(C)[C@@H](CO)N(C(=O)c1ccccc1-c1ccccc1)C1CC1]

A mixture of Intermediate 14c (2.2 g, 9.4 mmol), palladium hydroxide on carbon (0.40 g) and methanol (80 mL) in an autoclave was charged with hydrogen to a pressure of 1 bar, and the reaction mixture was stirred at ambient temperature for 1 hr. The reaction mixture was filtered through Celite® and concentrated in vacuo. The residue was dissolved in anhydrous DMF (10 mL) and treated with [1,1'-biphenyl]-2-carboxylic acid (2.3 g, 11 mmol), DIPEA (3.7 mL, 21 mmol) and HATU (4.4 g, 12 mmol) and the reaction mixture stirred at ambient temperature for 16 hrs, then at 40° C. for a further 2 hrs. The reaction mixture was allowed to cool, then diluted with diethyl ether (100 mL). The solution was washed with water (2×100 mL), brine (2×100 mL) and the organics dried over $Na_2SO_4$, filtered and concentrated in vacuo. The crude product was purified by chromatography on the Biotage Companion™ (120 g column, 50% EtOAc in isohexane) to afford the title compound as an oil (0.40 g).

LCMS (Method A): 2.31 min, 324 $[M+H]^+$

Preparation of (S)-2-(benzyl(methyl)amino)butan-1-ol (Intermediate 15a)

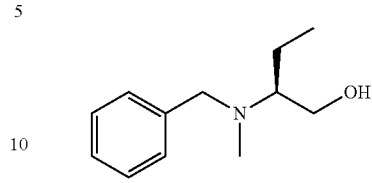

A mixture of (S)-2-aminobutan-1-ol (3.5 g, 39 mmol), benzaldehyde (4.2 g, 39 mmol), $NaBH(OAc)_3$ (18.6 g, 98 mmol) and AcOH (2.3 mL, 39 mmol) in DCE (200 mL) was stirred at ambient temperature for 1 hr. A 37% aqueous solution of formaldehyde (15 mL, 196 mmol) was added and the mixture was stirred for a further 16 hrs. The reaction mixture was quenched with saturated aqueous $NaHCO_3$, the organics separated, dried over $MgSO_4$, filtered, and concentrated in vacuo. The crude product was purified by flash column chromatography (40 to 66% EtOAc in heptane) to afford the title compound as an oil (4.6 g).

$^1$H NMR (400 MHz; $CDCl_3$) 7.51 (m, 5H), 3.72 (d, 1H), 3.59 (m, 1H), 3.57 (d, 1H), 3.42 (m, 1H), 2.72 (m, 1H), 2.23 (s, 3H), 1.67 (m, 1H), 1.20 (m, 1H) and 0.92 (t, 3H).

Preparation of (S)-tert-butyl (1-hydroxybutan-2-yl)(methyl)carbamate (Intermediate 15b)

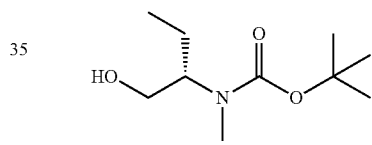

A mixture of Intermediate 15a (4.6 g, 24 mmol), di-tert-butyl dicarbonate (5.8 g, 26 mmol), palladium hydroxide on carbon (6.5 g) and methanol (135 mL) in an autoclave was charged with hydrogen and stirred at ambient temperature for 18 hrs. The reaction mixture was filtered through Celite® and concentrated in vacuo. The crude product was purified by flash column chromatography (40% EtOAc in heptane) to afford the title compound as an oil (4.4 g).

$^1$H NMR (400 MHz; $CDCl_3$) 3.98 (m, 1H), 3.57 (m, 2H), 2.72 (s, 3H), 1.86 (m, 1H), 1.45 (s, 9H), 1.44 (m, 2H) and 0.88 (t, 3H).

Preparation of (S)-tert-butyl (1-((5-chloropyridin-2-yl)amino)butan-2-yl)(methyl)carbamate (Intermediate 15c)

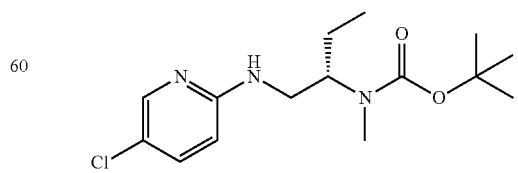

To a mixture of Intermediate 15b (4.4 g, 21 mmol) and $NaHCO_3$ (1.8 g, 84 mmol) in DCM (60 mL) at 0° C. was slowly added Dess-Martin periodinane (10 g, 424 mmol). The reaction mixture was allowed to warm to ambient temperature and was stirred for 18 hrs. The reaction mixture was quenched with saturated aqueous NaHCO₃, the organics separated, dried over MgSO₄, filtered and concentrated in vacuo. The residue was dissolved in DCE (200 mL) and 5-chloropyridin-2-amine (2.3 g, 18 mmol) was added. The reaction mixture was stirred for 5 hrs then NaBH(AcO)₃ (20 g, 108 mmol) was added and stirring continued for a further 20 hrs. The reaction mixture was quenched with saturated aqueous NaHCO₃, the organics separated, dried over MgSO₄, filtered and concentrated in vacuo. The crude product was purified by flash column chromatography (14% EtOAc in heptane) to afford the title compound as an oil (1.9 g).

$^1$H NMR (300 MHz; CDCl₃) 8.00 (bd, 1H), 7.26 (t, 1H), 7.31 (s, 1H), 6.30 (d, 1H), 4.84 (bs, 0.5H), 4.53 (bs, 0.5H), 4.20 (bm, 1.5H), 3.39 (bm, 1H), 3.19 (bm, 1H), 2.70 (s, 1.5H), 2.65 (s, 1.5H), 1.76 (bs, 0.5H), 1.61-1.29 (m, 9H), 0.91 (t, 3H).

Preparation of (S)—N$^1$-(5-chloropyridin-2-yl)-N$^2$-methylbutane-1,2-diamine Trihydrochloride (Intermediate 15)

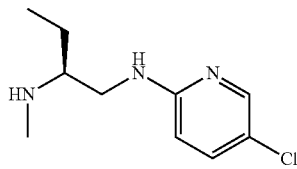

A mixture of Intermediate 15c (1.9 g, 6.3 mmol) and 4M HCl in dioxane (50 mL) was stirred at ambient temperature for 18 hrs. The reaction mixture was concentrated in vacuo to afford the title compound as a solid (1.47 g).

$^1$H NMR (400 MHz; MeOD) 8.06 (s, 1H), 7.89 (d, 1H), 7.08 (d, 1H), 3.75 (m, 2H), 3.62 (m, 1H), 3.40 (m, 1H), 2.76 (s, 3H), 1.81 (m, 2H) and 1.08 (t, 3H).

Preparation of methyl 5-nitro-2-(2H-1,2,3-triazol-2-yl)benzoate (Intermediate 16a)

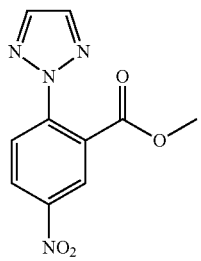 [SMILES: COC(=O)c1cc([N+](=O)[O-])ccc1-n1nccn1]

To a solution of methyl 2-bromo-5-nitrobenzoate (2.0 g, 7.7 mmol), copper(I) iodide (73 mg, 0.38 mmol) and potassium carbonate (2.7 g, 19 mmol) in a mixture of THF (56 mL) and DMF (12 mL) at 40° C. was added 2H-1,2,3-triazole (0.64 g, 9.2 mmol) and the reaction mixture was heated at reflux for 2 hrs. The reaction mixture was poured onto water (100 mL) and the precipitate collected by filtration. The crude product was purified by chromatography on the Biotage Companion™ (40 g column, 5 to 50% diethyl ether in isohexane) to afford the title compound as a solid (1.6 g).

Preparation of methyl 5-amino-2-(2H-1,2,3-triazol-2-yl)benzoate (Intermediate 16b)

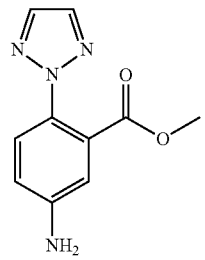 [SMILES: COC(=O)c1cc(N)ccc1-n1nccn1]

A mixture of Intermediate 16a (0.62 g, 2.5 mmol), iron (0.42 g, 7.5 mmol) and ammonium chloride (1.34 g, 25 mmol) in ethanol (20 mL) and water (10 mL) was heated at reflux for 1 hr. The reaction mixture was allowed to cool, poured onto water (100 mL) and the crude product extracted into EtOAc. The combined organics were concentrated in vacuo and the crude product was purified by chromatography on the Biotage Companion™ (12 g column, 0 to 50% diethyl ether in isohexane) to afford the title compound as a gum (0.43 g).

LCMS (Method A): 1.26 min, 219 [M+H]$^+$

Preparation of methyl 5-(dimethylamino)-2-(2H-1,2,3-triazol-2-yl)benzoate (Intermediate 16c)

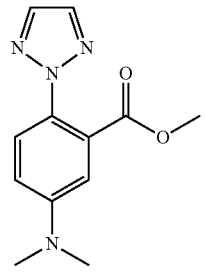 [SMILES: COC(=O)c1cc(N(C)C)ccc1-n1nccn1]

A mixture of Intermediate 16b (0.43 g, 2.0 mmol), 10% palladium on charcoal (0.21 g, 2.0 mmol), 37% aqueous solution of formaldehyde (1.5 mL, 20 mmol) and ethanol (20 mL) in an autoclave was charged with hydrogen to a pressure of 5 bar and the reaction mixture was stirred at ambient temperature for 4 hrs. The reaction mixture was filtered through Celite® and purified by ion-exchange chromatography using an SCX resin column (5 g, washing with 10 column volumes of methanol, then eluting with 5% methanolic ammonia) to afford the title compound as a solid (0.44 g).

LCMS (Method A): 1.86 min, 247 [M+H]$^+$

Preparation of 5-(dimethylamino)-2-(2H-1,2,3-triazol-2-yl)benzoic Acid (Intermediate 16)

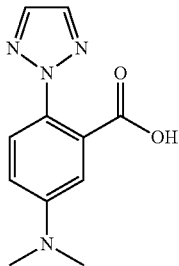 [SMILES: CN(C)c1ccc(-n2nccn2)c(C(=O)O)c1]

A mixture of Intermediate 16c (0.30 g, 1.2 mmol) and LiOH (0.12 g, 4.9 mmol) in water (10 mL) and THF (10 mL) was stirred at 40° C. for 1 hr. The reaction mixture was allowed to cool then was acidified with AcOH and concentrated in vacuo. The crude product was purified by ion-exchange chromatography using an SCX resin column (5 g, washing with 10 column volumes of methanol, then eluting with 5% methanolic ammonia) to afford the title compound as a solid (0.28 g).

LCMS (Method A): 1.44 min, 233 [M+H]$^+$

Preparation of 2-(2H-1,2,3-triazol-2-yl)-5-(trifluoromethyl)nicotinic Acid (Intermediate 17)

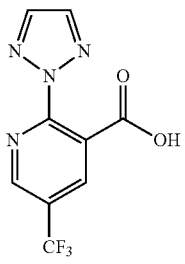 [SMILES: O=C(O)c1cc(C(F)(F)F)cnc1-n1nccn1]

A mixture of (1R,2R)—N$^1$,N$^2$-dimethylcyclohexane-1,2-diamine (63 mg, 0.44 mmol), 2H-1,2,3-triazole (0.61 g, 8.9 mmol), 2-chloro-5-(trifluoromethyl)nicotinic acid (1.0 g, 4.4 mmol), CuI (84 mg, 0.44 mmol) and Cs$_2$CO$_3$ (2.9 g, 8.9 mmol) in dioxane (10 mL) was heated at reflux for 4 hrs. The reaction mixture was allowed to cool, poured onto water (30 mL) and acidified to pH 1-2 with 1M hydrochloric acid. The crude product was extracted into EtOAc (3×50 mL) and then the combined organics were dried over Na$_2$SO$_4$, filtered and concentrated in vacuo. The crude product was purified by chromatography on the Biotage Companion™ (40 g column, 0 to 5% methanol (containing 0.1% AcOH) in DCM) to afford the title compound as a solid (0.27 g).

LCMS (Method A): 1.37 min, 259 [M+H]$^+$

Preparation of (S)-tert-butyl (1-((5-chloropyridin-2-yl)amino)-1-oxobutan-2-yl)carbamate (Intermediate 18a)

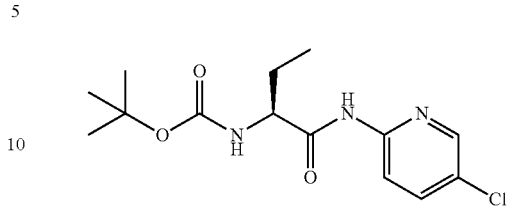

To a solution of (S)-2-((tert-butoxycarbonyl)amino)butanoic acid (10 g, 50 mmol) in DMF (120 mL) at 0° C. was added HBTU (20 g, 52 mmol) and DIPEA (17 mL, 100 mmol). After 20 mins, 2-amino-5-chloropyridine (6.4 g, 50 mmol) was added and then the reaction mixture was allowed to warm to ambient temperature and stirred for 5 days. The reaction mixture was partitioned between EtOAc and water, the organics separated, washed with saturated aqueous NaHCO$_3$ and brine. The organics were dried over MgSO$_4$, filtered and concentrated in vacuo. The crude product was purified by flash column chromatography (20 to 30% EtOAc in heptane) to afford the title compound as a solid (10 g).

$^1$H NMR (400 MHz; DMSO-d$_6$) 10.56 (s, 1H), 8.34 (s, 1H), 8.05 (d, 1H), 7.87 (d, 1H), 4.07 (bq, 1H), 1.65 (m, 2H), 1.39 (s, 9H), 0.85 (t, 3H).

Preparation of (S)-tert-butyl (1-((5-chloropyridin-2-yl)amino)butan-2-yl)carbamate (Intermediate 18b)

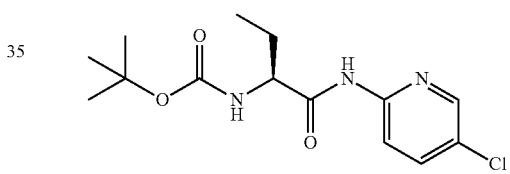

To a solution of Intermediate 18a (5.4 g, 17.4 mmol) in anhydrous THF (50 mL) at 0° C. was added LiAlH$_4$ (3.9 g, 104 mmol) portion wise maintaining the reaction temperature <5° C. The reaction mixture was stirred at 0° C. for 6 hrs and then quenched by the addition of Na$_2$SO$_4$·10H$_2$O. The reaction mixture was filtered and concentrated in vacuo. The crude product was purified by flash column chromatography (15 to 20% EtOAc in heptane) to afford the title compound as a solid (2.3 g).

$^1$H NMR (400 MHz; CDCl$_3$) 7.98 (s, 1H), 7.30 (d, 1H), 6.36 (d, 1H), 5.00 (bs, 1H), 4.59 (bs, 1H), 3.67 (m, 1H), 3.32 (m, 2H), 1.60 (m, 1H), 1.45 (m, 1H), 1.40 (s, 9H), 0.98 (t, 3H).

Preparation of (S)—N$^1$-(5-chloropyridin-2-yl)butane-1,2-diamine Trihydrochloride (Intermediate 18)

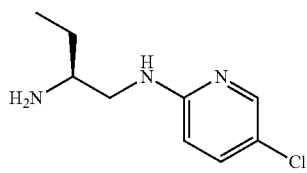

A solution of Intermediate 18b (1.4 g, 4.8 mmol) and 4M HCl in dioxane (25 mL) was stirred at ambient temperature for 18 hrs. The reaction mixture was concentrated in vacuo to afford the title compound as a solid (1.1 g).

$^1$H NMR (400 MHz; DMSO-$d_6$) 8.15 (m, 3H), 7.98 (s, 1H), 7.66 (d, 1H), 6.85 (d, 1H), 3.47 (m, 2H), 3.21 (m, 1H), 1.60 (m, 2H) and 0.93 (t, 3H).

Preparation of (S)-methyl 2-(benzyl(methyl)amino)-3-methylbutanoate (Intermediate 19a)

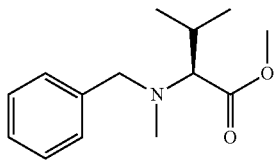 [SMILES: COC(=O)[C@H](C(C)C)N(C)Cc1ccccc1]

To a solution of Intermediate 14a (4.0 g, 18 mmol) in DCE (100 mL) was added molecular sieves (3 g), a 37% aqueous solution of formaldehyde (2.7 mL, 36 mmol) and NaBH(OAc)$_3$ (7.7 g, 36 mmol) and the reaction mixture was stirred at ambient temperature for 1 hr. The solution was then decanted and washed with saturated aqueous NaHCO$_3$, dried over Na$_2$SO$_4$, filtered and concentrated in vacuo to afford the title compound as an oil (4.2 g).

LCMS (Method A): 1.33 min, 236 [M+H]$^+$

Preparation of (S)-2-(benzyl(methyl)amino)-3-methylbutan-1-ol (Intermediate 19b)

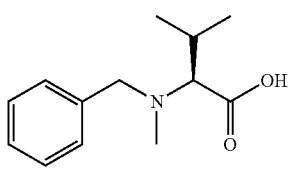 [SMILES: CC(C)[C@@H](C(=O)O)N(C)Cc1ccccc1]

To a solution of Intermediate 19a (4.3 g, 18 mmol) in anhydrous THF (100 mL), cooled in an ice bath, was slowly added a 2M solution of LiAlH$_4$ in THF (9.1 mL, 18 mmol). The mixture was allowed to warm to ambient temperature and stirred for 2 hrs. The reaction mixture was quenched with water (100 mL) whilst being cooled in an ice bath, and then the product was extracted into EtOAc (200 mL). The combined organics were washed with water, dried over Na$_2$SO$_4$, filtered and concentrated in vacuo to afford the title compound as an oil (3.7 g)

LCMS (Method A): 0.52 min, 208 [M+H]$^+$

Preparation of (S)-tert-butyl (1-hydroxy-3-methylbutan-2-yl)(methyl)carbamate (Intermediate 19c)

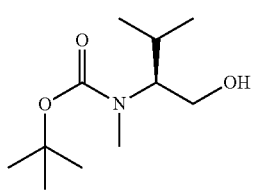

The title compound (3.7 g) was prepared as an oil from Intermediate 19b (3.7 g, 18 mmol) using the method described for Intermediate 15b. The crude product was purified by chromatography on the Biotage Companion™ (40 g column, 0 to 100% EtOAc in isohexane).

Preparation of (S)-tert-butyl (1-((5-chloropyridin-2-yl)amino)-3-methylbutan-2-yl)(methyl)carbamate (Intermediate 19d)

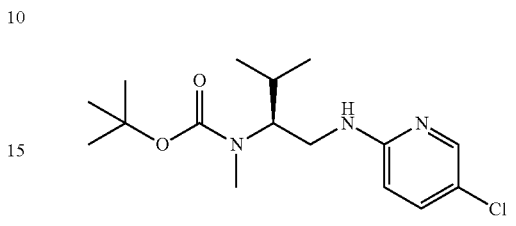

The title compound (0.71 g) was prepared as an oil from Intermediate 19c (0.8 g, 3.7 mmol) and 5-chloropyridin-2-amine (0.47 g, 3.7 mmol) using the method described for Intermediate 15c. The crude product was purified by ion-exchange chromatography using an SCX resin cartridge (10 g, washing with methanol, then eluting with 10% methanolic ammonia), followed by chromatography on the Biotage Companion™ (40 g column, 0 to 70% EtOAc in isohexane).

LCMS (Method A): 2.30 min, 328 [M+H]$^+$

Preparation of (S)—N$^1$-(5-chloropyridin-2-yl)-N$^2$,3-dimethylbutane-1,2-diamine (Intermediate 19)

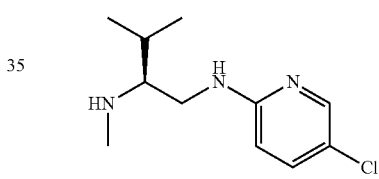

The title compound (0.42 g) was prepared as a gum from Intermediate 19d (0.7 g, 2.1 mmol) using the method described for Intermediate 15. The crude product was purified by ion-exchange chromatography using an SCX resin cartridge (10 g, washing with methanol, then eluting the product with 5% methanolic ammonia).

LCMS (Method A): 0.90 min, 228 [M+H]$^+$

Preparation of (S)-2-(benzylamino)-3-methylbutanamide (Intermediate 20a)

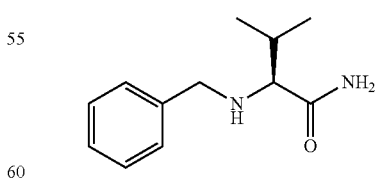

The title compound (12 g) was prepared as a solid from (S)-2-amino-3-methylbutanamide hydrochloride (10 g, 65 mmol) using the method described for Intermediate 14a. The crude product was used without further purification in subsequent reactions.

LCMS (Method C): 1.71 min, 207 [M+H]$^+$

Preparation of (S)-2-(benzyl(methyl)amino)-3-methylbutanamide (Intermediate 20b)

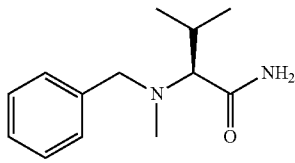 [SMILES: CC(C)[C@@H](C(N)=O)N(C)Cc1ccccc1]

The title compound (8.3 g) was prepared as a gum from Intermediate 20a (10 g, 65 mmol) using the method described for Intermediate 19a. The crude product was used without further purification in subsequent reactions.

LCMS (Method C): 1.73 min, 221 [M+H]$^+$

Preparation of (S)-tert-butyl (2-(benzyl(methyl)amino)-3-methylbutyl)carbamate (Intermediate 20c)

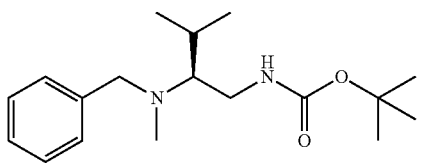 [SMILES: CC(C)[C@@H](CNC(=O)OC(C)(C)C)N(C)Cc1ccccc1]

To a solution of Intermediate 20b (4.0 g, 18 mmol) in anhydrous diethyl ether (100 mL) cooled in an ice/salt bath, was added a 1M solution of LiAlH$_4$ in THF (36 mL, 36 mmol). The reaction mixture was warmed to ambient temperature and was then heated at reflux for 18 hrs. It was then was cooled in an ice bath and quenched with water (1 mL) followed by 4M sodium hydroxide solution (3 mL). The reaction mixture was filtered through Celite® and concentrated in vacuo. The residue was dissolved in DCM (100 mL) and to this solution was added di-tert-butyl dicarbonate (4.2 mL, 18 mmol) and the mixture stirred for 16 hrs. The reaction mixture was concentrated in vacuo and the crude product was purified by chromatography on the Biotage Companion™ (120 g column, 0 to 100% ammonia solution in diethyl ether) to afford the title compound as a gum (3.8 g).

LCMS (Method A): 3.06 min, 307 [M+H]$^+$

Preparation of (S)-tert-butyl (3-methyl-2-(methylamino)butyl)carbamate (Intermediate 20d)

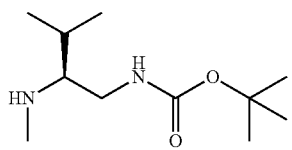

A mixture of Intermediate 20c (5.6 g, 18 mmol), 20% palladium hydroxide on carbon (2.6 g) and methanol (200 mL) in an autoclave was charged with hydrogen to a pressure of 4 bar and stirred at ambient temperature for 18 hrs. The reaction mixture was filtered through Celite® and concentrated in vacuo to afford the title compound as an oil (3.5 g).

LCMS (Method C): 1.56 min, 217 [M+H]$^+$

Preparation of (S)—N-(1-amino-3-methylbutan-2-yl)-N-methyl-[1,1'-biphenyl]-2-carboxamide (Intermediate 20)

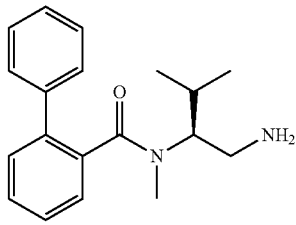 [SMILES: CC(C)[C@@H](CN)N(C)C(=O)c1ccccc1-c1ccccc1]

To a solution of Intermediate 20d (1.0 g, 4.6 mmol) and [1,1'-biphenyl]-2-carboxylic acid (1.0 g, 5.1 mmol), and DIPEA (2.4 mL, 14 mmol) in anhydrous DMF (10 mL) was added HATU (1.9 g, 5.1 mmol) and the mixture stirred for 3 days. The reaction mixture was poured onto water (40 mL) and the crude product extracted with diethyl ether (1×30 mL). The combined organics were washed with brine (2×20 mL), dried over Na$_2$SO$_4$, filtered and concentrated in vacuo. The residue was purified by chromatography on the Biotage Companion™ (40 g column, gradient 0 to 100% EtOAc in isohexane). The resulting intermediate was dissolved in 4M HCl in dioxane (10 mL) and allowed to stand at ambient temperature for 1 hr. The reaction mixture was concentrated in vacuo and the crude product purified by ion-exchange chromatography using an SCX resin cartridge (10 g column, washing with methanol, then eluting with 2% methanolic ammonia) to afford the title compound as an oil (0.58 g).

LCMS (Method A): 1.36 min, 297 [M+H]$^+$

Preparation of (S)-2-(benzyl(methyl)amino)butanamide (Intermediate 21a)

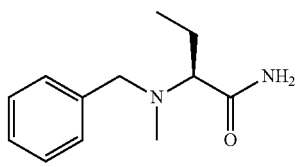

A mixture of triethylamine (10 mL, 72 mmol), benzaldehyde (7.7 g, 72 mmol), (S)-2-aminobutanamide hydrochloride (10 g, 72 mmol) and NaBH(OAc)$_3$ (30 g, 140 mmol) in DCE (200 mL) was stirred for 16 hrs. The reaction mixture was concentrated in vacuo, then the residue dissolved in diethyl ether (200 mL). The solution was washed with water (3×100 mL), and then the organics were separated and extracted into 1M hydrochloric acid (100 mL). The aqueous layer was separated, basified with 2M sodium hydroxide solution, and then the crude product was extracted into diethyl ether (200 mL) and washed with water (2×100 mL). The combined organics were dried over Na$_2$SO$_4$, filtered and concentrated in vacuo. The residue was dissolved in DCE (200 mL) and treated with a 37% aqueous solution of formaldehyde (5.4 mL, 72 mmol) and AcOH (4.1 mL, 72 mmol) and the reaction mixture was stirred for 1 hr. To this solution was added NaBH(OAc)$_3$ (31 g, 145 mmol) and the reaction mixture was stirred for a further 16 hrs. It was then quenched with saturated aqueous NaHCO$_3$ and the crude product was extracted into DCM. The combined organics were separated and concentrated in vacuo. The residue was partitioned between diethyl ether (400 mL) and 1M hydrochloric acid. The aqueous layer was separated, basified with 2M sodium hydroxide solution and the crude product extracted into EtOAc (2×300 mL). The combined organics were dried over Na$_2$SO$_4$, filtered and concentrated in vacuo to afford the title compound (13 g).

Alternative method: (S)-2-aminobutanamide hydrochloride (42 g, 0.30 mol), sodium hydroxide (12 g, 0.30 mol), 5% palladium on carbon (14 g, 50% water by mass) and benzaldehyde (33 mL, 0.32 mol) were combined in water (84 mL) and ethanol (0.34 L) under an atmosphere of hydrogen (2 bar) and stirred at ambient temperature for 24 hrs. After this time a 37% aqueous solution of formaldehyde (56 mL, 0.76 mol) was added and the hydrogen pressure restored for 24 hrs. The mixture was then filtered through Celite®. The liquors were concentrated to low volume and separated between water (0.84 L) and tBME (0.84 L). The aqueous was extracted with tBME (0.42 L) and the combined organics were dried over Na$_2$SO$_4$, filtered and concentrated in vacuo. The resulting oil was stirred in tBME (43 mL) and hexane (0.63 L) and heated to cause dissolution. The solution was then cooled to 5° C. and after stirring for 1 hr the product was filtered, washed with cold hexane (0.42 L) and dried to afford the title compound as a solid (42 g).

LCMS (Method B): 1.45 min, 207 [M+H]$^+$

LCMS (Method N): 1.21 min, 207 [M+H]$^+$

Preparation of (S)-tert-butyl (2-(benzyl(methyl) amino)butyl)carbamate (Intermediate 21b)

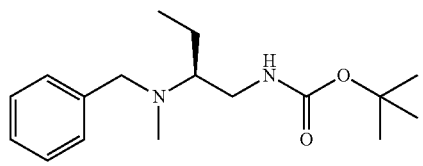 [SMILES: CC[C@@H](CNC(=O)OC(C)(C)C)N(C)Cc1ccccc1]

To an ice cooled solution of Intermediate 21a (13 g, 63 mmol) in anhydrous diethyl ether (100 mL) was added a 1M solution of LiAlH$_4$ in THF (126 mL, 126 mmol) and the reaction mixture was warmed to ambient temperature and then heated at reflux for 18 hrs. The reaction mixture was cooled in an ice bath and quenched with water (5 mL) followed by 4M sodium hydroxide solution (12 mL). The reaction mixture was then filtered through Celite® and concentrated in vacuo. The residue was dissolved in DCM (100 mL) and di-tert-butyl dicarbonate (14 mL, 63 mmol) was added. The reaction mixture was stirred for 16 hrs, then concentrated in vacuo and the crude product was purified by chromatography on the Biotage Companion™ (120 g column, gradient 0 to 5% ammonia solution in DCM) to afford the title compound as an oil (15 g).

LCMS (Method B): 2.77 min, 293 [M+H]$^+$

Preparation of (S)-tert-butyl (2-(methylamino)butyl) carbamate (Intermediate 21c)

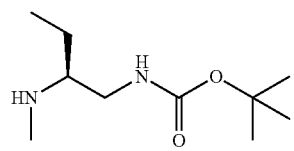

A mixture of Intermediate 21b (15 g, 52 mmol), 36 L paste palladium on carbon (1.1 g, 10 mmol) and methanol (100 mL) in an autoclave was charged with hydrogen to a pressure of 5 bar and stirred at ambient temperature for 18 hrs. The reaction mixture was filtered through Celite® and concentrated in vacuo to afford the title compound as an oil (10 g).

LCMS (Method A): 0.55 min, 203 [M+H]$^+$

Preparation of (S)—N-(1-aminobutan-2-yl)-5-chloro-N-methyl-2-(2H-1,2,3-triazol-2-yl)benzamide (Intermediate 21)

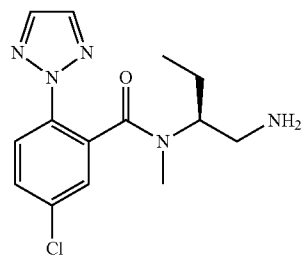 [SMILES: CC[C@@H](CN)N(C)C(=O)c1cc(Cl)ccc1-n1nccn1]

To a solution of 5-chloro-2-(2H-1,2,3-triazol-2-yl)benzoic acid (2.3 g, 10 mmol) [prepared as described in WO 2011/050198], Intermediate 21c (1.9 g, 9.3 mmol) and DIPEA (4.9 mL, 28 mmol) in anhydrous MeCN (60 mL) was added HATU (3.9 g, 10 mmol) and the reaction mixture was stirred for 16 hrs. It was concentrated in vacuo and the residue dissolved in EtOAc (300 mL). The solution was washed with saturated aqueous NaHCO$_3$ (2×100 mL), brine (100 mL), the organics were dried over Na$_2$SO$_4$, filtered and concentrated in vacuo. The crude intermediate was purified by chromatography on the Biotage Companion™ (220 g column, 0 to 40% EtOAc in isohexane). The resulting intermediate was dissolved in DCM (200 mL) and treated with TFA (40 mL) and the reaction mixture was allowed to stand at ambient temperature for 16 hrs. It was concentrated in vacuo and the crude product purified by ion-exchange chromatography using an SCX resin cartridge (50 g column, washing with methanol, then eluting with 10% methanolic ammonia) to afford the title compound (2.4 g).

LCMS (Method A): 1.09 min, 308/310 [M+H]$^+$

Preparation of (S)—N-(1-aminobutan-2-yl)-N,6-dimethyl-3-(2H-1,2,3-triazol-2-yl)picolinamide (Intermediate 22)

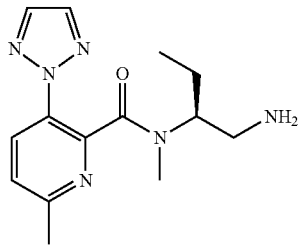 [SMILES: CC[C@@H](CN)N(C)C(=O)c1nc(C)ccc1-n1nccn1]

The title compound (510 mg) was prepared as an oil from 6-methyl-3-(2H-1,2,3-triazol-2-yl)picolinic acid hydrochloride (0.56 g, 2.3 mmol) [prepared as described in WO 2010/063662] and Intermediate 21c (0.47 g, 2.3 mmol) using the method described for Intermediate 21. The crude product was purified by ion-exchange chromatography using an SCX resin cartridge (20 g column, washing with methanol, then eluting with 10% methanolic ammonia).

LCMS (Method A): Two peaks at 0.53 min and 0.90 min, 289 [M+H]$^+$

Preparation of (S)—N-(1-amino-3-methylbutan-2-yl)-N,5-dimethyl-2-(2H-1,2,3-triazol-2-yl)benzamide (Intermediate 23)

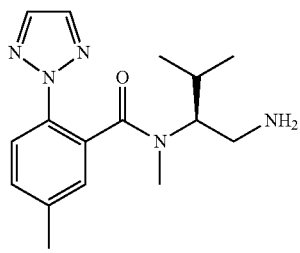 [SMILES: Cc1ccc(-n2nccn2)c(C(=O)N(C)[C@H](CN)C(C)C)c1]

To a solution of 5-methyl-2-(2H-1,2,3-triazol-2-yl)benzoic acid (0.38 g, 1.9 mmol) [prepared as described in WO 2012/148553], Intermediate 20d (0.41 g, 1.9 mmol) and DIPEA (0.98 mL, 5.6 mmol) in anhydrous DMF (10 mL) was added HATU (0.78 g, 2.1 mmol) and the reaction mixture was stirred for 3 days. It was then poured onto water (30 mL) and the crude product was extracted into EtOAc (2×20 mL). The combined organics were dried over Na$_2$SO$_4$, filtered and concentrated in vacuo. The crude intermediate was purified by chromatography on the Biotage Companion™ (12 g column, 0 to 100% ethyl acetate in isohexane). The resulting intermediate was dissolved in 4M HCl in dioxane (10 mL) and allowed to stand at ambient temperature for 1 hr. The reaction mixture was concentrated in vacuo, then 2M sodium hydroxide solution was added and the product was extracted into EtOAc. The combined organics were dried over Na$_2$SO$_4$, filtered and concentrated in vacuo to afford the title compound as an oil (0.29 g).

LCMS (Method A): 1.14 min, 302 [M+H]$^+$

Preparation of (S)—N-(1-amino-3-methylbutan-2-yl)-N,1-dimethyl-1H-indole-3-carboxamide (Intermediate 24)

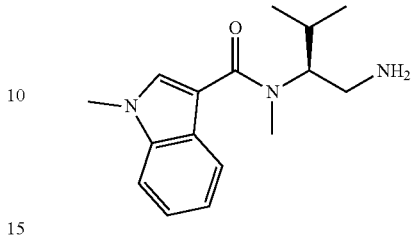

The title compound (0.38 g) was prepared as a gum from 1-methyl-1H-indole-3-carboxylic acid (0.30 g, 1.7 mmol) and Intermediate 20d (0.37 g, 1.7 mmol) using the method described for Intermediate 23. The reaction mixture was concentrated in vacuo, and then the residue was purified by ion-exchange chromatography using an SCX resin cartridge (10 g column, washing with methanol, then eluting with 2% methanolic ammonia).

LCMS (Method A): 1.05 min, 274 [M+H]$^+$

Preparation of (S)—N-(1-amino-3-methylbutan-2-yl)-N,2-dimethylquinoline-4-carboxamide (Intermediate 25)

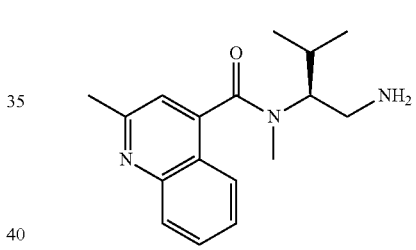

The title compound (0.37 g) was prepared from 2-methylquinoline-4-carboxylic acid (0.30 g, 1.6 mmol) and Intermediate 20d (0.35 g, 1.6 mmol) using the method described for Intermediate 23. The reaction mixture was concentrated in vacuo, and then the residue was purified by ion-exchange chromatography using an SCX resin cartridge (10 g column, washing with methanol, then eluting with 5% methanolic ammonia).

LCMS (Method A): 0.47 min, 286 [M+H]$^+$

Preparation of (S)—N-(1-amino-3-methylbutan-2-yl)-N-methyl-2-(trifluoromethoxy)benzamide (Intermediate 26)

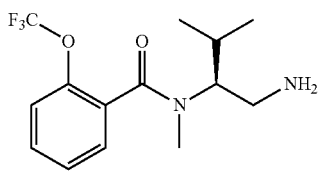 [SMILES: CC(C)[C@@H](CN)N(C)C(=O)c1ccccc1OC(F)(F)F]

The title compound (0.32 g) was prepared from 2-(trifluoromethoxy)benzoic acid (0.30 g, 1.5 mmol) and Intermediate 20d (0.31 g, 1.5 mmol) using the method described for Intermediate 23. The reaction mixture was concentrated in vacuo, and then the residue was purified by ion-exchange chromatography using an SCX resin cartridge (10 g column, washing with methanol, then eluting with 5% methanolic ammonia).

LCMS (Method A): 1.19 min, 305 [M+H]$^+$

Preparation of 5-methyl-2-morpholinobenzoic Acid (Intermediate 27)

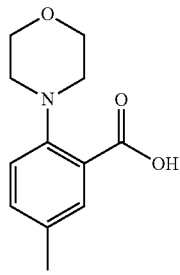 [SMILES: Cc1ccc(N2CCOCC2)c(C(=O)O)c1]

A mixture of ethyl 2-fluoro-5-methylbenzoate (0.5 g, 2.7 mmol) and morpholine (4.8 g, 55 mmol) was heated at reflux for 3 hrs. The mixture was then poured onto water (100 mL), acidified with AcOH and extracted into ether (2×30 mL). The combined organics were washed with water (20 mL), dried over Na$_2$SO$_4$, filtered and concentrated in vacuo. The residue was dissolved in THF (20 mL) and water (20 mL), treated with LiOH (0.2 g, 8.2 mmol) and heated at reflux for 3 hrs. The mixture was acidified with 1M hydrochloric acid and concentrated in vacuo such that the product could be collected by filtration and washed with ice-cold water to afford the title compound as a solid (0.52 g).

LCMS (Method A): 1.09 min, 220 [M+H]$^+$

Preparation of (S)—N-(1-amino-3-methylbutan-2-yl)-N,6-dimethyl-3-(2H-1,2,3-triazol-2-yl)picolinamide (Intermediate 28)

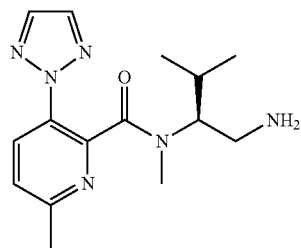 [SMILES: Cc1ccc(-n2nccn2)c(C(=O)N(C)[C@H](CN)C(C)C)n1]

To a solution of Intermediate 20d (0.34 g, 1.6 mmol), 6-methyl-3-(2H-1,2,3-triazol-2-yl)picolinic acid [prepared as described in WO 2011/023578] (0.35 g, 1.7 mmol) and DIPEA (0.82 mL, 4.72 mmol) in anhydrous DMF (7 mL) was added HATU (0.66 g, 1.7 mmol) and the mixture was stirred overnight. The reaction mixture was poured onto water (30 mL) and extracted with EtOAc. The combined organics were dried over MgSO$_4$, filtered and concentrated in vacuo. The crude intermediate was purified by chromatography on the Biotage Isolera Four™ (25 g column, 0 to 100% EtOAc in heptane). The resulting intermediate was dissolved in 4M HCl in dioxane (10 mL) and stirred at ambient temperature for 1 hr. The reaction mixture was concentrated in vacuo and then 2M sodium hydroxide solution was added and the product extracted into EtOAc. The combined organics were dried over MgSO$_4$, filtered and concentrated in vacuo to afford the title compound as a glass (0.27 g). The crude product was used without further purification in subsequent reactions.

LCMS (Method J): 1.36 min, 303 [M+H]$^+$

Preparation of methyl (2S)-2-aminobutanoate Hydrochloride (Intermediate 29a)

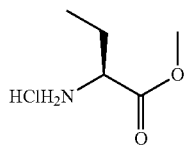

To a solution of (S)-2-aminobutanoic acid (5.0 g, 48 mmol) in methanol (50 mL) at −20° C. was added dropwise thionyl chloride (3.9 mL, 53 mmol) and the mixture allowed to warm to ambient temperature and stirred overnight. The reaction mixture was concentrated in vacuo, and then the residue was washed with diethyl ether, filtered and dried under vacuum to afford the title compound as a solid (6.2 g). The crude product was used without further purification in subsequent reactions.

LCMS (Method G): 0.16 min, 119 [M+H]$^+$

Preparation of (S)-methyl 2-(benzylamino)butanoate (Intermediate 29b)

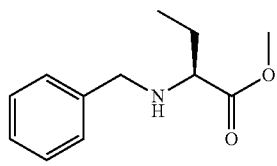

A mixture of triethylamine (0.91 mL, 6.5 mmol), benzaldehyde (0.66 mL, 6.5 mmol), Intermediate 29a (1.0 g, 6.5 mmol) and NaBH(OAc)$_3$ (2.1 g, 9.8 mmol) in DCE (5 mL) was stirred at ambient temperature overnight. The reaction mixture was concentrated in vacuo and the residue was dissolved in diethyl ether (30 mL). The organic phase was washed with water and the product was extracted into 1M hydrochloric acid. The aqueous phase was separated, basified to pH 9 with 2M sodium hydroxide solution and extracted with diethyl ether. The combined organics were washed with water, dried over Na$_2$SO$_4$, filtered and concentrated in vacuo. The crude product was purified by chromatography on the Biotage Isolera Four™ (50 g column, 10 to 50% EtOAc in heptane) to afford the title compound as an oil (0.63 g).

LCMS (Method J): 1.46 min, 208 [M+H]$^+$

Preparation of (S)-methyl 2-(benzyl(ethyl)amino)butanoate (Intermediate 29c)

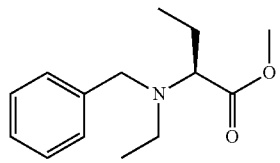 [SMILES: CC[C@@H](C(=O)OC)N(CC)Cc1ccccc1]

To a solution of Intermediate 29b (0.63 g, 3.0 mmol) in DCE (20 mL) was added acetaldehyde (0.34 mL, 6.1 mmol) and NaBH(OAc)$_3$ (1.29 g, 6.1 mmol) and the mixture was stirred for 3 hrs. The reaction mixture was diluted with DCM and washed with saturated aqueous NaHCO$_3$. The organic phase was dried over MgSO$_4$, filtered and concentrated in vacuo. The crude product was purified by chromatography on the Biotage Isolera Four™ (50 g column, 1 to 20% EtOAc in heptane) to afford the title compound as an oil (0.54 g).

LCMS (Method G): 0.78 min, 237 [M+H]$^+$

Preparation of (S)-2-(benzyl(ethyl)amino)butan-1-ol (Intermediate 29d)

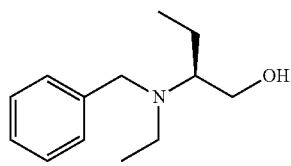

To an ice cooled solution of Intermediate 29c (0.55 g, 2.1 mmol) in anhydrous THF (12 mL) was added dropwise a 1M solution of LiAlH$_4$ in THF (4.1 mL, 4.1 mmol) and the mixture was stirred in an ice bath for 2 hrs. The reaction mixture was diluted with diethyl ether and quenched by sequential addition of water (0.15 mL) followed by 2M sodium hydroxide solution (0.15 mL) and water (0.5 mL). The organic phase was separated, and then dried over MgSO$_4$, filtered and concentrated in vacuo to afford the title compound as an oil (0.48 g). The crude product was used without further purification in subsequent reactions.

LCMS (Method G): 1.78 min, 208 [M+H]$^+$

Preparation of (S)-tert-butyl (2-(benzyl(ethyl)amino)butyl)carbamate (Intermediate 29e)

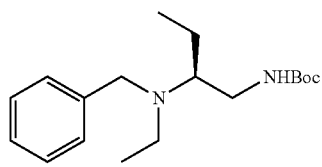 [SMILES: CC[C@@H](CNC(=O)OC(C)(C)C)N(CC)Cc1ccccc1]

A mixture of Intermediate 29d (0.48 g, 2.1 mmol), ethyl 2-{[(tert-butoxy)carbonyl]amino}-2-oxoacetate (0.45 g, 2.1 mmol) and triphenylphosphine (0.60 g, 2.3 mmol) in anhydrous THF (10 mL) was stirred at −10° C. followed by the slow addition of DEAD (0.33 mL, 2.1 mmol). The mixture was allowed to warm to ambient temperature and stirred for 3 hrs. The reaction mixture was poured onto brine (20 mL) and extracted with diethyl ether and the combined organics were concentrated in vacuo. The residue was dissolved in THF (10 mL) and then 1M LiOH solution (0.26 mL, 25 mmol) was added and the mixture was stirred at ambient temperature for 2 hrs. The reaction mixture was poured onto water (50 mL) and extracted with diethyl ether. The combined organic phases were concentrated in vacuo. The crude product was purified by chromatography on the Biotage Isolera Four™ (25 g column, 1 to 40% EtOAc in heptane) to afford title compound as an oil (0.44 g).

LCMS (Method G): 0.92 min, 308 [M+H]$^+$

Preparation of (S)-tert-butyl (2-(ethylamino)butyl)carbamate (Intermediate 29f)

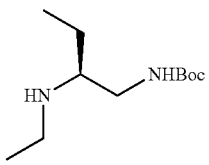

To a solution of Intermediate 29e (0.44 g, 1.4 mmol) in EtOH (10 mL) was added 10% palladium hydroxide on carbon (40 mg) and the mixture was stirred under an atmosphere of hydrogen for 18 hrs. The reaction mixture was filtered, and then concentrated in vacuo to afford the title compound (0.26 g). The crude product was used without further purification in subsequent reactions.

$^1$H NMR (500 MHz, CDCl$_3$) 4.99 (bs, 1H), 3.20 (bm, 1H), 3.04 (m, 1H), 2.63 (m, 2H), 2.55 (bm, 1H), 1.44 (s, 9H), 1.41 (m, 2H), 1.09 (t, 3H), 0.92 (t, 3H).

Preparation of (S)—N-(1-aminobutan-2-yl)-N-ethyl-6-methyl-3-(2H-1,2,3-triazol-2-yl)picolinamide (Intermediate 29)

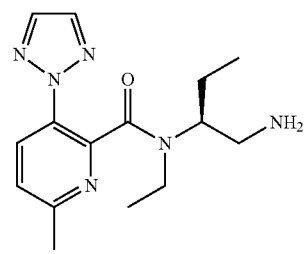 [SMILES: CC[C@@H](CN)N(CC)C(=O)c1nc(C)ccc1-n1nccn1]

To a solution of Intermediate 29f (0.26 g, 1.2 mmol), 6-methyl-3-(2H-1,2,3-triazol-2-yl)picolinic acid [prepared as described in WO 2011/023578] (0.34 g, 1.1 mmol) and DIPEA (0.45 mL, 3.3 mmol) in anhydrous DMF (5 mL) was added HATU (0.50 g, 1.3 mmol) and the mixture was stirred overnight. The reaction mixture was diluted with EtOAc and washed with water (2×100 mL). The organics were dried over Na$_2$SO$_4$, filtered and concentrated in vacuo. The crude intermediate was purified by chromatography on the Biotage Isolera Four™ (25 g column, 1 to 100% EtOAc in heptane). The resulting intermediate was dissolved in 4M HCl in dioxane (5 mL) and stirred at ambient temperature for 2 hrs. The reaction mixture was concentrated in vacuo and then 2M sodium hydroxide solution (30 mL) was added and the product was extracted into EtOAc (2×30 mL). The combined organics were dried over Na₂SO₄, filtered and concentrated in vacuo to afford the title compound as a solid (0.23 g). The crude product was used without further purification in subsequent reactions.

LCMS (Method G): 0.7 min, 303 [M+H]⁺

Preparation of
(S)-2-cyclopropyl-2-(methylamino)ethanol
(Intermediate 30a)

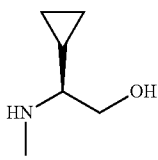

To an ice cooled solution of (S)-tert-butyl (1-cyclopropyl-2-hydroxyethyl)carbamate [prepared as described in WO 2013/046136] (0.61 g, 2.3 mmol) in anhydrous THF (10 mL) was added dropwise a 1M solution of LiAlH₄ in THF (4.6 mL, 4.6 mmol). The reaction mixture was warmed to ambient temperature and was then heated 55° C. for 2 hrs. It was then allowed to cool to ambient temperature, the mixture was diluted with diethyl ether (10 mL), and quenched by sequential addition of water (0.2 mL), 2M sodium hydroxide solution (0.2 mL), water (0.6 mL) and the mixture was stirred for 15 mins. The organic phase was separated and was dried over MgSO₄, filtered and concentrated in vacuo to afford the title compound as an oil (0.32 g). The crude product was used without further purification in subsequent reactions.

¹H NMR (500 MHz, CDCl₃) 3.71 (dd, 1H), 3.48 (dd, 1H), 2.48 (s, 3H), 1.76 (m, 1H), 0.77 (m, 1H), 0.59 (m, 1H), 0.48 (m, 1H), 0.27 (m, 1H), 0.14 (m, 1H).

Preparation of (S)—N-(1-cyclopropyl-2-hydroxyethyl)-N,6-dimethyl-3-(2H-1,2,3-triazol-2-yl)picolinamide (Intermediate 30b)

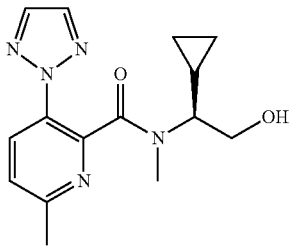 [SMILES: Cc1ccc(-n2nccn2)c(C(=O)N(C)[C@H](CO)C2CC2)n1]

To an ice-cooled solution of Intermediate 30a (0.27 g, 1.9 mmol), HATU (0.81 g, 2.1 mmol) and 6-methyl-3-(2H-1,2,3-triazol-2-yl)picolinic acid [prepared as described in WO 2011/023578] (0.68 g, 2.1 mmol) in anhydrous DMF (10 mL) was added DIPEA (1.7 mL, 9.7 mmol) and the mixture was stirred at ambient temperature overnight. The reaction mixture was concentrated in vacuo, and then the residue was dissolved in EtOAc and washed with water. The aqueous phase was extracted with EtOAc and the combined organics were washed with water and brine. The organics were dried over Na₂SO₄, filtered and concentrated in vacuo. The residue was purified by chromatography on the Biotage Isolera Four™ (25 g column, 0 to 100% EtOAc in heptane). The resulting crude product was dissolved in methanol (5 mL) and was added to a 0.5M LiOH solution (0.88 mL, 0.44 mmol) and the mixture was stirred for 2 hrs. The reaction mixture was neutralised with AcOH and then concentrated in vacuo. The residue was then re-dissolved in DCM (5 mL) and washed with saturated aqueous NaHCO₃. The organic phase was dried over Na₂SO₄, filtered and concentrated in vacuo. The crude product was purified by chromatography on the Biotage Isolera Four™ (25 g column, 0 to 10% methanol in DCM) to afford the title compound as an oil (0.29 g).

LCMS (Method G): 0.9 min, 302 [M+H]⁺

Preparation of (S)-tert-butyl (2-cyclopropyl-2-(N,6-dimethyl-3-(2H-1,2,3-triazol-2-yl)picolinamido)ethyl)carbamate (Intermediate 30c)

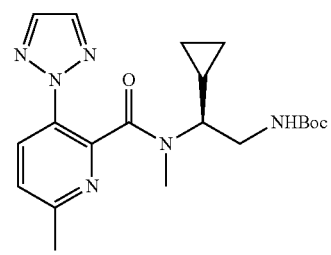 [SMILES: Cc1ccc(-n2nccn2)c(C(=O)N(C)[C@H](CNC(=O)OC(C)(C)C)C2CC2)n1]

To a solution of Intermediate 30b (0.29 g, 0.98 mmol), ethyl 2-{[(tert-butoxy)carbonyl]amino}-2-oxoacetate (0.20 mL, 0.98 mmol) and triphenylphosphine (0.28 g, 1.1 mmol) in anhydrous THF (12 mL) at −10° C. was slowly added DIAD (0.19 mL, 0.98 mmol). The mixture was stirred at ambient temperature for 3 hrs and then DIAD (0.39 mL, 2.0 mmol) and triphenylphosphine (0.56 g, 2.1 mmol) were added and stirring was continued for 16 hrs. Additional portions of DIAD (0.39 mL, 2.0 mmol) and triphenylphosphine (0.56 g, 2.1 mmol) were added and stirring was continued for a further 3 hrs. The mixture was then poured onto brine (12 mL) and extracted with diethyl ether. The combined organics were concentrated in vacuo. The residue was re-dissolved in THF (6 mL) and 1M LiOH (12 mL, 0.28 mmol) was added and the mixture was stirred at ambient temperature for 16 hrs. The reaction mixture was poured onto water (30 mL) and extracted with diethyl ether. The combined organics were concentrated in vacuo. The crude product was purified by chromatography on the Biotage Isolera Four™ (10 g column, 0 to 100% ethyl acetate in heptane) to afford the title compound as an oil (0.15 g).

¹H NMR (500 MHz, CDCl₃) 8.25 (d, 0.43H), 8.21 (d, 0.57H), 7.90 (s, 0.86H), 7.84 (s, 1.14H), 7.30 (m, 1H), 7.04 (bs, 0.57H), 5.53 (bs, 0.43H), 4.03 (m, 0.43H), 3.66 (m, 0.43H), 3.44 (m, 1H), 3.32 (m, 0.57H), 3.19 (m, 0.57H), 3.11 (s, 1.71H), 2.87 (s, 1.29H), 2.63 (m, 3H), 1.48 (s, 3.87H), 1.38 (s, 5.13H), 1 (m, 1.00H), 0.68 (m, 1H), 0.60 (m, 1.43H), 0.49 (m, 1H), 0.18 (m, 0.57H).

Preparation of (S)—N-(2-amino-1-cyclopropylethyl)-N,6-dimethyl-3-(2H-1,2,3-triazol-2-yl)picolinamide (Intermediate 30)

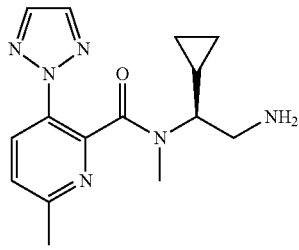 [SMILES: Cc1ccc(-n2nccn2)c(C(=O)N(C)[C@H](CN)C2CC2)n1]

A solution of Intermediate 30c (0.15 g, 0.29 mmol) in 4M HCl in dioxane (3 mL) was stirred at ambient temperature for 2 hrs. The reaction mixture was concentrated in vacuo, and then the residue was dissolved in 1M hydrochloric acid (10 mL) and extracted with EtOAc. The aqueous phase was adjusted to pH 12 with 2M sodium hydroxide solution. The aqueous phase was extracted with EtOAc, followed by IPA/Chloroform (1:9, 10 mL then 1:2, 10 mL). The combined organics were dried over Na$_2$SO$_4$, filtered and concentrated in vacuo. The crude product was purified on the Biotage Isolera Four™ (11 g KP—NH column, 0 to 100% EtOAc in heptane followed by 0 to 10% methanol in DCM) to afford the title compound as an oil (33 mg).

LCMS (Method G): 0.77 min, 302 [M+H]$^+$

Preparation of (S)—N$^2$-benzyl-N$^2$-methylbutane-1,2-diamine D-(−)-tartrate Salt (1:1) (Intermediate 31a)

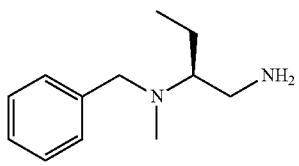

Intermediate 21a (50 g, 0.24 mol) was stirred in THF (0.42 L) and cooled to an internal temperature of 5° C. A 1M solution of LiAlH$_4$ in THF (0.36 L, 0.36 mol) was added. The mixture was then allowed to warm to ambient temperature and heated at 30° C. overnight. After this time the reaction was cooled. Water (14 mL) was added, followed by 15% sodium hydroxide solution (14 mL) and water (42 mL). tBME (52 mL) was added and the mixture stirred for 1 hr at ambient temperature. The mixture was then filtered through Celite® and the liquors were concentrated to give an oil. The oil was stirred in THF (820 mL) and D-(−)-tartaric acid (31 g, 0.21 mol) in methanol (180 mL) was added. The mixture was then heated to 60° C. and held for 1 hr before being allowed to cool back to ambient temperature and stirred for 1 hr. The product was filtered, washed with THF (2×333 mL) and dried to afford the title compound as a solid (50 g).

LCMS (Method N): 1.09 min, 193 [M+H]$^+$

Preparation of (S)—N$^2$-benzyl-N$^2$-methyl-N$^1$-(5-(trifluoromethyl)pyrimidin-2-yl)butane-1,2-diamine (Intermediate 31b)

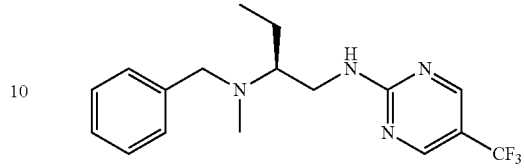

Intermediate 31a (89 g, 260 mmol) was stirred in water (710 mL). Potassium carbonate (108 g, 780 mmol) was added at approximately 22-25° C. A solution of 2-chloro-5-trifluoromethylpyrimidine (45 g, 250 mmol) in tBME (710 mL) was added and the mixture was stirred overnight at ambient temperature. The organic layer was separated, dried over Na$_2$SO$_4$, filtered and concentrated in vacuo to afford the title compound as an oil (78 g).

LCMS (Method N): 1.91 min, 339 [M+H]$^+$

Preparation of (S)—N$^2$-methyl-N$^1$-(5-(trifluoromethyl)pyrimidin-2-yl)butane-1,2-diamine (Intermediate 31)

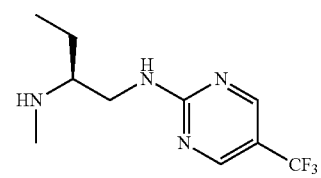 [SMILES: CC[C@@H](CNc1ncc(C(F)(F)F)cn1)NC]

Intermediate 31b (26 g, 77 mmol) and 10% palladium on carbon (2.6 g, 50% water by mass) were combined in ethanol (200 mL) under an atmosphere of hydrogen and stirred at ambient temperature for 48 hrs. The mixture was then filtered through Celite® and concentrated in vacuo. The residue was dissolved in isopropyl acetate (100 mL), dried over Na$_2$SO$_4$, filtered and concentrated to afford the title compound as an oil (18.5 g).

LCMS (Method N): 1.65 min, 249 [M+H]$^+$

Preparation of 1-bromo-N,N-dimethylisoquinolin-3-amine (Intermediate 32a)

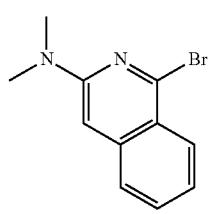

To a solution of 3-amino-1-bromoisoquinoline (685 mg, 3.1 mmol) in THF (12 mL) was added NaH (60% dispersion in oil) (294 mg, 7.4 mmol). After 30 mins, iodomethane (0.46 mL, 7.4 mmol) was added. The reaction was stirred at ambient temperature for 18 hrs. EtOAc (15 mL) and water (15 mL) were added and the aqueous phase was extracted with EtOAc (10 mL). The combined organics were washed with water (25 mL), dried over MgSO$_4$, filtered and concentrated in vacuo to afford the title compound as an oil (700 mg).

LCMS (Method K): 1.01 min, 251 [M+H]$^+$

Preparation of 3-(dimethylamino)isoquinoline-1-carboxylic Acid (Intermediate 32)

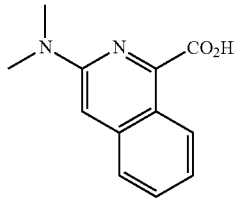 [SMILES: CN(C)c1cc2ccccc2c(C(=O)O)n1]

A mixture of Intermediate 32a (50 mg, 0.20 mmol), N-hydroxysuccinimide (46 mg, 0.40 mmol), triethylamine (40 mg, 0.40 mmol), xantphos (12 mg, 0.02 mmol) and Pd(OAc)$_2$ (4 mg, 0.02 mmol) in DMSO (10 mL) was heated at 85° C. in an autoclave with CO (g) (200 psi) for 18 hrs. The mixture was filtered through Celite® washing with THF (50 mL). The filtrate was concentrated in vacuo to give a crude residue, which was partitioned between EtOAc (10 mL) and water (10 mL). The aqueous phase was extracted with EtOAc (10 mL). The combined organics were washed with water (20 mL), dried over MgSO$_4$, filtered and concentrated in vacuo. The residue was purified by dry flash chromatography (0 to 50% EtOAc in heptane) to afford the title compound as a solid (17 mg).

LCMS (Method L): 0.46 min, 217 [M+H]$^+$

Preparation of (S)-tert-butyl methyl(1-((5-(trifluoromethyl)pyrimidin-2-yl)amino)butan-2-yl)carbamate (Intermediate 33a)

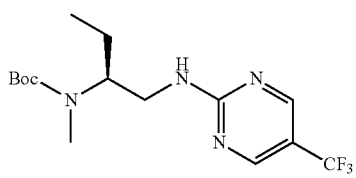 [SMILES: CC[C@@H](CNc1ncc(C(F)(F)F)cn1)N(C)C(=O)OC(C)(C)C]

To a solution of Intermediate 31 (300 mg, 1.2 mmol) and K$_2$CO$_3$ (167 mg, 1.2 mmol) in dioxane (3 mL) and water (3 mL) was added di-tert-butyl dicarbonate (290 mg, 1.3 mmol) and the mixture was stirred at ambient temperature overnight. The mixture was diluted with EtOAc and washed with water. The organic phase was dried over Na$_2$SO$_4$, filtered and concentrated in vacuo to afford the title compound as a solid (380 mg). The crude product was used without further purification in subsequent reactions.

LCMS (Method G): 1.28 min, 349 [M+H]$^+$

Preparation of (S)-tert-butyl methyl(1-(methyl(5-(trifluoromethyl)pyrimidin-2-yl)amino)butan-2-yl)carbamate (Intermediate 33b)

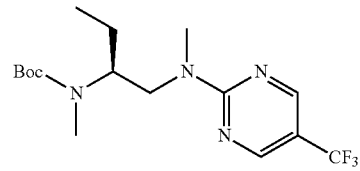

To a solution of Intermediate 33a (100 mg, 0.29 mmol), in anhydrous DMF (3 mL) was added sodium hydride, 60% dispersion in mineral oil (23 mg, 0.57 mmol) and the mixture was stirred at ambient temperature for 1 hr. Iodomethane (18 µL, 0.29 mmol) was added and stirring was continued overnight. The reaction mixture was diluted with EtOAc and the organic phase was washed with water. The aqueous phase was extracted with EtOAc and the combined organics were washed with water, brine and concentrated in vacuo. The crude product was purified by chromatography on the Biotage Isolera Four™ (25 g column, 0 to 100% EtOAc in heptane) to afford the title compound as an oil (101 mg).

LCMS (Method G): 1.40 min, 363 [M+H]$^+$

Preparation of (S)—N$^1$,N$^2$-dimethyl-N$^1$-(5-(trifluoromethyl)pyrimidin-2-yl)butane-1,2-diamine (Intermediate 33)

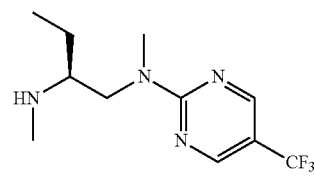 [SMILES: CC[C@@H](CN(C)c1ncc(C(F)(F)F)cn1)NC]

A solution of Intermediate 33b (101 mg, 0.29 mmol) in 4M HCl in dioxane (3 mL, 12 mmol) was stirred at ambient temperature for 2 hrs. The mixture was diluted with EtOAc and washed with 1M sodium hydroxide solution. The organic phase was dried over Na$_2$SO$_4$, filtered and concentrated in vacuo to afford the title compound as an oil (72 mg). The crude product was used without further purification in subsequent reactions.

LCMS (Method G): 0.80 min, 264 [M+H]$^+$

Preparation of (S)-tert-butyl (1-((2-methoxyethyl)(5-(trifluoromethyl)pyrimidin-2-yl)amino)butan-2-yl)(methyl)carbamate (Intermediate 34a)

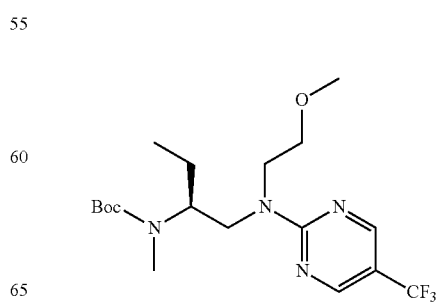

To a solution of Intermediate 33a (100 mg, 0.29 mmol), in anhydrous DMF (3 mL) was added sodium hydride, 60% dispersion in mineral oil (23 mg, 0.57 mmol) and the mixture was stirred at ambient temperature for 1 hr. 1-Bromo-2-methoxyethane (27 µL, 0.29 mmol) was added and stirring was continued overnight. The reaction mixture was diluted with EtOAc and the organic phase was washed with water. The aqueous phase was extracted with EtOAc and the combined organics were washed with water, brine and concentrated in vacuo. The crude product was purified by chromatography on the Biotage Isolera Four™ (25 g column, 0 to 100% EtOAc in heptane) to afford the title compound as an oil (126 mg).

LCMS (Method G): 1.42 min, 408 [M+H]$^+$

Preparation of (S)—N$^1$-(2-methoxyethyl)-N$^2$-methyl-N$^1$-(5-(trifluoromethyl)pyrimidin-2-yl)butane-1,2-diamine (Intermediate 34)

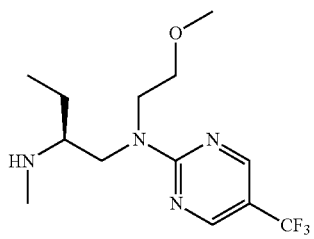 [SMILES: CC[C@@H](CN(CCOC)c1ncc(C(F)(F)F)cn1)NC]

A solution of Intermediate 34b (126 mg, 0.28 mmol) in 4M HCl in dioxane (3 mL, 12 mmol) was stirred at ambient temperature for 2 hrs. The mixture was diluted with EtOAc and washed with 1M sodium hydroxide solution. The organic phase was dried over Na$_2$SO$_4$, filtered and concentrated in vacuo to afford the title compound as an oil (49 mg). The crude product was used without further purification in subsequent reactions.

LCMS (Method G): 0.87 min, 308 [M+H]$^+$

Preparation of (S)-2-(benzylamino)-4,4,4-trifluorobutanamide (Intermediate 35a)

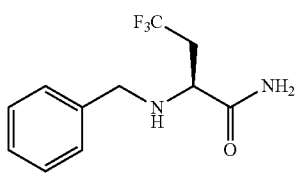

A mixture of (S)-2-amino-4,4,4-trifluorobutanamide hydrochloride (508 mg, 2.6 mmol), benzaldehyde (280 mg, 2.6 mmol) and triethylamine (280 mg, 2.6 mmol) in 2,2,2-trifluoroethanol (10 mL) was heated at 60° C. After 1 hr, NaBH$_4$ (300 mg, 7.9 mmol) was added and the reaction mixture was heated for a further 2 hrs before being allowed to cool to ambient temperature. DCM (20 mL) and water (20 mL) were added and the phases were separated. The organics were dried over MgSO$_4$, filtered and concentrated in vacuo. The residue was purified by dry flash chromatography (0 to 75% EtOAc in heptane) to afford the title compound as a solid (467 mg).

LCMS (Method K): 0.65 min, 247 [M+H]$^+$

Preparation of (S)-2-(benzyl(methyl)amino)-4,4,4-trifluorobutanamide (Intermediate 35b)

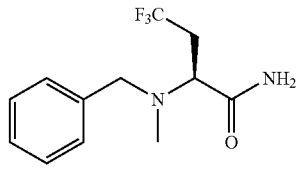 [SMILES: CN(Cc1ccccc1)[C@@H](CC(F)(F)F)C(N)=O]

To a mixture of Intermediate 35a (430 mg, 1.8 mmol), 37% aqueous solution of formaldehyde (106 mg, 3.5 mmol) and AcOH (0.11 mL, 1.8 mmol) in DCM (10 mL) was added NaBH(OAc)$_3$ (0.89 g, 4.2 mmol). The reaction mixture was stirred at ambient temperature for 2.5 hrs. Saturated aqueous NaHCO$_3$ (10 mL) was added and the phases were separated. The organics were dried over MgSO$_4$, filtered and concentrated in vacuo. The residue was purified by dry flash chromatography (0 to 60% EtOAc in heptane) to afford the title compound as an oil (431 mg).

LCMS (Method K): 0.75 min, 261 [M+H]$^+$

Preparation of (S)—N$^2$-benzyl-4,4,4-trifluoro-N$^2$-methylbutane-1,2-diamine (Intermediate 35c)

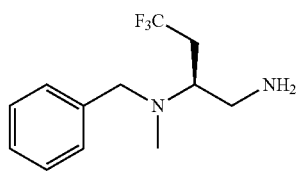 [SMILES: CN(Cc1ccccc1)[C@H](CN)CC(F)(F)F]

LiAlH$_4$ (203 mg, 5.3 mmol) was suspended in THF (8 mL) and heated at 50° C. for 18 hrs. It was then allowed to cool to ambient temperature, and a solution of Intermediate 35b (431 mg, 1.7 mmol) in THF (2 mL) was added. The reaction mixture was heated to 50° C. for 2.5 hrs, and was then cooled in an ice bath. Water (0.25 mL) was added dropwise, followed by 2M sodium hydroxide solution (0.25 mL) and water (0.75 mL). The mixture was stirred for 30 mins, filtered through Celite® and concentrated in vacuo. The residue was purified by dry flash chromatography (0 to 10% ammonia solution in DCM) to afford the title compound as an oil (120 mg).

LCMS (Method L): 2.09 min, 247 [M+H]$^+$

Preparation of (S)—N$^2$-benzyl-4,4,4-trifluoro-N$^2$-methyl-N$^1$-(5-(trifluoromethyl)pyrimidin-2-yl)butane-1,2-diamine (Intermediate 35d)

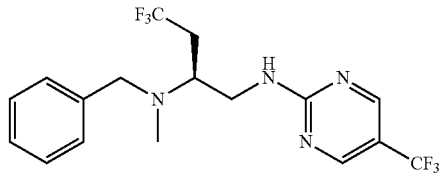 [SMILES: CN(Cc1ccccc1)[C@H](CNc1ncc(C(F)(F)F)cn1)CC(F)(F)F]

A mixture of Intermediate 35c (120 mg, 0.49 mmol), 2-chloro-5-(trifluoromethyl)pyrimidine (93 mg, 0.51 mmol) and DIPEA (0.17 mL, 0.97 mmol) in MeCN (10 mL) was heated at 60° C. for 2 hrs. EtOAc (10 mL) and water (10 mL) were added and the phases were separated. The organics were dried over MgSO$_4$, filtered and concentrated in vacuo. The residue was purified by dry flash chromatography (0 to 30% EtOAc in heptane) to afford the title compound as an oil (153 mg).

LCMS (Method K): 0.99 min, 393 [M+H]$^+$

Preparation of (S)-4,4,4-trifluoro-N$^2$-methyl-N$^1$-(5-(trifluoromethyl)pyrimidin-2-yl)butane-1,2-diamine (Intermediate 35)

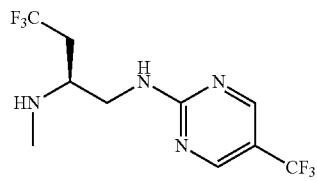

To a solution of Intermediate 35d (153 mg, 0.39 mmol) in methanol (8 mL) was added 10% palladium on charcoal (25 mg). The mixture was stirred under an atmosphere of hydrogen for 18 hrs. Additional 10% palladium on charcoal (50 mg) was added and the mixture stirred under an atmosphere of hydrogen for a further 18 hrs. The reaction mixture was filtered through Celite® and concentrated in vacuo. The residue was purified by dry flash chromatography (0 to 2.5% methanol in EtOAc) to afford the title compound as an oil (70 mg).

LCMS (Method K): 0.75 min, 303 [M+H]$^+$

Preparation of lithium 3-iodo-6-methylpicolinate (Intermediate 36a)

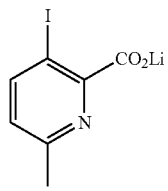

To a solution of methyl 3-iodo-6-methylpicolinate (0.5 g, 1.7 mmol) in methanol (10 mL) and THF (5 mL) was added 1M LiOH (3.4 mL, 3.4 mmol) and the reaction mixture was stirred at ambient temperature for 2 hrs. The reaction mixture was concentrated in vacuo and the residue was azeotroped from methanol (2×10 mL) to afford the title compound as a solid (0.5 g). The crude product was used without further purification in subsequent reactions.

LCMS (Method G): 0.38 min, 264 [M+H]$^+$

Preparation of (S)-3-iodo-N,6-dimethyl-N-(1-((5-(trifluoromethyl)pyrimidin-2-yl)amino)butan-2-yl) picolinamide (Intermediate 36)

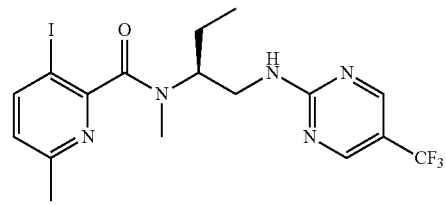 [SMILES: CC[C@@H](CNc1ncc(C(F)(F)F)cn1)N(C)C(=O)c1nc(C)ccc1I]

To a solution of Intermediate 36a (0.5 g, 1.7 mmol) and Intermediate 31 (0.42 g, 1.7 mmol) in DMF (10 mL) was added HATU (0.72 g, 1.88 mmol) followed by DIPEA (0.81 mL, 4.7 mmol) and the reaction mixture was stirred at ambient temperature for 3 days. The mixture was then diluted with EtOAc (80 mL) and washed with water. The organic phase was dried over Na$_2$SO$_4$, filtered and concentrated in vacuo. The crude product was purified by chromatography on the Biotage Isolera Four™ (100 g column, 10 to 100% EtOAc in heptane) to afford the title compound as a gum (0.73 g).

LCMS (Method G): 1.21 min, 495 [M+H]$^+$

Preparation of 2-methyl-5-(2H-1,2,3-triazol-2-yl) pyridine (Intermediate 37a)

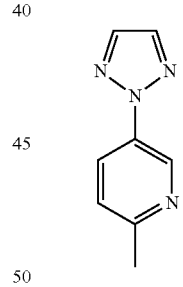

5-Bromo-2-methylpyridine (124 g, 720 mmol), 1H-1,2,3-triazole (210 mL, 3600 mmol), Rac-trans-N,N'-dimethyl-cyclohexane-1,2-diamine (26.0 g, 183 mmol), copper powder (46 g, 720 mmol) and potassium carbonate (200 g, 720 mmol) were combined in NMP (250 mL). The mixture was heated to 120° C. and stirred for 4 hrs. The mixture was allowed to cool to 50-90° C. and diluted with water (600 mL). The mixture was then added to an agitated mixture of water (1900 mL) and concentrated ammonia solution (124 mL). tBME (600 mL) was added and the mixture was stirred for 0.5 hrs and then filtered washing with tBME (300 mL). The biphasic filtrate was separated. The aqueous was extracted with tBME (2×500 mL) and the organics combined and used directly in the next step.

LCMS (Method N): 1.67 min, 161 [M+H]$^+$

Preparation of 2-methyl-5-(2H-1,2,3-triazol-2-yl) pyridine 1-oxide (Intermediate 37b)

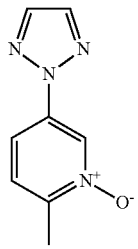

To the Intermediate 37a tBME solution was added 3-chloroperbenzoic acid (577%, 156 g, 670 mmol) and the mixture was stirred overnight at ambient temperature. The mixture was then heated to 45-50° C. Triethylamine (4 mL) was added and the mixture stirred for 15 mins. The mixture was then subjected to azeotropic drying with additions of tBME. The mixture was then cooled to 10-20° C. and the crude solid product was filtered, washed with tBME (300 mL) and dried. The crude product was stirred in IPA (680 mL) and heated to reflux to cause dissolution. The mixture was then allowed to cool to ambient temperature and stirred overnight. The mixture was then cooled to approximately 5° C. and stirred for 0.5 hrs. The mixture was filtered, washed with cold IPA (95 mL) and tBME (160 mL) and dried to afford the title compound as a solid (62.5 g).

LCMS (Method N): 1.56 min, 177 [M+H]$^+$

Preparation of 6-methyl-3-(2H-1,2,3-triazol-2-yl) picolinonitrile (Intermediate 37c)

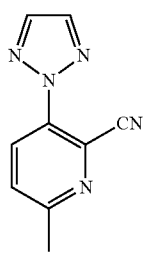

Trimethylsilyl cyanide (56.3 g, 568 mmol) was added to Intermediate 37b (50.0 g, 284 mmol) in DCM (250 mL) at ambient temperature. The mixture was stirred for 1 hr and then cooled to 10° C. Benzoyl chloride (59.8 g, 425 mmol) was added and the mixture was heated to 40° C. and stirred overnight. The mixture was then poured into saturated aqueous NaHCO$_3$ (750 mL). Triethylamine (7.5 mL) was added and the mixture stirred at 40° C. overnight. The aqueous phase was separated and extracted with DCM (100 mL). The combined organics were washed with water (200 mL), dried over Na$_2$SO$_4$, filtered and concentrated to give the crude product. This material was stirred in hexane (504 mL) and ethyl acetate (56 mL) overnight. The product was filtered, washed with hexane (100 mL) and dried to give the title compound as a solid (48.7 g).

LCMS (Method N): 1.99 min, 186 [M+H]$^+$

Preparation of 6-methyl-3-(2H-1,2,3-triazol-2-yl) picolinic Acid Lithium Salt (1:1) (Intermediate 37)

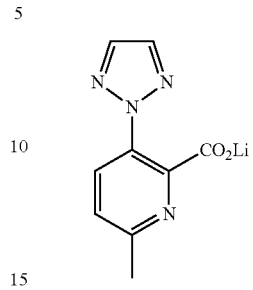

Lithium hydroxide monohydrate (16.5 g, 393 mmol) in water (130 mL) was added to Intermediate 37c (66.1 g, 357 mmol) in warm IPA (460 mL) and the mixture was heated to 80° C. and stirred overnight. The mixture was then subjected to azeotropic drying with additions of IPA. The resulting suspension was stirred overnight at ambient temperature. The product was filtered, washing with with IPA and dried to afford the title compound as a solid (67.8 g).

LCMS (Method N): 1.42 min, 205 [M+H]$^+$

Preparation of 2-fluoro-6-(2H-1,2,3-triazol-2-yl) benzoic Acid (Intermediate 38)

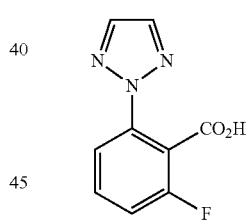

A suspension of 2-fluoro-6-iodobenzoic acid (300 mg, 1.1 mmol), (1R,2R)—N,N'-dimethylcyclohexane-1,2-diamine (32 mg, 0.23 mmol), Cs$_2$CO$_3$ (735 mg, 2.3 mmol), 1H-1,2,3-triazole (0.13 mL, 2.3 mmol), water (0.01 mL) in 1,4-dioxane (5 mL) was degassed under nitrogen for 10 mins. CuI (10.7 mg, 0.06 mmol) was added and the mixture was further degassed under nitrogen for 10 mins. The pressure tube was sealed and the mixture was heated to 100° C. for 18 hrs. After cooling, the reaction mixture was quenched with 13% wt NaCl in 2.5M hydrochloric acid (50 mL) and extracted with EtOAc. The combined organics were dried over MgSO$_4$, filtered and concentrated in vacuo. The crude product was purified by chromatography on the Biotage Isolera Four™ (25 g column, 0 to 75% (10% AcOH in EtOAc) in heptane) to afford the title compound as an oil (140 mg).

$^1$H NMR (250 MHz, MeOD) 7.94 (s, 2H), 7.80 (m, 1H), 7.62 (m, 1H), 7.29 (m, 1H).

Preparation of methyl 6-chloro-3-(2H-1,2,3-triazol-2-yl)picolinate (Intermediate 39a)

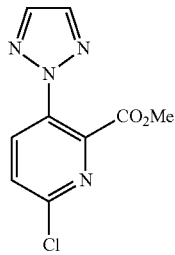

To a stirred suspension of 3-bromo-6-chloropyridine-2-carboxylic acid (3.6 g, 15. mmol) in 1,4-dioxane (35 mL) was added (1R,2R)—N,N'-dimethylcyclohexane-1,2-diamine (220 mg, 1.5 mol), $Cs_2CO_3$ (10 g, 31 mmol), 1H-1,2,3-triazole (2.1 g, 31 mmol), water (0.3 mL) and the mixture was degassed under nitrogen for 10 mins. CuI (295 mg, 1.6 mmol) was added and the mixture was heated at 100° C. for 6 hrs. The reaction mixture was then allowed to cool to ambient temperature, and concentrated in vacuo. MeOH (20 mL) was added to the residue and the mixture was acidified to pH 2 with 6N hydrochloric acid (approx 6 mL) and concentrated in vacuo. MeOH (20 mL) was added to the residue and concentrated in vacuo (×2). The residue was dissolved in MeOH (15 mL) and DCM (35 mL) and cooled to 0° C. TMS diazomethane (39 mL, 77 mmol) was added dropwise (over 15 mins) and the reaction mixture was stirred at ambient temperature for 18 hrs. The reaction mixture was concentrated in vacuo. The crude product was purified by chromatography on the Biotage Isolera Four™ (100 g column, 10 to 80% EtOAc in heptane) to afford the title compound as an oil (1.8 g).

LCMS (Method G): 1.03 min, 239 $[M+H]^+$

Preparation of sodium 6-methoxy-3-(2H-1,2,3-triazol-2-yl)picolinate (Intermediate 39)

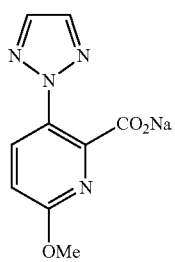

A suspension of Intermediate 39a (100 mg, 0.38 mmol) in a solution of NaOMe (5.4 M in MeOH; 2 mL, 10.8 mmol) was heated in a microwave reactor for 10 mins at 100° C. The reaction mixture was concentrated in vacuo to afford the title compound as a solid (110 mg). The crude product was used without further purification in subsequent reactions.

$^1$H NMR (250 MHz, DMSO-$d_6$) 8.12 (s, 2H), 8.05 (d, 1H), 6.99 (d, 1H), 4.08 (s, 3H).

Synthesis of Examples

Route 1: Typical Procedure for the Preparation of Examples by Reductive Amination as Exemplified by the Preparation of (S)—N-(1-((5-chloropyridin-2-yl)amino)butan-2-yl)-N,5-dimethyl-2-(2H-1,2,3-triazol-2-yl)benzamide (Example 1)

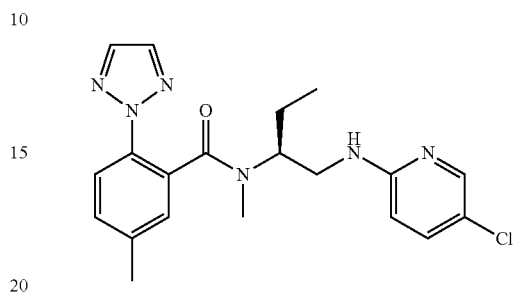

$NaHCO_3$ (0.26 g, 3.1 mmol), Intermediate 1 (0.60 g, 2.1 mmol) and Dess-Martin periodinane (0.97 g, 2.3 mmol) was stirred in anhydrous DCM (10 mL) for 2 hrs. The reaction mixture was diluted with diethyl ether, saturated aqueous $NaHCO_3$ and saturated aqueous sodium thiosulfate. After vigorous agitation for 1 hr the two layers were separated and the aqueous extracted with diethyl ether. The combined organics were washed with saturated aqueous $NaHCO_3$ and brine, dried over $MgSO_4$, filtered and concentrated in vacuo. The residue was dissolved in DCE (10 mL), 5-chloropyridin-2-amine (0.27 g, 2.1 mmol) and $NaBH(OAc)_3$ (0.88 g, 4.2 mmol) were added and the reaction mixture was stirred at ambient temperature for 18 hrs. The reaction mixture was purified by ion-exchange chromatography using an SCX resin cartridge (10 g column, washing with methanol, then eluting with 2% methanolic ammonia). The crude product was further purified by preparative HPLC (Waters, Acidic (0.1% Formic acid), Waters X-Bridge Prep-C18, 5 μm, 19×50 mm column, 40 to 80% MeCN in Water) to afford the title compound as a solid (145 mg).

LCMS (Method A): 2.11 min, 399 $[M+H]^+$ $^1$H NMR (400 MHz, DMSO-$d_6$, 375 K) 8.03-7.89 (m, 3H), 7.79 (bd, 0.15H), 7.77-7.66 (m, 1H), 7.43 (dd, 0.85H), 7.40-7.24 (m, 1.3H), 6.98 (bs, 0.85H), 6.58 (d, 0.85H), 6.44 (bs, 0.15H), 6.31 (bs, 0.85H), 4.56 (m, 1H), 3.47 (m, 2H), 3.16 (m, 0.15H), 2.84 (s, 0.45H), 2.64 (m, 2.55H), 2.38 (s, 2.7H), 2.19 (m, 0.3H), 1.63 (m, 1.7H), 0.97 (t, 3H), 0.67 (bs, 0.15H).

Preparation of (S)—N-(1-((5-chloropyridin-2-yl)amino)butan-2-yl)-5-methyl-2-(2H-1,2,3-triazol-2-yl)benzamide (Example 2)

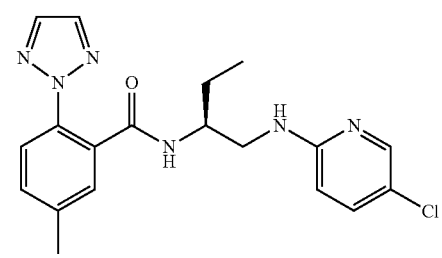 [SMILES: CC[C@@H](CNc1ccc(Cl)cn1)NC(=O)c1cc(C)ccc1-n1nccn1]

The title compound (98 mg) was prepared as a solid from Intermediate 1 (0.65 g, 2.4 mmol) and 5-chloropyridin-2-amine (0.30 g, 2.4 mmol) using the method described for Route 1. The crude product was purified by recrystallization from MeCN.

LCMS (Method A): 1.73 min, 385/387 [M+H]$^+$ $^1$H NMR (400 MHz, DMSO-d$_6$, 289 K) 8.16 (d, 1H), 7.98 (s, 2H), 7.96 (d, 1H), 7.64 (d, 1H), 7.47-7.38 (m, 2H), 7.25 (d, 1H), 6.65 (t, 1H), 6.54 (d, 1H), 3.88 (m, 1H), 3.31 (m, 2H), 2.39 (s, 3H), 1.54 (m, 1H), 1.42 (m, 1H), 0.90 (t, 3H).

Preparation of (S)—N-(1-((5-chloropyridin-2-yl)amino)butan-2-yl)-N-methyl-[1,1'-biphenyl]-2-carboxamide (Example 3)

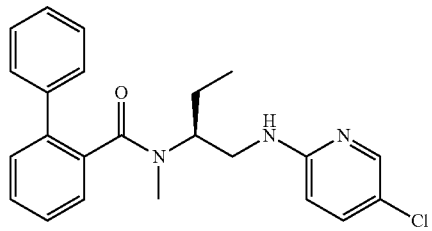 [SMILES: CC[C@@H](CNc1ccc(Cl)cn1)N(C)C(=O)c1ccccc1-c1ccccc1]

The title compound (63 mg) was prepared as a gum from Intermediate 2 (0.50 g, 1.8 mmol) and 5-chloropyridin-2-amine (0.23 g, 1.8 mmol) using the method described for Route 1. The crude product was purified by chromatography on the Biotage Companion™ (40 g column, gradient 0 to 100% EtOAc in isohexane).

LCMS (Method A): 2.33 min, 394/396 [M+H]$^+$ $^1$H NMR (400 MHz, DMSO-d$_6$, 374 K) 7.94 (bs, 0.62H), 7.76 (bs, 0.29H), 7.55-7.27 (m, 9.4H), 7.21-7.02 (m, 1.21H), 6.51 (d, 0.48H), 6.40 (bd, 0.32H), 6.17 (bs, 0.68H), 4.50 (bm, 0.82H), 3.30 (bm, 1.82H), 2.93 (bs, 0.85H), 2.71 (s, 1.15H), 2.56 (bm, 0.18H), 2.47-2.40 (m, 2.05H), 1.48 (bm, 0.59H), 1.34 (bm, 0.54H), 0.62 (bt, 1.95H), 0.46 (bs, 1.05H).

Preparation of (S)—N-(1-((5-chloropyridin-2-yl)amino)-3-methylbutan-2-yl)-[1,1'-biphenyl]-2-carboxamide (Example 4)

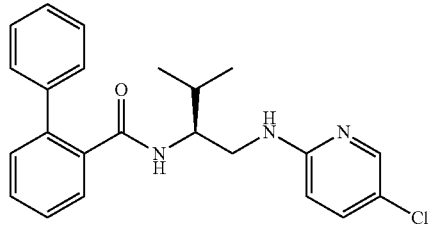

The title compound (0.10 g) was prepared as a glass from Intermediate 3 (0.27 g, 0.96 mmol) and 5-chloropyridin-2-amine (0.13 g, 0.98 mmol) using the method described for Route 1. The crude product was purified by chromatography on the Biotage Companion™ (40 g column, diethyl ether).

LCMS (Method A): 2.31 min, 394/396 [M+H]$^+$ $^1$H NMR (400 MHz, DMSO-d$_6$) 7.98 (d, 1H), 7.94 (dd, 1H), 7.52-7.46 (td, 1H), 7.46-7.27 (m, 9H), 6.56 (t, 1H), 6.53 (dd, 1H), 3.86 (m, 1H), 3.36-3.28 (m, 1H), 3.19 (m, 1H), 1.75 (m, 1H), 0.77 (t, 6H).

Preparation of (S)—N-(1-((5-chloropyridin-2-yl)amino)-4-methylpentan-2-yl)-[1,1'-biphenyl]-2-carboxamide (Example 5)

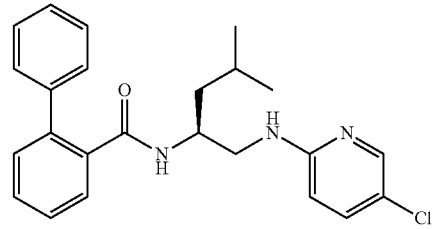 [SMILES: CC(C)C[C@@H](CNc1ccc(Cl)cn1)NC(=O)c1ccccc1-c1ccccc1]

The title compound (0.91 g) was prepared as a glass from Intermediate 4 (0.10 g, 0.31 mmol) and 5-chloropyridin-2-amine (65 mg, 0.51 mmol) using the method described for Route 1. The crude product was purified by chromatography on the Biotage Companion™ (12 g column, 10 to 40% EtOAc in isohexane).

LCMS (Method A): 2.41 min, 408/410 [M+H]$^+$ $^1$H NMR (400 MHz, DMSO-d$_6$) 7.93 (dd, 1H), 7.58 (dd, 1H), 7.47 (td, 1H), 7.43-7.29 (m, 8H), 6.34 (d, 1H), 5.34 (d, 1H), 5.04 (bt, 1H), 4.14 (m, 1H), 3.17 (m, 2H), 1.25 (m, 1H), 1.15 (m, 1H), 1.00 (m, 1H), 0.80 (d, 3H), 0.79 (d, 3H), Preparation of (S)—N-(1-((5-chloropyridin-2-yl)amino)-3-methylbutan-2-yl)-2-methyl-4-phenylthiazole-5-carboxamide (Example 6)

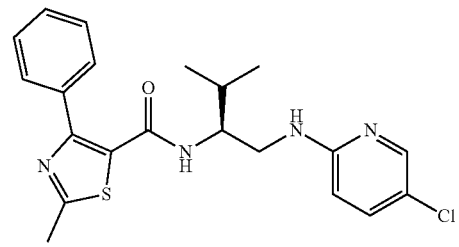 [SMILES: Cc1nc(-c2ccccc2)c(C(=O)N[C@H](CNc2ccc(Cl)cn2)C(C)C)s1]

The title compound (53 mg) was prepared as a glass from Intermediate 5 (0.20 g, 0.66 mmol) and 5-chloropyridin-2-amine (68 mg, 0.53 mmol) using the method described for Route 1. The crude product was purified by chromatography on the Biotage Companion™ (40 g column, 10 to 40% EtOAc in isohexane) then further purified by chromatography on the Biotage Companion™ (40 g column, diethyl ether).

LCMS (Method A): 2.17 min, 415/417 [M+H]$^+$ $^1$H NMR (400 MHz, DMSO-d$_6$) 8.04 (d, 1H), 7.92 (dd, 1H), 7.67-7.72 (m, 2H), 7.43 (dd, 1H), 7.39-7.34 (bm, 3H), 6.67 (t, 1H), 6.54 (dd, 1H), 3.97 (m, 1H), 3.37 (m, 1H), 3.24 (m, 1H), 2.69 (s, 3H), 1.81 (m, 1H), 0.87 (d, 3H), 0.80 (d, 3H).

Preparation of (S)—N-(1-((5-chloropyridin-2-yl)amino)-4-methylpentan-2-yl)-2-methyl-4-phenylthiazole-5-carboxamide (Example 7)

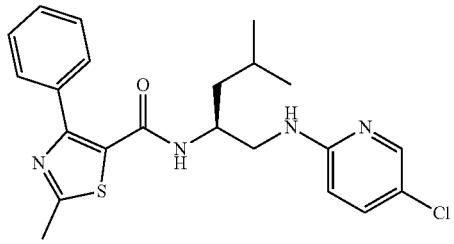

The title compound (71 mg) was prepared as a gum from Intermediate 6 (0.26 g, 0.82 mmol) and 5-chloropyridin-2-amine (0.11 g, 0.88 mmol) using the method described for Route 1. The crude product was purified by chromatography on the Biotage Companion™ (40 g column, diethyl ether).

LCMS (Method A): 2.32 min, 429 [M+H]$^+$ $^1$H NMR (400 MHz, DMSO-d$_6$) 7.85 (d, 1H), 7.59 (dd, 1H), 7.39-7.32 (m, 2H), 7.10 (dd, 1H), 7.06-6.99 (m, 3H), 6.45 (t, 1H), 6.20 (dd, 1H), 3.82 (bm, 1H), 2.94 (m, 2H), 2.37 (s, 3H), 1.23 (m, 1H), 1.02 (m, 1H), 0.92 (m, 1H), 0.53 (d, 6H).

Preparation of (S)—N-(1-((5-chloropyridin-2-yl)amino)-4-methylpentan-2-yl)-N-methyl-[1,1'-biphenyl]-2-carboxamide (Example 8)

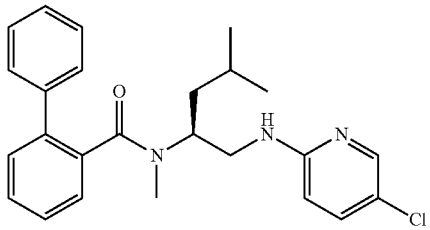 [SMILES: CC(C)C[C@@H](CNc1ccc(Cl)cn1)N(C)C(=O)c1ccccc1-c1ccccc1]

The title compound (94 mg) was prepared from Intermediate 7 (0.46 g, 1.47 mmol) and 5-chloropyridin-2-amine (0.17 g, 1.32 mmol) using the method described for Route 1. The crude product was purified by chromatography on the Biotage Companion™ (12 g column, diethyl ether).

LCMS (Method A): 2.72 min, 422/424 [M+H]$^+$ $^1$H NMR (400 MHz, DMSO-d$_6$) 8.15-8.04 (m, 0.61H), 7.96 (d, 0.05H), 7.79 (d, 0.12H), 7.73-7.43 (m, 9.76H), 7.40 (bm, 0.12H), 7.14-7.04 (m, 0.6H), 7.00 (bt, 0.54H), 6.94 (td, 0.13H), 6.86 (dd, 0.15H), 6.79 (bm, 0.05H), 6.72 (d, 0.65H), 6.62 (bd, 0.12H), 6.53 (d, 0.05H), 6.35 (bm, 0.05H), 4.97 (bm, 0.6H), 4.80 (bs, 0.05H), 3.63-3.45 (m, 1H), 3.38 (m, 0.84H), 3.13 (m, 0.15H), 3.00 (m, 0.18H), 2.89 (s, 0.6H), 2.84 (s, 0.15H), 2.61 (s, 0.45H), 2.46 (s, 1.8H), 1.84 (bm, 0.12H), 1.65 (bm, 0.21H), 1.42 (bm, 0.3H), 1.32 (bm, 0.87H), 1.15 (bm, 0.6H), 1.04 (bm, 0.87H), 0.94-0.79 (m, 4.08H), 0.79-0.70 (dd, 1.8H), 0.67 (d, 0.15H), −0.00 (m, 0.18H).

Preparation of (S)—N-(1-((5-chloropyridin-2-yl)amino)-4-methyl pentan-2-yl)-N,2-dimethyl-4-phenylthiazole-5-carboxamide (Example 9)

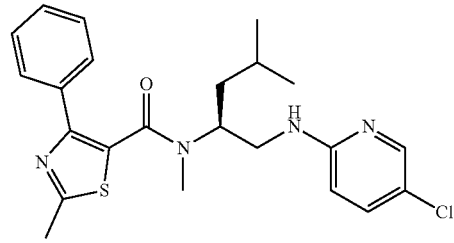 [SMILES: Cc1nc(-c2ccccc2)c(C(=O)N(C)[C@H](CNc2ccc(Cl)cn2)CC(C)C)s1]

The title compound (69 mg) was prepared as a gum from (Intermediate 8 (0.26 g, 0.8 mmol) and 5-chloropyridin-2-amine (94 mg, 0.73 mmol) using the method described for Route 1. The crude product was purified by chromatography on the Biotage Companion™ (12 g column, diethyl ether), and then further purified by chromatography on the Biotage Companion™ (12 g column, tBME).

LCMS (Method A): 2.60 min, 443/445 [M+H]$^+$ $^1$H NMR (400 MHz, DMSO-d$_6$) 7.94 (dd, 0.5H), 7.75 (dd, 0.5H), 7.69-7.63 (m, 2H), 7.47-7.40 (m, 2H), 7.40-7.32 (m, 2H), 6.96 (t, 0.5H), 6.86 (t, 0.5H), 6.53 (dd, 0.5H), 6.48 (dd, 0.5H), 4.90 (bm, 0.5H), 3.81 (m, 0.5H), 3.50-3.42 (m, 0.5H), 3.42-3.35 (m, 0.5H), 3.27 (m, 0.5H), 2.93 (m, 0.5H), 2.89 (s, 1H), 2.69 (s, 1H), 2.53 (s, 1.5H), 2.52 (s, 1.5H), 1.48 (m, 0.5H), 1.41-1.15 (m, 2H), 0.94 (d, 1.5H), 0.88 (d, 1.5H), 0.56 (m, 0.5H), 0.51 (d, 2H), 0.45 (d, 2H).

Preparation of (S)—N-(1-((5-chloropyridin-2-yl)amino)-3-methylbutan-2-yl)-N-methyl-[1,1'-biphenyl]-2-carboxamide (Example 10)

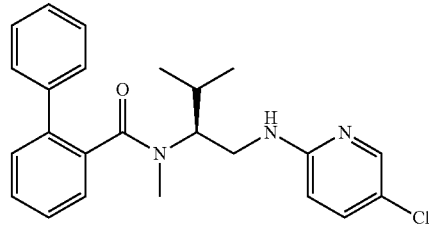 [SMILES: CC(C)[C@@H](CNc1ccc(Cl)cn1)N(C)C(=O)c1ccccc1-c1ccccc1]

The title compound (52 mg) was prepared from Intermediate 9 (0.38 g, 1.3 mmol) and 5-chloropyridin-2-amine (94 mg, 0.73 mmol) using the method described for Route 1. The crude product was purified by chromatography on the Biotage Companion™ (12 g column, tBME).

LCMS (Method A): 2.58 min, 408/410 [M+H]$^+$ $^1$H NMR (400 MHz, DMSO-d$_6$) 7.68 (d, 0.82H), 7.60 (bd, 0.18H), 7.54 (d, 0.18H), 7.38 (dd, 0.18H), 7.30 (bdd, 0.18H), 7.28-6.98 (m, 8.82H), 6.77-6.66 (m, 0.82H), 6.58-6.47 (bm, 0.82H), 6.34-6.19 (bm, 0.82H), 6.10 (bd, 0.18H), 4.09 (bm, 0.36H), 3.92 (bs, 0.18H), 3.39-3.20 (bm, 0.82H), 3.10-3.01 (bm, 0.82H), 2.83-2.82 (m, 0.18H), 2.66-2.59 (td, 0.18H), 2.51 (s, 0.36H), 2.12 (s, 2.02H), 1.72 (bs, 0.18H), 1.32 (b, 0.82H), 1.11-1.04 (bm, 0.18H), 1.00 (bm, 0.18H), 0.74 (bs, 0.36H), 0.66 (d, 2.46H), 0.55 (bs, 0.18H), 0.49 (bm, 0.18H), 0.42 (d, 0.54H), −0.01 (d, 2.46H), −0.42 (d, 0.54H).

Preparation of (S)—N-(1-((5-chloropyridin-2-yl)amino)-3-methylbutan-2-yl)-N,2-dimethyl-4-phenylthiazole-5-carboxamide (Example 11)

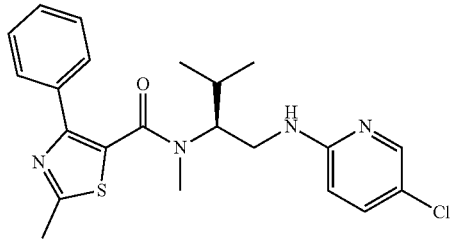

The title compound (45 mg) was prepared as a gum from Intermediate 10 (0.40 g, 1.26 mmol) and 5-chloropyridin-2-amine (98 mg, 0.77 mmol) using the method described for Route 1. The crude product was purified by chromatography on the Biotage Companion™ (12 g column, tBME).

LCMS (Method A): 2.40 min, 429/431 [M+H]$^+$ $^1$H NMR (400 MHz, DMSO-d$_6$, 374 K) 7.93 (bs, 1H), 7.79-7.67 (m, 2H), 7.46-7.28 (m, 4H), 6.64-6.36 (bs, 1H), 6.33-6.13 (bm, 1H), 4.42 (bs, 0.5H), 3.61-3.41 (m, 2H), 2.67 (bs, 6H), 1.91 (bs, 0.5H), 1.15-0.68 (bm, 6H), 0.46 (bm, 1H).

Preparation of (S)—N-(1-((5-chloropyridin-2-yl)amino)-3,3-dimethylbutan-2-yl)-N-methyl-[1,1'-biphenyl]-2-carboxamide (Example 12)

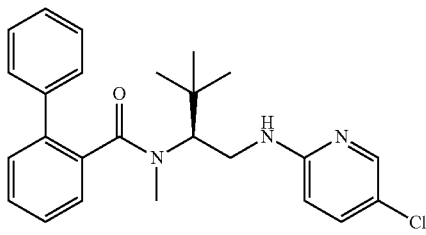

The title compound (59 mg) was prepared as a solid from Intermediate 11 (0.30 g, 0.95 mmol) and 5-chloropyridin-2-amine (0.12 g, 0.92 mmol) using the method described for Route 1. The crude product was purified by preparative HPLC (Waters, Acidic (0.1% Formic acid), Waters X-Bridge Prep-C18, 5 μm, 19×50 mm column, 5 to 95% MeCN in Water).

LCMS (Method A): 2.71 min, 422 [M+H]$^+$ $^1$H NMR (400 MHz, DMSO-d$_6$, 374 K) 8.40 (s, 0.1H), 7.98 (bm, 0.1H), 7.94 (d, 0.9H), 7.89 (bm, 0.1H), 7.83 (bm, 0.1H), 7.58 (bm, 0.2H), 7.50-7.24 (m, 9.4H), 7.07 (bs, 0.9H), 6.52 (d, 0.9H), 5.99 (bm, 0.3H), 4.68 (bs, 0.9H), 3.65-3.39 (m, 1.8H), 2.96 (bs, 0.1H), 2.84 (bs, 0.1H), 2.60 (bs, 0.1H), 2.55 (bs, 2.7H), 2.46 (bs, 0.3H), 0.85 (bs, 8.1H), 0.62 (bs, 0.9H).

Preparation of (S)—N-(2-((5-chloropyridin-2-yl)amino)-1-cyclopropylethyl)-N-methyl-[1,1'-biphenyl]-2-carboxamide (Example 13)

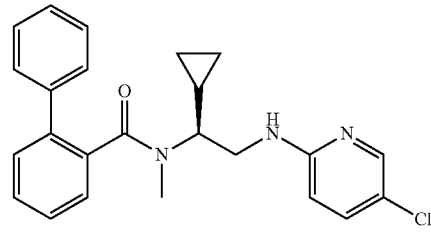 [SMILES: CN(C(=O)c1ccccc1-c1ccccc1)[C@H](CNc1ccc(Cl)cn1)C1CC1]

The title compound (0.16 g) was prepared from Intermediate 12 (0.67 g, 2.3 mmol) and 5-chloropyridin-2-amine (0.29 g, 2.3 mmol) using the method described for Route 1. The crude product was purified by preparative HPLC (Waters, Acidic (0.1% Formic acid), Waters X-Bridge Prep-C18, 5 μm, 19×50 mm column, 5 to 95% MeCN in Water).

LCMS (Method A): 2.38 min, 406 [M+H]$^+$ $^1$H NMR (400 MHz, DMSO-d$_6$, 374 K) 8.05 (s, 0.2H), 7.72 (s, 0.8H), 7.55 (s, 0.2H), 7.35-7.06 (m, 9H), 6.92 (m, 1H), 6.29 (d, 0.8H), 6.12 (bd, 0.2H), 5.95 (bs, 0.8H), 3.63 (m, 0.8H), 3.25 (m, 2H), 3.08 (bm, 0.2H), 2.68 (bm, 1H), 2.65 (bs, 0.6H), 2.35 (s, 2.4H), 0.66 (bm, 0.8H), 0.28 (m, 1H), 0.04 (m, 1.2H), −0.30 (bm, 1H).

Preparation of (S)—N-(1-((5-chloropyridin-2-yl)amino)propan-2-yl)-N-methyl-[1,1'-biphenyl]-2-carboxamide (Example 14)

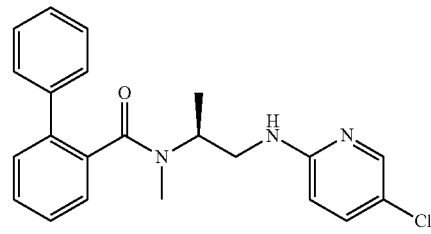 [SMILES: C[C@@H](CNc1ccc(Cl)cn1)N(C)C(=O)c1ccccc1-c1ccccc1]

The title compound (0.17 g) was prepared as a gum from Intermediate 13 (0.48 g, 1.8 mmol) and 5-chloropyridin-2-amine (0.23 g, 1.8 mmol) using the method described for Route 1. The crude product was purified by chromatography on the Biotage Companion™ (40 g column, 0 to 100% EtOAc in isohexane).

LCMS (Method A): 2.09 min, 380/382 [M+H]$^+$ $^1$H NMR (400 MHz, DMSO-d$_6$, 374 K) 7.93 (bs, 0.4H), 7.71 (bs, 0.49H), 7.54-7.28 (m, 8.58H), 7.22 (bm, 0.76H), 7.04 (bm, 0.78H), 6.52 (bd, 0.49H), 6.40 (bd, 0.68H), 6.22 (bs, 0.82H), 4.65 (bm, 0.45H), 3.60 (bm, 0.64H), 3.27 (bm, 0.74H), 3.12 (bm, 0.46H), 3.04-2.85 (bm, 0.82H), 2.70 (bs, 1.2H), 2.55 (m, 0.18H), 2.46 (bs, 0.3H), 2.42 (bs, 1.02H), 0.91 (bm, 1.9H), 0.32 (bs, 1.29H).

Preparation of (S)—N-(1-((5-chloropyridin-2-yl)amino)-3-methylbutan-2-yl)-N-cyclopropyl-[1,1'-biphenyl]-2-carboxamide (Example 15)

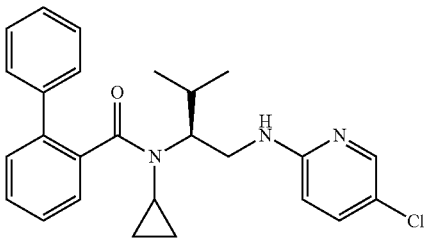 [SMILES: CC(C)[C@@H](CNc1ccc(Cl)cn1)N(C(=O)c1ccccc1-c1ccccc1)C1CC1]

The title compound (0.12 g) was prepared as a gum from Intermediate 14 (0.36 g, 1.1 mmol) and 5-chloropyridin-2-amine (0.14 g, 1.1 mmol) using the method described for Route 1. The crude product was purified by chromatography on the Biotage Companion™ (40 g column, 0 to 70% EtOAc in isohexane).

LCMS (Method A): 2.79 min, 434/436 [M+H]$^+$ $^1$H NMR (400 MHz, DMSO-d$_6$, 374 K) 7.94 (d, 1H), 7.54-7.28 (m, 10H), 6.45 (d, 1H), 5.91 (bs, 1H), 3.74-3.48 (bm, 3H), 2.30-2.11 (m, 2H), 0.95 (d, 3H), 0.57 (d, 3H), 0.37-0.15 (m, 4H).

Route 2: Typical Procedure for the Preparation of Examples by Amide Coupling as Exemplified by the Preparation of (S)-5-chloro-N-(1-((5-chloropyridin-2-yl)amino)butan-2-yl)-N-methyl-2-(2H-1,2,3-triazol-2-yl)benzamide (Example 16)

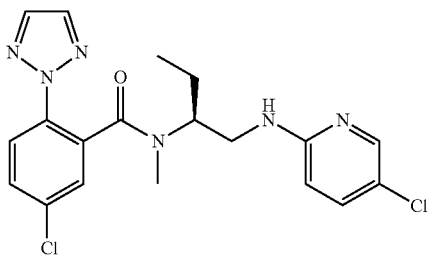

To a solution of 5-chloro-2-(2H-1,2,3-triazol-2-yl)benzoic acid (91 mg, 0.41 mmol) [prepared as described in WO 2011/050198], Intermediate 15 (0.12 g, 0.37 mmol) and DIPEA (0.32 mL, 1.8 mmol) in anhydrous DMF (2 mL) was added HATU (0.15 g, 0.41 mmol) and the reaction mixture was stirred overnight. The reaction mixture was concentrated in vacuo and the residue dissolved in methanol (10 ml). It was purified by ion-exchange chromatography using an SCX resin cartridge (2 g column, washing with 10 column volumes of methanol, then eluting with 2% methanolic ammonia). The crude product was further purified by chromatography on the Biotage Companion™ (12 g column, 0 to 5% ammonia solution in DCM) to afford the title compound (43 mg).

LCMS (Method A): 2.26 min, 419/421 [M+H]$^+$ $^1$H NMR (400 MHz, DMSO-d$_6$) 8.11 (m, 1.21H), 8.06 (s, 0.76H), 8.00 (bm, 0.18H), 7.96 (bd, 0.42H), 7.89 (bd, 0.42H), 7.77 (d, 0.29H), 7.72 (d, 0.33H), 7.71-7.61 (m, 0.65H), 7.51-7.37 (m, 1.4H), 7.27 (dd, 0.1H), 7.04 (d, 0.9H), 6.98 (m, 0.65H), 6.88 (s, 0.1H), 6.65 (s, 0.1H), 6.64-6.53 (bm, 0.84H), 6.49 (d, 0.35H), 6.45 (dd, 0.1H), 6.23 (d, 0.1H), 6.13 (bs, 0.1H), 4.62 (bm, 0.48H), 4.45 (bs, 0.12H), 3.63 (bs, 0.1H), 3.56-3.35 (m, 1.65H), 3.32-3.31 (m, 0.9H), 3.12-2.95 (m, 0.4H), 2.87 (s, 0.24H), 2.80 (s, 0.75H), 2.66 (s, 1.59H), 1.64 (bm, 0.27H), 1.55 (m, 0.87H), 1.36 (s, 0.42H), 1.27 (m, 0.3H), 0.95 (t, 1.65H), 0.83 (t, 0.21H), 0.75 (m, 0.27H), 0.47 (t, 0.78H).

Preparation of (S)—N-(1-((5-chloropyridin-2-yl)amino)butan-2-yl)-N-methyl-2-(2H-1,2,3-triazol-2-yl)-5-(trifluoromethyl)benzamide (Example 17)

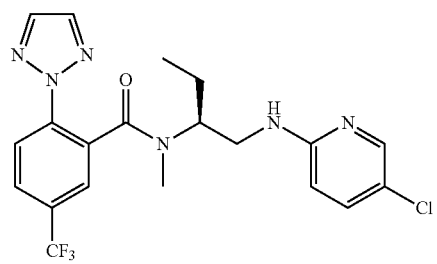 [SMILES: CC[C@@H](CNc1ccc(Cl)cn1)N(C)C(=O)c1cc(C(F)(F)F)ccc1-n1nccn1]

The title compound (39 mg) was prepared as a gum from 2-(2H-1,2,3-triazol-2-yl)-5-(trifluoromethyl)benzoic acid (50 mg, 0.19 mmol) [prepared as described in WO 2012/085857] and Intermediate 15 (63 mg, 0.19 mmol) using the method described for Route 2. The crude product was purified by chromatography on the Biotage Companion™ (12 g column, 0 to 10% methanol in DCM).

LCMS (Method A): 2.41 min, 453/455 [M+H]$^+$ $^1$H NMR (400 MHz, DMSO-d$_6$) 8.34 (dd, 0.12H), 8.16-8.11 (m, 0.88H), 8.07-7.92 (s, 0.25H), 8.14 (m, 1.44H), 8.00 (m, 1.64H), 7.82 (ddd, 0.25H), 7.71 (bs, 0.12H), 7.69 (d, 0.27H), 7.65 (bd, 0.12H), 7.60 (dd, 0.10H), 7.51-7.38 (m, 1.44H), 7.35 (dd, 0.25H), 7.26 (dd, 0.10H), 7.03 (t, 0.51H), 6.91 (t, 0.24H), 6.70-6.95 (m, 0.23H), 6.57 (dd, 0.65H), 6.44 (dd, 0.25H), 6.21 (dd, 0.14H), 4.67 (bm, 0.59H), 4.48 (bm, 0.16H), 3.64-3.35 (m, 1.71H), 3.26-3.11 (m, 0.45H), 3.06 (m, 0.26H), 2.91 (s, 0.30H), 2.84 (s, 0.75H), 2.64 (m, 1.95H), 1.67 (m, 0.33H), 1.56 (m, 1.25H), 1.30 (m, 0.25H), 0.99 (m, 1.95H), 0.81 (m, 0.30H), 0.46 (t, 0.75H).

Preparation of (S)—N-(1-((5-chloropyridin-2-yl)amino)butan-2-yl)-5-fluoro-N-methyl-2-(2H-1,2,3-triazol-2-yl)benzamide (Example 18)

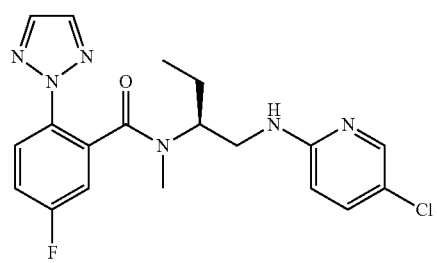 [SMILES: CC[C@@H](CNc1ccc(Cl)cn1)N(C)C(=O)c1cc(F)ccc1-n1nccn1]

The title compound (115 mg) was prepared as a gum from 5-fluoro-2-(2H-1,2,3-triazol-2-yl)benzoic acid (75 mg, 0.33 mmol) [prepared as described in WO 2012/145581 and Intermediate 15 (70 mg, 0.36 mmol) using the method described for Route 2. The crude product was purified by chromatography on the Biotage Companion™ (12 g column, 0 to 60% EtOAc in isohexane).

LCMS (Method A): 2.09 min, 403/405 [M+H]+

$^{1}$H NMR (400 MHz, DMSO-d$_{6}$) 8.09 (bm, 1.12H), 8.03 (bs, 0.8H), 7.96 (bs, 0.5H), 7.88 (bm, 0.52H), 7.76 (dd, 0.42H), 7.70 (d, 0.4H), 7.53-7.34 (bm, 1.62H), 7.34-7.19 (bm, 0.83H), 6.96 (bm, 1.27H), 6.80 (dd, 0.85H), 6.58 (d, 0.28H), 6.48 (d, 0.28H), 6.25 (d, 0.11H), 4.61 (t, 0.45H), 4.46 (bs, 0.10H), 3.64 (bs, 0.15H), 3.41 (m, 1.32H), 3.29 (m, 0.63H), 3.10-2.84 (m, 0.45H), 2.85 (s, 0.10H), 2.79 (s, 0.81H), 2.70 (s, 0.36H), 2.67 (bs, 1.73H), 1.72-1.46 (m, 1.30H), 1.35-1.20 (m, 0.45H), 0.93 (t, 1.73H), 0.84 (bt, 0.32H), 0.74 (m, 0.25H), 0.48 (t, 0.85H).

Preparation of (S)-5-bromo-N-(1-((5-chloropyridin-2-yl)amino)butan-2-yl)-N-methyl-2-(2H-1,2,3-triazol-2-yl)benzamide (Example 19)

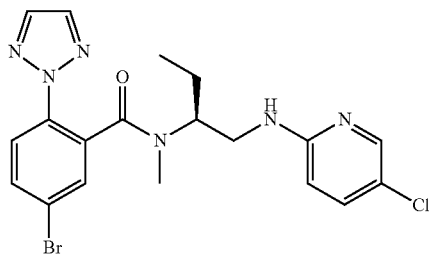

The title compound (59 mg) was prepared as a gum from 5-bromo-2-(2H-1,2,3-triazol-2-yl)benzoic acid (97 mg, 0.36 mmol) [prepared as described in WO 2008/147518] and Intermediate 15 (70 mg, 0.33 mmol) using the method described for Route 2. The crude product was purified by chromatography on the Biotage Companion™ (12 g column, 0 to 70% EtOAc in isohexane).

LCMS (Method A): 2.36 min, 463/465 [M+H]+

$^{1}$H NMR (400 MHz, DMSO-d$_{6}$) 8.16-8.11 (m, 0.82H), 8.10 (s, 0.15H), 8.09-7.99 (m, 1H), 7.96 (m, 0.52H), 7.92 (bd, 0.07H), 7.86-7.73 (m, 1.44H), 7.71 (d, 0.28H), 7.65 (d, 0.07H), 7.61 (dd, 0.28H), 7.58 (bs, 0.12H), 7.50 (d, 0.09H), 7.49-7.39 (m, 1H), 7.27 (dd, 0.06H), 7.23-7.18 (m, 0.85H), 7.02-6.92 (m, 0.92H), 6.63-6.53 (d, 1H), 6.49 (d, 0.24H), 6.23 (d, 0.09H), 4.62 (bm, 0.51H), 4.45 (bm, 0.2H), 3.63 (bm, 0.06H), 3.56-3.33 (m, 1.35H), 3.28 (m, 0.28H), 3.23-3.07 (bm, 0.21H), 3.02 (m, 0.27H), 2.87 (s, 0.18H), 2.80 (s, 0.81H), 2.70 (s, 0.21H), 2.66 (bs, 1.86H), 1.65 (bm, 0.3H), 1.55 (m, 0.99H), 1.34-1.21 (m, 0.5H), 0.99-0.91 (t, 1.92H), 0.84 (m, 0.27H), 0.76 (m, 0.29H), 0.47 (t, 0.79H).

Preparation of (S)—N-(1-((5-chloropyridin-2-yl)amino)butan-2-yl)-N-methyl-2-(2H-1,2,3-triazol-2-yl)-5-(trifluoromethoxy)benzamide (Example 20)

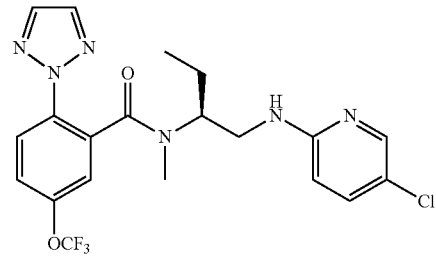 [SMILES: CC[C@@H](CNc1ccc(Cl)cn1)N(C)C(=O)c1cc(OC(F)(F)F)ccc1-n1nccn1]

The title compound (110 mg) was prepared as a solid from 2-(2H-1,2,3-triazol-2-yl)-5-(trifluoromethoxy)benzoic acid (98 mg, 0.36 mmol) [prepared as described in WO 2012/085857] and Intermediate 15 (70 mg, 0.33 mmol) using the method described for Route 2. The crude product was purified by chromatography on the Biotage Companion™ (12 g column, 0 to 60% EtOAc in isohexane).

LCMS (Method A): 2.47 min, 469/471 [M+H]+

$^{1}$H NMR 400 MHz, DMSO-d$_{6}$) 8.18 (d, 0.11H), 8.13 (m, 0.82H), 8.12-8.05 (m, 1.25H), 8.00 (d, 0.51H), 7.95 (bd, 0.45H), 7.90 (d, 0.09H), 7.72 (dd, 0.27H), 7.63 (m, 0.92H), 7.41 (m, 1.48H), 7.34 (bd, 0.09H), 7.27 (dd, 0.09H), 6.98 (m, 1.53H), 6.55 (m, 1.3H), 6.22 (d, 0.09H), 4.63 (bm, 0.46H), 4.46 (bm, 0.1H), 3.64 (bm, 0.09H), 3.57-3.33 (m, 1.51H), 3.28 (m, 0.35H), 3.20 (m, 0.09H), 3.16-2.95 (m, 0.27H), 2.87 (s, 0.24H), 2.81 (s, 0.81H), 2.66 (m, 1.95H), 1.65 (bs, 0.24H), 1.55 (m, 1.11H), 1.29 (m, 0.39H), 0.96 (t, 1.83H), 0.91-0.77 (m, 0.63H), 0.47 (t, 0.93H).

Preparation of (S)—N-(1-((5-chloropyridin-2-yl)amino)butan-2-yl)-N,6-dimethyl-3-(2H-1,2,3-triazol-2-yl)picolinamide (Example 21)

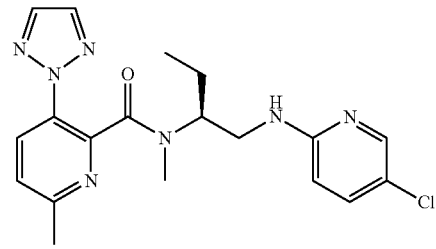 [SMILES: CC[C@@H](CNc1ccc(Cl)cn1)N(C)C(=O)c1nc(C)ccc1-n1nccn1]

The title compound (42 mg) was prepared as a gum from 6-methyl-3-(2H-1,2,3-triazol-2-yl)picolinic acid (87 mg, 0.36 mmol) [prepared as described in WO 2010/063662] and Intermediate 15 (70 mg, 0.33 mmol) using the method described for Route 2. The crude product was purified by preparative HPLC (Waters, Acidic (0.1% Formic acid), Waters X-Bridge Prep-C18, 5 μm, 19×50 mm column, 35 to 65% MeCN in Water).

LCMS (Method A): Two peaks at 1.79 min and 1.98 min, 400/402 [M+H]+

$^{1}$H NMR (400 MHz, DMSO-d$_{6}$) 8.24 (d, 0.5H), 8.22 (d, 0.5H), 8.12 (m, 2H), 7.99 (dd, 0.5H), 7.73 (d, 0.5H), 7.51 (dd, 0.5H), 7.48 (dd, 0.5H), 7.46 (dd, 0.5H), 7.34 (dd, 0.5H), 6.79 (bt, 0.5H), 6.60 (t, 0.5H), 6.55 (dd, 0.5H), 6.34 (d, 0.5H), 4.54 (m, 0.5H), 3.65 (m, 0.5H), 3.34-3.21 (m, 2H), 2.85 (s, 1.5H), 2.71 (s, 1.5H), 2.56 (s, 1.5H), 2.48 (s, 1.5H), 1.71-1.38 (m, 2H), 0.95 (t, 1.5H), 0.77 (t, 1.5H).

Preparation of (S)—N-(1-((5-chloropyridin-2-yl)amino)butan-2-yl)-N,5-dimethyl-2-morpholinobenzamide (Example 22)

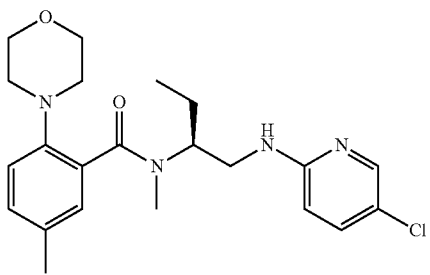 [SMILES: CC[C@@H](CNc1ccc(Cl)cn1)N(C)C(=O)c1cc(C)ccc1N1CCOCC1]

The title compound (54 mg) was prepared as a glass from Intermediate 27 (90 mg, 0.41 mmol) and Intermediate 15 (120 mg, 0.41 mmol) using the method described for Route 2. The crude product was purified by chromatography on the Biotage Companion™ (12 g column, 0 to 5% ammonia solution in DCM).

LCMS (Method A): 2.21 min, 417/419 [M+H]$^+$ $^1$H NMR (400 MHz, DMSO-d$_6$, 374 K) 7.95 (bd, 0.6H), 7.83 (bs, 0.35H), 7.77 (bs, 0.35H), 7.42 (dd, 0.6H), 7.35 (dd, 0.42H), 7.14 (dd, 0.58H), 7.06-6.99 (m, 0.99H), 6.93 (bd, 0.35H), 6.88 (bd, 0.35H), 6.64 (bs, 0.35H), 6.58 (d, 0.66H), 6.45 (d, 0.54H), 6.38 (bt, 0.51H), 6.24 (bs, 0.35H), 4.67 (bs, 0.7H), 3.77-3.32 (bm, 6.72H), 3.29-2.98 (bm, 2.09H), 2.87-2.66 (s, 1.1H), 2.74 (bm, 1.05H), 2.59 (bm, 2.28H), 2.25 (bs, 2.04H), 2.00 (s, 0.65H), 1.64 (bm, 2.01H), 1.00 (bt, 1.95H), 0.86 (bt, 1.05H), 0.74 (bm, 0.36H).

Preparation of (S)—N-(1-((5-chloropyridin-2-yl)amino)butan-2-yl)-5-(dimethylamino)-N-methyl-2-(2H-1,2,3-triazol-2-yl)benzamide (Example 23)

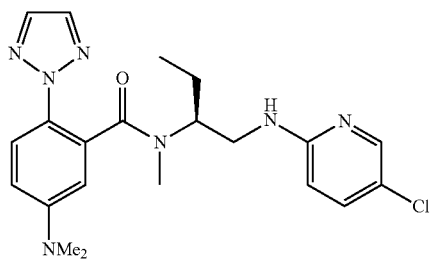

The title compound (45 mg) was prepared as a gum from Intermediate 16 (84 mg, 0.62 mmol) and Intermediate 15 (117 mg, 0.36 mmol) using the method described for Route 2. The crude product was purified by chromatography on the Biotage Companion™ (12 g column, 0 to 10% methanol in DCM).

LCMS (Method A): 2.18 min, 428/430 [M+H]$^+$ $^1$H NMR (400 MHz, DMSO-d$_6$) 8.03-7.96 (bm, 0.60H), 7.96-7.93 (bm, 0.83H), 7.92 (s, 0.15H), 7.91 (bs, 0.72H), 7.80 (d, 0.12H), 7.74 (d, 0.12H), 7.72-7.64 (m, 0.43H), 7.56 (bd, 0.43H), 7.51-7.47 (dd, 0.45H), 7.47-7.38 (dd, 0.52H), 7.33 (dd, 0.13H), 7.30 (dd, 0.22H), 6.98-6.78 (m, 1.50H), 6.73 (d, 0.03H), 6.67 (dd, 0.33H), 6.60-6.40 (m, 1.20H), 6.43 (d, 0.35H), 6.38 (d, 0.35H), 6.26 (m, 0.52H), 4.63 (bm, 0.50H), 4.48 (bs, 0.15H), 3.76 (bm, 0.13H), 3.52 (bm, 0.56H), 3.40 (bm, 0.80H), 3.31 (bm, 0.50H), 3.08 (m, 0.12H), 3.03-2.94 (m, 1.86H), 2.91 (bs, 2.32H), 2.84 (s, 1.24H), 2.82 (s, 0.30H), 2.75 (s, 0.80H), 2.63 (m, 1.86H), 2.19 (s, 0.15H), 1.62 (m, 0.48H), 1.50 (m, 0.84H), 1.36 (s, 0.84H), 1.30-1.17 (bm, 0.55H), 0.90 (bm, 2.13H), 0.51 (bm, 0.87H).

Preparation of (S)—N-(1-((5-chloropyridin-2-yl)amino)butan-2-yl)-N-methyl-2-(2H-1,2,3-triazol-2-yl)-5-(trifluoromethyl)nicotinamide (Example 24)

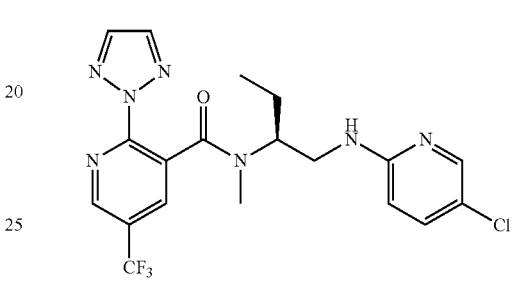

The title compound (49 mg) was prepared as a solid from Intermediate 17 (93 mg, 0.36 mmol) and Intermediate 15 (70 mg, 0.33 mmol) using the method described for Route 2. The crude product was purified by preparative HPLC (Waters, Acidic (0.1% Formic acid), Waters X-Bridge Prep-C18, 5 μm, 19×50 mm column, 20 to 50% MeCN in Water).

LCMS (Method A): 2.14 min, 454/456 [M+H]$^+$ $^1$H NMR (400 MHz, DMSO-d$_6$) 9.12-9.04 (bm, 0.75H), 8.95 (m, 0.27H), 8.39 (bs, 0.12H), 8.29 (bd, 0.12H), 8.27-8.22 (m, 0.81H), 8.22-8.16 (m, 1.2H), 8.01 (bdd, 0.9H), 7.95 (bd, 0.44H), 7.70 (dd, 0.27H), 7.62 (dd, 0.09H), 7.50-7.40 (bdd, 0.63H), 7.37 (dd, 0.23H), 7.26 (dd, 0.12H), 7.04 (bt, 0.47H), 6.88 (t, 0.3H), 6.71-6.62 (m, 0.21H), 6.59-6.53 (d, 0.68H), 6.45 (dd, 0.27H), 6.25 (dd, 0.12H), 4.64 (bm, 0.43H), 4.41 (bs, 0.15H), 3.59 (bm, 0.09H), 3.52-3.35 (m, 1.39H), 3.19 (m, 0.4H), 3.10 (m, 0.28H), 2.92 (s, 0.27H), 2.85 (s, 0.81H), 2.72 (m, 1.92H), 1.67 (bm, 0.21H), 1.59 (m, 1.23H), 1.41-1.28 (m, 0.29H), 0.99 (m, 2.06H), 0.88 (m, 0.23H), 0.81 (t, 0.39H), 0.49 (t, 0.85H).

Preparation of (S)-5-chloro-N-(1-((5-chloropyridin-2-yl)amino)butan-2-yl)-2-(2H-1,2,3-triazol-2-yl)benzamide (Example 25)

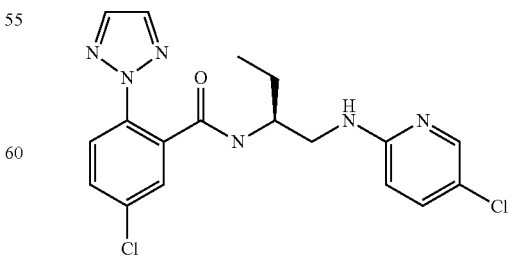

The title compound (53 mg) was prepared as a solid from 5-chloro-2-(2H-1,2,3-triazol-2-yl)benzoic acid (56 mg, 0.25 mmol) [prepared as described in WO 2011/050198] and Intermediate 18 (70 mg, 0.23 mmol) using the method described for Route 2. The crude product was purified by trituration with MeCN.

LCMS (Method A): 1.92 min, 405/407 [M+H]$^+$ $^1$H NMR (400 MHz, DMSO-d$_6$) 8.34 (d, 1H), 8.04 (s, 2H), 7.96 (dd, 1H), 7.81 (d, 1H), 7.69 (dd, 1H), 7.54 (dd, 1H), 7.43 (d, 1H), 6.73 (t, 1H), 6.55 (dd, 1H), 3.88 (m, 1H), 3.38 (m, 1H), 3.28 (m, 1H), 1.56 (m, 1H), 1.42 (m, 1H), 0.92 (m, 3H).

Preparation of (S)—N-(1-((5-chloropyridin-2-yl)amino)-3-methylbutan-2-yl)-N,2-dimethyl-5-phenylthiazole-4-carboxamide (Example 26)

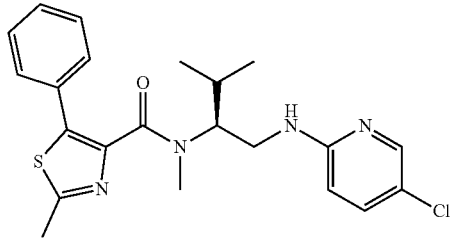 [SMILES: Cc1nc(C(=O)N(C)[C@H](CNc2ccc(Cl)cn2)C(C)C)c(-c2ccccc2)s1]

The title compound (89 mg) was prepared as a gum from 2-methyl-4-phenylthiazole-5-carboxylic acid (120 mg, 0.53 mmol) and Intermediate 19 (120 mg, 0.53 mmol) using the method described for Route 2. The crude product was purified by preparative HPLC (Waters, Acidic (0.1% Formic acid), Waters X-Bridge Prep-C18, 5 µm, 19×50 mm column, 5 to 95% MeCN in Water).

LCMS (Method A): 2.30 min, 429 [M+H]$^+$ $^1$H NMR (400 MHz, DMSO-d$_6$, 374 K) 8.13 (s, 0.5H), 7.95 (bs, 1H), 7.86 (bs, 0.5H), 7.56-7.43 (m, 1.5H), 7.43-7.24 (m, 4H), 6.49 (d, 0.5H), 6.31 (m, 0.5H), 6.07 (bs, 0.5H), 4.39 (m, 0.5H), 3.67-3.28 (m, 2.5H), 2.85 (s, 1.5H), 2.69 (m, 3H), 2.62 (s, 1.5H), 1.97 (m, 0.5H), 1.80 (m, 0.5H), 1.05 (d, 1.5H), 0.88 (m, 3H), 0.64 (d, 1.5H).

Preparation of (S)—N-(1-((5-chloropyridin-2-yl)amino)-3-methylbutan-2-yl)-N-methyl-2-phenyl-1H-indole-3-carboxamide (Example 27)

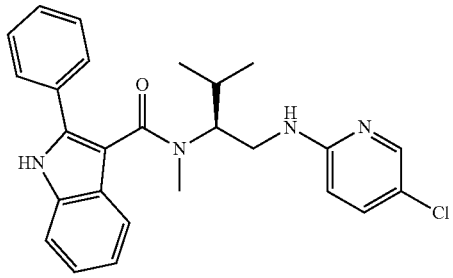 [SMILES: CC(C)[C@@H](CNc1ccc(Cl)cn1)N(C)C(=O)c1c(-c2ccccc2)[nH]c2ccccc12]

The title compound (89 mg) was prepared as a solid from 2-phenyl-1H-indole-3-carboxylic acid (300 mg, 0.88 mmol) and Intermediate 19 (200 mg, 0.88 mmol) using the method described for Route 2. The crude product was purified by chromatography on the Biotage Companion™ (40 g column, 0 to 50% EtOAc in isohexane).

LCMS (Method A): 2.83 min, 447 [M+H]$^+$ $^1$H NMR (400 MHz, DMSO-d$_6$, 375 K) 7.95 (bs, 1H), 7.74 (m, 2H), 7.48-7.29 (m, 7H), 7.14 (td, 1H), 6.98 (t, 1H), 6.57 (bs, 1H), 6.24 (bs, 1H), 4.61 (bm, 1H), 3.57 (bs, 2H), 2.67 (bs, 3H), 1.97 (bs, 1H), 1.09 (bs, 3H), 0.96 (bs, 3H).

Preparation of (S)—N-(1-((5-chloropyridin-2-yl)amino)-3-methylbutan-2-yl)-N-methyl-2-(2H-1,2,3-triazol-2-yl)benzamide (Example 28)

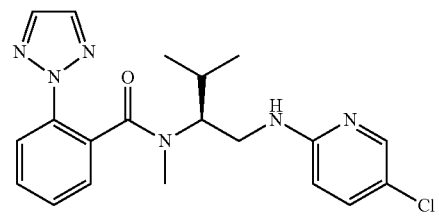 [SMILES: CC(C)[C@@H](CNc1ccc(Cl)cn1)N(C)C(=O)c1ccccc1-n1nccn1]

The title compound (91 mg) was prepared as a solid from 2-(2H-1,2,3-triazol-2-yl)benzoic acid (100 mg, 0.53 mmol) and Intermediate 19 (120 mg, 0.53 mmol) using the method described for Route 2. The reaction mixture was poured onto water and the solid collected by filtration. It was purified by chromatography on the Biotage Companion™ (12 g column, 10 to 70% EtOAc in isohexane).

LCMS (Method A): Two peaks at 2.12 min and 2.21 min, 399 [M+H]$^+$ $^1$H NMR (400 MHz, DMSO-d$_6$, 375 K) 8.00 (m, 2.8H), 7.94-7.80 (m, 1H), 7.58 (td, 1H), 7.48 (t, 1H), 7.44 (dd, 1H), 7.35 (bd, 0.1H), 7.25 (bd, 1H), 6.58 (d, 1H), 6.39 (bm, 0.1H), 6.16 (bs, 1H), 4.35 (td, 0.9H), 3.64 (dt, 0.9H), 3.50 (m, 1H), 3.23 (m, 0.1H), 2.95 (bs, 0.3H), 2.70 (s, 2.7H), 2.02 (m, 0.9H), 1.80 (bm, 0.1H), 1.08 (d, 2.7H), 1.01 (d, 3H), 0.90 (bm, 0.3H), 0.68 (bm, 0.1H).

Route 3: Typical Procedure for the Preparation of Examples by Nucleophilic Displacement with an Alcohol as Exemplified by the Preparation of (S)—N-(1-((4-fluorobenzyl)oxy)-3-methylbutan-2-yl)-N-methyl-[1,1'-biphenyl]-2-carboxamide (Example 29)

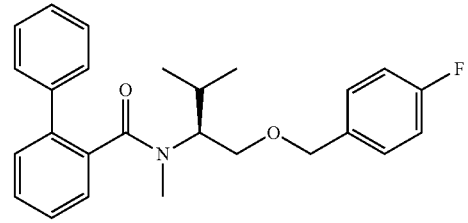 [SMILES: CC(C)[C@@H](COCc1ccc(F)cc1)N(C)C(=O)c1ccccc1-c1ccccc1]

To a solution of Intermediate 9 (150 mg, 0.50 mmol) in anhydrous THF (3 mL) was added sodium hydride, 60% dispersion in oil (50 mg, 1.3 mmol) and the reaction mixture was stirred at ambient temperature for 30 mins. To the reaction was added 1-(bromomethyl)-4-fluorobenzene (240 mg, 1.3 mmol) and the reaction mixture stirred at ambient temperature for a further 1 hr. The reaction mixture was quenched with water (2 mL) and the crude product extracted into diethyl ether (20 mL). The combined organics were washed with water (2×10 mL), dried over Na$_2$SO$_4$, filtered and concentrated in vacuo. The crude product was purified by chromatography on the Biotage Companion™ (12 g column, 0 to 100% isohexane in EtOAc) to afford the title compound as a gum (185 mg).

LCMS (Method A): 2.86 min, 406 [M+H]$^+$ $^1$H NMR (400 MHz, DMSO-d$_6$, 374 K) 7.69-7.25 (m, 11H), 7.25-7.11 (m, 2H), 4.49-4.34 (m, 1.45H), 4.30 (m, 1H), 3.59 (dd, 1H), 3.47 (bm, 0.55H), 2.97 (m, 1H), 2.79 (s, 1H), 2.51 (s, 2H), 1.89 (bm, 1H), 0.92 (d, 3H), 0.67 (bm, 3H).

Preparation of (S)—N-(1-((4,6-dimethylpyrimidin-2-yl)oxy)-3-methylbutan-2-yl)-N-methyl-[1,1'-biphenyl]-2-carboxamide (Example 30)

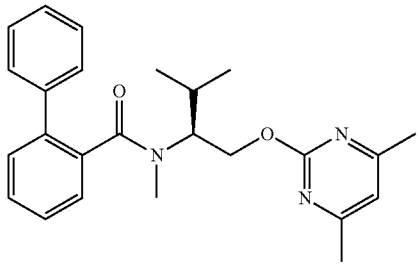 [SMILES: Cc1cc(C)nc(OC[C@H](C(C)C)N(C)C(=O)c2ccccc2-c2ccccc2)n1]

The title compound (45 mg) was prepared as a foam from Intermediate 9 (150 mg, 0.50 mmol) and 2-chloro-4,6-dimethylpyrimidine (120 mg, 0.84 mmol) using the method described for Route 3. The crude product was purified by chromatography on the Biotage Companion™ (12 g column, 0 to 100% EtOAc in isohexane).

LCMS (Method A): 2.51 min, 280 [M-(4,6-dimethylpyrimidin-2-one)+H]$^+$ $^1$H NMR (400 MHz, DMSO-d$_6$) 7.60-6.95 (m, 10H), 4.57-4.47 (d, 0.27H), 4.47-4.33 (dd, 0.44H), 4.33-4.12 (bm, 1H), 4.05-3.94 (d, 0.25H), 3.63-3.36 (bm, 0.9H), 3.11 (bd, 0.2H), 2.84 (bm, 0.1H), 2.76-2.63 (m, 3H), 2.45 (s, 3H), 2.38 (s, 3H), 1.95 (m, 0.4H), 1.64 (bs, 0.3H), 1.50 (bs, 0.14H), 0.98-0.71 (m, 3H), 0.67 (d, 0.5H), 0.62 (d, 0.5H), 0.54 (d, 0.5H), 0.27 (d, 1H), −0.19 (d, 0.5H).

Preparation of (S)—N-methyl-N-(3-methyl-1-(quinazolin-2-yloxy)butan-2-yl)-[1,1'-biphenyl]-2-carboxamide (Example 31)

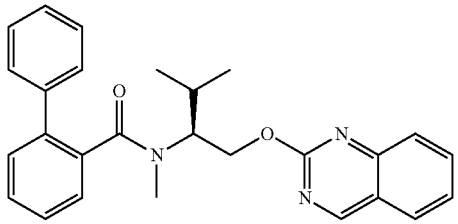 [SMILES: CC(C)[C@@H](COc1ncc2ccccc2n1)N(C)C(=O)c1ccccc1-c1ccccc1]

The title compound (105 mg) was prepared as a foam from Intermediate 9 (150 mg, 0.50 mmol) and 2-chloroquinazoline (180 mg, 1.1 mmol) using the method described for Route 3. The crude product was purified by chromatography on the Biotage Companion™ (12 g column, 0 to 100% EtOAc in isohexane).

LCMS (Method A): 2.62 min, 280 [M-(quinazolin-2-one)+H]$^+$ $^1$H NMR (400 MHz, DMSO-d$_6$, 374 K) 9.47-9.38 (bs, 1H), 8.07 (dd, 1H), 7.93 (td, 1H), 7.79 (d, 0.8H), 7.74 (bd, 0.2H), 7.62-7.12 (m, 10H), 4.72-4.42 (m, 3.2H), 3.28 (bs, 0.2H), 2.84 (s, 0.6H), 2.58 (s, 2.4H), 2.02 (bs, 1.2H), 1.03 (bd, 2.4H), 0.78 (bd, 0.6H), 0.67 (bs, 2.4H).

Preparation of (S)—N-methyl-N-(3-methyl-1-((4-phenylpyrimidin-2-yl)oxy)butan-2-yl)-[1,1'-biphenyl]-2-carboxamide (Example 32)

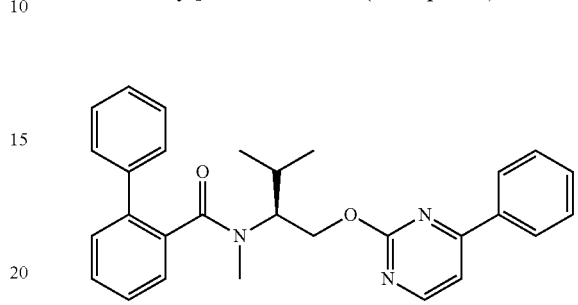

The title compound (98 mg) was prepared as a foam from Intermediate 9 (130 mg, 0.4 mmol) and 2-chloro-4-phenylpyrimidine (210 mg, 1.1 mmol) using the method described for Route 3. The crude product was purified by chromatography on the Biotage Companion™ (12 g column, 0 to 100% EtOAc in isohexane).

LCMS (Method A): 2.81 min, 280 [M-(4-phenylpyrimidin-2-one)+H]$^+$ $^1$H NMR (400 MHz, DMSO-d$_6$, 374 K) 8.65 (d, 0.8H), 8.61 (bs, 0.2H), 8.18 (td, 1.8H), 8.12 (bs, 0.6H), 7.70-7.10 (m, 12.6H), 4.70-4.41 (m, 3.2H), 3.27 (bs, 0.4H), 2.85 (s, 0.6H), 2.57 (s, 2.4H), 2.00 (bs, 1.2H), 1.02 (d, 2.4H), 0.77 (bd, 0.6H), 0.66 (bs, 2.2H).

Preparation of (S)—N-methyl-N-(3-methyl-1-((1-methyl-1H-benzo[d]imidazol-2-yl)oxy)butan-2-yl)-[1,1'-biphenyl]-2-carboxamide (Example 33)

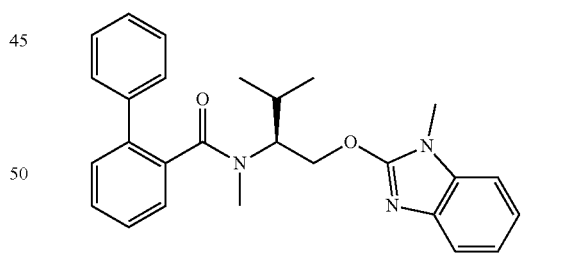

The title compound (132 mg) was prepared as a foam from Intermediate 9 (150 mg, 0.50 mmol) and 2-chloro-1-methyl-1H-benzo[d]imidazole (84 mg, 0.50 mmol) using the method described for Route 3. The crude product was purified by chromatography on the Biotage Companion™ (12 g column, 0 to 100% EtOAc in isohexane).

LCMS (Method A): 2.17 min, 280 [M-(1-methyl-1H-benzo[d]imidazol-2-one)+H]$^+$ $^1$H NMR (400 MHz, DMSO-d$_6$, 374 K) 7.60-7.26 (m, 9.8H), 7.26-6.96 (m, 3.2H), 4.69 (dd, 1H), 4.58 (d, 1H), 4.42 (bt, 1H), 3.49 (s, 3H), 2.87 (s, 0.6H), 2.58 (s, 2.4H), 2.02 (bs, 1H), 1.00 (d, 2.4H), 0.75 (bd, 0.6H), 0.63 (bs, 3H).

Preparation of (S)—N-(1-((5-chloropyridin-2-yl)oxy)-3-methylbutan-2-yl)-N-methyl-[1,1'-biphenyl]-2-carboxamide (Example 34)

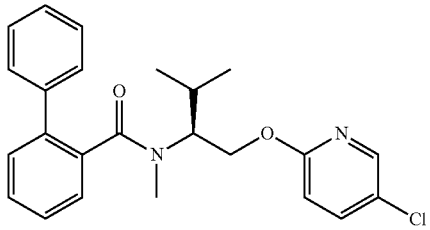 [SMILES: CC(C)[C@@H](COc1ccc(Cl)cn1)N(C)C(=O)c1ccccc1-c1ccccc1]

The title compound (105 mg) was prepared as a gum from Intermediate 9 (150 mg, 0.50 mmol) and 2,5-dichloropyridine (187 mg, 1.3 mmol) using the method described for Route 3. The crude product was purified by chromatography on the Biotage Companion™ (12 g column, 0 to 100% EtOAc in isohexane).

LCMS (Method A): 2.90 min, 280 [M-(5-dichloropyridin-2-one)+H]$^+$ $^1$H NMR (400 MHz, DMSO-d$_6$, 375 K) 8.16 (d, 1H), 8.09 (bs, 0.1H), 7.75 (dd, 1H), 7.55-7.38 (m, 5.1H), 7.38-7.24 (m, 3H), 7.19 (d, 0.9H), 6.77 (d, 0.9H), 4.37 (bm, 2.7H), 3.17 (bs, 0.3H), 2.92 (s, 2.7H), 2.79 (s, 0.3H), 1.95 (bs, 1H), 0.96 (d, 3H), 0.75-0.54 (bm, 3H).

Route 4: Typical Procedure for the Preparation of Examples by Nucleophilic Displacement with an Amine as Exemplified by the Preparation of (S)—N-methyl-N-(3-methyl-1-((4-phenylpyrimidin-2-yl)amino)butan-2-yl)-[1,1'-biphenyl]-2-carboxamide (Example 35)

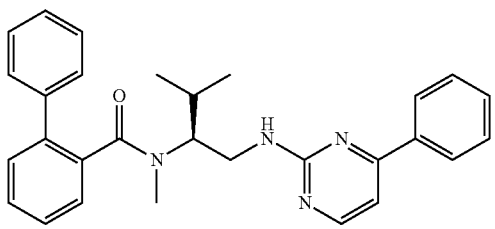 [SMILES: CC(C)[C@@H](CNc1nccc(-c2ccccc2)n1)N(C)C(=O)c1ccccc1-c1ccccc1]

A mixture of 2-chloro-4-phenylpyrimidine (71 mg, 0.37 mmol), Intermediate 20 (100 mg, 0.34 mmol) and DIPEA (120 µL, 0.68 mmol) in NMP (1 mL) was heated at 130° C. for 3 hrs. The reaction mixture was allowed to cool to ambient temperature and diluted with water (10 mL). The crude product was extracted into diethyl ether (20 mL), dried over Na$_2$SO$_4$, filtered and concentrated in vacuo. The residue was purified by chromatography on the Biotage Companion™ (12 g column, 0 to 100% diethyl ether in isohexane) to afford the title compound as a gum (65 mg)

LCMS (Method A): Two peaks at 2.45 min and 2.66 min, 451 [M+H]$^+$ $^1$H NMR (400 MHz, DMSO-d$_6$, 374 K) 8.36 (d, 0.8H), 8.30 (bd, 0.2H), 8.15-8.07 (m, 1.6H), 7.97 (bm, 0.3H), 7.56-7.46 (m, 3.92H), 7.46-7.24 (m, 7.38H), 7.16-7.05 (m, 1.8H), 6.33 (bs, 1H), 4.41 (td, 1H), 3.71 (m, 1H), 3.50 (m, 1.1H), 3.26 (bm, 0.2H), 2.84 (s, 0.3H), 2.82 (s, 0.3H), 2.63 (s, 0.3H), 2.48 (s, 2.1H), 1.82 (bm, 0.7H), 1.00 (d, 2.5H), 0.78 (bd, 0.5H), 0.56 (bs, 3H).

Preparation of (S)—N-methyl-N-(3-methyl-1-(quinazolin-2-ylamino)butan-2-yl)-[1,1'-biphenyl]-2-carboxamide (Example 36)

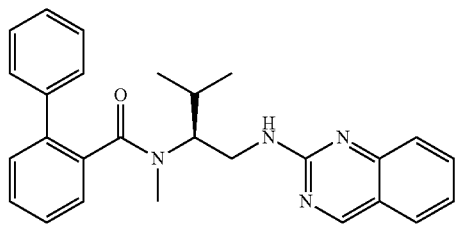

The title compound (67 mg) was prepared as a solid from Intermediate 20 (100 mg, 0.34 mmol) and 2-chloroquinazoline (61 mg, 0.37 mmol) using the method described for Route 4. The crude product was purified by chromatography on the Biotage Companion™ (12 g column, 0 to 100% diethyl ether in isohexane).

LCMS (Method A): 2.31 min, 425 [M+H]$^+$ $^1$H NMR (400 MHz, DMSO-d$_6$, 374 K) 9.10 (s, 0.8H), 9.06 (bs, 0.1H), 7.80 (dd, 1H), 7.69 (m, 1H), 7.53 (bd, 0.3H), 7.47 (d, 1H), 7.44-7.33 (m, 6H), 7.33-7.20 (m, 3H), 7.14-6.98 (bd, 1H), 6.52 (bs, 0.8H), 4.40 (td, 1H), 3.71 (m, 1H), 3.55 (m, 1H), 3.28 (bm, 0.2H), 2.82 (s, 0.4H), 2.54 (m, 2.4H), 1.83 (bm, 1H), 1.01 (d, 2.4H), 0.80 (d, 0.6H), 0.55 (bs, 3H).

Preparation of (S)—N-(1-((4,6-dimethylpyrimidin-2-yl)amino)-3-methylbutan-2-yl)-N-methyl-[1,1'-biphenyl]-2-carboxamide (Example 37)

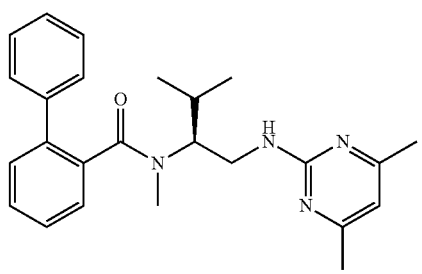 [SMILES: Cc1cc(C)nc(NC[C@H](C(C)C)N(C)C(=O)c2ccccc2-c2ccccc2)n1]

The title compound (33 mg) was prepared as a gum from Intermediate 20 (150 mg, 0.51 mmol) and 2-chloro-4,6-dimethylpyrimidine (72 mg, 0.51 mmol) using the method described for Route 4. The crude product was purified by chromatography on the Biotage Companion™ (40 g column, 0 to 100% EtOAc in isohexane).

LCMS (Method A): Two peaks at 1.83 min and 1.98 min, 403 [M+H]$^+$ $^1$H NMR (400 MHz, DMSO-d$_6$, 374 K) 8.14 (s, 0.45H), 7.54 (bd, 0.3H), 7.48-7.27 (m, 7.71H), 7.08 (bd, 1H), 6.37 (s, 0.9H), 6.33 (bs, 0.22H), 5.93 (bm, 0.42H), 4.29 (td, 0.7H), 3.57 (m, 1H), 3.44 (m, 1H), 3.19 (bm, 0.2H), 2.77 (s, 0.4H), 2.47 (s, 2.4H), 2.22 (s, 5.4H), 2.16 (s, 0.9H), 1.77 (bs, 1H), 0.96 (d, 2.7H), 0.74 (d, 0.3H), 0.55 (bs, 3H).

Preparation of (S)—N-methyl-N-(3-methyl-1-((1-methyl-1H-benzo[d]imidazol-2-yl)amino)butan-2-yl)-[1,1'-biphenyl]-2-carboxamide (Example 38)

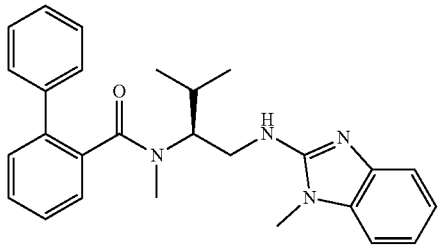 [SMILES: CC(C)[C@@H](CNc1nc2ccccc2n1C)N(C)C(=O)c1ccccc1-c1ccccc1]

The title compound (26 mg) was prepared as a solid from Intermediate 20 (150 mg, 0.51 mmol) and 2-chloro-1-methyl-1H-benzo[d]imidazole (93 mg, 0.56 mmol) using the method described for Route 4. The crude product was purified by chromatography on the Biotage Companion™ (40 g column, 0 to 100% EtOAc in isohexane).

LCMS (Method A): 1.69 min, 427 [M+H]$^+$ $^1$H NMR (400 MHz, DMSO-d$_6$, 374 K) 7.55 (bd, 0.2H), 7.46-7.37 (m, 3H), 7.37-7.16 (m, 5.4H), 7.16-7.11 (m, 1.2H), 7.05-6.90 (m, 3.1H), 6.08 (bs, 1.1H), 4.33 (td, 1H), 3.70-3.55 (m, 2.7H), 3.51 (bs, 0.3H), 3.47 (s, 2.7H), 2.83 (s, 0.3H), 2.54 (s, 2.7H), 1.84 (bm, 0.3H), 0.99 (d, 2.7H), 0.78 (bd, 0.3H), 0.53 (bd, 3H).

Preparation of (S)-5-chloro-N-methyl-2-(2H-1,2,3-triazol-2-yl)-N-(1-((5-(trifluoromethyl)pyrimidin-2-yl)amino)butan-2-yl)benzamide (Example 39)

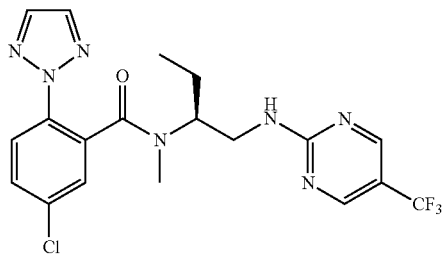 [SMILES: CC[C@@H](CNc1ncc(C(F)(F)F)cn1)N(C)C(=O)c1cc(Cl)ccc1-n1nccn1]

The title compound (201 mg) was prepared as a solid from Intermediate 21 (150 mg, 0.49 mmol) and 2-chloro-5-(trifluoromethyl)pyrimidine (89 mg, 0.49 mmol) using the method described for Route 4. The crude product was purified by chromatography on the Biotage Companion™ (12 g column, 0 to 5%, methanol in DCM), and then further purified by trituration in diethyl ether.

LCMS (Method D): Two peaks at 2.25 min and 2.54 min, 454/456 [M+H]$^+$ $^1$H NMR (400 MHz, DMSO-d$_6$)) 8.73-8.62 (m, 1.62H), 8.48 (bs, 0.07H), 8.39 (bd, 0.34H), 8.37-8.28 (m, 0.85H), 8.18 (bs, 0.34H), 8.13 (s, 0.63H), 8.09-8.07 (m, 0.15H), 8.06 (bs, 0.81H), 8.01 (bd, 0.09H), 7.90 (d, 0.47H), 7.77 (d, 0.4H), 7.73-7.60 (m, 0.86H), 7.46 (bs, 0.13H), 7.44-7.40 (m, 0.44H), 7.20 (d, 0.43H), 6.95 (d, 0.37H), 4.73 (m, 0.43H), 4.61 (bm, 0.12H), 3.76-3.61 (m, 0.18H), 3.58-3.37 (m, 1.38H), 3.31 (m, 0.61H), 3.07 (m, 0.33H), 2.87 (s, 0.18H), 2.81 (s, 0.99H), 2.68 (s, 1.83H), 1.71-1.48 (m, 1.35H), 1.29 (m, 0.33H), 0.96 (t, 1.83H), 0.85 (t, 0.15H), 0.70 (m, 0.3H), 0.48 (t, 0.99H).

Preparation of (S)-5-chloro-N-methyl-2-(2H-1,2,3-triazol-2-yl)-N-(1-((5-(trifluoromethyl)pyrazin-2-yl)amino)butan-2-yl)benzamide (Example 40)

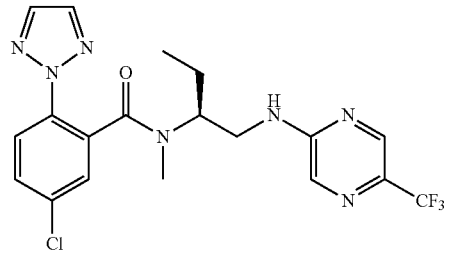 [SMILES: CC[C@@H](CNc1cnc(C(F)(F)F)cn1)N(C)C(=O)c1cc(Cl)ccc1-n1nccn1]

The title compound (104 mg) was prepared as a solid from Intermediate 21 (150 mg, 0.49 mmol) and 2-chloro-5-(trifluoromethyl)pyrazine (89 mg, 0.49 mmol) using the method described for Route 4. The crude product was collected by filtration following addition of water to the reaction mixture and was purified by trituration with diethyl ether.

LCMS (Method A): Two peaks at 2.25 min and 2.49 min, 454/456 [M+H]$^+$ $^1$H NMR (400 MHz, DMSO-d$_6$) 8.44-8.39 (bm, 0.67H), 8.23-8.14 (m, 0.76H), 8.13 (s, 0.54H), 8.11-8.00 (m, 3.09H), 7.97 (bd, 0.1H), 7.90 (d, 0.45H), 7.78 (d, 0.27H), 7.76-7.63 (m, 0.93H), 7.47 (bs, 0.12H), 7.43 (dd, 0.32H), 7.40 (d, 0.09H), 7.24 (bd, 0.39H), 7.07 (d, 0.27H), 4.70 (bm, 0.65H), 4.49 (bs, 0.2H), 3.69 (bt, 0.12H), 3.62-3.45 (m, 1.53H), 3.29 (m, 0.62H), 3.16 (m, 0.43H), 2.89 (s, 0.22H), 2.84 (s, 0.94H), 2.68 (s, 1.87H), 1.73-1.50 (m, 0.21H), 1.33 (m, 0.34H), 0.96 (t, 1.98H), 0.86 (t, 0.37H), 0.81 (m, 0.35H), 0.49 (t, 1.17H).

Preparation of (S)-5-chloro-N-methyl-2-(2H-1,2,3-triazol-2-yl)-N-(1-((6-(trifluoromethyl)pyridazin-3-yl)amino)butan-2-yl)benzamide (Example 41)

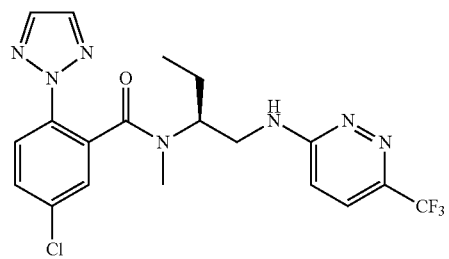 [SMILES: CC[C@@H](CNc1ccc(C(F)(F)F)nn1)N(C)C(=O)c1cc(Cl)ccc1-n1nccn1]

The title compound (62 mg) was prepared as a gum from Intermediate 21 (150 mg, 0.49 mmol) and 3-chloro-6-(trifluoromethyl)pyridazine (89 mg, 0.49 mmol) using the method described for Route 4. The crude product was purified by chromatography on the Biotage Companion™ (12 g column, 0 to 60%, EtOAc in isohexane).

LCMS (Method A): Two peaks at 2.12 min and 2.38 min, 454/456 [M+H]$^+$ $^1$H NMR (400 MHz, DMSO-d$_6$) 8.17-8.14 (m, 0.75H), 8.14-8.09 (bm, 0.34H), 8.09-8.04 (m, 1.1H), 7.98 (m, 0.12H), 7.93-7.79 (m, 0.86H), 7.78-7.62 (m, 2.28H), 7.61-7.54 (bm, 0.25H), 7.52-7.45 (bm, 0.23H), 7.44 (bd, 0.06H), 7.36 (dd, 0.38H), 7.20 (bs, 0.39H), 7.03 (d, 0.57H), 6.98 (d, 0.46H), 6.97 (bs, 0.15H), 6.83 (d, 0.03H), 6.63 (d, 0.03H), 4.73 (bm, 0.39H), 4.51 (bs, 0.09H), 3.81-3.56 (m, 1.49H), 3.36 (bm, 0.4H), 3.19-3.08 (m, 0.35H), 2.90 (s, 0.12H), 2.87 (s, 0.06H), 2.84 (s, 0.99H), 2.70 (s, 1.83H), 1.69 (bm, 0.24H), 1.60 (m, 0.99H), 1.43 (m, 0.06H), 1.38-1.22 (m, 0.52H), 0.98 (t, 1.83H), 0.92-0.87 (m, 0.32H), 0.69 (bm, 0.3H), 0.53 (t, 1.02H).

Preparation of (S)-5-chloro-N-methyl-2-(2H-1,2,3-triazol-2-yl)-N-(1-((5-(trifluoromethyl)pyridin-2-yl)amino)butan-2-yl)benzamide (Example 42)

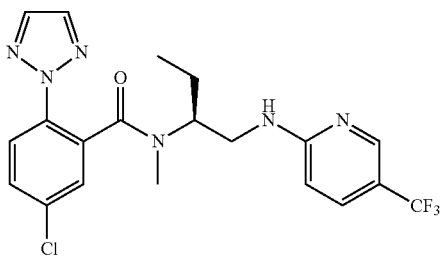

The title compound (55 mg) was prepared as a gum from Intermediate 21 (150 mg, 0.49 mmol) and 2-bromo-5-(trifluoromethyl)pyridine (110 mg, 0.49 mmol) using the method described for Route 4. The crude product was purified by chromatography on the Biotage Companion™ (12 g column, 0 to 60%, EtOAc in isohexane).

LCMS (Method A): 2.58 min, 453/455 [M+H]$^+$ $^1$H NMR (400 MHz, DMSO-d$_6$) 8.40 (bs, 0.05H), 8.34 (bs, 0.18H), 8.30 (bs, 0.52H), 8.13 (s, 0.83H), 8.10-8.03 (m, 1.61H), 7.98 (bs, 0.18H), 7.92-7.85 (d, 0.52H), 7.76 (d, 0.24H), 7.73-7.61 (m, 1.65H), 7.56 (bt, 0.42H), 7.52-7.49 (bm, 0.54H), 7.43-7.38 (m, 0.35H), 7.20 (bs, 0.15H), 7.14 (bt, 0.09H), 7.07 (bs, 0.42H), 7.04 (d, 0.3H), 6.66 (d, 0.69H), 6.57 (bd, 0.21H), 6.32 (d, 0.05H), 4.65 (bm, 0.53H), 4.47 (bs, 0.1H), 3.65-3.41 (bm, 1.46H), 3.29 (m, 0.4H), 3.12-3.03 (m, 0.35H), 2.88 (s, 0.15H), 2.82 (s, 0.75H), 2.68 (m, 2.1H), 1.66 (bm, 0.35H), 1.57 (m, 1.22H), 1.29 (m, 0.34H), 0.96 (m, 2.05H), 0.85 (t, 0.21H), 0.77 (m, 0.15H), 0.49 (t, 0.84H).

Preparation of (S)—N-(1-(benzo[d]oxazol-2-ylamino)butan-2-yl)-5-chloro-N-methyl-2-(2H-1,2,3-triazol-2-yl)benzamide (Example 43)

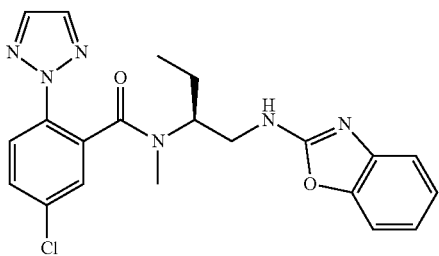 [SMILES: CC[C@@H](CNc1nc2ccccc2s1)N(C)C(=O)c1cc(Cl)ccc1-n1nccn1]

The title compound (300 mg) was prepared as a solid from Intermediate 21 (700 mg, 2.3 mmol) and 2-chlorobenzo[d]oxazole (420 mg, 2.3 mmol) using ethanol (10 mL) as solvent at reflux, and the method described for Route 4. The crude product was purified by preparative HPLC (Waters, Acidic (10 mM Ammonium formate+0.1% Formic acid), YMC ODS Prep C-18, 10 μm, 500×30 mm column, 20 to 60% MeCN in Water).

LCMS (Method E): Two peaks at 2.31 min and 2.55 min, 425 [M+H]$^+$ $^1$H NMR (400 MHz, DMSO-d$_6$) 8.93-8.72 (m, 1H), 8.72-8.62 (m, 0.9H), 8.34-8.00 (m, 5H), 8.00-7.88 (m, 0.9H), 7.88-7.76 (m, 0.9H), 6.98 (bm, 0.3H), 6.60 (bm, 0.1H), 5.88 (bm, 0.9H), 5.16 (bm, 0.2H), 4.86-4.67 (bm, 0.9H), 4.61 (bm, 0.9H), 4.50 (bm, 0.1H), 4.34 (m, 1.1H), 3.79 (s, 0.3H), 2.71-2.41 (m, 1.8H), 2.34 (s, 2.7H), 0.78 (m, 3H).

Preparation of (S)—N-(1-(benzo[d]thiazol-2-ylamino)butan-2-yl)-5-chloro-N-methyl-2-(2H-1,2,3-triazol-2-yl)benzamide (Example 44)

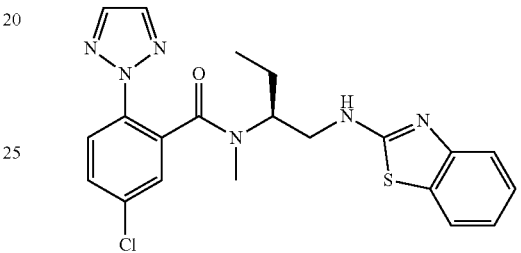

The title compound (15 mg) was prepared as a solid from Intermediate 21 (200 mg, 0.65 mmol) and 2-bromobenzo[d]thiazole (153 mg, 0.72 mmol) using ethanol (5 mL) as solvent at reflux, and the method described for Route 4. The crude product was purified by preparative HPLC ((Waters, Acidic (0.1% Formic acid), YMC ODS Prep C-18, 10 μm, 500×30 mm column, 10 to 50% MeCN in Water).

LCMS (Method F) Two peaks at 3.11 min and 3.37 min, 441 [M+H]$^+$ $^1$H NMR (400 MHz, DMSO-d$_6$) 8.29-8.20 (m, 0.72H), 8.20-8.14 (m, 1H), 8.14-8.07 (m, 1H), 8.05-7.88 (m, 1H), 7.81 (d, 0.39H), 7.77-7.67 (m, 1.3H), 7.67-7.58 (m, 0.43H), 7.54 (bs, 0.2H), 7.48-7.40 (m, 0.75H), 7.38 (dd, 0.2H), 7.34-7.16 (m, 2.05H), 7.12-6.98 (m, 0.86H), 6.83-6.76 (m, 0.1H), 4.76 (bs, 0.25H), 4.49 (bm, 0.05H), 3.80 (bm, 0.1H), 3.72-3.44 (m, 2H), 2.92 (s, 0.05H), 2.86 (s, 0.45H), 2.75 (m, 1.5H), 2.04 (m, 0.05H), 1.79-1.70 (bm, 0.05H), 1.70-1.56 (m, 1H), 1.44-1.17 (m, 2.1H), 1.01 (t, 2.1H), 0.95-0.81 (m, 1H), 0.56 (t, 0.3H).

Preparation of (S)-5-chloro-N-(1-((5-chloro-3-nitropyridin-2-yl)amino)butan-2-yl)-N-methyl-2-(2H-1,2,3-triazol-2-yl)benzamide (Example 45)

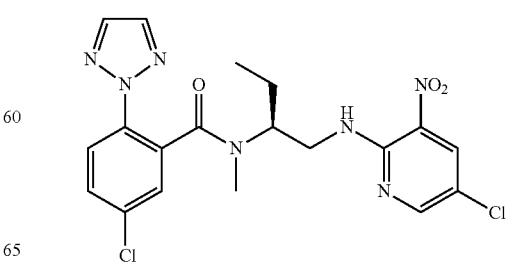

The title compound (520 mg) was prepared as a solid from Intermediate 21 (500 mg, 1.6 mmol) and 5-chloro-2-fluoro-3-nitropyridine (290 mg, 1.6 mmol) using MeCN (10 mL) as solvent at reflux, and the method described for Route 4. The crude product was purified by column chromatography (50 to 100% EtOAc in hexane).

LCMS (Method E): Two peaks at 2.87 min and 3.09 min, 464 [M+H]$^+$ $^1$H NMR (400 MHz, DMSO-d$_6$) 9.06-8.90 (m, 0.95H), 8.74 (bt, 0.31H), 8.67 (bt, 0.35H), 8.63-8.47 (m, 1.35H), 8.46-8.33 (m, 0.2H), 8.31-8.25 (m, 0.2H), 8.22 (d, 0.24H), 8.09-7.99 (m, 1H), 8.03 (s, 0.35H), 7.98-7.85 (m, 0.7H), 7.80-7.73 (m, 0.35H), 7.73-7.60 (m, 0.7H), 7.48-7.38 (m, 0.35H), 7.35 (d, 0.15H), 7.25 (d, 0.15H), 7.02 (bs, 0.35H), 6.79 (d, 0.3H), 4.78 (bm, 0.2H), 3.70 (m, 0.55H), 3.44 (m, 0.8H), 2.89 (s, 0.1H), 2.83 (s, 0.6H), 2.67 (m, 1.35H), 1.71-1.48 (m, 0.9H), 1.37-1.21 (m, 0.9H), 1.17 (m, 3H), 0.95 (t, 1.2H), 0.85 (m, 0.6H), 0.68 (bm, 0.2H), 0.50 (t, 0.6H).

Preparation of (S)—N,6-dimethyl-3-(2H-1,2,3-triazol-2-yl)-N-(1-((5-(trifluoromethyl)pyrimidin-2-yl)amino)butan-2-yl)picolinamide (Example 46)

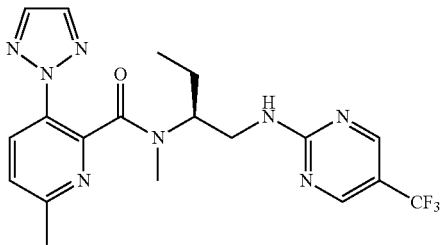 [SMILES: CC[C@@H](CNc1ncc(C(F)(F)F)cn1)N(C)C(=O)c1nc(C)ccc1-n1nccn1]

The title compound (81 mg) was prepared as a solid from Intermediate 22 (120 mg, 0.42 mmol) and 2-chloro-5-(trifluoromethyl)pyrimidine (84 mg, 0.46 mmol) using the method described for Route 4. The crude product was purified by ion exchange chromatography using an SCX resin cartridge (5 g column, washing with methanol, then eluting with 5% methanolic ammonia) and further purified by chromatography on the Biotage Companion™ (12 g column, 0 to 5%, methanol in DCM).

Alternative method: Intermediate 37 (2.5 g, 12 mmol) was stirred in thionyl chloride (12.5 mL) and heated at reflux for 1 hr. The mixture was then concentrated in vacuo, toluene (10 mL) was added and the mixture was concentrated to a residue. This residue was taken up in isopropyl acetate (40 mL) and treated with a solution of triethylamine (3.3 mL, 24 mmol) in isopropyl acetate (20 mL) and the mixture was cooled. A solution of Intermediate 31 (2.7 g, 11 mmol) in isopropyl acetate (20 mL) was added and the mixture was stirred at ambient temperature for 30 mins. Water (40 mL) was then added and stirred. The organic layer was separated, washed with saturated aqueous NaHCO$_3$ (40 mL), dried over Na$_2$SO$_4$, filtered and concentrated in vacuo. The crude product was heated in ethyl acetate (19 mL) and hexane (56 mL) to cause dissolution. The mixture was then allowed to cool and the product was collected by filtration and dried to afford the title compound as a solid (3.6 g, 77%).

LCMS (Method A): 2.32 min, 435 [M+H]$^+$

LCMS (Method N): 2.46 min, 435 [M+H]$^+$; 2.51 min, 435 [M+H]$^+$ $^1$H NMR (400 MHz, DMSO-d$_6$) 8.71 (m, 1H), 8.59 (bd, 0.5H), 8.45 (bd, 0.5H), 8.27 (s, 0.5H), 8.24 (s, 0.5H), 8.19 (bs, 0.5H), 8.18 (bs, 1H), 8.14 (s, 1H), 7.77 (bt, 0.5H), 7.53 (d, 0.5H), 7.50 (d, 0.5H), 4.69 (m, 0.5H), 3.75 (m, 0.5H), 3.62 (t, 1H), 3.48 (m, 0.5H), 3.39 (m, 0.5H), 2.89 (s, 1.5H), 2.76 (s, 1.5H), 2.55 (s, 1.5H), 2.49 (s, 1.5H), 1.65 (m, 1H), 1.53 (m, 1H), 1.00 (t, 1.5H), 0.80 (t, 1.5H).

Preparation of (S)—N,6-dimethyl-3-(2H-1,2,3-triazol-2-yl)-N-(1-((5-(trifluoromethyl)pyrazin-2-yl)amino)butan-2-yl)picolinamide (Example 47)

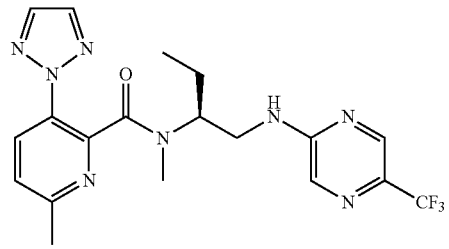 [SMILES: CC[C@@H](CNc1cnc(C(F)(F)F)cn1)N(C)C(=O)c1nc(C)ccc1-n1nccn1]

The title compound (81 mg) was prepared as a gum from Intermediate 22 (120 mg, 0.42 mmol) and 2-chloro-5-(trifluoromethyl)pyrimidine (84 mg, 0.46 mmol) using the method described for Route 4. The crude product was purified by ion exchange chromatography using an SCX resin cartridge (5 g column, washing with methanol, then eluting with 5% methanolic ammonia) and further purified by chromatography on the Biotage Companion™ (12 g column, 0 to 5%, methanol in DCM).

LCMS (Method A): 2.17 min, 435 [M+H]$^+$ $^1$H NMR (400 MHz, DMSO-d$_6$) 8.42 (s, 0.5H), 8.22 (d, 0.5H), 8.17 (d, 0.5H), 8.15-8.10 (m, 2.5H), 8.07 (s, 0.5H), 8.08-7.90 (bm, 1H), 7.88 (s, 0.5H), 7.51 (d, 0.5H), 7.43 (d, 0.5H), 4.65 (m, 0.5H), 3.70 (m, 1H), 3.52 (m, 0.5H), 3.43 (m, 1H), 2.90 (s, 1.5H), 2.74 (s, 1.5H), 2.51 (s, 1.5H), 2.40 (s, 1.5H), 2.21 (t, 0.5H), 1.67 (m, 1H), 1.52 (m, 0.5H), 1.00 (t, 1.5H), 0.78 (t, 1.5H).

Preparation of (S)—N,6-dimethyl-3-(2H-1,2,3-triazol-2-yl)-N-(1-((5-(trifluoromethyl)pyridin-2-yl)amino)butan-2-yl)picolinamide (Example 48)

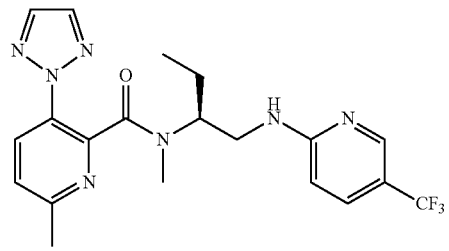

The title compound (61 mg) was prepared as a gum from Intermediate 22 (120 mg, 0.42 mmol) and 2-chloro-5-(trifluoromethyl)pyridine (103 mg, 0.46 mmol) using the method described for Route 4. The crude product was purified by ion exchange chromatography using an SCX resin cartridge (5 g column, washing with methanol, then eluting with 5% methanolic ammonia) and further purified by chromatography on the Biotage Companion™ (12 g column, 0 to 5%, methanol in DCM).

LCMS (Method A): 2.27 min, 434 [M+H]$^+$

¹H NMR (400 MHz, DMSO-d₆) 8.35 (m, 0.5H), 8.25 (d, 0.5H), 8.23 (d, 0.5H), 8.16-8.13 (m, 2H), 8.08 (bs, 0.5H), 7.70 (dd, 0.5H), 7.57 (dd, 0.5H), 7.54 (dd, 0.5H), 7.47 (d, 0.5H), 7.37 (bs, 0.5H), 7.24 (bs, 0.5H), 6.67 (d, 0.5H), 6.46 (d, 0.5H), 4.60 (m, 0.5H), 3.71 (m, 0.5H), 3.58 (t, 0.5H), 3.42 (m, 1H), 2.89 (s, 1.5H), 2.75 (s, 1.5H), 2.56 (s, 1.5H), 2.47 (s, 1.5H), 2.21 (t, 0.5H), 1.67 (m, 1H), 1.51 (m, 1H), 0.99 (t, 1.5H), 0.80 (t, 1.5H).

Route 5: Typical Procedure for the Preparation of Examples by Palladium Catalyzed Coupling of an Amine and an Aryl Halide as Exemplified by the Preparation of (S)—N-(1-((5-chloropyridin-2-yl)amino)-3-methylbutan-2-yl)-N,5-dimethyl-2-(2H-1,2,3-triazol-2-yl)benzamide (Example 49)

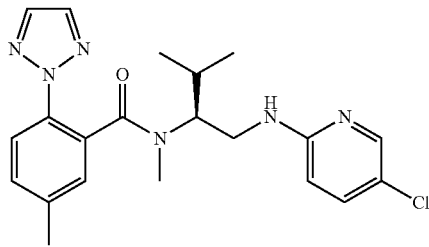 [SMILES: Cc1ccc(-n2nccn2)c(C(=O)N(C)[C@H](CNc2ccc(Cl)cn2)C(C)C)c1]

A mixture of 2,5-dichloropyridine (0.26 g, 1.7 mmol), Intermediate 23 (0.44 g, 1.4 mmol), Pd₂(dba)₃ (66 mg, 0.07 mmol), BINAP (45 mg, 0.07 mmol) and NaOᵗBu (0.17 g, 1.7 mmol) in toluene (20 mL) was heated at reflux for 20 hrs. The reaction mixture was allowed to cool to ambient temperature and then purified by ion exchange chromatography using an SCX resin cartridge (10 g column, washing with methanol, then eluting with 2% methanolic ammonia) and then further purified by preparative HPLC (Waters, Acidic (0.1% Formic acid), Waters X-Select Prep-C18, 5 μm, 19×50 mm column, 5 to 95% MeCN in Water) to afford the title compound as a glass (145 mg)

LCMS (Method A): Two peaks at 2.28 min and 2.40 min, 413/415 [M+H]⁺

¹H NMR (400 MHz, DMSO-d₆, 374 K) 8.00 (d, 0.85H), 7.95 (s, 2H), 7.86 (bs, 0.15H), 7.78-7.69 (m, 1H), 7.44 (dd, 1H), 7.37 (bd, 1H), 7.29 (bs, 0.15H), 7.04 (bs, 0.15H), 6.95 (bs, 0.85H), 6.58 (d, 1H), 6.18 (bs, 0.85H), 4.33 (m, 1H), 3.59 (m, 2H), 2.93 (s, 0.45H), 2.89 (s, 0.45H), 2.70 (s, 2.55H), 2.37 (s, 2.55H), 2.20 (bm, 0.15H), 2.01 (m, 0.85H), 1.07 (d, 3H), 0.99 (d, 2.55H), 0.90 (bm, 0.45H).

Preparation of (S)—N-(1-((5-chloropyridin-2-yl)amino)-3-methylbutan-2-yl)-N,1-dimethyl-1H-indole-3-carboxamide (Example 50)

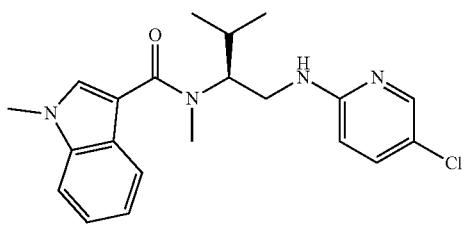 [SMILES: CC(C)[C@@H](CNc1ccc(Cl)cn1)N(C)C(=O)c1cn(C)c2ccccc12]

The title compound (131 mg) was prepared as a glass from Intermediate 24 (0.20 g, 0.73 mmol) and 2,5-dichloropyridine (130 mg, 0.88 mmol) using the method described for Route 5. The crude product was purified by chromatography on the Biotage Companion™ (40 g column, 0 to 100%, EtOAc in isohexane).

LCMS (Method A): 2.26 min, 385/387 [M+H]⁺

¹H NMR (400 MHz, DMSO-d₆, 374 K) 7.97 (dd, 1H), 7.87 (dt, 1H), 7.57 (s, 1H), 7.41 (dt, 1H), 7.39 (dd, 1H), 7.18 (m, 1H), 7.07 (m, 1H), 7.05 (bs, 1H), 6.64 (bdd, 1H), 4.48 (m, 1H), 3.76 (s, 3H), 3.69 (m, 1H), 3.51 (m, 1H), 2.89 (s, 3H), 2.02 (m, 1H), 1.10 (d, 3H), 0.83 (d, 3H).

Preparation of (S)—N-(1-((5-chloropyridin-2-yl)amino)-3-methylbutan-2-yl)-N,2-dimethylquinoline-4-carboxamide (Example 51)

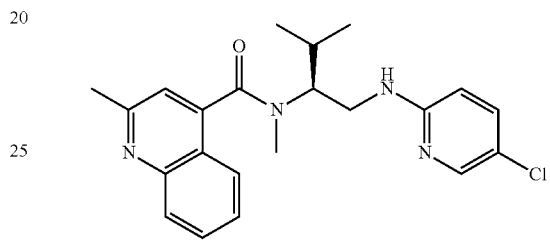

The title compound (98 mg) was prepared as a solid from Intermediate 25 (0.32 g, 1.12 mmol) and 2,5-dichloropyridine (0.20 g, 1.3 mmol) using the method described for Route 5. The crude product was purified by chromatography on the Biotage Companion™ (40 g column, 0 to 100%, EtOAc in isohexane).

LCMS (Method A): Two peaks at 1.58 min and 1.66 min, 397/399 [M+H]⁺

¹H NMR (400 MHz, DMSO-d₆, 375 K) 8.01-7.92 (m, 1.3H), 7.88 (bd, 0.3H), 7.78-7.60 (m, 2.4H), 7.50-7.38 (m, 2.1H), 7.28 (s, 0.3H), 7.05 (s, 0.6H), 6.97 (bs, 0.3H), 6.67 (d, 0.7H), 6.53 (bs, 1H), 4.62 (m, 0.6H), 3.80-3.57 (m, 1.6H), 3.32 (bm, 0.6H), 3.07 (s, 0.7H), 2.92 (bs, 0.7H), 2.67 (s, 2.1H), 2.63 (s, 2.1H), 2.43 (bs, 0.7H), 2.03 (bm, 0.6H), 1.87 (bm, 0.3H), 1.16 (d, 2.1H), 1.07 (d, 2.1H), 0.84 (bd, 1.8H).

Preparation of (S)—N-(1-((5-chloropyridin-2-yl)amino)-3-methylbutan-2-yl)-N-methyl-2-(trifluoromethoxy)benzamide (Example 52)

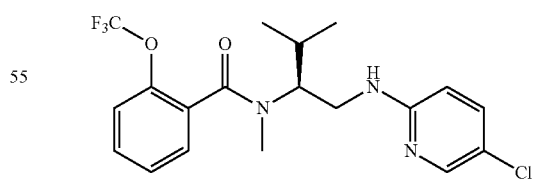

The title compound (95 mg) was prepared as a gum from Intermediate 26 (0.22 g, 0.72 mmol) and 2,5-dichloropyridine (0.13 g, 0.87 mmol) using the method described for Route 5. The crude product was purified by chromatography on the Biotage Companion™ (40 g column, 0 to 60%, EtOAc in isohexane).

LCMS (Method A): 2.48 min, 416 [M+H]⁺

$^1$H NMR (400 MHz, DMSO-d$_6$, 375 K) 7.96 (d, 0.6H), 7.79 (bs, 0.3H), 7.52 (btd, 0.7H), 7.46-7.34 (m, 2.8H), 7.29-7.17 (m, 1H), 7.11 (bs, 0.3H), 7.03 (bs, 0.3H), 6.63-6.43 (m, 1.4H), 6.26 (bs, 0.6H), 4.42 (m, 1H), 3.66 (m, 1H), 3.54 (m, 1H), 3.25 (bm, 0.6H), 2.65 (s, 2.1H), 1.99 (m, 1H), 1.87 (bm, 0.3H), 1.10 (d, 2.1H), 0.96 (d, 2.1H), 0.93 (bd, 0.9H), 0.89 (bd, 0.9H).

Preparation of (S)-5-chloro-N-methyl-N-(1-((6-methylpyridin-2-yl)amino)butan-2-yl)-2-(2H-1,2,3-triazol-2-yl)benzamide (Example 53)

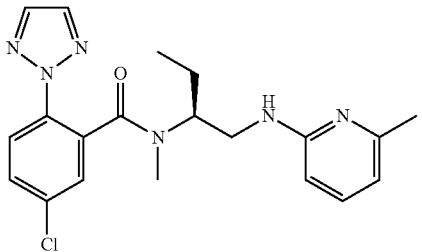 [SMILES: CC[C@@H](CNc1cccc(C)n1)N(C)C(=O)c1cc(Cl)ccc1-n1nccn1]

The title compound (25 mg) was prepared as a gum from Intermediate 21 (0.15 g, 0.49 mmol) and 2-bromo-6-methylpyridine (0.10 g, 0.59 mmol) using the method described for Route 5. The crude product was purified by ion exchange chromatography using an SCX resin cartridge (10 g column, washing with methanol, then eluting with 5% methanolic ammonia) and then further purified by preparative HPLC (Waters, Acidic (0.1% Formic acid), Waters X-Select Prep-C18, 5 µm, 19×50 mm column, 0 to 35% MeCN in water).

LCMS (Method A): 1.42 min, 399/401 [M+H]$^+$ $^1$H NMR (400 MHz, DMSO-d$_6$) 8.24 (s, 0.3H), 8.20 (s, 0.24H), 8.17 (s, 0.12H), 8.15 (s, 0.48H), 8.09 (s, 0.9H), 8.06-7.98 (m, 0.18H), 7.91 (d, 0.45H), 7.77 (d, 0.31H), 7.75-7.68 (m, 0.21H), 7.65 (dd, 0.45H), 7.52-7.47 (bs, 0.15H), 7.47-7.41 (m, 0.31H), 7.39-7.28 (m, 0.62H), 7.25 (td, 0.26H), 7.15-7.01 (m, 0.06H), 7.09 (d, 0.24H), 6.91 (d, 0.48H), 6.56 (m, 0.78H), 6.43 (d, 0.24H), 6.39 (d, 0.45H), 6.34 (d, 0.72H), 6.31-6.26 (m, 0.54H), 6.20 (d, 0.3H), 6.08 (bm, 0.15H), 5.96 (d, 0.06H), 4.69-4.52 (m, 0.56H), 3.64 (m, 0.3H), 3.52-3.23 (m, 3.5H), 3.01 (m, 0.1H), 2.90 (s, 0.12H), 2.81 (s, 0.5H), 2.73-2.68 (m, 1.6H), 2.33 (s, 0.6H), 2.27 (s, 1.2H), 2.10 (m, 0.93H), 1.69 (bm, 0.4H), 1.58 (m, 0.8H), 1.28 (bm, 0.1H), 0.99 (t, 2.19H), 0.91 (t, 0.15H), 0.69 (bm, 0.2H), 0.57 (t, 0.75H).

Route 6: Alternative Procedure for the Preparation of Examples by Palladium Catalyzed Coupling of an Amine and an Aryl Halide as Exemplified by the Preparation of (S)-5-chloro-N-methyl-2-(2H-1,2,3-triazol-2-yl)-N-(1-((6-(trifluoromethyl)pyridin-3-yl)amino)butan-2-yl)benzamide (Example 54)

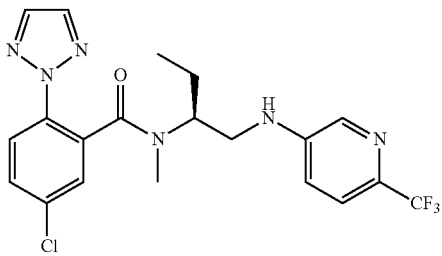 [SMILES: CC[C@@H](CNc1ccc(C(F)(F)F)nc1)N(C)C(=O)c1cc(Cl)ccc1-n1nccn1]

A mixture of 5-iodo-2-(trifluoromethyl)pyridine (0.11 g, 0.39 mmol), Intermediate 21 (100 mg, 0.33 mmol), Pd$_2$(dba)$_3$ (15 mg, 0.02 mmol), xantphos (9.4 mg, 0.02 mmol) and Cs$_2$CO$_3$ (0.21 g, 0.65 mmol) in anhydrous dioxane (10 mL) was heated at 100° C. for 19 hrs. The reaction mixture was cooled to ambient temperature, concentrated in vacuo and the crude product purified by chromatography on the Biotage Companion™ (40 g column, 0 to 60%, EtOAc in isohexane) and the further purified by chromatography on the Biotage Companion™ (12 g column, 0 to 5% methanol in DCM) to afford the title compound as a solid (45 mg).

LCMS (Method A): Two peaks at 2.25 min and 2.49 min, 453/455 [M+H]$^+$ $^1$H NMR (400 MHz, DMSO-d$_6$) 8.17-8.10 (m, 1.59H), 8.06 (s, 0.91H), 8.03-7.95 (m, 0.32H), 7.95-7.86 (m, 0.62H), 7.83 (d, 0.08H), 7.79 (d, 0.32H), 7.74-7.64 (m, 0.81H), 7.54 (d, 0.67H), 7.50-7.40 (m, 1.07H), 7.36 (d, 0.12H), 7.16-7.07 (m, 1.03H), 6.92-6.81 (m, 0.84H), 6.81-6.72 (m, 0.46H), 6.70 (bdd, 0.08H), 6.40 (bm, 0.08H), 4.62 (bm, 0.32H), 4.43 (bm, 0.15H), 3.58 (bm, 0.09H), 3.35 (bm, 0.52H), 3.19 (bm, 0.42H), 3.01 (bm, 0.08H), 2.88 (s, 2.39H), 2.83 (s, 0.62H), 2.68 (bm, 2.12H), 1.78-1.52 (bm, 1.21H), 1.35 (bm, 0.15H), 0.97 (m, 1.98H), 0.89 (t, 0.39H), 0.51 (t, 0.56H).

Preparation of (S)—N,6-dimethyl-3-(2H-1,2,3-triazol-2-yl)-N-(1-((6-(trifluoromethyl) pyridin-3-yl)amino)butan-2-yl)picolinamide (Example 55)

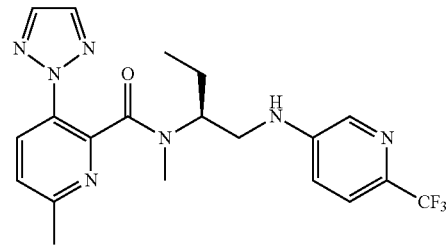

The title compound (58 mg) was prepared as a solid from Intermediate 22 (90 mg, 0.31 mmol) and 5-iodo-2-(trifluoromethyl)pyridine (0.10 g, 0.38 mmol) using the method described for Route 6. The crude product was purified by ion exchange chromatography using an SCX resin cartridge (10 g column, washing with methanol, then eluting with 5% methanolic ammonia) and then further purified chromatography on the Biotage Companion™ (12 g column, 0 to 70%, EtOAc in isohexane).

LCMS (Method A): 2.14 min, 434 [M+H]$^+$ $^1$H NMR (400 MHz, DMSO-d$_6$) 8.27 (d, 0.5H), 8.25 (d, 0.5H), 8.18 (s, 1H), 8.15 (d, 0.5H), 8.14 (s, 1H), 7.96 (d, 0.5H), 7.56 (dd, 1H), 7.51 (dd, 0.5H), 7.45 (d, 0.5H), 7.15 (dd, 0.5H), 6.83 (dd, 0.5H), 6.73 (m, 1H), 4.55 (m, 0.5H), 3.66 (m, 0.5H), 3.37 (m, 1.5H), 3.28 (m, 0.5H), 2.89 (s, 1.5H), 2.77 (s, 1.5H), 2.60 (s, 1.5H), 2.50 (s, 1.5H), 1.82-1.53 (m, 2H), 0.99 (t, 1.5H), 0.84 (t, 1.5H).

Preparation of (S)—N-(1-(4-fluorobenzamido)-3-methylbutan-2-yl)-N-methyl-[1,1'-biphenyl]-2-carboxamide (Example 56)

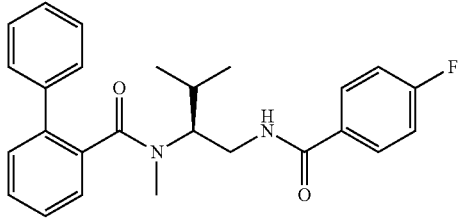 [SMILES: CC(C)[C@@H](CNC(=O)c1ccc(F)cc1)N(C)C(=O)c1ccccc1-c1ccccc1]

To a solution of Intermediate 20 (0.11 g, 0.39 mmol), 4-fluorobenzoic acid (59 mg, 0.42 mmol) and DIPEA (0.13 mL, 0.77 mmol) in anhydrous DMF (10 mL) was added HATU (0.16 g, 0.42 mmol) and the reaction mixture was stirred for 2 hrs. It was poured onto water and the product collected by filtration, washed with water (20 mL) and dried in vacuo to afford the title compound as a solid (102 mg).

LCMS (Method A): 2.44 min, 419 [M+H]$^+$ $^1$H NMR (400 MHz, DMSO-d$_6$, 374 K) 7.99 (bs, 0.95H), 7.94-7.84 (td, 1.8H), 7.55 (bd, 0.05H), 7.51-7.21 (m, 10.25H), 7.07 (d, 0.95H), 4.29 (td, 1H), 3.57-3.35 (m, 1.8H), 2.81 (s, 0.25H), 2.53 (m, 3H), 1.78 (bm, 0.95H), 0.95 (d, 3H), 0.74 (bd, 0.15H), 0.48 (d, 2.85H).

Preparation of (S)—N-(1-((4-fluorobenzyl)amino)-3-methylbutan-2-yl)-N-methyl-[1,1'-biphenyl]-2-carboxamide (Example 57)

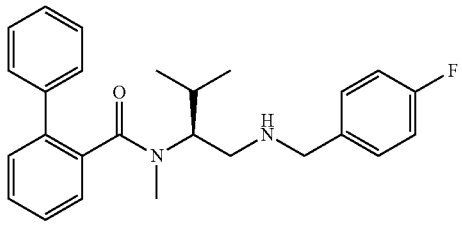 [SMILES: CC(C)[C@@H](CNCc1ccc(F)cc1)N(C)C(=O)c1ccccc1-c1ccccc1]

To a solution of Intermediate 20 (0.12 g, 0.42 mmol) and 4-fluorobenzaldehyde (52 mg, 0.42 mmol) in anhydrous DCE (10 mL) was added NaBH(OAc)$_3$ (0.13 g, 0.63 mmol) and the reaction mixture was stirred for 4 hrs. It was then washed with saturated aqueous NaHCO$_3$ (2×5 mL), dried over Na$_2$SO$_4$, filtered and concentrated in vacuo. The crude product was purified by chromatography on the Biotage Companion™ to afford the title compound as a gum (56 mg).

LCMS (Method A): 1.68 min, 405 [M+H]$^+$ $^1$H NMR (400 MHz, DMSO-d$_6$, 374 K) 7.56 (bd, 0.1H), 7.52-7.17 (m, 11.9H), 7.14-7.04 (m, 2H), 4.23 (td, 0.9H), 3.72-3.53 (dd, 2H), 3.42 (bm, 0.2H), 2.74 (s, 0.3H), 2.69-2.52 (m, 2H), 2.42 (s, 2.7H), 1.70 (m, 0.9H), 0.85 (d, 3H), 0.63 (bs, 3H).

Preparation of (S)—N-methyl-N-(3-methyl-1-(3-phenyl ureido)butan-2-yl)-[1,1'-biphenyl]-2-carboxamide (Example 58)

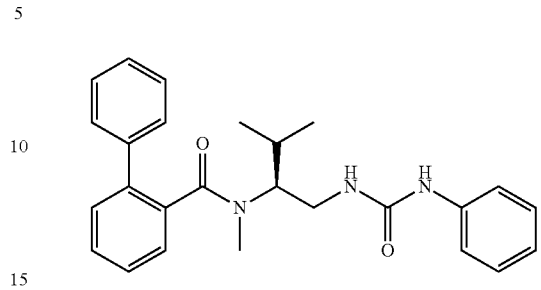

A mixture of Intermediate 20 (0.12 g, 0.42 mmol) and isocyanatobenzene (50 mg, 0.42 mmol) in toluene (10 mL) was heated at 60° C. for 30 mins. The reaction mixture was concentrated in vacuo and the crude product purified by chromatography on the Biotage Companion™ (12 g column, 0 to 100% EtOAc in isohexane) to afford the title compound as a solid (0.14 g).

LCMS (Method A): Two peaks at 2.29 min and 2.44 min, 416 [M+H]$^+$ $^1$H NMR (400 MHz, DMSO-d$_6$, 374 K) 7.57 (bd, 0.2H), 7.48-7.34 (m, 8.9H), 7.34-7.28 (m, 2.7H), 7.28-7.21 (m, 2.3H), 6.93 (tt, 1H), 5.81 (bm, 0.9H), 4.16 (bm, 0.9H), 3.41-3.24 (m, 1.8H), 2.78 (s, 0.3H), 2.47 (s, 2.7H), 1.72 (bm, 1H), 0.92 (d, 3H), 0.70 (bd, 0.3H), 0.47 (bd, 3H).

Preparation of (S)—N-(1-((4-chlorophenyl)amino)-3-methylbutan-2-yl)-N-methyl-[1,1'-biphenyl]-2-carboxamide (Example 59)

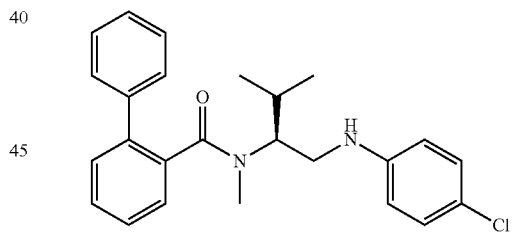

A mixture of Intermediate 20 (0.16 g, 0.54 mmol), DIPEA (0.47 mL, 2.7 mmol), copper(II) acetate (98 mg, 0.54 mmol) and (4-chlorophenyl)boronic acid (0.17 g, 1.1 mmol) in anhydrous DCM (10 mL) was stirred at ambient temperature for 16 hrs. The reaction mixture was concentrated in vacuo and the crude product purified by chromatography on the Biotage Companion™ (40 g column, 0 to 100% EtOAc in isohexane) to afford the title compound as a solid (76 mg).

LCMS (Method A): 2.94 min, 407 [M+H]$^+$ $^1$H NMR (400 MHz, DMSO-d$_6$, 374 K) 7.55 (bd, 0.1H), 7.51-7.29 (m, 8.6H), 7.25-7.15 (bdd, 1H), 7.08 (m, 2H), 7.02 (bd, 0.2H), 6.79 (d, 0.1H), 6.56 (d, 1.8H), 6.34 (bs, 0.2H), 4.95 (bs, 0.3H), 4.23 (m, 1H), 3.22 (m, 0.9H), 3.12 (m, 0.9H), 2.77 (s, 0.3H), 2.46 (s, 2.7H), 1.85 (bm, 0.9H), 0.96 (d, 2.7H), 0.73 (bd, 0.3H), 0.61 (bs, 3H).

Preparation of (S)—N-(1-((3-amino-5-chloropyridin-2-yl)amino)butan-2-yl)-5-chloro-N-methyl-2-(2H-1,2,3-triazol-2-yl)benzamide (Example 60)

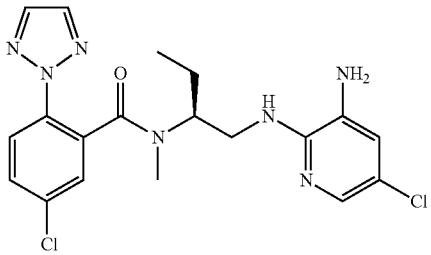 [SMILES: CC[C@@H](CNc1ncc(Cl)cc1N)N(C)C(=O)c1cc(Cl)ccc1-n1nccn1]

To a solution of Example 45 (0.36 g, 0.79 mmol) in ethanol (10 mL) was added SnCl$_2$·2H$_2$O (0.44 g, 2.0 mmol) and the reaction mixture was heated at reflux for 2 hrs. It was then was cooled to ambient temperature and concentrated in vacuo to afford a residue, which was neutralized with saturated aqueous NaHCO$_3$ (20 mL) and extracted into EtOAc (2×10 mL). The combined organics were dried over Na$_2$SO$_4$, filtered and concentrated in vacuo to afford the title compound as a solid (0.26 g).

LCMS (Method E): Two peaks at 2.40 min and 2.57 min, 434 [M+H]$^+$ $^1$H NMR (400 MHz, DMSO-d$_6$) 8.14 (d, 0.3H), 8.09 (s, 0.6H), 8.07-7.91 (m, 1.3H), 7.91-7.81 (m, 0.5H), 7.75-7.56 (m, 0.8H), 7.51-7.26 (m, 1H), 7.13 (m, 0.2H), 7.10 (bs, 0.4H), 7.02 (d, 0.3H), 6.97 (d, 0.4H), 6.92 (m, 0.1H), 6.72 (m, 0.7H), 6.67 (d, 0.2H), 6.54 (m, 0.2H), 5.92 (bm, 0.6H), 5.86-5.53 (m, 0.4H), 5.18-5.0 (m, 0.83H), 4.87 (s, 0.05H), 4.66 (bm, 0.19H), 4.42 (bm, 0.05H), 4.19-3.96 (m, 0.13H), 3.75 (m, 0.05H), 2.79 (s, 0.4H), 2.69-2.59 (m, 1.5H), 2.33 (s, 0.45H), 1.65 (bm, 0.27H), 1.59-1.42 (m, 0.87H), 1.32-1.04 (m, 3.4H), 0.94 (t, 1.14H), 0.83 (m, 0.93H), 0.70 (bm, 0.34H), 0.47 (t, 0.4H).

Preparation of (S)—N,6-dimethyl-N-(1-(quinazolin-2-ylamino)butan-2-yl)-3-(2H-1,2,3-triazol-2-yl)picolinamide (Example 61)

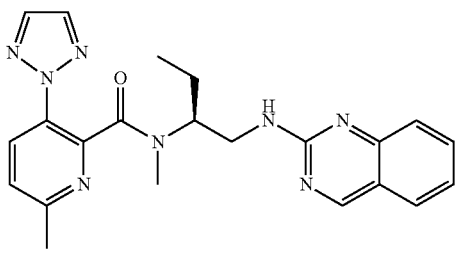 [SMILES: CC[C@@H](CNc1ncc2ccccc2n1)N(C)C(=O)c1nc(C)ccc1-n1nccn1]

A mixture of Intermediate 22 (30 mg, 0.09 mmol), 2-chloroquinazoline (28 mg, 0.17 mmol) and DIPEA (36 mg, 0.27 mmol) in DMSO (2 mL) was heated at 120° C. for 18 hrs. The reaction mixture was allowed to cool to ambient temperature and then EtOAc (10 mL) and water (10 mL) were added and the layers were separated. The aqueous phase was extracted with EtOAc (10 mL). The combined organics were washed with water (20 mL), dried over MgSO$_4$, filtered and concentrated in vacuo. The residue was purified by dry flash chromatography (0 to 2.5% methanol in EtOAc) and then by reverse phase column chromatography (C18 30 g cartridge, 5 to 95% pH 10 NH$_4$HCO$_3$ in MeCN) to afford the title compound as a solid (8 mg).

LCMS (Method L): Two peaks at 2.04 and 2.22 min, 417 [M+H]$^+$ $^1$H NMR (400 MHz, DMSO-d$_6$) 9.37 (bs, 0.5H), 9.25 (bs, 0.5H), 8.50-8.20 (bm, 3H), 8.00 (bdd, 1H), 7.88 (bm, 2H), 7.69 (bm, 1H), 7.60-7.30 (bm, 1.5H), 7.18 (bs, 0.5H), 4.90 (bs, 0.5H), 4.15-4.00 (bs, 0.5H), 3.97-3.82 (bs, 1H), 3.82-3.67 (bm, 1H), 3.06 (bm, 1.5H), 2.96 (bm, 1.5H), 2.66 (bs, 1.5H), 2.61 (bs, 1.5H), 1.77 (bm, 2H), 1.18 (bt, 1.5H), 1.00 (bt, 1.5H).

Preparation of (S)—N-(1-(benzo[d]oxazol-2-ylamino)butan-2-yl)-N,6-dimethyl-3-(2H-1,2,3-triazol-2-yl)picolinamide (Example 62)

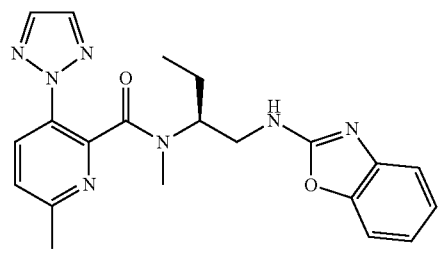

A mixture of Intermediate 22 (20 mg, 0.062 mmol), 2-chlorobenzoxazole (9 mg, 0.055 mmol) and DIPEA (24 mg, 0.19 mmol) in MeCN (1.5 mL) was heated at 70° C. for 18 hrs. The reaction mixture was allowed to cool to ambient temperature and then DCM (10 mL) and water (10 mL) were added and the layers were separated. The organic phase was dried over MgSO$_4$, filtered and concentrated in vacuo. The residue was purified by dry flash chromatography (0 to 100% EtOAc in heptane) to afford the title compounds as a solid (17 mg).

LCMS (Method L): Two peaks at 1.95 and 2.03 min, 406 [M+H]$^+$ $^1$H NMR (300 MHz, DMSO-d$_6$) 8.39 (m, 1H), 8.30 (m, 2H), 8.16 (bm, 0.5H), 8.03 (bm, 0.5H), 7.67 (d, 0.5H), 7.57 (m, 1H), 7.46 (bm, 1H), 7.29 (m, 1.5H), 7.16 (m, 1H), 4.85 (bm, 0.5H), 4.01-3.85 (bm, 0.5H), 3.85-3.63 (bm, 2H), 3.07 (s, 1.5H), 2.95 (s, 1.5H), 2.55 (m, 3H), 1.75 (m, 2H), 1.17 (t, 1.5H), 0.97 (t, 1.5H).

Preparation of (S)—N-(1-(benzo[d]thiazol-2-ylamino)butan-2-yl)-N,6-dimethyl-3-(2H-1,2,3-triazol-2-yl)picolinamide (Example 63)

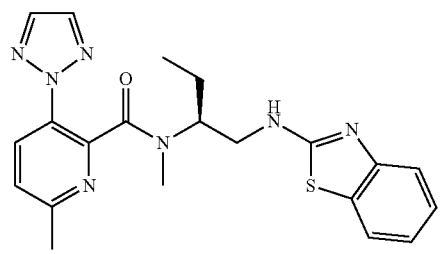 [SMILES: CC[C@@H](CNc1nc2ccccc2o1)N(C)C(=O)c1nc(C)ccc1-n1nccn1]

A mixture of Intermediate 22 (100 mg, 0.31 mmol), 2-chlorobenzothiazole (78 mg, 0.46 mmol) and DIPEA (0.16 mL, 0.92 mmol) in DMSO (3 mL) was heated at 70° C. for 18 hrs. The reaction mixture was allowed to cool to ambient temperature and then DCM (10 mL) and water (10 mL) were added and the layers were separated. The organic phase was dried over MgSO$_4$, filtered and concentrated in vacuo. The residue was purified by dry flash chromatography (50 to 100% EtOAc in heptane) to afford the title compound as a solid (44 mg).

LCMS (Method L): Two peaks at 1.95 and 1.98 min, 422 [M+H]$^+$ $^1$H NMR (400 MHz, DMSO-d$_6$) 8.42 (m, 1H), 8.33 (m, 2H), 8.19 (m, 1H), 7.88 (d, 0.39H), 7.82 (d, 0.61H), 7.69 (d, 0.39H), 7.61 (m, 1H), 7.40 (m, 1.61H), 7.20 (m, 1H), 4.80 (m, 0.39H), 3.96 (m, 0.61H), 3.79 (m, 1.39H), 3.64 (m, 0.61H), 3.07 (s, 1.83H), 2.94 (s, 1.17H), 2.67 (s, 1.17H), 2.61 (s, 1.83H), 1.76 (m, 2H), 1.16 (t, 1.17H), 0.99 (t, 1.83H).

Preparation of (S)—N-(1-((5-chlorobenzo[d]oxazol-2-yl)amino)butan-2-yl)-N,6-dimethyl-3-(2H-1,2,3-triazol-2-yl)picolinamide (Example 64)

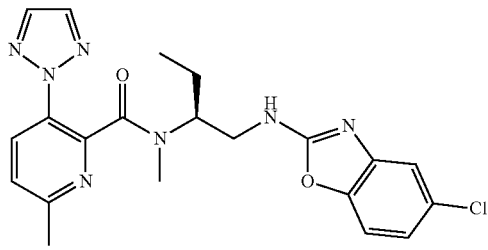 [SMILES: CC[C@@H](CNc1nc2cc(Cl)ccc2o1)N(C)C(=O)c1nc(C)ccc1-n1nccn1]

A mixture of Intermediate 22 (30 mg, 0.09 mmol), 2,5-dichlorobenzoxazole (13 mg, 0.08 mmol) and DIPEA (36 mg, 0.27 mmol) in MeCN (2 mL) was heated at 70° C. for 18 hrs. The reaction mixture was allowed to cool to ambient temperature and then DCM (10 mL) and water (10 mL) were added and the layers were separated. The organic phase was dried over MgSO$_4$, filtered and concentrated in vacuo. The residue was purified by dry flash chromatography (50 to 100% EtOAc in heptane) to afford the title compound as a solid (11 mg).

LCMS (Method L): Two peaks at 2.31 and 2.37 min, 440 [M+H]$^+$ $^1$H NMR (300 MHz, DMSO-d$_6$) 8.32 (m, 4H), 7.67 (d, 0.53H), 7.59 (d, 1H), 7.49 (bm, 1H), 7.36 (bm, 0.47H), 7.19 (m, 1H), 4.85 (m, 0.47H), 4.00-3.59 (m, 2.53H), 3.07 (s, 1.41H), 2.94 (s, 1.59H), 2.53 (m, 3H), 1.74 (m, 2H), 1.17 (t, 1.59H), 0.96 (t, 1.41H).

Route 7: Alternative Procedure for the Preparation of Examples by Nucleophilic Displacement with an Amine as Exemplified by the Preparation of (S)—N,6-dimethyl-N-(1-(quinoxalin-2-ylamino)butan-2-yl)-3-(2H-1,2,3-triazol-2-yl)picolinamide (Example 65)

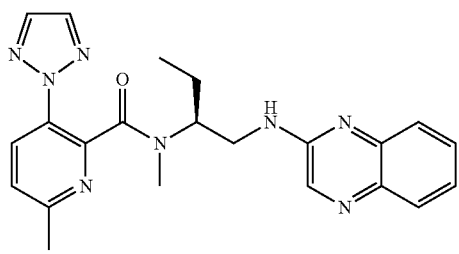 [SMILES: CC[C@@H](CNc1cnc2ccccc2n1)N(C)C(=O)c1nc(C)ccc1-n1nccn1]

A mixture of Intermediate 22 (100 mg, 0.31 mmol), 2-chloroquinoxaline (76 mg, 0.46 mmol) and DIPEA (0.27 mL, 1.54 mmol) in NMP (3 mL) was heated to 100° C. for 8 hrs. 2-chloroquinoxaline (51 mg, 0.31 mmol) was added and heating was continued for a further 8 hrs. The reaction mixture was allowed to cool to ambient temperature and then the mixture was diluted with EtOAc and water and the layers were separated. The aqueous phase was extracted with EtOAc. The combined organics were washed with saturated aqueous NaHCO$_3$, brine, dried over MgSO$_4$, filtered and concentrated in vacuo. The crude product was purified by chromatography on the Biotage Isolera Four™ (25 g column, 0 to 10% methanol in DCM). The crude product was further purified by chromatography on the Biotage Isolera Four™ (25 g column, 0 to 100% EtOAc in heptane followed by 0 to 10% methanol in DCM), followed by purification by preparative HPLC (Gilson, Acidic (0.1% Formic acid), Waters Sunfire Prep-C18, 10 μm, 30×100 mm column, 10 to 95% MeCN in Water) to afford the title compound as a solid (29 mg).

LCMS (Method H): 3.79 min, 417 [M+H]$^+$ $^1$H NMR (500 MHz, CDCl$_3$) 8.16 (bm, 1.6H), 7.84-7.80 (bm, 1.6H), 7.79-7.75 (bd, 0.6H), 7.70-7.65 (s, 0.8H), 7.63-7.55 (bm, 1H), 7.48 (bm, 1.6H), 7.34-7.26 (bm, 1.4H), 7.25-7.21 (bm, 1H), 5.92 (bm, 0.4H), 4.82 (bs, 0.6H), 3.94 (m, 0.4H), 3.81-3.44 (m, 2H), 2.94 (s, 1.8H), 2.73 (bs, 1.2H), 2.57 (bs, 1.8H), 2.51 (bs, 1.2H), 1.88-1.71 (bm, 1.2H), 1.70-1.58 (bm, 0.8H), 1.08 (t, 1.2H), 0.89 (bt, 1.8H).

Preparation of (S)—N,6-di methyl-N-(3-methyl-1-((5-(trifluoromethyl)pyrimidin-2-yl)amino)butan-2-yl)-3-(2H-1,2,3-triazol-2-yl)picolinamide (Example 66)

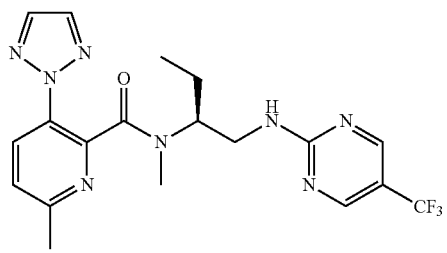 [SMILES: CC[C@@H](CNc1ncc(C(F)(F)F)cn1)N(C)C(=O)c1nc(C)ccc1-n1nccn1]

The title compound (30 mg) was prepared as a solid from Intermediate 28 (50 mg, 0.17 mmol) and 2-chloro-5-(trifluoromethyl)pyrimidine (45 mg, 0.25 mmol) using the method described for Route 7. The crude product was purified by chromatography on the Biotage Isolera Four™ (11 g KP—NH column, 0 to 100% EtOAc in heptane). The crude product was further purified by washing with diethyl ether.

LCMS (Method I): Two peaks at 3.68 and 3.85 min, 449 [M+H]$^+$ $^1$H NMR (500 MHz, CDCl$_3$) 8.46 (bd, 1.76H), 8.39 (bd, 0.24H), 8.21 (d, 0.88H), 8.15 (bd, 0.12H), 8.11 (s, 1.76H), 7.83 (s, 0.24H), 7.27 (d, 0.12H), 7.23 (d, 1.00H), 6.69 (bd, 0.88H), 4.55 (bm, 0.88H), 4.04 (m, 0.88H), 3.68-3.46 (bm, 0.24H), 3.45-3.33 (bm, 1H), 2.92 (s, 0.36H), 2.77 (s, 2.64H), 2.62 (s, 0.36H), 2.54 (s, 2.64H), 1.96 (bm, 0.88H), 1.30-1.17 (bm, 0.12H), 1.11 (d, 2.64H), 1.07 (d, 2.64H), 0.98 (bd, 0.36H), 0.93 (bd, 0.36H).

Preparation of (S)—N,6-dimethyl-N-(3-methyl-1-((5-(trifluoromethyl)pyrazin-2-yl)amino)butan-2-yl)-3-(2H-1,2,3-triazol-2-yl)picolinamide (Example 67)

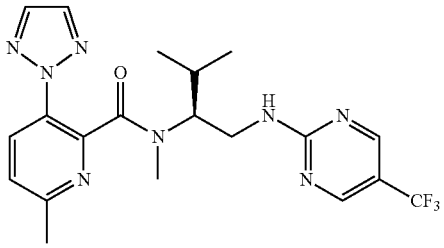 [SMILES: Cc1ccc(-n2nccn2)c(C(=O)N(C)[C@H](CNc2ncc(C(F)(F)F)cn2)C(C)C)n1]

The title compound (13 mg) was prepared as a solid from Intermediate 28 (50 mg, 0.17 mmol) and 2-chloro-5-(trifluoromethyl)pyrazine (30 μL, 0.25 mmol) using the method described for Route 7. The crude product was purified by chromatography on the Biotage Isolera Four™ (11 g KP—NH column, 0 to 100% EtOAc in heptane). The crude product was further purified by washing with diethyl ether.

LCMS (Method I): Two peaks at 4.38 and 4.45 min, 449 [M+H]$^+$ $^1$H NMR (500 MHz, CDCl$_3$) 8.27 (s, 0.85H), 8.21 (s, 0.15H), 8.18 (d, 1H), 7.87 (d, 0.85H), 7.85-7.78 (m, 0.45H), 7.78-7.75 (m, 1.85H), 7.28 (d, 0.15H), 7.25 (d, 0.85H), 6.09 (bm, 0.85H), 4.43 (bm, 0.85H), 3.84 (m, 0.85H), 3.63 (bm, 0.15H), 3.58-3.44 (m, 1H), 2.90 (s, 0.45H), 2.73 (s, 2.55H), 2.57 (s, 0.45H), 2.53 (s, 2.55H), 2.01 (m, 0.85H), 1.92 (m, 0.15H), 1.21 (dd, 0.15H), 1.10 (d, 2.55H), 1.07 (d, 2.55H), 0.95 (m, 0.9H).

Preparation of (S)—N,6-dimethyl-N-(3-methyl-1-(quinazolin-2-ylamino)butan-2-yl)-3-(2H-1,2,3-triazol-2-yl)picolinamide (Example 68)

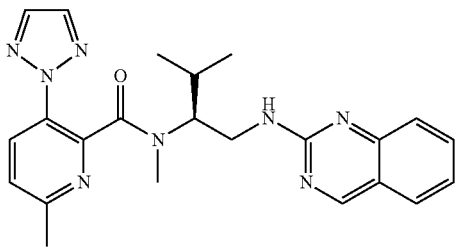 [SMILES: Cc1ccc(-n2nccn2)c(C(=O)N(C)[C@H](CNc2ncc3ccccc3n2)C(C)C)n1]

The title compound (4 mg) was prepared as a solid from Intermediate 28 (30 mg, 0.1 mmol) and 2-chloroquinazoline (25 mg, 0.15 mmol) using the method described for Route 7. The crude product was purified by chromatography on the Biotage Isolera Four™ (11 g KP—NH column, 0 to 100% EtOAc in heptane). The crude product was further purified by preparative HPLC (Gilson, Basic (0.2% Ammonium hydroxide), Waters Xbridge Prep-C18, 10 μm, 30×100 mm column, 10 to 95% MeCN in Water).

LCMS (Method O): Two peaks at 4.83 and 5.08 min, 431 [M+H]$^+$ $^1$H NMR (500 MHz, CDCl$_3$) 9.31 (s, 0.03H), 9.01 (s, 0.69H), 8.95 (s, 0.03H), 8.92 (s, 0.25H), 8.26 (m, 2H), 8.17 (d, 0.26H), 7.99 (m, 0.12H), 7.95 (s, 0.45H), 7.82 (bm, 0.31H), 7.72-7.68 (m, 0.24H), 7.68 (s, 0.65H), 7.67-7.65 (m, 0.72H), 7.65-7.63 (m, 0.81H), 7.63-7.60 (bm, 0.39H), 7.57 (bd, 0.27H), 7.51 (m, 0.03H), 7.40 (d, 0.03H), 7.29 (d, 0.72H), 7.26 (d, 0.24H), 7.24-7.22 (m, 0.5H), 7.22-7.20 (m, 0.27H), 7.20-7.19 (t, 0.12H), 7.18 (d, 0.06H), 7.05 (s, 0.03H), 6.77 (m, 0.03H), 6.46 (s, 0.75H), 4.70 (bs, 0.7H), 4.31 (m, 0.05H), 4.19 (m, 0.72H), 3.81-3.72 (m, 0.25H), 3.72-3.63 (bm, 0.56H), 3.56 (t, 0.72H), 3.11 (s, 0.03H), 3.02 (s, 0.75H), 2.87 (s, 2.22H), 2.73 (s, 0.03H), 2.68 (s, 0.72H), 2.65 (s, 0.06H), 2.61 (s, 2.19H), 2.32 (m, 0.02H), 2.07 (m, 0.87H), 1.56 (d, 0.09H), 1.53 (d, 0.02H), 1.30 (d, 0.2H), 1.26 (bm, 0.15H), 1.19 (m, 3.95H), 1.14-1.10 (bm, 0.09H), 1.05 (m, 1.45H), 0.99 (d, 0.08H), 0.89 (m, 0.05H), 0.79 (m, 0.03H).

Preparation of (S)—N,6-dimethyl-N-(3-methyl-1-((5-(trifluoromethyl)pyridin-2-yl)amino)butan-2-yl)-3-(2H-1,2,3-triazol-2-yl)picolinamide (Example 69)

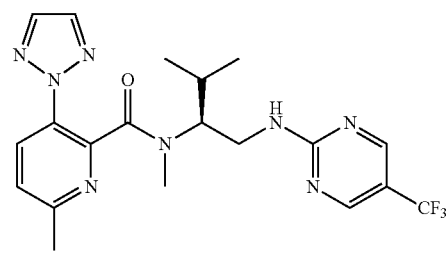 [SMILES: Cc1ccc(-n2nccn2)c(C(=O)N(C)[C@H](CNc2ncc(C(F)(F)F)cn2)C(C)C)n1]

The title compound (44 mg) was prepared as a solid from Intermediate 28 (45 mg, 0.15 mmol) and 2-fluoro-5-(trifluoromethyl)pyridine (27 μL, 0.22 mmol) using the method described for Route 7. The crude product was purified by chromatography on the Biotage Isolera Four™ (11 g KP—NH column, 0 to 100% EtOAc in heptane). The crude product was further purified by preparative HPLC (Gilson, Acidic (0.1% Formic acid), Waters Sunfire Prep-C18, 10 μm, 30×100 mm column, 10 to 95% MeCN in Water).

LCMS (Method O): Two peaks at 5.25 and 5.32 min, 448 [M+H]$^+$ $^1$H NMR (500 MHz, CDCl$_3$) 8.30 (bs, 0.67H), 8.24 (bs, 0.33H), 8.18 (m, 1H), 7.87 (m, 1.33H), 7.80 (s, 0.67H), 7.50 (dd, 0.67H), 7.40 (dd, 0.33H), 7.27 (d, 0.33H), 7.24 (d, 0.67H), 6.46-6.29 (m, 1H), 5.92 (bm, 1H), 4.47 (bm, 0.67H), 3.76 (bm, 0.66H), 3.63-3.48 (bm, 1H), 3.48-3.37 (bm, 0.67H), 2.90 (s, 0.99H), 2.74 (s, 2.01H), 2.57 (s, 0.99H), 2.54 (s, 2.01H), 2.06-1.95 (bm, 0.67H), 1.95-1.85 (m, 0.33H), 1.10 (d, 2.01H), 1.07 (d, 2.01H), 0.92 (bm, 1.98H).

Preparation of (S)—N-ethyl-6-methyl-3-(2H-1,2,3-triazol-2-yl)-N-(1-((5-(trifluoromethyl)pyrazin-2-yl)amino)butan-2-yl)picolinamide (Example 70)

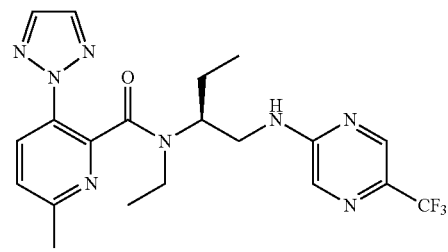 [SMILES: CC[C@@H](CNc1cnc(C(F)(F)F)cn1)N(CC)C(=O)c1nc(C)ccc1-n1nccn1]

The title compound (56 mg) was prepared as an oil from Intermediate 29 (50 mg, 0.17 mmol) and 2-chloro-5-(trifluoromethyl)pyrazine (44 mg, 0.24 mmol) using the method described for Route 7. The crude product was purified by chromatography on the Biotage Isolera Four™ (10 g column, 20 to 100% EtOAc in heptane).

LCMS (Method I): Two peaks at 4.18 and 4.35 min, 450 $[M+H]^+$ $^1$H NMR (250 MHz, DMSO-$d_6$, 353K) 8.37 (bs, 0.45H), 8.20 (d, 0.45H), 8.17-8.11 (bm, 1.1H), 8.06 (d, 0.45H), 8.03 (bs, 2H), 7.88 (m, 0.55H), 7.59 (bm, 1H), 7.50 (d, 0.45H), 7.43 (d, 0.55H), 3.95 (m, 0.45H), 3.76 (m, 1.45H), 3.54-3.33 (m, 2H), 3.24 (m, 1H), 2.56 (s, 1.35H), 2.48 (s, 1.65H), 2.08-1.85 (m, 0.55H), 1.85-1.65 (m, 0.45H), 1.57 (m, 1.1H), 1.22 (t, 1.65H), 1.03 (t, 2.7H), 0.84 (t, 1.65H).

Preparation of (S)—N-ethyl-6-methyl-3-(2H-1,2,3-triazol-2-yl)-N-(1-((5-(trifluoromethyl)pyridin-2-yl)amino)butan-2-yl)picolinamide (Example 71)

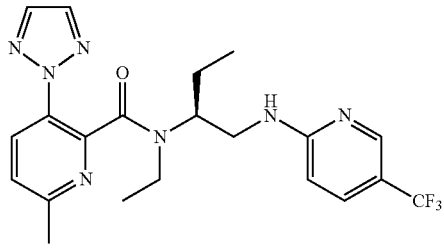 [SMILES: CC[C@@H](CNc1ccc(C(F)(F)F)cn1)N(CC)C(=O)c1nc(C)ccc1-n1nccn1]

The title compound (49 mg) was prepared as a solid from Intermediate 29 (50 mg, 0.16 mmol) and 2-fluoro-5-(trifluoromethyl)pyridine (30 µL, 0.24 mmol) using the method described for Route 7. The crude product was purified by chromatography on the Biotage Isolera Four™ (10 g column, 20 to 100% EtOAc in heptane).

LCMS (Method H): Two peaks at 4.35 and 4.39 min, 448 $[M+H]^+$ $^1$H NMR (250 MHz, DMSO-$d_6$, 353K) 8.32 (bm, 0.4H), 8.23-8.16 (m, 1H), 8.12 (bm, 0.6H), 8.05 (m, 2H), 7.64 (dd, 0.4H), 7.57-7.42 (m, 1.6H), 7.08 (bm, 0.6H), 6.94 (bm, 0.4H), 6.66 (d, 0.4H), 6.46 (d, 0.6H), 3.94 (m, 0.4H), 3.74 (m, 1.4H), 3.55-3.29 (m, 2H), 3.24 (m, 1H), 2.58 (s, 1.2H), 2.52 (s, 1.8H), 2.05-1.85 (m, 0.6H), 1.85-1.68 (m, 0.4H), 1.68-1.52 (m, 1.2H), 1.21 (t, 1.8H), 1.04 (m, 2.4H), 0.85 (t, 1.8H).

Preparation of (S)—N-ethyl-6-methyl-N-(1-(quinazolin-2-ylamino)butan-2-yl)-3-(2H-1,2,3-triazol-2-yl)picolinamide (Example 72)

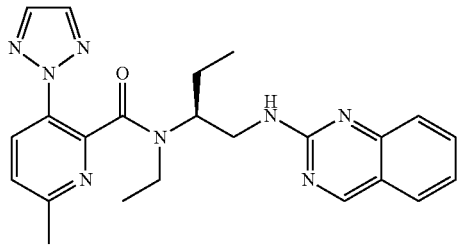 [SMILES: CC[C@@H](CNc1ncc2ccccc2n1)N(CC)C(=O)c1nc(C)ccc1-n1nccn1]

The title compound (90 mg) was prepared as a glass from Intermediate 29 (80 mg, 0.26 mmol) and 2-chloroquinazoline (66 mg, 0.40 mmol) using the method described for Route 7. The crude product was purified by chromatography on the Biotage Isolera Four™ (10 g column, 20 to 100% EtOAc in heptane).

LCMS (Method H): 3.53 min, 431 $[M+H]^+$ $^1$H NMR (250 MHz, DMSO-$d_6$, 353K) 9.14 (s, 0.45H), 9.03 (s, 0.55H), 8.28-8.20 (d, 0.45H), 8.20-8.15 (d, 0.55H), 8.14-8.12 (s, 0.9H), 8.08 (s, 1.1H), 7.87-7.61 (m, 2H), 7.57-7.44 (m, 1H), 7.44-7.32 (m, 1.45H), 7.31-7.18 (m, 1H), 6.85 (bs, 0.55H), 4.14-3.99 (m, 0.55H), 3.99-3.72 (m, 1.45H), 3.70-3.48 (m, 1H), 3.49-3.36 (m, 1H), 3.35-3.24 (m, 1H), 2.58 (s, 1.35H), 2.53 (s, 1.65H), 2.12-1.88 (m, 0.55H), 1.88-1.76 (m, 0.45H), 1.76-1.58 (m, 1H), 1.22 (t, 1.65H), 1.07 (m, 2.7H), 0.89 (t, 1.65H).

Preparation of (S)—N-ethyl-6-methyl-3-(2H-1,2,3-triazol-2-yl)-N-(1-((5-(trifluoromethyl)pyrimidin-2-yl)amino)butan-2-yl)picolinamide (Example 73)

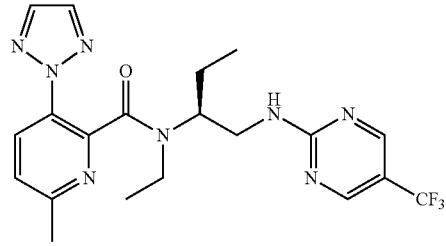

The title compound (28 mg) was prepared as a glass from Intermediate 29 (50 mg, 0.16 mmol) and 2-chloro-5-(trifluoromethyl)pyrimidine (45 mg, 0.25 mmol) using the method described for Route 7. The crude product was purified by chromatography on the Biotage Isolera Four™ (11 g KP—NH column, 0 to 10% methanol in DCM).

LCMS (Method H): Two peaks at 4.36 and 4.50 min, 449 $[M+H]^+$ $^1$H NMR (250 MHz, DMSO-$d_6$) 8.88 (s, 0.35H), 8.85 (s, 0.35H), 8.76 (s, 0.65H), 8.64 (s, 0.65H), 8.48-8.36 (m, 1.65H), 8.34 (s, 0.7H), 8.30 (s, 1.3H), 8.03 (bm, 0.35H), 7.72 (d, 0.35H), 7.67 (d, 0.65H), 4.09 (bm, 0.65H), 3.94 (m, 1.35H), 3.83-3.63 (bm, 1H), 3.62-3.54 (m, 1H), 3.42 (d, 1H), 2.75 (s, 1.05H), 2.70 (s, 1.95H), 2.25-2.02 (bm, 0.65H), 1.96-1.81 (bm, 0.35H), 1.73 (m, 1H), 1.36 (t, 1.95H), 1.21 (m, 2.1H), 0.99 (t, 1.95H).

Preparation of (S)—N-(1-cyclopropyl-2-((5-(trifluoromethyl)pyrimidin-2-yl)amino)ethyl)-N,6-dimethyl-3-(2H-1,2,3-triazol-2-yl)picolinamide (Example 74)

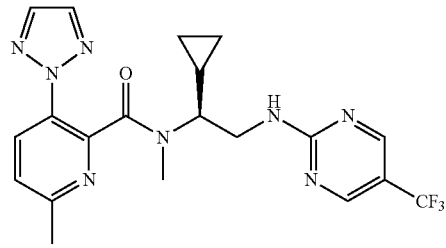 [SMILES: Cc1ccc(-n2nccn2)c(C(=O)N(C)[C@H](CNc2ncc(C(F)(F)F)cn2)C2CC2)n1]

The title compound (10 mg) was prepared as an oil from Intermediate 30 (33 mg, 0.1 mmol) and 2-chloro-5-(trifluoromethyl)pyrimidine (18 mg, 0.1 mmol) using the method described for Route 7. The crude product was purified by chromatography on the Biotage Isolera Four™ (11 g KP—NH column, 0 to 100% EtOAc in heptane).

LCMS (Method I): 3.39 min, 447 [M+H]⁺

¹H NMR (250 MHz, DMSO-d₆, 353K) 8.62 (s, 1.1H), 8.43 (s, 0.9H), 8.18 (m, 1H), 8.08 (s, 1.1H), 8.04 (s, 0.9H), 7.85 (bm, 0.45H), 7.55-7.42 (m, 1H), 7.42-7.32 (bm, 0.55H), 4.02 (m, 0.55H), 3.75 (m, 1.55H), 3.55 (m, 0.45H), 3.35 (m, 0.45H), 3.02 (s, 1.35H), 2.86 (s, 1.65H), 2.55 (s, 1.65H), 2.53 (s, 1.35H), 1.10 (m, 1H), 0.49 (m, 3.55H), 0.15 (m, 0.45H).

Preparation of (S)—N,6-dimethyl-N-(1-(quinolin-2-ylamino)butan-2-yl)-3-(2H-1,2,3-triazol-2-yl)picolinamide (Example 75)

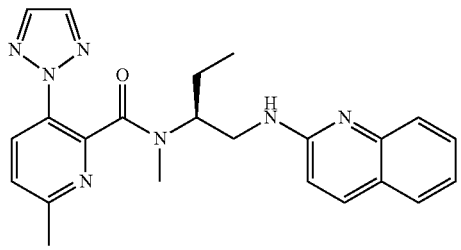 [SMILES: CC[C@@H](CNc1ccc2ccccc2n1)N(C)C(=O)c1nc(C)ccc1-n1nccn1]

To a mixture of Intermediate 22 (65 mg, 0.20 mmol), 2-chloroquinoline (29 mg, 0.18 mmol), NaOᵗBu (48 mg, 0.50 mmol) and BINAP (12 mg, 0.02 mmol) in degassed dioxane (12 mL) was added Pd₂(dba)₃ (9 mg, 0.01 mmol). The reaction mixture was heated at 100° C. for 18 hrs. EtOAc (10 mL) and water (10 mL) were added and the layers were separated. The aqueous phase was extracted with EtOAc (10 mL). The combined organics were washed with water (20 mL), dried over MgSO₄, filtered and concentrated in vacuo. The residue was purified by dry flash chromatography (50 to 100% EtOAc in heptane) and then by reverse phase column chromatography (C18 30 g cartridge, 5 to 95% pH 10 NH₄HCO₃ in MeCN) to afford the title compound as a solid (23 mg).

LCMS (Method B): Two peaks at 2.27 and 2.31 min, 416 [M+H]⁺

¹H NMR (400 MHz, DMSO-d₆) 8.41 (d, 0.55H), 8.34 (s, 1H), 8.33-8.28 (m, 1.45H), 8.07 (d, 0.45H), 7.97 (d, 0.55H), 7.85-7.74 (dd, 1H), 7.74-7.57 (m, 2H), 7.46 (m, 1H), 7.33 (m, 1H), 7.22 (bm, 0.55H), 7.11 (bm, 0.45H), 7.00 (d, 0.45H), 6.81 (bd, 0.55H), 4.80 (m, 0.45H), 4.12-3.96 (m, 0.55H), 3.92-3.76 (m, 0.9H), 3.76-3.61 (m, 1.1H), 3.07 (s, 1.65H), 2.96 (s, 1.35H), 2.69 (s, 1.35H), 2.56 (bs, 1.65H), 1.76 (m, 2H), 1.18 (bt, 1.35H), 1.02 (bt, 1.65H).

Preparation of (S)—N-(1-((1,5-naphthyridin-2-yl)amino)butan-2-yl)-N,6-dimethyl-3-(2H-1,2,3-triazol-2-yl)picolinamide (Example 76)

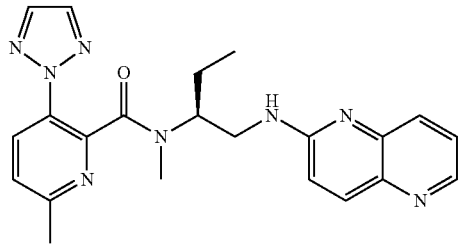 [SMILES: CC[C@@H](CNc1ccc2ncccc2n1)N(C)C(=O)c1nc(C)ccc1-n1nccn1]

A mixture of Intermediate 22 (100 mg, 0.31 mmol), 2-bromo-1,5-naphthyridine (64 mg, 0.31 mmol), NaOᵗBu (71 mg, 0.74 mmol) and BINAP (4 mg, 0.01 mmol) in toluene (3 mL) was degassed under nitrogen for 5 mins. Pd₂dba₃ (11 mg, 0.01 mmol) was added and the mixture was degassed under nitrogen for 5 mins. The mixture was heated to 120° C. for 4 hrs. The reaction mixture was allowed to cool to ambient temperature, and then BINAP (4 mg, 0.01 mmol), Pd₂dba₃ (11 mg, 0.01 mmol) and NaOᵗBu (27 mg, 0.31 mmol) were added and the mixture was degassed for 5 mins. Heating was continued at 120° C. for 3 hrs. The reaction mixture was then allowed to cool to ambient temperature, and the mixture was diluted with EtOAc/water and the phases were separated. The aqueous phase was extracted with EtOAc. The combined organics were washed with saturated aqueous NaHCO₃ and brine, dried over MgSO₄, filtered and concentrated in vacuo. The crude product was purified by preparative HPLC (Gilson, Acidic (0.1% Formic acid), Waters Sunfire Prep-C18, 10 µm, 30×100 mm column, 10 to 95% MeCN in Water) to afford the title compound as a glass (23 mg).

LCMS (Method I): Two peaks at 1.64 and 1.69 min, 417 [M+H]⁺

¹H NMR (500 MHz, CDCl₃) 8.53 (dd, 0.4H), 8.50 (dd, 0.6H), 8.30-8.20 (bm, 0.6H), 8.19-8.12 (m, 1.4H), 7.97 (m, 1H), 7.90 (d, 1H), 7.81 (s, 1.2H), 7.71 (s, 0.8H), 7.41-7.38 (dd, 0.4H), 7.38-7.33 (dd, 0.6H), 7.25-7.21 (bm, 1H), 6.94 (bm, 0.4H), 6.81 (bm, 0.6H), 4.76 (m, 0.4H), 3.88 (bm, 0.6H), 3.86-3.67 (bm, 1H), 3.67-3.45 (bm, 1H), 2.93 (s, 1.8H), 2.72 (s, 1.2H), 2.57 (s, 1.8H), 2.51 (s, 1.2H), 1.75 (m, 1.2H), 1.61 (m, 0.8H), 1.06 (t, 1.2H), 0.86 (t, 1.8H).

Preparation of (S)-5-chloro-N-methyl-N-(1-(quinolin-2-ylamino)butan-2-yl)-2-(2H-1,2,3-triazol-2-yl)benzamide (Example 77)

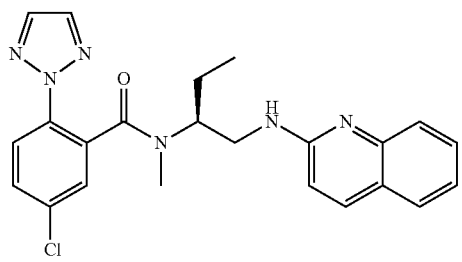 [SMILES: CC[C@@H](CNc1ccc2ccccc2n1)N(C)C(=O)c1cc(Cl)ccc1-n1nccn1]

To a solution of Intermediate 21 (400 mg, 1.3 mmol) in dioxane (8 mL) was added 2-bromoquinoline (300 mg, 1.4 mmol) and NaO^tBu (310 mg, 3.2 mmol) and the mixture was degassed under argon for 20 mins. tBuXPhos (110 mg, 0.26 mmol) and Pd₂(dba)₃ (120 mg, 0.13 mmol) were added and the mixture was degassed under argon for a further 10 mins. The reaction mixture was heated at 120° C. for 3 hrs in a microwave reactor and was then allowed to cool to ambient temperature. EtOAc was added and the organics were washed with water and brine, dried over Na₂SO₄, filtered and concentrated in vacuo. The residue was purified by column chromatography (5% methanol in DCM) to afford the title compound as a solid (90 mg).

LCMS (Method E): Two peaks at 2.32 and 2.72 min, 435 $[M+H]^+$ $^1$H NMR (400 MHz, DMSO-d₆) 8.12 (s, 1H), 8.05 (s, 1H), 8.02-7.92 (bm, 0.35H), 7.92-7.74 (bm, 1.47H), 7.74-7.33 (bm, 3.9H), 7.28-6.95 (bm, 2.83H), 6.92-6.79 (bm, 1.1H), 6.73 (d, 0.35H), 4.68 (bm, 0.34H), 4.51 (bm, 0.07H), 3.78 (bm, 0.6H), 3.63-3.41 (m, 0.63H), 3.25-3.04 (bm, 1.32H), 2.91 (s, 0.08H), 2.83 (s, 0.8H), 2.74 (m, 1.2H), 2.72-2.63 (m, 0.6H), 2.33 (m, 0.17H), 1.72 (bm, 0.19H), 1.62 (t, 0.78H), 1.39-1.16 (m, 1.25H), 0.99 (m, 1.42H), 0.89 (m, 0.6H), 0.74 (bm, 0.25H), 0.62 (t, 0.7H).

Preparation of (S)—N,3-dimethyl-N-(1-((5-(trifluoromethyl)pyrimidin-2-yl)amino)butan-2-yl)isoquinoline-1-carboxamide (Example 78)

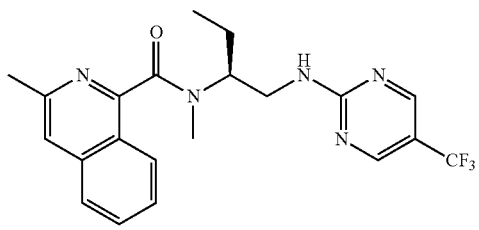 [SMILES: CC[C@@H](CNc1ncc(C(F)(F)F)cn1)N(C)C(=O)c1nc(C)cc2ccccc12]

To a mixture of 3-methylisoquinoline-1-carboxylic acid [prepared as described in J. Med. Chem. 2014, 57, 1976-1994] (40 mg, 0.21 mmol) and triethylamine (43 mg, 0.43 mmol) in DMF (1 mL) was added HATU (97 mg, 0.26 mmol). After 15 mins, Intermediate 31 (53 mg, 0.21 mmol) was added and the reaction mixture was stirred at ambient temperature for 30 mins. EtOAc (10 mL) and water (10 mL) were added. The layers were separated, and then the aqueous phase was extracted with EtOAc (10 mL). The combined organics were washed with water (20 mL), dried over MgSO₄, filtered and concentrated in vacuo. The residue was purified by dry flash chromatography (50 to 100% EtOAc in heptane) to afford the title compound as a solid (20.4 mg).

LCMS (Method L): 2.47 min, 418 $[M+H]^+$ $^1$H NMR (400 MHz, CDCl₃) 8.70 (bs, 0.5H), 8.54-8.41 (m, 2.1H), 8.07 (d, 0.9H), 7.84 (bd, 0.1H), 7.77 (d, 1.15H), 7.67 (t, 1.05H), 7.58-7.48 (m, 2.2H), 5.09 (bm, 0.1H), 3.85-3.65 (m, 2.4H), 3.61 (m, 0.2H), 3.48 (m, 0.15H), 3.22 (m, 0.8H), 3.06 (s, 2.55H), 2.79 (s, 2.55H), 2.74-2.69 (m, 0.33H), 2.68 (s, 0.33H), 1.82-1.69 (m, 0.21H), 1.41 (m, 1.2H), 1.33-1.21 (bm, 0.18H), 1.16 (t, 0.3H), 1.06 (t, 0.09H), 0.92 (t, 0.09H), 0.77 (t, 2.52H).

Preparation of (S)—N-methyl-N-(1-((5-(trifluoromethyl)pyrimidin-2-yl)amino)butan-2-yl)quinoline-8-carboxamide (Example 79)

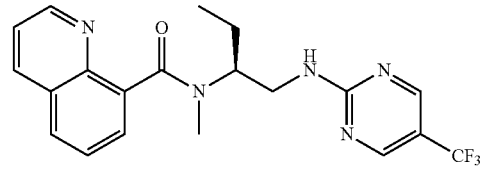 [SMILES: CC[C@@H](CNc1ncc(C(F)(F)F)cn1)N(C)C(=O)c1cccc2cccnc12]

To a mixture of 8-quinoline carboxylic acid (35 mg, 0.20 mmol) and triethylamine (22 mg, 0.22 mmol) in MeCN (0.5 mL) was added HATU (92 mg, 0.20 mmol). After 15 mins, Intermediate 31 (50 mg, 0.20 mmol) was added and the reaction mixture was stirred at ambient temperature for 2 hrs. EtOAc (10 mL) and water (10 mL) were added. The organic phase was washed with water (20 mL), dried over MgSO₄, filtered and concentrated in vacuo. The residue was purified by dry flash chromatography (0 to 10% MeOH in EtOAc) to afford the title compound as a solid (35.2 mg).

LCMS (Method L): Peaks at 1.79, 1.83 and 2.03 min, 404 $[M+H]^+$ $^1$H NMR (400 MHz, CDCl₃) 9.37 (bd, 0.5H), 9.31 (bd, 0.5H), 8.69 (bs, 0.5H), 8.53 (m, 1.5H), 8.46-8.37 (m, 1H), 8.23 (d, 1H), 7.90 (d, 1H), 7.77 (d, 0.5H), 7.74 (d, 0.5H), 7.62 (t, 1H), 7.51 (m, 1H), 5.26 (bm, 0.5H), 4.09 (bm, 0.5H), 3.72 (bm, 0.5H), 3.55 (m, 0.5H), 3.23 (bt, 0.5H), 3.16-3.10 (bm, 0.5H), 3.09 (s, 1.5H), 2.60 (s, 1.5H), 1.77-1.62 (m, 1H), 1.55-1.40 (m, 0.5H), 1.11 (t, 1.5H), 0.92 (t, 1.5H), 0.83 (bm, 0.5H).

Preparation of (S)-6-chloro-N-methyl-N-(1-((5-(trifluoromethyl)pyrimidin-2-yl)amino)butan-2-yl)quinoline-8-carboxamide (Example 80)

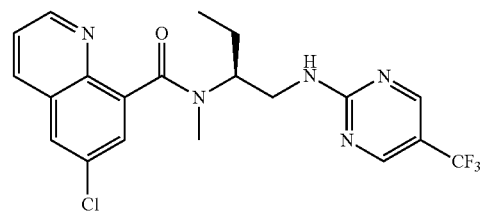 [SMILES: CC[C@@H](CNc1ncc(C(F)(F)F)cn1)N(C)C(=O)c1cc(Cl)cc2cccnc12]

To a mixture of 6-chloroquinoline-8-carboxylic acid (42 mg, 0.20 mmol) and triethylamine (22 mg, 0.22 mmol) in MeCN (0.5 mL) was added HATU (92 mg, 0.20 mmol). After 15 mins, Intermediate 31 (50 mg, 0.20 mmol) was added and the reaction mixture was stirred at ambient temperature for 2 hrs. EtOAc (10 mL) and water (10 mL) were added and the layers were separated. The aqueous phase was extracted with EtOAc (10 mL). The combined organics were washed with water (20 mL), dried over MgSO₄, filtered and concentrated in vacuo. The residue was purified by dry flash chromatography (50 to 100% EtOAc in heptane) to afford the title compound as a solid (23.6 mg).

LCMS (Method A): Peaks at 0.80, 0.86 and 0.94 min, 438 $[M+H]^+$ $^1$H NMR (400 MHz, CDCl₃) 9.36 (dd, 0.39H), 9.29 (dd, 0.39H), 9.25 (bd, 0.1H), 8.53 (bm, 1.41H), 8.48 (bm, 0.45H), 8.44 (m, 0.36H), 8.23 (bs, 0.18H), 8.21 (bs, 0.18H), 8.16 (t, 0.84H), 8.14 (t, 0.45H), 8.12 (d, 0.06H), 7.88 (d, 0.89H), 7.85 (d, 0.15H), 7.72 (d, 0.39H), 7.67 (d, 0.5H), 7.59 (d, 0.11H), 7.53 (m, 1.15H), 5.22 (m, 0.4H), 4.09 (m, 0.4H), 3.68 (m, 0.45H), 3.55 (m, 0.62H), 3.24 (t, 0.4H), 3.19-3.12 (m, 0.52H), 3.08 (s, 1.41H), 2.70 (s, 0.28H), 2.62 (s, 1.29H), 1.77-1.60 (m, 1.47H), 1.25 (bs, 0.39H), 1.17 (t, 0.18H), 1.10 (t, 1.29H), 0.95 (t, 1.32H), 0.83 (bm, 0.48H), 0.73 (t, 0.1H).

Preparation of (S)-3-(dimethylamino)-N-methyl-N-(1-((5-(trifluoromethyl)pyrimidin-2-yl)amino)butan-2-yl)isoquinoline-1-carboxamide (Example 81)

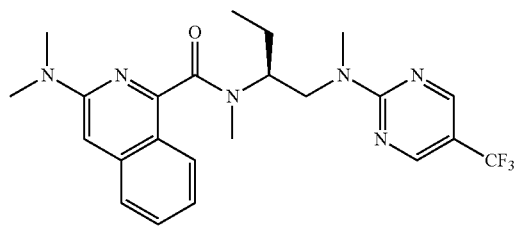 [SMILES: CC[C@@H](CN(C)c1ncc(C(F)(F)F)cn1)N(C)C(=O)c1nc(N(C)C)cc2ccccc12]

To a mixture of Intermediate 32 (17 mg, 0.08 mmol) and triethylamine (16 mg, 0.16 mmol) in MeCN (1 mL) was added HATU (36 mg, 0.09 mmol). After 15 mins, Intermediate 31 (20 mg, 0.08 mmol) was added and the reaction mixture was stirred at ambient temperature for 30 mins. EtOAc (10 mL) and water (10 mL) were added and the aqueous phase was extracted with EtOAc (10 mL). The combined organics were washed with water (20 mL), dried over MgSO$_4$, filtered and concentrated in vacuo. The residue was purified by dry flash chromatography (0 to 100% EtOAc in heptane) to afford the title compound as a solid (22.2 mg).

LCMS (Method B): Two peaks at 2.64 and 2.89 min, 447 [M+H]$^+$ $^1$H NMR (400 MHz, DMSO-d$_6$) 8.90 (d, 0.25H), 8.81 (d, 0.25H), 8.44 (m, 1H), 8.22 (t, 0.75H), 8.17 (bs, 0.75H), 7.83 (d, 0.25H), 7.69-7.57 (m, 1.75H), 7.50 (t, 1H), 7.21 (t, 0.25H), 7.10 (t, 0.75H), 6.96 (s, 0.25H), 6.84 (s, 0.75H), 5.16 (bm, 0.25H), 4.02 (bm, 0.5H), 3.89 (bm, 0.25H), 3.52 (s, 2.25H), 3.43 (bm, 0.75H), 3.24 (s, 3.75H), 3.23 (s, 0.75H), 3.19 (s, 2.25H), 2.76 (s, 0.75H), 1.80 (m, 1.5H), 1.70 (m, 0.75H), 1.43 (m, 0.25H), 1.18 (t, 0.75H), 1.09 (t, 2.25H).

Preparation of (S)—N,6-dimethyl-N-(1-(methyl(5-(trifluoromethyl)pyrimidin-2-yl)amino)butan-2-yl)-3-(2H-1,2,3-triazol-2-yl)picolinamide (Example 82)

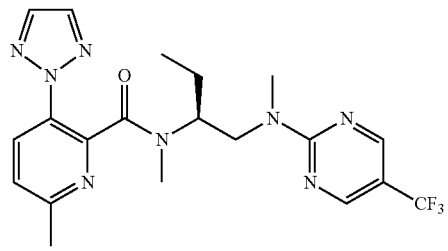 [SMILES: CC[C@@H](CN(C)c1ncc(C(F)(F)F)cn1)N(C)C(=O)c1nc(C)ccc1-n1nccn1]

To a solution of Intermediate 33 (72 mg, 0.28 mmol), HATU (115 mg, 0.3 mmol) and 6-methyl-3-(2H-1,2,3-triazol-2-yl)picolinic acid [prepared as described in WO2011023578](97 mg, 0.3 mmol) in anhydrous DMF (2 mL) was added DIPEA (0.24 mL, 1.38 mmol) and the mixture was stirred at ambient temperature overnight. The reaction mixture was then concentrated in vacuo and the residue was purified by preparative HPLC (Gilson, Acidic (0.1% Formic acid), Waters Sunfire Prep-C18, 10 μm, 30×100 mm column, 10 to 95% MeCN in Water). The crude product was further purified by chromatography on the Biotage Isolera Four™ (11 g KP—NH column, 0 to 100% EtOAc in heptane) to afford the title compound as a solid (20 mg).

LCMS (Method H): Two peaks at 4.23 and 4.62 min, 449 [M+H]$^+$ $^1$H NMR (500 MHz, DMSO-d$_6$) 8.92 (s, 0.85H), 8.85 (s, 0.85H), 8.77 (s, 0.15H), 8.48 (s, 0.15H), 8.36-8.31 (m, 1H), 8.26 (s, 0.3H), 8.23 (s, 1.7H), 7.64 (d, 0.85H), 7.56 (d, 0.15H), 5.04 (m, 0.85H), 4.40 (dd, 0.85H), 3.97-3.89 (bm, 0.15H), 3.97-3.89 (d, 0.15H), 3.83-3.77 (dd, 0.15H), 3.77-3.71 (dd, 0.85H), 3.42 (s, 2.55H), 3.23 (s, 0.45H), 3.11 (s, 0.45H), 2.91 (s, 2.55H), 2.61 (s, 2.55H), 2.58 (s, 0.45H), 1.90-1.80 (m, 0.85H), 1.80-1.70 (m, 0.85H), 1.63-1.47 (m, 0.3H), 1.19 (t, 2.55H), 0.91 (t, 0.45H).

Preparation of (S)—N-(1-((2-methoxyethyl)(5-(trifluoromethyl)pyrimidin-2-yl)amino)butan-2-yl)-N,6-dimethyl-3-(2H-1,2,3-triazol-2-yl)picolinamide (Example 83)

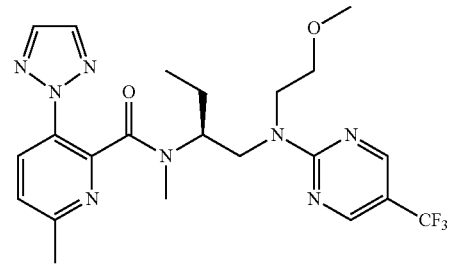 [SMILES: CC[C@@H](CN(CCOC)c1ncc(C(F)(F)F)cn1)N(C)C(=O)c1nc(C)ccc1-n1nccn1]

To a solution of Intermediate 34 (49 mg, 0.16 mmol), HATU (65 mg, 0.17 mmol) and 6-methyl-3-(2H-1,2,3-triazol-2-yl)picolinic acid [prepared as described in WO2011023578](55 mg, 0.17 mmol) in anhydrous DMF (2 mL) was added DIPEA (0.14 mL, 0.78 mmol) and the reaction mixture was stirred at ambient temperature for 5 hrs. The reaction mixture was concentrated in vacuo and the residue was dissolved in EtOAc (25 mL) and washed with water. The aqueous phase was extracted with EtOAc and the combined organics were washed with water, brine, dried over Na$_2$SO$_4$, filtered and concentrated in vacuo. The crude product was purified by chromatography on the Biotage Isolera Four™ (11 g KP—NH column, 0 to 100% EtOAc in heptane). The crude product was further purified by preparative HPLC (Gilson, Acidic (0.1% Formic acid), Waters Sunfire Prep-C18, 10 μm, 30×100 mm column, 10 to 95% MeCN in Water) to afford the title compound as a solid (31 mg).

LCMS (Method I): Two peaks at 3.54 and 3.99 min, 493 [M+H]$^+$ $^1$H NMR (500 MHz, DMSO-d$_6$) 8.92 (s, 0.6H), 8.87 (s, 0.6H), 8.77 (s, 0.4H), 8.49 (s, 0.4H), 8.38-8.32 (d, 0.6H), 8.32-8.30 (d, 0.4H), 8.27 (s, 0.8H), 8.23 (s, 1.2H), 7.65 (d, 0.6H), 7.55 (d, 0.4H), 5.01 (bm, 1H), 4.30 (dd, 0.6H), 4.17-3.95 (m, 1.4H), 3.95-3.81 (m, 1.4H), 3.77 (m, 1.6H), 3.63 (m, 1H), 3.46 (s, 1.8H), 3.36 (s, 1.2H), 3.10 (s, 1.2H), 2.91 (s, 1.8H), 2.63 (s, 1.8H), 2.60 (s, 1.2H), 1.79 (m, 1.4H), 1.55 (m, 0.6H), 1.18 (t, 1.8H), 0.89 (t, 1.2H).

Preparation of (S)—N,6-dimethyl-3-(pyrimidin-2-yl)-N-(1-((5-(trifluoromethyl)pyrimidin-2-yl)amino)butan-2-yl)picolinamide Formic Acid Salt (Example 84)

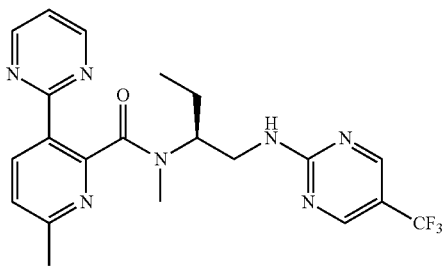 [SMILES: CC[C@@H](CNc1ncc(C(F)(F)F)cn1)N(C)C(=O)c1nc(C)ccc1-c1ncccn1]

To a solution of lithium 6-methyl-3-(pyrimidin-2-yl)picolinate [prepared as described in WO 2012/089607] (29 mg, 0.13 mmol), Intermediate 31 (32 mg, 0.13 mmol) and HATU (54 mg, 0.14 mmol) in DMF (5 mL) at 0° C. was added DIPEA (62 µL, 0.36 mmol) and the reaction mixture was allowed to warm to ambient temperature and stirred for 88 hrs. The mixture was diluted with EtOAc (30 mL) and washed with saturated aqueous NaHCO₃. The organic phase was dried over Na₂SO₄, filtered and concentrated in vacuo. The crude product was purified by chromatography on the Biotage Isolera Four™ (10 g column, 1 to 10% methanol in DCM). The crude product was further purified by preparative HPLC (Gilson, Acidic (0.1% Formic acid), Waters Sunfire Prep-C18, 10 µm, 30×100 mm column, 10 to 95% MeCN in Water) and lyophilised from 10% MeCN in water (3 mL) to give the title compound as a solid (39 mg)

LCMS (Method I): 3.30 min, 446 [M+H]⁺

¹H NMR (500 MHz, DMSO-d₆) 9.11 (d, 1.2H), 9.09 (d, 0.8H), 8.87 (s, 0.4H), 8.82 (s, 0.4H), 8.71 (s, 0.6H), 8.67 (s, 0.6H), 8.64-8.62 (d, 0.4H), 8.62-8.59 (d, 0.6H), 8.49 (bm, 0.6H), 8.02 (t, 0.4H), 7.66 (m, 1H), 7.62 (m, 1H), 4.84 (m, 0.4H), 3.98 (m, 0.6H), 3.87-3.75 (m, 1H), 3.75-3.66 (m, 1H), 3.06 (s, 1.8H), 2.92 (s, 1.2H), 2.72 (s, 1.8H), 2.70 (s, 1.2H), 1.80 (m, 2H), 1.20 (t, 1.2H), 1.03 (t, 1.8H).

Preparation of (S)—N-methyl-N-(1-((5-(trifluoromethyl)pyrimidin-2-yl)amino)butan-2-yl)isoquinoline-1-carboxamide (Example 85)

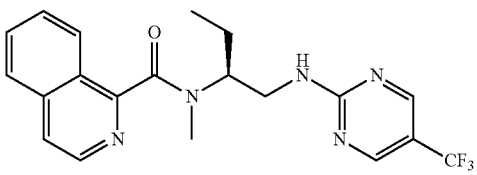 [SMILES: CC[C@@H](CNc1ncc(C(F)(F)F)cn1)N(C)C(=O)c1nccc2ccccc12]

To a mixture of isoquinoline-1-carboxylic acid (150 mg, 0.87 mmol) in DMF (1 mL) was added CDI (140 mg, 0.87 mmol). After 10 mins, Intermediate 31 (195 mg, 0.79 mmol) was added and the reaction mixture was stirred at ambient temperature for 18 hrs and was then partitioned between EtOAc (10 mL) and water (10 mL). The aqueous layer was extracted with EtOAc (10 mL) and the combined organics were washed with water (20 mL), dried over MgSO₄, filtered and concentrated in vacuo. The residue was purified by dry flash chromatography (50 to 100% EtOAc in heptane) to afford the title compound as a solid (76.4 mg).

LCMS (Method B): Two peaks at 2.23 and 2.28 min, 404 [M+H]⁺

¹H NMR (400 MHz, CDCl₃) 8.56 (d, 0.85H), 8.53-8.45 (m, 1.3H), 8.43 (bs, 0.85H), 8.35 (bs, 0.85H), 8.13 (d, 0.85H), 7.90-7.82 (m, 1H), 7.77-7.68 (m, 2H), 7.68-7.65 (d, 0.15H), 7.65-7.60 (td, 0.85H), 7.50 (tt, 0.15H), 6.24 (m, 0.15H), 5.11 (m, 0.15H), 3.91-3.61 (m, 1.85H), 3.24 (m, 0.85H), 3.07 (s, 2.55H), 2.67 (s, 0.45H), 1.75 (m, 0.3H), 1.70-1.62 (m, 0.85H), 1.42 (m, 0.85H), 1.15 (t, 0.45H), 0.78 (m, 2.7H).

Preparation of (S)—N-(1-((5-chloropyridin-2-yl)amino)butan-2-yl)-N,4,5-trimethyl-2-(2H-1,2,3-triazol-2-yl)benzamide (Example 86)

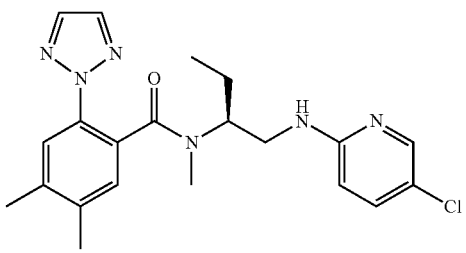 [SMILES: CC[C@@H](CNc1ccc(Cl)cn1)N(C)C(=O)c1cc(C)c(C)cc1-n1nccn1]

To a solution of 4,5-dimethyl-2-(2H-1,2,3-triazol-2-yl)benzoic acid [prepared as described in WO 2014/141065] (30 mg, 0.14 mmol) in DCM (2 mL) was added oxalyl chloride (35 mg, 0.28 mmol). The reaction mixture was stirred at ambient temperature for 1 hr. Toluene (2 mL) was added and the reaction mixture was concentrated in vacuo. The residue was dissolved in DCM (1 mL) and added to an ice-cooled solution of Intermediate 15 (30 mg, 0.14 mmol) and triethylamine (28 mg, 0.28 mmol) in DCM (1 mL). The reaction was allowed to warm to ambient temperature and stirred for 1 hr. EtOAc (10 mL) and saturated aqueous NaHCO₃ (10 mL) were added and the layers were separated. The aqueous phase was extracted with EtOAc (10 mL) and the combined organics were washed with water (20 mL), dried over MgSO₄, filtered and concentrated in vacuo. The residue was purified by dry flash chromatography (0 to 100% EtOAc in heptane) to afford the title compound as a solid (11.1 mg).

LCMS (Method B): Two peaks at 2.52 and 2.79 min, 413 [M+H]⁺

¹H NMR (400 MHz, DMSO-d₆) 8.26 (bm, 0.24H), 8.23 (s, 0.64H), 8.18 (bm, 0.80H), 8.14 (bm, 0.31H), 7.96 (bm, 0.06H), 7.95-7.85 (m, 0.63H), 7.79 (bm, 0.47H), 7.70-7.63 (m, 1.03H), 7.62 (d, 0.16H), 7.59 (d, 0.22H), 7.35-7.25 (bm, 0.34H), 7.20-7.10 (bm, 0.88H), 6.89 (s, 0.41H), 6.80-6.70 (bm, 1.50H), 6.65 (d, 0.31H), 4.85-4.70 (bm, 0.52H), 3.85-3.70 (bm, 0.23H), 3.52 (m, 3.50H), 3.25-3.05 (bm, 0.18H), 3.01 (s, 0.16H), 2.95 (s, 0.79H), 2.79 (s, 1.38H), 2.55-2.45 (m, 2.42H), 2.40 (m, 1.68H), 2.27 (s, 0.45H), 2.11 (s, 0.84H), 1.71 (bm, 0.77H), 1.43 (bm, 1.09H), 1.11 (t, 1.51H), 1.08-0.98 (bt, 0.55H), 0.86 (bt, 0.10H), 0.67 (t, 0.84H).

Preparation of (S)—N-(1-((5-chloropyridin-2-yl) amino)butan-2-yl)-5-methoxy-N,4-dimethyl-2-(2H-1,2,3-triazol-2-yl)benzamide (Example 87)

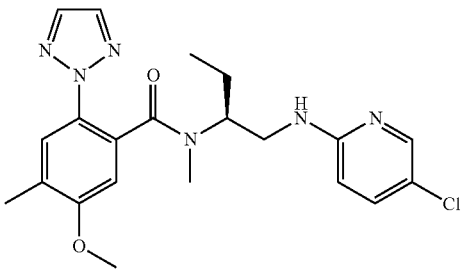 [SMILES: CC[C@@H](CNc1ccc(Cl)cn1)N(C)C(=O)c1cc(OC)c(C)cc1-n1nccn1]

To a solution of 5-methoxy-4-methyl-2-(2H-1,2,3-triazol-2-yl)benzoic acid [prepared as described in WO 2014/141065] (30 mg, 0.13 mmol) in DCM (2 mL) was added oxalyl chloride (33 mg, 0.26 mmol). The reaction mixture was stirred at ambient temperature for 1 hr. Toluene (2 mL) was added and the reaction mixture was concentrated in vacuo. The residue was dissolved in DCM (1 mL) and added to an ice-cooled solution of Intermediate 15 (27 mg, 0.13 mmol) and triethylamine (26 mg, 0.26 mmol) in DCM (1 mL). The reaction was allowed to warm to ambient temperature and stirred for 1 hr. EtOAc (10 mL) and saturated aqueous NaHCO₃ (10 mL) were added and the layers were separated. The aqueous phase was extracted with EtOAc (10 mL) and the combined organics were washed with water (20 mL), dried over MgSO₄, filtered and concentrated in vacuo. The residue was purified by dry flash chromatography (0 to 100% EtOAc in heptane) to afford the title compound as a solid (6.2 mg).

LCMS (Method B): Two peaks at 2.50 and 2.75 min, 429 [M+H]⁺

¹H NMR (400 MHz, DMSO-d₆) 8.19 (m, 2H), 7.98-7.92 (m, 0.2H), 7.92-7.83 (m, 0.49H), 7.79 (bs, 0.46H), 7.67 (s, 0.33H), 7.65-7.55 (bm, 0.49H), 7.55-7.45 (m, 0.46H), 7.20-7.10 (bm, 0.52H), 7.10-6.95 (bm, 0.62H), 6.85 (s, 0.33H), 6.83-6.70 (bm, 1.63H), 6.61 (d, 0.36H), 6.44 (d, 0.13H), 4.87-4.77 (bs, 0.41H), 4.75-4.60 (bs, 0.12H), 4.09-4.03 (bm, 0.53H), 4.02 (s, 0.26H), 3.96 (bs, 1.17H), 3.87 (s, 0.99H), 3.75-3.60 (bm, 1H), 3.25-3.15 (bm, 0.43H), 3.02 (s, 0.26H), 2.94 (s, 1.08H), 2.85-2.75 (bm, 2.08H), 2.47-2.37 (bm, 2.36H), 2.34 (s, 0.90H), 2.27 (s, 0.15H), 1.90-1.75 (bm, 0.23H), 1.75-1.65 (bm, 0.81H), 1.50-1.35 (bm, 0.38H), 1.15-0.95 (bm, 2.90H), 0.68 (t, 0.93H).

Preparation of (S)—N,6-dimethyl-3-(2H-1,2,3-triazol-2-yl)-N-(4,4,4-trifluoro-1-((5-(trifluoromethyl) pyrimidin-2-yl)amino)butan-2-yl)picolinamide (Example 88)

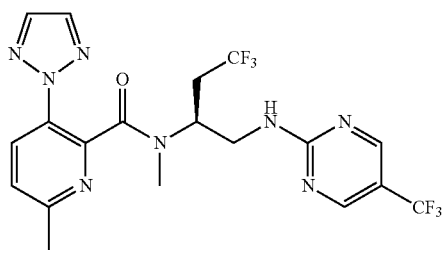 [SMILES: Cc1ccc(-n2nccn2)c(C(=O)N(C)[C@H](CNc2ncc(C(F)(F)F)cn2)CC(F)(F)F)n1]

To a solution of 6-methyl-3-(2H-1,2,3-triazol-2-yl)picolinic acid [prepared as described in WO 2010/063662] (20 mg, 0.10 mmol) in DCM (1.5 mL) was added oxalyl chloride (37 mg, 0.29 mmol). The reaction mixture was stirred at ambient temperature for 2 hrs. Toluene (2 mL) was added and the mixture was concentrated in vacuo. The residue was dissolved in DCM (1 mL) and added to an ice-cooled solution of Intermediate 35 (35 mg, 0.12 mmol) and triethylamine (30 mg, 0.29 mmol) in DCM (1 mL). The reaction mixture was allowed to warm to ambient temperature and stirred for 1 hr. DCM (10 mL) and saturated aqueous NaHCO₃ (10 mL) were added and the layers were separated. The organics were dried over MgSO₄, filtered and concentrated in vacuo. The residue was purified by dry flash chromatography (50 to 100% EtOAc in heptane) to afford the title compound as a solid (37 mg).

LCMS (Method L): Two peaks at 2.37 and 2.48 min, 489 [M+H]⁺

¹H NMR (400 MHz, DMSO-d₆) 8.90 (m, 1H), 8.78 (bs, 0.58H), 8.55 (bs, 0.42H), 8.44 (m, 1H), 8.41-8.36 (bm, 0.42H), 8.35-8.32 (m, 1.16H), 8.26 (m, 0.84H), 8.20 (bm, 0.58H), 7.71 (m, 0.58H), 7.65 (m, 0.42H), 5.13 (bs, 0.58H), 4.41 (bs, 0.42H), 4.00-3.60 (m, 2H), 3.15 (s, 1.26H), 2.99 (s, 1.74H), 2.87 (bm, 2H), 2.69 (s, 1.74H), 2.51 (s, 1.26H).

Route 8: Procedure for the Preparation of Examples by Copper Catalysed Coupling of an Aryl Halide with a Heterocycle, as Exemplified by the Preparation of (S)—N,6-dimethyl-3-(1H-1,2,4-triazol-1-yl)-N-(1-((5-(trifluoromethyl)pyrimidin-2-yl)amino) butan-2-yl)picolinamide Formic Acid Salt (Example 89)

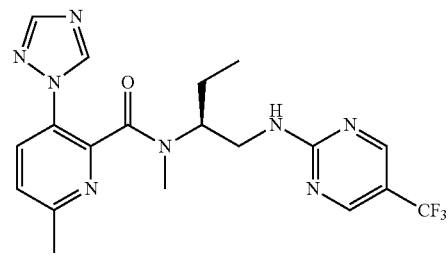 [SMILES: CC[C@@H](CNc1ncc(C(F)(F)F)cn1)N(C)C(=O)c1nc(C)ccc1-n1cncn1]

A suspension of Intermediate 36 (250 mg, 0.42 mmol), (1R,2R)—N,N'-dimethylcyclohexane-1,2-diamine (6 mg, 0.04 mmol), CuI (8 mg, 0.04 mmol), Cs₂CO₃ (274 mg, 0.84 mmol) and 1,2,4-triazole (58 mg, 0.84 mmol) in DMF (3 mL) was degassed under nitrogen for 10 mins at ambient temperature in a sealed tube. The mixture was then heated at 100° C. for 18 hrs. The mixture was allowed to cool to ambient temperature, and then CuI (8 mg, 0.04 mmol) and 1,2,4-triazole (58 mg, 0.84 mmol) were added and the mixture was degassed under nitrogen for 10 mins before heating was continued at 100° C. for a further 6 hrs. The reaction mixture was concentrated in vacuo. EtOAc (50 mL) was added and the organic phase was washed with saturated aqueous NaHCO₃. The organic phase was dried over Na₂SO₄, filtered and concentrated in vacuo. The crude product was purified by chromatography on the Biotage Isolera Four™ (10 g column, 1 to 10% methanol in DCM). The product was further purified by preparative TLC (3×3% methanol in DCM) followed by preparative HPLC (Gilson, Acidic (0.1% Formic acid), Waters Sunfire Prep-C18, 10

µm, 30×100 mm column, 10 to 95% MeCN in Water) to afford the title compound as a gum (28 mg).

LCMS (Method O): Two peaks at 4.28 and 4.34 min, 435 [M+H]$^+$ $^1$H NMR (500 MHz, DMSO-d$_6$) 9.08 (s, 0.45H), 8.99 (s, 0.55H), 8.84 (s, 0.45H), 8.85 (s, 0.45H), 8.71 (s, 0.55H), 8.62 (s, 0.55H), 8.44-8.42 (s, 0.45H), 8.42-8.41 (s, 0.55H), 8.41-8.36 (m, 0.55H), 8.25 (d, 0.45H), 8.18 (d, 0.55H), 8.01 (m, 0.45H), 7.70 (d, 0.45H), 7.64 (d, 0.55H), 4.79 (m, 0.45H), 3.97 (bm, 0.55H), 3.71 (m, 1H), 3.54 (m, 1H), 3.03 (s, 1.65H), 2.89 (s, 1.35H), 2.70 (s, 1.35H), 2.65 (s, 1.65H), 1.70 (m, 2H), 1.01 (t, 1.35H), 0.91 (t, 1.65H).

Preparation of (S)—N,6-dimethyl-3-(1H-pyrazol-1-yl)-N-(1-((5-(trifluoromethyl)pyrimidin-2-yl)amino)butan-2-yl)picolinamide Formic Acid Salt (Example 90)

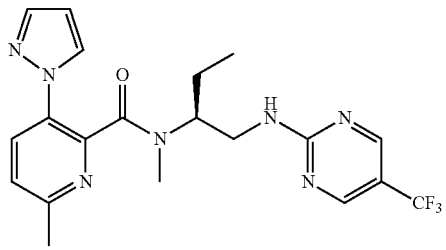 [SMILES: CC[C@@H](CNc1ncc(C(F)(F)F)cn1)N(C)C(=O)c1nc(C)ccc1-n1cccn1]

The title compound (70 mg) was prepared as a solid from Intermediate 36 (250 mg, 0.42 mmol) and 1H-pyrazole (57 mg, 0.84 mmol) using the method described for Route 8. The crude product was purified by chromatography on the Biotage Isolera Four™ (25 g column, 10 to 100% EtOAc in heptane). The product was further purified by preparative HPLC (Gilson, Acidic (0.1% Formic acid), Waters Sunfire Prep-C18, 10 µm, 30×100 mm column, 10 to 95% MeCN in Water).

LCMS (Method H): 4.16 min, 435 [M+H]$^+$ $^1$H NMR (500 MHz, DMSO-d$_6$) 8.66 (m, 1H), 8.58 (m, 0.4H), 8.47 (m, 0.6H), 8.23 (t, 0.6H), 8.12 (d, 0.4H), 8.10 (d, 0.6H), 8.00 (d, 0.4H), 7.98 (d, 0.6H), 7.83-7.75 (m, 1.4H), 7.44 (d, 0.4H), 7.39 (d, 0.6H), 6.51 (t, 0.6H), 6.48 (t, 0.4H), 4.64 (m, 0.6H), 3.62 (bm, 0.6H), 3.58-3.50 (m, 1H), 2.82 (s, 1.8H), 2.66 (s, 1.2H), 2.65 (m, 0.4H), 2.49 (s, 1.2H), 2.41 (s, 1.8H), 2.37 (m, 0.4H), 1.63-1.51 (m, 1H), 1.45 (bm, 0.6H), 1.34 (bm, 0.4H), 0.89 (t, 1.2H), 0.64 (bm, 1.8H).

Preparation of (S)-2-fluoro-N-methyl-6-(2H-1,2,3-triazol-2-yl)-N-(1-((5-(trifluoromethyl)pyrimidin-2-yl)amino)butan-2-yl)benzamide (Example 91)

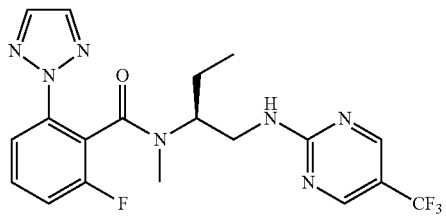 [SMILES: CC[C@@H](CNc1ncc(C(F)(F)F)cn1)N(C)C(=O)c1c(F)cccc1-n1nccn1]

The title compound (158 mg) was prepared as a solid from Intermediate 31 (168 mg, 0.68 mmol), Intermediate 38 (140 mg, 0.68 mmol), HATU (0.26 g, 0.68 mmol) and DIPEA (0.29 mL, 1.69 mmol) using the method described in Route 2. The crude product was isolated by extraction into EtOAc, then purified by chromatography on the Biotage Isolera Four™ (25 g column, 0 to 10% MeOH in DCM). The product was further purified by preparative HPLC (Gilson, Acidic (0.1% Formic acid), Waters Sunfire Prep-C18, 10 µm, 30×100 mm column, 10 to 95% MeCN in Water).

LCMS (Method I): Four peaks at 3.11, 3.37, 3.52 and 3.82 min, 438 [M+H]$^+$ $^1$H NMR (250 MHz, DMSO-d$_6$, 353 K) 8.65 (s, 0.82H), 8.59 (s, 0.65H), 8.41 (bs, 0.12H), 8.35 (bs, 0.13H), 8.16 (s, 0.9H), 8.06 (s, 0.35H), 8.05-8.02 (m, 0.75H), 7.92-7.83 (m, 0.57H), 7.81-7.69 (m, 0.72H), 7.68 (t, 0.31H), 7.66-7.55 (m, 0.75H), 7.54-7.19 (m, 1.81H), 6.95 (td, 0.12H), 4.77 (m, 0.42H), 4.59 (m, 0.58H), 3.82-3.67 (m, 0.54H), 3.67-3.41 (m, 1.18H), 3.40-3.19 (m, 0.48H), 2.92 (s, 0.29H), 2.87 (s, 0.39H), 2.79 (s, 1.46H), 2.78 (s, 0.98H), 1.79-1.55 (m, 1.56H), 1.33 (m, 0.12H), 0.98 (m, 2.25H), 0.85 (t, 0.39H), 0.48 (t, 0.36H).

Preparation of (S)-6-methoxy-N-methyl-3-(2H-1,2,3-triazol-2-yl)-N-(1-((5-(trifluoromethyl)pyrimidin-2-yl)amino)butan-2-yl)picolinamide (Example 92)

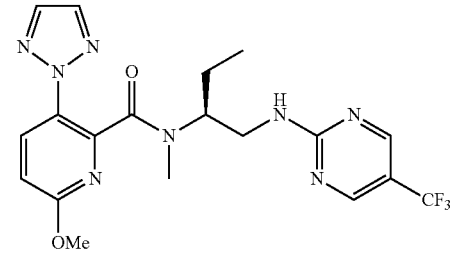 [SMILES: CC[C@@H](CNc1ncc(C(F)(F)F)cn1)N(C)C(=O)c1nc(OC)ccc1-n1nccn1]

The title compound (30 mg) was prepared as a solid from Intermediate 39 (110 mg, 0.34 mmol), Intermediate 31 (84 mg, 0.34 mmol), HATU (141 mg, 0.37 mmol) and DIPEA (160 µL, 0.92 mmol) using the method described in Route 2. The crude product was isolated by extraction into EtOAc, then purified by preparative HPLC (Gilson, Basic (0.2% Ammonium hydroxide), Waters Xbridge Prep-C18, 10 µm, 30×100 mm column, 10 to 95% MeCN in Water) followed by lyophilisation.

LCMS (Method H): Two peaks at 3.92 and 4.11 min, 451 [M+H]$^+$ $^1$H NMR (250 MHz, DMSO-d$_6$, 353 K) 8.62 (s, 1.6H), 8.43 (s, 0.6H), 8.26-8.13 (m, 1H), 8.03 (d, 1.8H), 7.66 (bs, 0.4H), 7.35 (bs, 0.6H), 7.04 (d, 0.6H), 6.98 (d, 0.4H), 4.65 (m, 0.6H), 3.91 (s, 1.2H), 3.89 (s, 1.8H), 3.81 (m, 0.6H), 3.64 (m, 1.2H), 3.50 (m, 0.6H), 2.87 (s, 1.2H), 2.79 (s, 1.8H), 1.60 (m, 2H), 0.99 (t, 1.8H), 0.82 (t, 1.2H).

Biological Assays

Antagonism against orexin receptors has been measured for each example compound using at least one of the following procedures. Antagonism is reported as a pIC$_{50}$, where pIC$_{50}$=–log$_{10}$ (IC$_{50}$) and where IC$_{50}$ is the concentration of example compound needed to inhibit 50% of the agonist response. These values may fluctuate depending on the daily cellular assay performance. Fluctuations of this kind are known to those skilled in the art. Data reported as less than (<) represents either the highest measurable pIC$_{50}$, or the highest concentration tested that failed to achieve 50% inhibition of agonist response. Data highlighted with an asterix (*) is derived from a single experiment, otherwise all data reported is an average of at least two independent replicate experiments.

Intracellular Calcium Measurements Using Division-Arrested Cells (Table 1):

Test compounds are prepared as 10 mM stock solutions in DMSO, then serially diluted in half log concentrations with DMSO followed by dilution with assay buffer (HBSS (Sigma-Aldrich, H8264) containing 20 mM HEPES (Sigma-Aldrich, H4034), 0.1% (w/v) bovine serum albumin and adjusted to pH 7.4) to a top final assay concentration of 10 µM.

Human $OX_1$ (CT-A474) and human $OX_2$ (CT-A475) receptor-expressing division-arrested cells are plated into 384 well black, clear bottom, cell-bind plates at a seeding density of 10,000 cells/50 µL growth media. The seeded plates are incubated at 37° C. in air supplemented with 5% $CO_2$ for 16 hrs.

The media is removed and replaced with 30 µL/well of cell loading buffer (a vial of Calcium 5 is solubilized in 22 mL of assay buffer to which a freshly prepared 250 mM solution of probenecid in 1:1 1M NaOH to assay buffer (200 µL) is added) and the cells incubated for 1 hr at 37° C. The serially diluted test compounds (10 µL/well) are added to the plate, which is then incubated for 10 mins and placed in a FlexStation III reader. Finally 10 µL of agonist, orexin A for $OX_1$ and orexin B for $OX_2$, is added at a concentration of $2 \times EC_{50}$ which is determined for each assay run. Fluorescence is measured at excitation and emission wavelengths of 485 nm and 525 nm respectively and this data analyzed using GraphPad Prism to determine an $IC_{50}$ value for each compound.

TABLE 1

| Example Number | $pIC_{50}$ $OX_1$ | $pIC_{50}$ $OX_2$ |
| --- | --- | --- |
| 1 | 7.7 | 6.0 |
| 2 | 7.4 | 5.7 |
| 3 | 7.7 | 6.0 |
| 4 | 6.8 | <5.0 |
| 5 | 6.0 | <5.0 |
| 6 | 6.3 | <5.0 |
| 7 | 5.8 | 5.3 |
| 8 | 6.1 | <5.0 |
| 9 | 6.6 | <5.0 |
| 10 | 7.1 | 5.2 |
| 11 | 7.1 | <5.1 |
| 12 | 6.0 | <5.0 |
| 13 | 7.4 | 5.6 |
| 14 | 8.3 | 6.8 |
| 15 | 5.7 | <5.0 |
| 16 | 7.9 | 5.9 |
| 17 | 6.7 | 5.5 |
| 18 | 7.1 | <5.0 |
| 19 | 7.6* | 5.8* |
| 20 | 6.7* | 5.3* |
| 21 | 8.1 | 5.5 |
| 22 | 5.7 | <5.0 |
| 23 | 7.6 | 5.6 |
| 24 | 5.7* | <5.0* |
| 25 | 6.2 | <5.0 |
| 26 | 7.5 | 5.7 |
| 27 | 6.8 | 6.3 |
| 28 | 6.7 | <5.0 |
| 29 | 5.8 | 5.4 |
| 30 | 5.8 | <5.3 |
| 31 | 6.7 | 5.2 |
| 32 | 6.7 | 5.5 |
| 33 | 7.0 | 5.1 |
| 34 | 6.7 | <5.5 |
| 35 | 7.1 | 5.7 |
| 36 | 7.2 | 5.4 |
| 37 | 7.1 | 5.4 |
| 38 | 7.1 | <5.4 |
| 39 | 8.2 | 6.0 |
| 40 | 7.8 | 5.6 |
| 41 | 6.7* | <5.0* |
| 42 | 7.9 | 6.0 |
| 46 | 7.7 | 5.1 |
| 47 | 7.5 | 5.2 |
| 48 | 7.9 | 5.6 |
| 49 | 7.5 | <5.3 |
| 50 | 6.2 | 5.5 |
| 51 | 6.2 | <5.0 |
| 52 | 6.0 | <5.1 |
| 53 | 6.6 | 5.4 |
| 54 | 7.7 | 5.9 |
| 55 | 7.1 | 5.1 |
| 56 | 6.9 | <5.5 |
| 57 | 5.7 | 5.3 |
| 58 | 6.9 | <5.3 |
| 59 | 6.8 | <5.2 |

Intracellular Calcium Measurements Using Stable-Replicating Cells:

Method A (Table 2): Test compounds are prepared as 10 mM stock solutions in DMSO, warmed briefly for 20 seconds at 37° C. and serially diluted in half log concentrations with DMSO followed by dilution with assay buffer (HBSS (Sigma-Aldrich, H8264) containing 10 mM HEPES (Invitrogen, 15630080) and pH adjusted to 7.4) to a top final assay concentration of 10 µM.

Human $OX_1$ (CT-A674) and human $OX_2$ (CT-A675) receptor-expressing stable-replicating cells are grown in a culture medium, Ham F12 (Invitrogen, 31765-035) containing 10% fetal bovine serum (Invitrogen, 16000044), 1% non-essential amino acids (Invitrogen, 11140-050), 100 U/mL Penicillin/Streptomycin (Invitrogen, 15140-122) and G418 (Invitrogen, 11811023) at a concentration of 400 µg/mL. The cells are seeded at a density of 7,000 cells/well into black, clear bottom 384-well plates (Corning, 3683) and incubated at 37° C. in air supplemented with 5% $CO_2$ for 16 hrs.

Loading dye (25 UL/well), prepared from a FLIPR Calcium 6 Assay kit (Molecular Devices, R8190-Explorer) according to the manufacturer's instructions, and the serially diluted test compounds (10 µL/well) are added to the plate. The plate is then incubated for 30 mins at 37° C. in 5% $CO_2$, then for 30 mins at ambient temperature and placed into a FlexStation III reader. Finally orexin-A is added to each well at a concentration of $4 \times EC_{50}$ which is determined for each assay run. Fluorescence is measured at excitation and emission wavelengths of 485 nm and 525 nm respectively and this data analyzed using GraphPad Prism to determine an $IC_{50}$ value for each compound.

TABLE 2

| Example Number | $pIC_{50}$ $OX_1$ | $pIC_{50}$ $OX_2$ |
| --- | --- | --- |
| 1 | 8.1 | 5.9 |
| 6 | 5.5 | <5.0* |
| 9 | 5.7 | <5.0 |
| 14 | 7.8 | 7.2 |
| 39 | 7.7 | <5.0* |
| 43 | 8.0 | 6.0 |
| 44 | 8.1 | 6.2 |
| 45 | 6.9 | <5.0 |

TABLE 2-continued

| Example Number | pIC$_{50}$ OX$_1$ | pIC$_{50}$ OX$_2$ |
|---|---|---|
| 46 | 7.5 | <5.0 |
| 47 | 8.4 | <5.1 |
| 60 | 7.4 | <5.0 |
| 61 | 8.4* | 5.8* |
| 62 | 8.3* | 5.1* |
| 63 | 8.8* | 5.9* |
| 64 | 8.3* | 5.6* |
| 75 | 8.2* | 5.7* |
| 77 | 8.1 | 5.9 |
| 78 | 7.6* | 6.0* |
| 79 | 7.0* | 5.8* |
| 80 | 7.6* | 6.7* |
| 81 | 7.4* | 6.6* |
| 85 | 7.3* | 5.5* |
| 86 | 8.1* | 6.5* |
| 87 | 6.8* | 6.4* |
| 88 | 7.4 | <5.0* |

Method B (Table 3): Test compounds are prepared as 20 mM stock solutions in DMSO, then serially diluted in half log concentrations with DMSO followed by dilution with assay buffer (HBSS Gibco, 14065-049) containing 20 mM HEPES (Gibco, 15630-56), 2.5 mM Probenecid; 0.1% (w/v) pluronic F127 (Sigma, P2443) and adjusted to pH 7.4) to a top final assay concentration of 1 µM or 10 µM, depending on the potency at a given human OX receptor. Human OX$_1$ or human OX$_2$ receptor expressing CHO cells are plated into 384 well black, clear bottom, CellBIND plates at a seeding density of 10,000 cells/75 µL growth media. The seeded plates are incubated at 37° C. in air supplemented with 5% CO$_2$ overnight.

The next day media is removed and replaced with 30 µL/well of cell loading buffer (a vial of Calcium 5 is solubilized in 20 mL of assay buffer) and the cells incubated for 1 hr at 37° C. The serially diluted test compounds (10 µL/well) are added to the cell plate by the FLIPR Tetra and the addition is monitored for 5 mins by the instrument. The cell plate is then removed and incubated for additional 25 mins in a humidified incubator at 37° C. prior to being placed back into the FLIPR Tetra. Finally 10 µL of orexin A in assay buffer+0.1% (w/v) bovine serum albumin is dispensed by the FLIPR Tetra at an EC$_{75}$ concentration determined for each assay run. Fluorescence is measured at excitation and emission wavelengths of 485 nm and 525 nm respectively and data analyzed using GraphPad Prism for the EC$_{75}$ value of orexin A and Aplus to determine an IC$_{50}$ value for each test compound.

TABLE 3

| Example Number | pIC$_{50}$ OX$_1$ | pIC$_{50}$ OX$_2$ |
|---|---|---|
| 19 | 8.8 | 6.3 |
| 20 | 7.0 | 5.5 |
| 24 | 5.4 | <5.0 |
| 39 | 9.1 | 5.8 |
| 41 | 7.7 | <5.3 |
| 43 | 9.1 | 6.1 |
| 44 | 8.8 | 6.4 |
| 46 | 8.5 | <5.0 |
| 47 | 8.6 | <5.4 |
| 49 | 8.3 | <5.4 |
| 61 | 8.6 | 5.5 |
| 62 | 8.5 | 5.6 |
| 63 | 8.8 | 6.3 |
| 65 | 8.7 | 6.1 |
| 66 | 7.9 | <6.2 |
| 67 | 8.1 | 5.3 |
| 68 | 7.8 | <6.0 |
| 69 | 8.5 | 5.5 |
| 70 | 8.8 | 5.3 |
| 71 | 9.0 | 6.5 |
| 72 | 8.8 | 6.4 |
| 73 | 8.8 | <6.0 |
| 74 | 5.7 | <5.0 |
| 75 | 8.9 | 5.6 |
| 76 | 7.6 | <5.7 |
| 77 | 9.1 | 6.3 |
| 78 | 7.8 | 6.2 |
| 79 | 7.1 | 5.6 |
| 80 | 8.0 | 6.5 |
| 81 | 8.3 | 6.6 |
| 82 | 8.1 | <5.0 |
| 83 | 7.9 | <6.0 |
| 84 | 8.7 | 6.0 |
| 85 | 7.0 | 5.3 |
| 87 | 8.4 | 6.8 |
| 88 | 8.0 | 5.4 |
| 89 | 5.7 | <5.0 |
| 90 | 8.7 | <6.0 |
| 91 | 7.6 | <5.1 |
| 92 | 7.5 | 5.1 |

As indicated herein, by whole cell FLIPR functional assay data and by comparison with reference compounds not claimed within the present invention, the compounds of the present invention provide increased selectivity for the orexin-1 receptor over the orexin-2 receptor.

Selectivity 80x

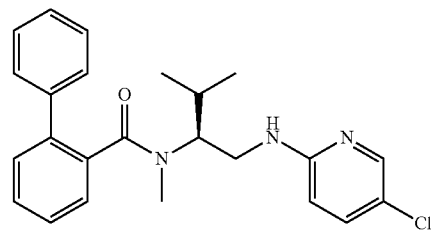

Example 10
hOX1R pIC$_{50}$ = 7.1
hOX2R pIC$_{50}$ = 5.2

Selectivity 1.9x

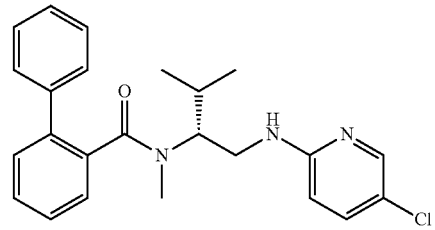

hOX1R pIC$_{50}$ = 6.0
hOX2R pIC$_{50}$ = 5.7

-continued

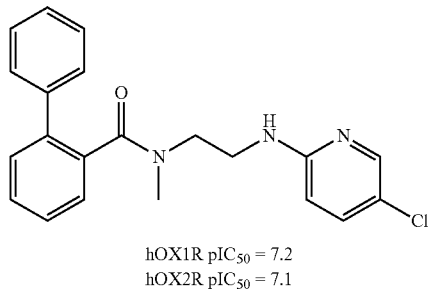

Selectivity 1.1x hOX1R pIC$_{50}$ = 7.2
hOX2R pIC$_{50}$ = 7.1

The increased selectivity for the orexin-1 receptor over the orexin-2 receptor in the whole cell FLIPR functional assay provides enhanced predictive value for determining in vivo efficacy. Increasing the functional selectivity for the orexin-1 receptor reduces the potential for dual receptor antagonism in vivo. Such greater functional selectivity may provide benefits over other orexin receptor antagonists that are known in the art.

In general, the compounds of the present invention possess IC$_{50}$ values of 10 µM (pIC$_{50}$ 5) or less against orexin-1 in the above identified assays and showed selectivity for orexin 1 over orexin 2 in the above assays that is greater than or equal to 0.4 log units. Preferred compounds of the invention possess IC$_{50}$ values of 3 µM (pIC$_{50}$ 5.5) or less against orexin 1 in the above identified assays and showed selectivity for orexin 1 over orexin 2 in the above assays that is greater than or equal to 1.0 log units. The most preferred compounds possess IC$_{50}$ values of 500 nM (pIC$_{50}$ 6.3) or less against orexin-1 in the above identified assays and showed selectivity for orexin 1 over orexin 2 in the above assays that is greater than or equal to 1.5 log units.

The following compounds did not show any activity (i.e. they have an IC$_{50}$ of greater than 10 µM) against orexin-1 in the aforementioned assays:
(S)-5-methyl-N-(1-((1-methyl-1H-benzo[d]imidazol-2-yl)oxy)butan-2-yl)-2-(2H-1,2,3-triazol-2-yl)benzamide;
(S)—N,5-dimethyl-N-(1-((1-methyl-1H-benzo[d]imidazol-2-yl)oxy)butan-2-yl)-2-(2H-1,2,3-triazol-2-yl)benzamide;
N-(2-((5-chloropyridin-2-yl)amino)-1-(oxetan-3-yl)ethyl)-N,5-dimethyl-2-(2H-1,2,3-triazol-2-yl)benzamide;
(S)—N-(1-((5-chloropyridin-2-yl)amino)butan-2-yl)-5-methyl-2-(4-methylpiperazin-1-yl)benzamide;
(S)—N-(1-((5-chloropyridin-2-yl)amino)butan-2-yl)-5-methyl-2-morpholinobenzamide;
(S)—N-(1-((5-chloropyridin-2-yl)amino)butan-2-yl)-N,5-dimethyl-2-(4-methylpiperazin-1-yl)benzamide;
(S)—N-(1-((5-chloropyridin-2-yl)amino)butan-2-yl)-N,2-dimethyl-5-(2H-1,2,3-triazol-2-yl)pyrimidine-4-carboxamide;
(S)—N-(2-(5-chloro-N-methyl-2-(2H-1,2,3-triazol-2-yl)benzamido)butyl)picolinamide;
(S)-5-chloro-N-(1-(imidazo[1,2-a]pyridin-6-ylamino)butan-2-yl)-N-methyl-2-(2H-1,2,3-triazol-2-yl)benzamide;
(S)-ethyl 6-((2-(5-chloro-N-methyl-2-(2H-1,2,3-triazol-2-yl)benzamido)butyl)amino) nicotinate;
(S)-6-(2-hydroxypropan-2-yl)-N-methyl-3-(2H-1,2,3-triazol-2-yl)-N-(1-((5-(trifluoromethyl)pyrimidin-2-yl)amino)butan-2-yl)picolinamide.

In an embodiment, the present invention provides a compound of formula I as defined herein which is not selected from one of the compounds listed in the paragraph above.

The following compound possessed an IC$_{50}$ of 4.9 µM in the aforementioned assays: (S)—N-(1-((5-chloropyridin-2-yl)amino)butan-2-yl)-N-methyl-2-(1H-1,2,3-triazol-1-yl)-5-(trifluoromethyl)benzamide. In an embodiment, the present invention provides a compound of formula I which excludes this particular compound.

REFERENCES

1. De Lecea, L. (1998). The hypocretins: Hypothalamus-specific peptides with neuroexcitatory activity. *Proceedings of the National Academy of Sciences*, 95(1), 322-327. doi:10.1073/pnas.95.1.322
2. Sakurai, T., Amemiya, A., Ishii, M., Matsuzaki, I., Chemelli, R. M., Tanaka, H., Williams, S. C., et al. (1998). Orexins and orexin receptors: a family of hypothalamic neuropeptides and G protein-coupled receptors that regulate feeding behavior. *Cell*, 92(4), 573-85. Retrieved from http://www.ncbi.nlm.nih.gov/pubmed/9491897
3. Lee, J.-H., Bang, E., Chae, K.-J., Kim, J.-Y., Lee, D. W., & Lee, W. (1999). Solution structure of a new hypothalamic neuropeptide, human hypocretin-2/orexin-B. *European Journal of Biochemistry*, 266(3), 831-839. doi:10.1046/j.1432-1327.1999.00911.x
4. Peyron, C., Tighe, D. K., Van den Pol, A. N., De Lecea, L., Heller, H. C., Sutcliffe, J. G., & Kilduff, T. S. (1998). Neurons Containing Hypocretin (Orexin) Project to Multiple Neuronal Systems. *J. Neurosci.*, 18(23), 9996-10015. Retrieved from http://www.jneurosci.org/content/18/23/9996.long
5. Van den Pol, A. N., Gao, X.-B., Obrietan, K., Kilduff, T. S., & Belousov, A. B. (1998). Presynaptic and Postsynaptic Actions and Modulation of Neuroendocrine Neurons by a New Hypothalamic Peptide, Hypocretin/Orexin. *J. Neurosci.*, 18(19), 7962-7971. Retrieved from http://www.jneurosci.org/content/18/19/7962.long
6. Boss, C., Brisbare-Roch, C., & Jenck, F. (2009). Biomedical application of orexin/hypocretin receptor ligands in neuroscience. *Journal of Medicinal Chemistry*, 52(4), 891-903. doi:10.1021/jm801296d
7. Brisbare-Roch, C., Dingemanse, J., Koberstein, R., Hoever, P., Aissaoui, H., Flores, S., Mueller, C., et al. (2007). Promotion of sleep by targeting the orexin system in rats, dogs and humans. *Nature Medicine*, 13(2), 150-5. doi:10.1038/nm1544
8. Urbańska, A., Sokołowska, P., Woldan-Tambor, A., Biegańska, K., Brix, B., Jöhren, O., Namiecińska, M., et al. (2012). Orexins/hypocretins acting at Gi protein-coupled OX 2 receptors inhibit cyclic AMP synthesis in the primary neuronal cultures. *Journal of Molecular Neuroscience: MN*, 46(1), 10-7. doi:10.1007/s12031-011-9526-2
9. Matsuki, T., & Sakurai, T. (2008). Orexins and orexin receptors: from molecules to integrative physiology. *Results and Problems in Cell Differentiation*, 46, 27-55. doi:10.1007/400_2007_047
10. Chemelli, R. M., Willie, J. T., Sinton, C. M., Elmquist, J. K., Scammell, T., Lee, C., Richardson, J. A., et al. (1999). Narcolepsy in orexin Knockout MiceMolecular Genetics of Sleep Regulation. *Cell*, 98(4), 437-451. doi:10.1016/S0092-8674(00)81973-X
11. Mieda, M. (2002). Sleep, feeding, and neuropeptides: roles of orexins and orexin receptors. *Current Opinion in Neurobiology*, 12(3), 339-345. doi:10.1016/S0959-4388(02)00331-8
12. Lin, L., Faraco, J., Li, R., Kadotani, H., Rogers, W., Lin, X., Qiu, X., et al. (1999). The Sleep Disorder Canine Narcolepsy Is Caused by a Mutation in the Hypocretin (Orexin) Receptor 2 Gene. *Cell,* 98(3), 365-376. doi: 10.1016/S0092-8674(00)81965-0

13. Nishino, S., Ripley, B., Overeem, S., Nevsimalova, S., Lammers, G. J., Vankova, J., Okun, M., et al. (2001). Low cerebrospinal fluid hypocretin (Orexin) and altered energy homeostasis in human narcolepsy. *Annals of Neurology,* 50(3), 381-8. Retrieved from http://www.ncbi.nlm.nih.gov/pubmed/11558795

14. Peyron, C., Faraco, J., Rogers, W., Ripley, B., Overeem, S., Charnay, Y., Nevsimalova, S., et al. (2000). A mutation in a case of early onset narcolepsy and a generalized absence of hypocretin peptides in human narcoleptic brains. *Nature Medicine,* 6(9), 991-7. doi:10.1038/79690

15. Gatfield, J., Brisbare-Roch, C., Jenck, F., & Boss, C. (2010). Orexin receptor antagonists: a new concept in CNS disorders? *Chem Med Chem,* 5(8), 1197-214. doi: 10.1002/cmdc.201000132

16. Herring, W. J., Snyder, E., Budd, K., Hutzelmann, J., Snavely, D., Liu, K., Lines, C., et al. (2012). Orexin receptor antagonism for treatment of insomnia: a randomized clinical trial of suvorexant. *Neurology,* 79(23), 2265-74. doi:10.1212/WNL.0b013e31827688ee 17. Willie, J. T., Chemelli, R. M., Sinton, C. M., Tokita, S., Williams, S. C., Kisanuki, Y. Y., Marcus, J. N., et al. (2003). Distinct Narcolepsy Syndromes in Orexin Receptor-2 and Orexin Null Mice. *Neuron,* 38(5), 715-730. doi:10.1016/S0896-6273(03)00330-1

18. Hoever, P., Dorffner, G., Beneš, H., Penzel, T., Danker-Hopfe, H., Barbanoj, M. J., Pillar, G., et al. (2012). Orexin receptor antagonism, a new sleep-enabling paradigm: a proof-of-concept clinical trial. *Clinical Pharmacology and Therapeutics,* 91(6), 975-85. doi:10.1038/clpt.2011.370

19. Bernardis, L. L., & Bellinger, L. L. (1993). The lateral hypothalamic area revisited: Neuroanatomy, body weight regulation, neuroendocrinology and metabolism. *Neuroscience & Biobehavioral Reviews,* 17(2), 141-193. doi: 10.1016/S0149-7634(05)80149-6

20. Haynes, A. C., Jackson, B., Overend, P., Buckingham, R. E., Wilson, S., Tadayyon, M., & Arch, J. R. (1999). Effects of single and chronic intracerebroventricular administration of the orexins on feeding in the rat. *Peptides,* 20(9), 1099-1105. doi:10.1016/S0196-9781(99) 00105-9

21. Yamada, H., Okumura, T., Motomura, W., Kobayashi, Y., & Kohgo, Y. (2000). Inhibition of food intake by central injection of anti-orexin antibody in fasted rats. *Biochemical and Biophysical Research Communications,* 267(2), 527-31. doi:10.1006/bbrc.1999.1998

22. Rodgers, R. J., Halford, J. C. G., Nunes de Souza, R. L., Canto de Souza, A. L., Piper, D. C., Arch, J. R. S., Upton, N., et al. (2001). SB-334867, a selective orexin-1 receptor antagonist, enhances behavioural satiety and blocks the hyperphagic effect of orexin-A in rats. *European Journal of Neuroscience,* 13(7), 1444-1452. doi:10.1046/j.0953-816x.2001.01518.x 23. Piccoli, L., Vittoria, M., Di, M., Cifani, C., Costantini, V. J. A., Massagrande, M., Montanari, D., et al. (2012). Role of Orexin-1 Receptor Mechanisms on Compulsive Food Consumption in a Model of Binge Eating in Female Rats. *Neuropsychopharmacology,* 37(9), 1999-2011. doi: 10.1038/npp.2012.48

24. López, M., Seoane, L., García, M. C., Lago, F., Casanueva, F. F., Señaris, R., & Diéguez, C. (2000). Leptin regulation of prepro-orexin and orexin receptor mRNA levels in the hypothalamus. *Biochemical and Biophysical Research Communications,* 269(1), 41-5. doi:10.1006/bbrc.2000.2245

25. Pizza, F., Magnani, M., Indrio, C., & Plazzi, G. (2013). The Hypocretin System and Psychiatric Disorders. *Current Psychiatry Reports,* 16(2), 433. doi:10.1007/s11920-013-0433-9

26. Von der Goltz, C., Koopmann, A., Dinter, C., Richter, A., Grosshans, M., Fink, T., . . . Kiefer, F. (2011). Involvement of orexin in the regulation of stress, depression and reward in alcohol dependence. *Hormones and Behavior,* 60(5), 644-50. doi:10.1016/j.yhbeh.2011.08.017

27. Johnson, P. L., Truitt, W., Fitz, S. D., Minick, P. E., Dietrich, A., Sanghani, S., . . . Shekhar, A. (2009). A key role for orexin in panic anxiety. *Nature Medicine,* 16(1), 111-115. doi:10.1038/nm.2075

28. Harris, G. C., Wimmer, M., & Aston-Jones, G. (2005). A role for lateral hypothalamic orexin neurons in reward seeking. *Nature,* 437(7058), 556-9. doi:10.1038/nature04071

29. Boutrel, B., Kenny, P. J., Specio, S. E., Martin-Fardon, R., Markou, A., Koob, G. F., & de Lecea, L. (2005). Role for hypocretin in mediating stress-induced reinstatement of cocaine-seeking behavior. *Proceedings of the National Academy of Sciences of the United States of America,* 102(52), 19168-73. doi:10.1073/pnas.0507480102

30. Lawrence, A. J., Cowen, M. S., Yang, H.-J., Chen, F., & Oldfield, B. (2006). The orexin system regulates alcohol-seeking in rats. *British Journal of Pharmacology,* 148(6), 752-9. doi:10.1038/sj.bjp.0706789

31. Harris, G. C., & Aston-Jones, G. (2006). Arousal and reward: a dichotomy in orexin function. *Trends in Neurosciences,* 29(10), 571-7. doi:10.1016/j.tins.2006.08.002

32. Harris, G. C., Wimmer, M., & Aston-Jones, G. (2005). A role for lateral hypothalamic orexin neurons in reward seeking. *Nature,* 437(7058), 556-9. doi:10.1038/nature04071

33. Hollander, J. A., Lu, Q., Cameron, M. D., Kamenecka, T. M. & Kenny P. J. (2008). Insular hypocretin transmission regulates nicotine reward. *PNAS,* 105(49), 19480-19485.

34. LeSage, M. G., Perry, J. L., Kotz, C. M., Shelley, D. & Corrigall, W. A. (2010). Nicotine self-administration in the rat: effects of hypocretin antagonists and changes in hypocretin mRNA. *Psychopharmacology,* 209, 203-212.

35. Plaza-Zabala, A., Martín-García, E., de Lecea, L., Maldonado, R. & Berrendero, F. Hypocretins regulate the anxiogenic-like effects of nicotine and induce reinstatement of nicotine-seeking behaviour. (2010). *J Neurosci.,* 30(6), 2300-2310.

36. Plaza-Zabala, A., Martín-García, E., de Lecea, L., Maldonado, R. & Berrendero, F. A role for Hypocretin/Orexin Receptor-1 in Cue-Induced Reinstatement of Nicotine-seeking behaviour. (2013). *Neuropsychopharmacology,* 38, 1724-1736.

The invention claimed is:

1. A method of alleviating a disease or condition selected from anxiety disorders; panic disorders; mood disorders; addiction including substance dependence, alcohol dependence, nicotine dependence or gambling disorder; and eating disorders, said method comprising administering to a subject in need of such treatment a therapeutically effective amount of a compound of formula I, or a pharmaceutically acceptable salt or solvate thereof:

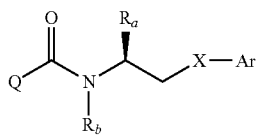

(I)

wherein:
$R_a$ is ethyl, propyl, isopropyl, cyclopropyl, n-butyl, isobutyl, sec-butyl, t-butyl, or cyclopropylmethyl, each of which is optionally substituted by one or more fluoro;
$R_b$ is:
  (i) hydrogen;
  (ii) a (1-4C)alkyl which is optionally substituted by one or more fluoro;
  (iii) a (3-6C)cycloalkyl which is optionally substituted by one or more fluoro; or
  (iv) a (3-6C)cycloalkyl(1-2C)alkyl which is optionally substituted by one or more fluoro;
X is a group:

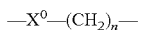

wherein
$X^0$ is —O—, —N($R^1$)—, —C(O)—N($R^1$)—, —N($R^1$)C(O)N($R^1$)— or —S—;
n is 0 or 1;
$R^1$ is hydrogen or a (1-2C)alkyl group which is optionally substituted by one or more substituents selected from fluoro, hydroxyl, $NR^{1a}R^{1b}$, (1-2C)alkoxy and (1-2C)haloalkoxy;
$R^{1a}$ and $R^{1b}$ are each independently hydrogen or (1-2C)alkyl; or $R^{1a}$ and $R^{1b}$ are linked such that, together with the nitrogen atom to which they are attached, they form a 4, 5 or 6 membered heterocyclic ring;
Ar is aryl or heteroaryl, each of which is optionally substituted with one or more substituents selected from halo, cyano, nitro and a group of the formula:

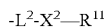

wherein
$L^1$ is absent or a linker group of the formula —[$CR^7R^8$]$_r$— in which r is an integer selected from 1, 2, 3 and 4, and $R^7$ and $R^8$ are each independently selected from hydrogen, halo, hydroxy and a (1-4C)alkyl, (3-6C)cycloalkyl, (3-6C)cycloalkyl(1-2C)alkyl group which is optionally substituted by one or more fluoro substituents; or $R^7$ and $R^8$ are optionally linked such that, together with the carbon atom to which they are attached, they form a (3-6C)cycloalkyl ring which is optionally substituted by one or more fluoro substituents;
$X^1$ is absent or selected from —O—, —C(O)—, —C(O)O—, —OC(O)—, —N($R^9$)—, —N($R^9$)—C(O)—, —C(O)—N($R^9$)—, —N($R^9$)—C(O)O—, —OC(O)—N($R^9$)—, —N($R^9$)C(O)N($R^{10}$)—, —S—, —SO—, —SO$_2$—, —S(O)$_2$N($R^9$)—, —N($R^9$)SO$_2$— and —S(O)(=N$R^{10}$)—, wherein $R^9$ and $R^{10}$ are hydrogen, (1-4C)alkyl, (1-4C)fluoroalkyl or (3-6C)cycloalkyl; and
$R^6$ is hydrogen, (1-6C)alkyl, (2-6C)alkenyl, (2-6C)alkynyl, aryl, aryl(1-2C)alkyl, (3-6C)cycloalkyl, (3-6C)cycloalkyl(1-2C)alkyl, heterocyclyl, heterocyclyl-(1-2C)alkyl, heteroaryl, or heteroaryl-(1-2C)alkyl, and wherein $R^6$ is optionally further substituted by one or more substituent groups independently selected from oxo, halo, cyano, nitro, and a group of the formula:

-$L^2$-$X^2$—$R^{11}$ wherein
$L^2$ is absent or a linker group of the formula —[$CR^{12}R^{13}$]$_s$— in which s is an integer selected from 1, 2, 3 and 4, and $R^{12}$ and $R^{13}$ are each independently hydrogen or a (1-4C)alkyl, (3-6C)cycloalkyl, (3-6C)cycloalkyl(1-2C)alkyl group which is optionally substituted by one or more fluoro substituents; or $R^{12}$ and $R^{13}$ are optionally linked such that, together with the carbon atom to which they are attached, they form a (3-6C)cycloalkyl ring which is optionally substituted by one or more fluoro substituents;
$X^2$ is absent or selected from —O—, —C(O)—, —C(O)O—, —OC(O)—, —N($R^{14}$)—, —N($R^{14}$)—C(O)—, —C(O)—N($R^{14}$)—, —N($R^{14}$)—C(O)O—, —OC(O)—N($R^{14}$)—, —N($R^{14}$)C(O)N($R^{15}$)—, —S—, —SO—, —SO$_2$—, —S(O)$_2$N($R^{14}$)—, —N($R^{14}$)SO$_2$— and —S(O)(=N$R^{14}$)—, wherein $R^{14}$ and $R^{15}$ are hydrogen, (1-4C)alkyl, (1-4C)fluoroalkyl or (3-6C)cycloalkyl; and
$R^{11}$ is hydrogen or a (1-6C)alkyl (3-6C)cycloalkyl, (3-6C)cycloalkyl(1-2C)alkyl group which is optionally substituted by one or more fluoro substituents;
Q is aryl or heteroaryl, each of which is optionally substituted with one or more $R^z$ substituents, wherein $R^z$ is halo, cyano, nitro, or a group of the formula:

-$L^3$-$X^3$—$R^{30}$ wherein
$L^3$ is absent or a linker group of the formula —[$CR^{31}R^{32}$]$_t$— in which t is an integer selected from 1, 2, 3 and 4, and $R^{31}$ and $R^{32}$ are each independently hydrogen or a (1-4C)alkyl, (3-6C)cycloalkyl, (3-6C)cycloalkyl(1-2C)alkyl group which is optionally substituted by one or more fluoro substituents; or $R^{31}$ and $R^{32}$ are optionally linked such that, together with the carbon atom to which they are attached, they form a (3-6C)cycloalkyl ring which is optionally substituted by one or more fluoro substituents;
$X^3$ is absent, —O—, —C(O)—, —C(O)O—, —OC(O)—, —N($R^{33}$)—, —N($R^{33}$)—C(O)—, —C(O)—N($R^{33}$)—, —N($R^{33}$)—C(O)O—, —OC(O)—N($R^{33}$)—, —N($R^{33}$)C(O)N($R^{34}$)—, —S—, —SO—, —SO$_2$—, —S(O)$_2$N($R^{33}$)—, —N($R^{33}$)SO$_2$— or —S(O)(=N$R^{33}$)—, wherein $R^{33}$ and $R^{34}$ are selected from hydrogen, (1-4C)alkyl, (1-4C)fluoroalkyl and (3-6C)cycloalkyl; and
$R^{30}$ is hydrogen, (1-6C)alkyl, (2-6C)alkenyl, (2-6C)alkynyl, aryl, aryl(1-2C)alkyl, (3-6C)cycloalkyl, (3-6C)cycloalkyl(1-2C)alkyl, heterocyclyl, heterocyclyl-(1-2C)alkyl, heteroaryl, or heteroaryl-(1-2C)alkyl,
and wherein $R^{30}$ is optionally further substituted by one or more substituent groups independently selected from oxo, halo, cyano, nitro, and a group of the formula:

-$L^4$-$X^4$—$R^{35}$ wherein
- $L^4$ is absent or a linker group of the formula —[$CR^{36}R^{37}$]$_u$— in which u is an integer selected from 1, 2, 3 and 4, and $R^{36}$ and $R^{37}$ are each independently hydrogen or a (1-4C)alkyl, (3-6C)cycloalkyl, (3-6C)cycloalkyl(1-2C)alkyl group which is optionally substituted by one or more fluoro substituents; or $R^{36}$ and $R^{37}$ are optionally linked such that, together with the carbon atom to which they are attached, they form a (3-6C)cycloalkyl ring which is optionally substituted by one or more fluoro substituents;
- $X^4$ is absent or selected from —O—, —C(O)—, —C(O)O—, —OC(O)—, —N($R^{38}$)—, —N($R^{38}$)—C(O)—, —C(O)—N($R^{38}$)—, —N($R^{38}$)—C(O)O—, —OC(O)—N($R^{38}$)—, —N($R^{38}$)C(O)N($R^{39}$)—, —S—, —SO—, —SO$_2$—, —S(O)$_2$N($R^{38}$)—, —N($R^{38}$)SO$_2$— and —S(O)(=N$R^{38}$)—, wherein $R^{38}$ and $R^{39}$ are hydrogen, (1-4C)alkyl, (1-4C)fluoroalkyl or (3-6C)cycloalkyl; and
- $R^{35}$ is hydrogen or a (1-6C)alkyl, (3-6C)cycloalkyl, (3-6C)cycloalkyl(1-2C)alkyl group which is optionally substituted by one or more fluoro substituents;

or a pharmaceutically acceptable salt or solvate thereof.

2. The method according to claim 1, wherein $R_a$ is ethyl or cyclopropyl, each of which is optionally substituted by one or more fluoro.

3. The method according to claim 1, wherein $R_a$ is ethyl optionally substituted by one or more fluoro.

4. The method according to claim 1, wherein $R_a$ is ethyl.

5. The method according to claim 1, wherein $R_b$ is:
hydrogen; or
a (1-4C)alkyl which is optionally substituted by one or more fluoro.

6. The method according to claim 1, wherein $R_b$ is hydrogen or methyl.

7. The method according to claim 1, wherein $R_b$ is methyl.

8. The method according to claim 1, wherein Ar is aryl or heteroaryl, each of which is optionally substituted with one or more substituents selected from halo, cyano, nitro and a group of the formula:

-$L^1$-$X^1$—$R^6$ wherein
- $L^1$ is absent or a linker group of the formula —[$CR^7R^8$]$_r$— in which r is an integer 1 or 2, and $R^7$ and $R^8$ are each independently hydrogen, halo, or a (1-2C)alkyl group which is optionally substituted by one or more fluoro substituents;
- $X^1$ is absent or selected from —O—, —N($R^9$)—, —S—, —SO—, and —SO$_2$—, wherein $R^9$ is hydrogen or (1-2C)alkyl; and
- $R^6$ is hydrogen, (1-4C)alkyl, phenyl, phenyl(1-2C)alkyl, (3-4C)cycloalkyl, (3-4C)cycloalkyl(1-2C)alkyl, 3-6-membered heterocyclyl, 3-6-membered heterocyclyl-(1-2C)alkyl, 5-6-membered heteroaryl, or 5-6-membered heteroaryl-(1-2C)alkyl,
and wherein $R^6$ is optionally further substituted by one or more substituent groups independently selected from oxo, halo, cyano, nitro, and a group of the formula:

-$L^2$-$X^2$—$R^{11}$ wherein
- $L^2$ is absent or a linker group of the formula —[$CR^{12}R^{13}$]$_s$— in which s is an integer 1 or 2, and $R^{12}$ and $R^{13}$ are each independently hydrogen or a (1-2C)alkyl group;
- $X^2$ is absent or selected from —O—, —N($R^{14}$)—, —S—, —SO—, and —SO$_2$—, wherein $R^{14}$ is hydrogen or (1-2C)alkyl; and
- $R^{11}$ is hydrogen or a (1-4C)alkyl group which is optionally substituted by one or more fluoro substituents.

9. The method according to claim 1, wherein Ar is phenyl, naphthyl or a mono or bicyclic heteroaryl, each of which is optionally substituted with one or more substituents selected from halo, cyano, nitro and a group of the formula:

-$L^1$-$X^1$—$R^6$ wherein
- $L^1$ is absent or a linker group of the formula —[$CR^7R^8$]$_r$— in which r is an integer 1 or 2, and $R^7$ and $R^8$ are each independently hydrogen, halo, or a (1-2C)alkyl group which is optionally substituted by one or more fluoro substituents;
- $X^1$ is absent or selected from —O—, —N($R^9$)—, —S—, —SO—, and —SO$_2$—, wherein $R^9$ is hydrogen or (1-2C)alkyl; and
- $R^6$ is hydrogen, (1-4C)alkyl, phenyl, phenyl(1-2C)alkyl, (3-4C)cycloalkyl, (3-4C)cycloalkyl(1-2C)alkyl, 3-6-membered heterocyclyl, 3-6-membered heterocyclyl-(1-2C)alkyl, 5-6-membered heteroaryl, or 5-6-membered heteroaryl-(1-2C)alkyl,
and wherein $R^6$ is optionally further substituted by one or more substituent groups independently selected from oxo, halo, cyano, nitro, and a group of the formula:

-$L^2$-$X^2$—$R^{11}$ wherein
- $L^2$ is absent or a linker group of the formula —[$CR^{12}R^{13}$]$_s$— in which s is an integer 1 or 2, and $R^{12}$ and $R^{13}$ are each independently hydrogen or a (1-2C)alkyl group;
- $X^2$ is absent or selected from —O—, —N($R^{14}$)—, —S—, —SO—, and —SO$_2$—, wherein $R^{14}$ hydrogen or (1-2C)alkyl; and
- $R^{11}$ is hydrogen or a (1-4C)alkyl group which is optionally substituted by one or more fluoro substituents.

10. The method according to claim 1, wherein Q is aryl or heteroaryl, each of which is optionally substituted with one or more $R^z$ substituents, wherein $R^z$ is halo, cyano, nitro, or a group of the formula:

-$L^3$-$X^3$—$R^{30}$ wherein
- $L^3$ is absent or a linker group of the formula —[$CR^{31}R^{32}$]$_t$— in which t is an integer selected from 1 or 2, and $R^{31}$ and $R^{32}$ are each independently hydrogen or a (1-4C)alkyl group;
- $X^3$ is absent, or selected from —O—, —N($R^{33}$)—, —N($R^{33}$)—C(O)—, —C(O)—N($R^{33}$)—, —S—, —SO—, and —SO$_2$—, wherein $R^{33}$ is hydrogen or (1-2C)alkyl; and
- $R^{30}$ is hydrogen, (1-4C)alkyl, phenyl, phenyl(1-2C)alkyl, (3-4C)cycloalkyl, (3-4C)cycloalkyl(1-2C)alkyl, 3-6-membered heterocyclyl, 3-6-membered heterocyclyl-(1-2C)alkyl, 5-6-membered heteroaryl, or 5-6-membered heteroaryl-(1-2C)alkyl, and wherein $R^{30}$ is optionally further substituted by one or more substituent groups independently selected from oxo, halo, cyano, nitro, and a group of the formula:

-$L^4$-$X^4$—$R^{35}$ wherein
$L^4$ is absent or a linker group of the formula —[$CR^{36}R^{37}$]$_u$— in which u is an integer 1 or 2, and $R^{36}$ and $R^{37}$ are each independently hydrogen or a (1-2C)alkyl group;
$X^4$ is absent or selected from —O—, —N($R^{38}$)—, —S—, —SO—, and —SO$_2$—, wherein $R^{38}$ is hydrogen or (1-2C)alkyl; and
$R^{35}$ is hydrogen or a (1-4C)alkyl group which is optionally substituted by one or more fluoro substituents.

11. The method according to claim 1, wherein Q is a group having the following structure:

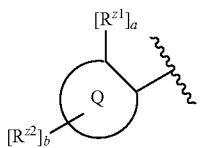

wherein ring Q is selected from phenyl, 5-6 membered monocyclic heteroaryl, and 9-10 membered bicyclic heteroaryl; a is an integer 0-1; and b is an integer 0-5; and
$R^{z1}$ is a substituent group of the formula:

-$L^3$-$X^3$—$R^{30}$ wherein
$L^3$ is absent;
$X^3$ is absent or selected from —O—, —N($R^{33}$)—, —S—, —SO— and —SO$_2$—, wherein $R^{33}$ is hydrogen or (1-2C)alkyl; and
$R^{30}$ is hydrogen, (1-4C)alkyl, phenyl, (3-4C)cycloalkyl, (3-4C)cycloalkyl(1-2C)alkyl, 3-6-membered heterocyclyl, 3-6-membered heterocyclyl-(1-2C)alkyl, 5-6-membered heteroaryl, or 5-6-membered heteroaryl-(1-2C)alkyl,
and wherein $R^{30}$ is optionally further substituted by one or more substituent groups independently selected from oxo, halo, cyano, nitro, and a group of the formula:

-$L^4$-$X^4$—$R^{35}$ wherein
$L^4$ is absent or a linker group of the formula —[$CR^{36}R^{37}$]$_u$— in which u is an integer selected from 1, 2 and 3, and $R^{36}$ and $R^{37}$ are each independently hydrogen or a (1-4C)alkyl group which is optionally substituted by one or more fluoro substituents; or $R^{36}$ and $R^{37}$ are optionally linked such that, together with the carbon atom to which they are attached, they form a (3-4C)cycloalkyl ring which is optionally substituted by one or more fluoro substituents;
$X^4$ is absent or selected from —O—, —C(O)—, —N($R^{38}$)—, —N($R^{38}$)—C(O)—, —C(O)—N($R^{38}$)—, —N($R^{38}$)C(O)N($R^{39}$)—, —S—, —SO—, —SO$_2$—, —S(O)$_2$N($R^{38}$)—, —N($R^{38}$)SO$_2$— and —S(O)(=N$R^{38}$)—, wherein $R^{38}$ and $R^{39}$ are selected from hydrogen, (1-4C)alkyl, (1-4C)fluoroalkyl and (3-6C)cycloalkyl; and $R^{35}$ is hydrogen or a (1-6C)alkyl, (3-6C)cycloalkyl, (3-6C)cycloalkyl(1-2C)alkyl group which is optionally substituted by one or more fluoro substituents, $R^{z2}$ is selected from halo, cyano, nitro, and a group of the formula:

-$L^3$-$X^3$—$R^{30}$ wherein
$L^3$ is absent;
$X^3$ is absent, or selected from —O—, —N($R^{33}$)—, —N($R^{33}$)—C(O)—, —C(O)—N($R^{33}$)—, —S—, —SO—, and —SO$_2$—, wherein $R^{33}$ is hydrogen or (1-2C)alkyl; and
$R^{30}$ is hydrogen, (1-4C)alkyl, (3-4C)cycloalkyl, (3-4C)cycloalkyl(1-2C)alkyl, 3-6-membered heterocyclyl, 3-6-membered heterocyclyl-(1-2C)alkyl, 5-6-membered heteroaryl, or 5-6-membered heteroaryl-(1-2C)alkyl,
and wherein $R^{30}$ is optionally further substituted by one or more substituent groups independently selected from oxo, halo, cyano, nitro, and a group of the formula:

-$L^4$-$X^4$—$R^{35}$ wherein
$L^4$ is absent or a linker group of the formula —[$CR^{36}R^{37}$]$_u$— in which u is an integer selected from 1, 2 and 3, and $R^{36}$ and $R^{37}$ are each independently hydrogen or a (1-4C)alkyl group which is optionally substituted by one or more fluoro substituents; or $R^{36}$ and $R^{37}$ are optionally linked such that, together with the carbon atom to which they are attached, they form a (3-4C)cycloalkyl ring which is optionally substituted by one or more fluoro substituents;
$X^4$ is absent or selected from —O—, —C(O)—, —N($R^{38}$)—, —N($R^{38}$)—C(O)—, —C(O)—N($R^{38}$)—, —N($R^{38}$)C(O)N($R^{39}$)—, —S—, —SO—, —SO$_2$—, —S(O)$_2$N($R^{38}$)—, —N($R^{38}$)SO$_2$— and —S(O)(=N$R^{38}$)—, wherein $R^{38}$ and $R^{39}$ are selected from hydrogen, (1-4C)alkyl, (1-4C)fluoroalkyl and (3-6C)cycloalkyl; and
$R^{35}$ is hydrogen or a (1-6C)alkyl, (3-6C)cycloalkyl, (3-6C)cycloalkyl(1-2C)alkyl group which is optionally substituted by one or more fluoro substituents.

12. The method according to claim 11, wherein ring Q is a group having any one of the following structures, W1-W7:

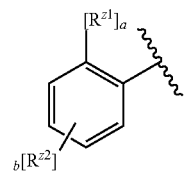

W1

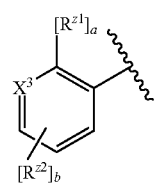

W2

-continued

W3
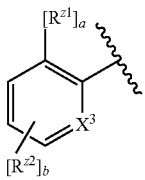

W4
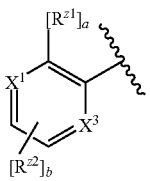

W5
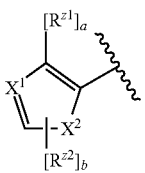

W6
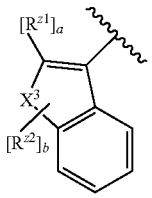

W7
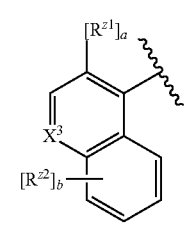

wherein $X^1$, $X^2$ and $X^3$ are each a heteroatom selected from O, N and S; a is an integer 0-1; and b is an integer 0-5.

13. The method according to claim 11, wherein a is 1 and b is 0 or 1.

14. The method according to claim 11, wherein $R^{z1}$ is a substituent group of the formula:

-L$^3$-X$^3$—R$^{30}$ wherein
L$^3$ is absent;
X$^3$ is absent; and
R$^{30}$ is phenyl or a C- or N-linked 5-6 membered heteroaryl,
and wherein R$^{30}$ is optionally further substituted by one or more substituent groups independently selected from halo, cyano and a group of the formula:

-L$^4$-X$^4$—R$^{35}$ wherein
L$^4$ is absent;
X$^4$ is absent; and
R$^{35}$ is hydrogen or a (1-2C)alkyl group which is optionally substituted by one or more fluoro substituents.

15. The method according to claim 11, wherein $R^{z2}$ is selected from halo, cyano, and a group of the formula:

-L$^3$-X$^3$—R$^{30}$ wherein
L$^3$ is absent;
X$^3$ is absent, or selected from —O—, —N(R$^{33}$)—, —N(R$^{33}$)—C(O)—, —C(O)—N(R$^{33}$)—, —S—, —SO—, and —SO$_2$—, wherein R$^{33}$ is hydrogen or (1-2C)alkyl; and
R$^{30}$ is hydrogen or (1-4C)alkyl,
and wherein R$^{30}$ is optionally further substituted by one or more fluoro atoms.

16. The method according to claim 1, wherein said compound has the structural formula IA shown below (IA)

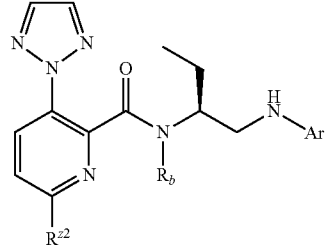

wherein
$R_b$ is selected from:
(i) (1-4C)alkyl which is optionally substituted by one or more fluoro;
(ii) (3-6C)cycloalkyl which is optionally substituted by one or more fluoro; or
(iii) (3-6C)cycloalkyl(1-2C)alkyl which is optionally substituted by one or more fluoro;
$R^{z2}$ is selected from halo, cyano, nitro, and a group of the formula:

-L$^3$-X$^3$—R$^{30}$ wherein
L$^3$ is absent;
X$^3$ is absent, or selected from —O—, —N(R$^{33}$)—, —N(R$^{33}$)—C(O)—, —C(O)—N(R$^{33}$)—, —S—, —SO—, and —SO$_2$—, wherein R$^{33}$ is hydrogen or (1-2C)alkyl; and
R$^{30}$ is hydrogen, (1-4C)alkyl, (3-4C)cycloalkyl, (3-4C)cycloalkyl(1-2C)alkyl, 3-6-membered heterocyclyl, 3-6-membered heterocyclyl-(1-2C)alkyl, 5-6-membered heteroaryl, or 5-6-membered heteroaryl-(1-2C)alkyl,
and wherein R$^{30}$ is optionally further substituted by one or more substituent groups independently selected from oxo, halo, cyano, nitro, and a group of the formula:

-L$^4$-X$^4$—R$^{35}$ wherein
L$^4$ is absent or a linker group of the formula —[CR$^{36}$R$^{37}$]$_u$— in which u is an integer selected from 1, 2 and 3, and R$^{36}$ and R$^{37}$ are each independently hydrogen or a (1-4C)alkyl group which is optionally substituted by one or more fluoro substituents; or R$^{36}$ and R$^{37}$ are optionally linked such that, together with the carbon atom to which they are attached, they form a (3-4C)cycloalkyl ring which is optionally substituted by one or more fluoro substituents;
X$^4$ is absent or selected from —O—, —C(O)—, —N(R$^{38}$)—, —N(R$^{38}$)—C(O)—, —C(O)—N(R$^{38}$)—, —N(R$^{38}$)C(O)N(R$^{39}$)—, —S—, —SO—, —SO$_2$—, —S(O)$_2$N(R$^{38}$)—, —N(R$^{38}$)SO$_2$— and —S(O) (=NR$^{38}$)—, wherein R$^{38}$ and R$^{39}$ are selected from hydrogen, (1-4C)alkyl, (1-4C)fluoroalkyl and (3-6C) cycloalkyl; and R$^{35}$ is hydrogen or a (1-6C)alkyl, (3-6C)cycloalkyl, (3-6C)cycloalkyl(1-2C)alkyl group which is optionally substituted by one or more fluoro substituents.

17. The method according to claim 16, wherein
R$_b$ is (1-4C)alkyl optionally substituted by fluoro;
R$^{z2}$ is selected from halo, cyano, nitro, and a group of the formula:

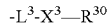

wherein
L$^3$ is absent;
X$^3$ is absent, or selected from —O—, —N(R$^{33}$)—, —N(R$^{33}$)—C(O)—, —C(O)—N(R$^{33}$)—, —S—, —SO—, or —SO$_2$—, wherein R$^{33}$ is hydrogen or (1-2C)alkyl; and
R$^{30}$ is hydrogen or (1-4C)alkyl;
and wherein R$^{30}$ is optionally further substituted by one or more fluoro atoms.

18. The method according to claim 16, wherein
R$_b$ is methyl optionally substituted by fluoro;
R$^{z2}$ is halo, methyl, methoxy, CF$_3$ or OCF$_3$;
Ar is pyridyl, pyrimidinyl, pyrazinyl, which is optionally substituted by one or more substituent groups selected from halo, cyano, hydroxyl, mercapto, amino, carbamoyl, sulphamoyl, (1-2C)alkyl, (1-2C)haloalkyl, (1-2C)alkoxy, (1-2C)haloalkoxy, (1-2C)alkylamino, di-[(1-2C)alkyl]amino, (1-2C)alkylthio, (1-2C)alkylsulphinyl, (1-2C)alkylsulphonyl, (1-2C)alkoxycarbonyl, N-(1-2C)alkylcarbamoyl, N,N-di-[(1-2C)alkyl]carbamoyl, (2C)alkanoyl, (2C)alkanoyloxy, (2C)alkanoylamino, N-(1-2C)alkylsulphamoyl and N,N-di-[(1-2C)alkyl]sulphamoyl.

19. The method of claim 1, wherein the compound is selected from:
(S)—N-(1-(5-chloropyridin-2-yl)amino)butan-2-yl)-N,5-dimethyl-2-(2H-1,2,3-triazol-2-yl)benzamide;
(S)—N-(1-(5-chloropyridin-2-yl)amino)butan-2-yl)-5-methyl-2-(2H-1,2,3-triazol-2-yl)benzamide;
(S)—N-(1-(5-chloropyridin-2-yl)amino)butan-2-yl)-N-methyl-[1,1'-biphenyl]-2-carboxamide;
(S)—N-(1-((5-chloropyridin-2-yl)amino)-3-methylbutan-2-yl)-[1,1'-biphenyl]-2-carboxamide;
(S)—N-(1-(5-chloropyridin-2-yl)amino)-4-methylpentan-2-yl)-[1,1'-biphenyl]-2-carboxamide;
(S)—N-(1-((5-chloropyridin-2-yl)amino)-3-methylbutan-2-yl)-2-methyl-4-phenylthiazole-5-carboxamide;
(S)—N-(1-(5-chloropyridin-2-yl)amino)-4-methylpentan-2-yl)-2-methyl-4-phenylthiazole-5-carboxamide;
(S)—N-(1-(5-chloropyridin-2-yl)amino)-4-methylpentan-2-yl)-N-methyl-[1,1'-biphenyl]-2-carboxamide;
(S)—N-(1-(5-chloropyridin-2-yl)amino)-4-methylpentan-2-yl)-N,2-dimethyl-4-phenylthiazole-5-carboxamide;
(S)—N-(1-(5-chloropyridin-2-yl)amino)-3-methylbutan-2-yl)-N-methyl-[1,1'-biphenyl]-2-carboxamide;
(S)—N-(1-((5-chloropyridin-2-yl)amino)-3-methylbutan-2-yl)-N,2-dimethyl-4-phenylthiazole-5-carboxamide;
(S)—N-(1-((5-chloropyridin-2-yl)amino)-3,3-dimethylbutan-2-yl)-N-methyl-[1,1'-biphenyl]-2-carboxamide;
(S)—N-(2-((5-chloropyridin-2-yl)amino)-1-cyclopropylethyl)-N-methyl-[1,1'-biphenyl]-2-carboxamide;
(S)—N-(1-((5-chloropyridin-2-yl)amino)propan-2-yl)-N-methyl-[1,1'-biphenyl]-2-carboxamide;
(S)—N-(1-((5-chloropyridin-2-yl)amino)-3-methylbutan-2-yl)-N-cyclopropyl-[1,1'-biphenyl]-2-carboxamide;
(S)-5-chloro-N-(1-((5-chloropyridin-2-yl)amino)butan-2-yl)-N-methyl-2-(2H-1,2,3-triazol-2-yl)benzamide;
(S)—N-(1-((5-chloropyridin-2-yl)amino)butan-2-yl)-N-methyl-2-(2H-1,2,3-triazol-2-yl)-5-(trifluoromethyl)benzamide;
(S)—N-(1-((5-chloropyridin-2-yl)amino)butan-2-yl)-5-fluoro-N-methyl-2-(2H-1,2,3-triazol-2-yl)benzamide;
(S)-5-bromo-N-(1-((5-chloropyridin-2-yl)amino)butan-2-yl)-N-methyl-2-(2H-1,2,3-triazol-2-yl)benzamide;
(S)—N-(1-((5-chloropyridin-2-yl)amino)butan-2-yl)-N-methyl-2-(2H-1,2,3-triazol-2-yl)-5-(trifluoromethoxy)benzamide;
(S)—N-(1-((5-chloropyridin-2-yl)amino)butan-2-yl)-N,6-dimethyl-3-(2H-1,2,3-triazol-2-yl)picolinamide;
(S)—N-(1-((5-chloropyridin-2-yl)amino)butan-2-yl)-N,5-dimethyl-2-morpholinobenzamide;
(S)—N-(1-((5-chloropyridin-2-yl)amino)butan-2-yl)-5-(dimethylamino)-N-methyl-2-(2H-1,2,3-triazol-2-yl)benzamide;
(S)—N-(1-((5-chloropyridin-2-yl)amino)butan-2-yl)-N-methyl-2-(2H-1,2,3-triazol-2-yl)-5-(trifluoromethyl)nicotinamide;
(S)-5-chloro-N-(1-((5-chloropyridin-2-yl)amino)butan-2-yl)-2-(2H-1,2,3-triazol-2-yl)benzamide;
(S)—N-(1-((5-chloropyridin-2-yl)amino)-3-methylbutan-2-yl)-N,2-dimethyl-5-phenylthiazole-4-carboxamide;
(S)—N-(1-((5-chloropyridin-2-yl)amino)-3-methylbutan-2-yl)-N-methyl-2-phenyl-1H-indole-3-carboxamide;
(S)—N-(1-((5-chloropyridin-2-yl)amino)-3-methylbutan-2-yl)-N-methyl-2-(2H-1,2,3-triazol-2-yl)benzamide;
(S)—N-(1-((4-fluorobenzyl)oxy)-3-methylbutan-2-yl)-N-methyl-[1,1'-biphenyl]-2-carboxamide;
(S)—N-(1-((4,6-dimethylpyrimidin-2-yl)oxy)-3-methylbutan-2-yl)-N-methyl-[1,1'-biphenyl]-2-carboxamide;
(S)—N-methyl-N-(3-methyl-1-(quinazolin-2-yloxy)butan-2-yl)-[1,1'-biphenyl]-2-carboxamide;
(S)—N-methyl-N-(3-methyl-1-((4-phenylpyrimidin-2-yl)oxy)butan-2-yl)-[1,1'-biphenyl]-2-carboxamide;
(S)—N-methyl-N-(3-methyl-1-((1-methyl-1H-benzo[d]imidazol-2-yl)oxy)butan-2-yl)-[1,1'-biphenyl]-2-carboxamide;
(S)—N-(1-((5-chloropyridin-2-yl)oxy)-3-methylbutan-2-yl)-N-methyl-[1,1'-biphenyl]-2-carboxamide;
(S)—N-methyl-N-(3-methyl-1-((4-phenylpyrimidin-2-yl)amino)butan-2-yl)-[1,1'-biphenyl]-2-carboxamide;
(S)—N-methyl-N-(3-methyl-1-(quinazolin-2-ylamino)butan-2-yl)-[1,1'-biphenyl]-2-carboxamide;
(S)—N-(1-((4,6-dimethylpyrimidin-2-yl)amino)-3-methylbutan-2-yl)-N-methyl-[1,1'-biphenyl]-2-carboxamide;
(S)—N-methyl-N-(3-methyl-1-((1-methyl-1H-benzo[d]imidazol-2-yl)amino)butan-2-yl)-[1,1'-biphenyl]-2-carboxamide;
(S)-5-chloro-N-methyl-2-(2H-1,2,3-triazol-2-yl)-N-(1-((5-(trifluoromethyl)pyrimidin-2-yl)amino)butan-2-yl)benzamide;
(S)-5-chloro-N-methyl-2-(2H-1,2,3-triazol-2-yl)-N-(1-((5-(trifluoromethyl)pyrazin-2-yl)amino)butan-2-yl)benzamide;
(S)-5-chloro-N-methyl-2-(2H-1,2,3-triazol-2-yl)-N-(1-((6-(trifluoromethyl)pyridazin-3-yl)amino)butan-2-yl)benzamide;

(S)-5-chloro-N-methyl-2-(2H-1,2,3-triazol-2-yl)-N-(1-((5-(trifluoromethyl)pyridin-2-yl)amino)butan-2-yl)benzamide;
(S)—N-(1-(benzo[d]oxazol-2-ylamino)butan-2-yl)-5-chloro-N-methyl-2-(2H-1,2,3-triazol-2-yl)benzamide;
(S)—N-(1-(benzo[d]thiazol-2-ylamino)butan-2-yl)-5-chloro-N-methyl-2-(2H-1,2,3-triazol-2-yl)benzamide;
(S)-5-chloro-N-(1-((5-chloro-3-nitropyridin-2-yl)amino)butan-2-yl)-N-methyl-2-(2H-1,2,3-triazol-2-yl)benzamide;
(S)—N,6-dimethyl-3-(2H-1,2,3-triazol-2-yl)-N-(1-((5-(trifluoromethyl)pyrimidin-2-yl)amino)butan-2-yl)picolinamide;
(S)—N,6-dimethyl-3-(2H-1,2,3-triazol-2-yl)-N-(1-((5-(trifluoromethyl)pyrazin-2-yl)amino)butan-2-yl)picolinamide;
(S)—N,6-dimethyl-3-(2H-1,2,3-triazol-2-yl)-N-(1-((5-(trifluoromethyl)pyridin-2-yl)amino)butan-2-yl)picolinamide;
(S)—N-(1-((5-chloropyridin-2-yl)amino)-3-methylbutan-2-yl)-N,5-dimethyl-2-(2H-1,2,3-triazol-2-yl)benzamide;
(S)—N-(1-((5-chloropyridin-2-yl)amino)-3-methylbutan-2-yl)-N,1-dimethyl-1H-indole-3-carboxamide;
(S)—N-(1-((5-chloropyridin-2-yl)amino)-3-methylbutan-2-yl)-N,2-dimethylquinoline-4-carboxamide;
(S)—N-(1-((5-chloropyridin-2-yl)amino)-3-methylbutan-2-yl)-N-methyl-2-(trifluoromethoxy)benzamide;
(S)-5-chloro-N-methyl-N-(1-((6-methylpyridin-2-yl)amino)butan-2-yl)-2-(2H-1,2,3-triazol-2-yl)benzamide;
(S)-5-chloro-N-methyl-2-(2H-1,2,3-triazol-2-yl)-N-(1-((6-(trifluoromethyl)pyridin-3-yl)amino)butan-2-yl)benzamide;
(S)—N,6-dimethyl-3-(2H-1,2,3-triazol-2-yl)-N-(1-((6-(trifluoromethyl)pyridin-3-yl)amino)butan-2-yl)picolinamide;
(S)—N-(1-(4-fluorobenzamido)-3-methylbutan-2-yl)-N-methyl-[1,1'-biphenyl]-2-carboxamide;
(S)—N-(1-((4-fluorobenzyl)amino)-3-methylbutan-2-yl)-N-methyl-[1,1'-biphenyl]-2-carboxamide;
(S)—N-methyl-N-(3-methyl-1-(3-phenylureido)butan-2-yl)-[1,1'-biphenyl]-2-carboxamide;
(S)—N-(1-((4-chlorophenyl)amino)-3-methylbutan-2-yl)-N-methyl-[1,1'-biphenyl]-2-carboxamide;
(S)—N-(1-((3-amino-5-chloropyridin-2-yl)amino)butan-2-yl)-5-chloro-N-methyl-2-(2H-1,2,3-triazol-2-yl)benzamide;
(S)—N,6-dimethyl-N-(1-(quinazolin-2-ylamino)butan-2-yl)-3-(2H-1,2,3-triazol-2-yl)picolinamide;
(S)—N-(1-(benzo[d]oxazol-2-ylamino)butan-2-yl)-N,6-dimethyl-3-(2H-1,2,3-triazol-2-yl)picolinamide;
(S)—N-(1-(benzo[d]thiazol-2-ylamino)butan-2-yl)-N,6-dimethyl-3-(2H-1,2,3-triazol-2-yl)picolinamide;
(S)—N-(1-((5-chlorobenzo[d]oxazol-2-yl)amino)butan-2-yl)-N,6-dimethyl-3-(2H-1,2,3-triazol-2-yl)picolinamide;
(S)—N,6-dimethyl-N-(1-(quinoxalin-2-ylamino)butan-2-yl)-3-(2H-1,2,3-triazol-2-yl)picolinamide;
(S)—N,6-dimethyl-N-(3-methyl-1-((5-(trifluoromethyl)pyridin-2-yl)amino)butan-2-yl)-3-(2H-1,2,3-triazol-2-yl)picolinamide;
(S)—N,6-dimethyl-N-(3-methyl-1-((5-(trifluoromethyl)pyrazin-2-yl)amino)butan-2-yl)-3-(2H-1,2,3-triazol-2-yl)picolinamide;
(S)—N,6-dimethyl-N-(3-methyl-1-(quinazolin-2-ylamino)butan-2-yl)-3-(2H-1,2,3-triazol-2-yl)picolinamide;
(S)—N,6-dimethyl-N-(3-methyl-1-((5-(trifluoromethyl)pyridin-2-yl)amino)butan-2-yl)-3-(2H-1,2,3-triazol-2-yl)picolinamide;
(S)—N-ethyl-6-methyl-3-(2H-1,2,3-triazol-2-yl)-N-(1-((5-(trifluoromethyl)pyrazin-2-yl)amino)butan-2-yl)picolinamide;
(S)—N-ethyl-6-methyl-3-(2H-1,2,3-triazol-2-yl)-N-(1-((5-(trifluoromethyl)pyridin-2-yl)amino)butan-2-yl)picolinamide;
(S)—N-ethyl-6-methyl-N-(1-(quinazolin-2-ylamino)butan-2-yl)-3-(2H-1,2,3-triazol-2-yl)picolinamide;
(S)—N-ethyl-6-methyl-3-(2H-1,2,3-triazol-2-yl)-N-(1-((5-(trifluoromethyl)pyrimidin-2-yl)amino)butan-2-yl)picolinamide;
(S)—N-(1-cyclopropyl-2-((5-(trifluoromethyl)pyrimidin-2-yl)amino)ethyl)-N,6-dimethyl-3-(2H-1,2,3-triazol-2-yl)picolinamide;
(S)—N,6-dimethyl-N-(1-(quinolin-2-ylamino)butan-2-yl)-3-(2H-1,2,3-triazol-2-yl)picolinamide;
(S)—N-(1-((1,5-naphthyridin-2-yl)amino)butan-2-yl)-N,6-dimethyl-3-(2H-1,2,3-triazol-2-yl)picolinamide;
(S)-5-chloro-N-methyl-N-(1-(quinolin-2-ylamino)butan-2-yl)-2-(2H-1,2,3-triazol-2-yl)benzamide;
(S)—N,3-dimethyl-N-(1-((5-(trifluoromethyl)pyrimidin-2-yl)amino)butan-2-yl)isoquinoline-1-carboxamide;
(S)—N-methyl-N-(1-((5-(trifluoromethyl)pyrimidin-2-yl)amino)butan-2-yl)quinoline-8-carboxamide;
(S)-6-chloro-N-methyl-N-(1-((5-(trifluoromethyl)pyrimidin-2-yl)amino)butan-2-yl)quinoline-8-carboxamide;
(S)-3-(dimethylamino)-N-methyl-N-(1-((5-(trifluoromethyl)pyrimidin-2-yl)amino)butan-2-yl)isoquinoline-1-carboxamide;
(S)—N,6-dimethyl-N-(1-(methyl(5-(trifluoromethyl)pyrimidin-2-yl)amino)butan-2-yl)-3-(2H-1,2,3-triazol-2-yl)picolinamide;
(S)—N-(1-((2-methoxyethyl)(5-(trifluoromethyl)pyrimidin-2-yl)amino)butan-2-yl)-N,6-dimethyl-3-(2H-1,2,3-triazol-2-yl)picolinamide;
(S)—N,6-dimethyl-3-(pyrimidin-2-yl)-N-(1-((5-(trifluoromethyl)pyrimidin-2-yl)amino)butan-2-yl)picolinamide formic acid salt;
(S)—N-methyl-N-(1-((5-(trifluoromethyl)pyrimidin-2-yl)amino)butan-2-yl)isoquinoline-1-carboxamide;
(S)—N-(1-((5-chloropyridin-2-yl)amino)butan-2-yl)-N,4,5-trimethyl-2-(2H-1,2,3-triazol-2-yl)benzamide;
(S)—N-(1-((5-chloropyridin-2-yl)amino)butan-2-yl)-5-methoxy-N,4-dimethyl-2-(2H-1,2,3-triazol-2-yl)benzamide;
(S)—N,6-dimethyl-3-(2H-1,2,3-triazol-2-yl)-N-(4,4,4-trifluoro-1-((5-(trifluoromethyl)pyrimidin-2-yl)amino)butan-2-yl)picolinamide;
(S)—N,6-dimethyl-3-(1H-1,2,4-triazol-1-yl)-N-(1-((5-(trifluoromethyl)pyrimidin-2-yl)amino)butan-2-yl)picolinamide formic acid salt;
(S)—N,6-dimethyl-3-(1H-pyrazol-1-yl)-N-(1-((5-(trifluoromethyl)pyrimidin-2-yl)amino)butan-2-yl)picolinamide formic acid salt;
(S)-2-fluoro-N-methyl-6-(2H-1,2,3-triazol-2-yl)-N-(1-((5-(trifluoromethyl)pyrimidin-2-yl)amino)butan-2-yl)benzamide; and
(S)-6-methoxy-N-methyl-3-(2H-1,2,3-triazol-2-yl)-N-(1-((5-(trifluoromethyl)pyrimidin-2-yl)amino)butan-2-yl)picolinamide;
or a pharmaceutically acceptable salt or solvate thereof.

20. The method of claim 1, wherein the substance dependence is cocaine, opiates, *cannabis* or prescription drug dependence.

21. The method of claim 1, wherein the anxiety disorder is selected from generalized anxiety disorder, post-traumatic stress disorder, acute stress disorder, social anxiety disorder, agoraphobia, obsessive compulsive disorder, trichotillomania and body dysmorphic disorder.

22. The method of claim 1, wherein the mood disorder is selected from depressive disorders, bipolar disorders, bipolar mania and bipolar depression.

23. The method of claim 1, wherein the eating disorder is selected from binge eating, bulimia nervosa and anorexia nervosa.

\* \* \* \* \*

UNITED STATES PATENT AND TRADEMARK OFFICE
CERTIFICATE OF CORRECTION

PATENT NO. : 12,024,509 B2
APPLICATION NO. : 16/814328
DATED : July 2, 2024
INVENTOR(S) : Emma Louise Blaney et al.

It is certified that error appears in the above-identified patent and that said Letters Patent is hereby corrected as shown below:

In the Claims

In Claim 19, at Column 167, Line 40, please cancel the portion of the claim reading:
"(S)-N-(1-(5-chloropyridin-2-yl)amino)butan-2-yl)-N,5-dimethyl-2-(2H-1,2,3-triazol-2-yl)benzamide;"
And insert the following:
--(S)-N-(1-((5-chloropyridin-2-yl)amino)butan-2-yl)-N,5-dimethyl-2-(2H-1,2,3-triazol-2-yl)benzamide;--

In Claim 19, at Column 167, Line 42, please cancel the portion of the claim reading:
"(S)-N-(1-(5-chloropyridin-2-yl)amino)butan-2-yl)-5-methyl-2-(2H-1,2,3-triazol-2-yl)benzamide;"
And insert the following:
--(S)-N-(1-((5-chloropyridin-2-yl)amino)butan-2-yl)-5-methyl-2-(2H-1,2,3-triazol-2-yl)benzamide;--

In Claim 19, at Column 167, Line 44, please cancel the portion of the claim reading:
"(*S*)-*N*-(1-(5-chloropyridin-2-yl)amino)butan-2-yl)-*N*-methyl-[1,1'-biphenyl]-2-carboxamide;"
And insert the following:
--(S)-N-(1-((5-chloropyridin-2-yl)amino)butan-2-yl)-N-methyl-[1,1'-biphenyl]-2-carboxamide;--

In Claim 19, at Column 167, Line 48, please cancel the portion of the claim reading:
"(*S*)-*N*-(1-(5-chloropyridin-2-yl)amino)-4-methylpentan-2-yl)-[1,1'-biphenyl]-2-carboxamide;"
And insert the following:
--(S)-N-(1-((5-chloropyridin-2-yl)amino)-4-methylpentan-2-yl)-[1,1'-biphenyl]-2-carboxamide;--

In Claim 19, at Column 167, Line 52, please cancel the portion of the claim reading:
"(*S*)-*N*-(1-(5-chloropyridin-2-yl)amino)-4-methylpentan-2-yl)-2-methyl-4-phenylthiazole-5-carboxamide;"
And insert the following:
--(S)-N-(1-((5-chloropyridin-2-yl)amino)-4-methylpentan-2-yl)-2-methyl-4-phenylthiazole-5-carboxamide;--

Signed and Sealed this
First Day of October, 2024

*Katherine Kelly Vidal*

Katherine Kelly Vidal
*Director of the United States Patent and Trademark Office*

CERTIFICATE OF CORRECTION (continued)
U.S. Pat. No. 12,024,509 B2

In Claim 19, at Column 167, Line 54, please cancel the portion of the claim reading:
"(*S*)-*N*-(1-(5-chloropyridin-2-yl)amino)-4-methylpentan-2-yl)-*N*-methyl-[1,1'-biphenyl]-2-carboxamide;"
And insert the following:
--(S)-N-(1-((5-chloropyridin-2-yl)amino)-4-methylpentan-2-yl)-N-methyl-[1,1'-biphenyl]-2-carboxamide;--

In Claim 19, at Column 167, Line 56, please cancel the portion of the claim reading:
"(*S*)-*N*-(1-(5-chloropyridin-2-yl)amino)-4-methylpentan-2-yl)-*N*,2-dimethyl-4-phenylthiazole-5-carboxamide;"
And insert the following:
--(S)-N-(1-((5-chloropyridin-2-yl)amino)-4-methylpentan-2-yl)-N,2-dimethyl-4-phenylthiazole-5-carboxamide;--

In Claim 19, at Column 167, Line 58, please cancel the portion of the claim reading:
"(*S*)-*N*-(1-(5-chloropyridin-2-yl)amino)-3-methylbutan-2-yl)-*N*-methyl-[1,1'-biphenyl]-2-carboxamide;"
And insert the following:
--(S)-N-(1-((5-chloropyridin-2-yl)amino)-3-methylbutan-2-yl)-N-methyl-[1,1'-biphenyl]-2-carboxamide;--